United States Patent
Slater et al.

(10) Patent No.: US 9,485,989 B2
(45) Date of Patent: Nov. 8, 2016

(54) METHOD OF CONTROLLING NEONICOTINOID RESISTANT HEMIPTERA

(75) Inventors: Russell Slater, Stein (CH); Alfred Rindlisbacher, Stein (CH); Peter Maienfisch, Stein (CH); Phillippe Camblin, Stein (CH); Alain Gaume, Stein (CH)

(73) Assignee: Syngenta Participations AG, Basel (CH)

( * ) Notice: Subject to any disclaimer, the term of this patent is extended or adjusted under 35 U.S.C. 154(b) by 76 days.

(21) Appl. No.: 13/988,480

(22) PCT Filed: May 26, 2011

(86) PCT No.: PCT/EP2011/058628
§ 371 (c)(1),
(2), (4) Date: Oct. 30, 2013

(87) PCT Pub. No.: WO2011/151249
PCT Pub. Date: Dec. 8, 2011

(65) Prior Publication Data
US 2014/0057930 A1    Feb. 27, 2014

(30) Foreign Application Priority Data

May 31, 2010   (EP) .................... 10164509
Oct. 14, 2010   (EP) .................... 10187533

(51) Int. Cl.
*A01N 53/00*    (2006.01)
*A01N 43/40*    (2006.01)
*A01N 43/90*    (2006.01)
*A01N 47/06*    (2006.01)

(52) U.S. Cl.
CPC .............. *A01N 53/00* (2013.01); *A01N 43/40* (2013.01); *A01N 43/90* (2013.01); *A01N 47/06* (2013.01)

(58) Field of Classification Search
None
See application file for complete search history.

(56) References Cited

U.S. PATENT DOCUMENTS 6,458,965 B1    10/2002  Lieb et al.
2008/0234328 A1*  9/2008  Schlatter et al. ............. 514/341
2011/0301031 A1  12/2011  Muehlebach et al.

FOREIGN PATENT DOCUMENTS

WO         2009/049851        4/2009
WO    WO 2009049851 A1 *   4/2009

OTHER PUBLICATIONS

Hagedorn, Pea Enation Mosaic: Ecology and Control, The Plant Viruses, 1996, Business Media New York, pp. 345-356.*
International Search Report, International Application No. PCT/EP2011/058628, completion date Nov. 29, 2011.
Elbert A et al: "Resistance management guidelines for the new ketoenol insecticide Movento", Announcement Bayer Cropscience, jXX, XX, vol. 61, No. 2, Apr. 16, 2008, pp. 407-409.
Database WPI, Thomson Scientific, London, GB; AN 2001-040951.

* cited by examiner

*Primary Examiner* — San-Ming Hui
*Assistant Examiner* — Andrew Lee
(74) *Attorney, Agent, or Firm* — James Cueva

(57) ABSTRACT

The invention relates to a method of controlling insects from the order hemiptera that resistant to neo-nicotinoid insecticides using spiroheterocyclic pyrrolidine dione derivatives.

14 Claims, No Drawings

METHOD OF CONTROLLING NEONICOTINOID RESISTANT HEMIPTERA

This application is a 371 of International Application No. PCT/EP2011/058628 filed May 26, 2011, which claims priority to EP 10164509.1 filed May 31, 2010, and EP 10187533.4 filed Oct. 14, 2010, the contents of which are incorporated herein by reference.

The present invention relates to a method of controlling Hemiptera that are resistant to neo-nicotinoid insecticides.

Plants exhibiting aphid damage can have a variety of symptoms, such as decreased growth rates, mottled leaves, yellowing, stunted growth, curled leaves, browning, wilting, low yields and death. The removal of sap creates a lack of vigour in the plant, and aphid saliva is toxic to plants. Hemiptera, in particular aphids, frequently transmit disease-causing organisms like plant viruses to their hosts. The green peach aphid (*Myzus persicae*) is a vector for more than 110 plant viruses. Cotton aphids (*Aphis gossypii*) often infect sugarcane, papaya and groundnuts with viruses. Aphids contributed to the spread of late blight (*Phytophthora infestans*) among potatoes in the Great Irish Potato Famine of the 1840s.

The cherry aphid or black cherry aphid, *Myzus cerasi*, is responsible for some leaf curl of cherry trees. This can easily be distinguished from 'leaf curl' caused by *Taphrina* fungus species due to the presence of aphids beneath the leaves.

The coating of plants with honeydew can contribute to the spread of fungi which can damage plants. Honeydew produced by aphids has been observed to reduce the effectiveness of fungicides as well.

The damage of plants, and in particular commercial crops, has resulted in large amounts of resources and efforts being spent attempting to control the activities of Hemiptera. The neonicotinoids represent the fastest-growing class of insecticides introduced to the market since the commercialization of pyrethroids (Nauen & Denholm, 2005: Archives of Insect Biochemistry and Physiology 58:200-215) and are extremely valuable insect control agents not least because they had exhibited little or no cross-resistance to the older insecticide classes, which suffer markedly from resistance problems. However, reports of insect resistance to the neo-nicotinoid class of insecticides are on the increase. The increase in resistance of such insects to neonicotinoid insecticides thus poses a significant threat to the cultivation of a number of commercially important crops, and there is thus a need to find alternative insecticides capable of controlling neonicotinoid resistant insects (i.e. to find insecticides that do not exhibit any cross-resistance with the neonicotinoid class).

The present invention is based on the finding that a compound selected from the chemical class of cyclic diones can be successfully used to control neonicotinoid resistant populations of insects in the Hemiptera order.

Thus in the first aspect of the invention there is provided a method of controlling insects from the Hemiptera order which are resistant to a neonicotinoid insecticide, which method comprises applying to said neonicotinoid resistant insects a compound of formula I

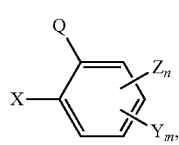

(I)

in which Q is
i or ii or iii

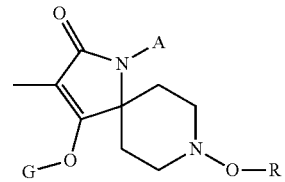

i

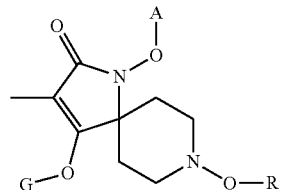

ii

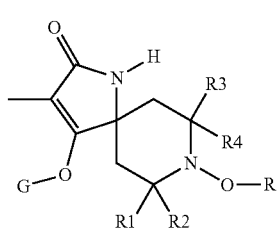

iii

X, Y and Z independently of each other are $C_{1-4}$alkyl, $C_{3-6}$cycloalkyl, $C_{1-4}$haloalkyl, $C_{1-4}$ alkoxy, halogen, phenyl or phenyl substituted by $C_{1-4}$alkyl, $C_{1-4}$haloalkyl, halogen or cyano;

m and n, independently of each other, are 0, 1, 2 or 3 and m+n is 0, 1, 2 or 3;

G is hydrogen, a metal, an ammonium, a sulfonium or a latentiating group;

R is hydrogen, $C_{1-6}$alkyl, $C_{1-6}$haloalkyl, $C_{1-6}$cyanoalkyl, benzyl, $C_{1-4}$alkoxy($C_{1-4}$)alkyl, $C_{1-4}$alkoxy($C_{1-4}$)alkoxy ($C_{1-4}$)alkyl or a group selected from G;

A is $C_{1-6}$alkyl, $C_{1-6}$haloalkyl, $C_{3-6}$cycloalkyl, $C_{3-6}$cycloalkyl ($C_{1-4}$)alkyl, or $C_{3-6}$cycloalkyl-($C_{1-4}$)alkyl where in the cycloalkyl moiety a methylene group is replaced by O, S or $NR_0$, where $R_0$ is $C_{1-6}$alkyl or $C_{1-6}$alkoxy, or A is $C_{2-6}$alkenyl, $C_{2-6}$haloalkenyl, $C_{3-6}$alkynyl, $C_{1-6}$cyanoalkyl, benzyl, $C_{1-4}$alkoxy($C_{1-4}$)alkyl, $C_{1-4}$alkoxy($C_{1-4}$) alkoxy($C_{1-4}$)alkyl, oxetanyl, tetrahydrofuranyl, tetrahydropyranyl, $C_{1-6}$alkylcarbonyl, $C_{1-6}$alkoxycarbonyl, $C_{3-6}$cycloalkylcarbonyl, N-di($C_{1-6}$alkyl)carbamoyl, benzoyl, $C_{1-6}$alkylsulfonyl, phenylsulfonyl, $C_{1-4}$alkylthio ($C_{1-4}$)alkyl, $C_{1-4}$alkylsulfinyl($C_{1-4}$)alkyl or $C_{1-4}$alkylsulfonyl($C_{1-4}$)alkyl; and when Q is ii A may also be hydrogen, furanyl-($C_{1-4}$)alkyl, tetrahydro-thiofuranyl, tetrahydro-thiopyranyl or 1-($C_{1-4}$)alkoxy-piperidin-4-yl; and $R_1$, $R_2$, $R_3$ and $R_4$, independently of each other, are hydrogen or methyl;

or an agrochemically acceptable salt or an N-oxide thereof.

Preferably, the insects from the Hemiptera order, which are controlled by the method according to the present invention, are insects from the Aphididae family.

By virtue of the surprising ability of a compound of formula I to control such neonicotinoid resistant insects, the invention also provides a method of protecting a crop of useful plants, wherein said crop is susceptible to and/or under attack from such insects. Such a method involves applying to said crop, treating a plant propagation material of said crop with, and/or applying to said insects, a compound of formula I.

Since the compound of formula I does not exhibit cross-resistance to neonicotinoid resistant Hemiptera, it may be used in a resistance management strategy with a view to controlling resistance to the neonicotinoid class of insecticides. Such a strategy may involve alternating applications of a compound of formula I and a neonicotinoid insecticide, either on an application by application alternation (including different types of application, such as treatment of plant propagation material and foliar spray), or seasonal/crop alternation basis (e.g. use a compound of formula I on a first crop/for control in a first growing season, and use a neonicotinoid insecticide for a subsequent crop/growing season, or vice versa), and this forms yet a further aspect of the invention.

As mentioned herein, not only are insects from the Hemiptera order pests of a number of commercially important crops, the viruses that these insects carry also pose a threat. With the emergence of resistance to neonicotinoid insecticides, the severity of this threat has increased. Thus, a further aspect of the invention provides a method of controlling a plant virus in a crop of useful plants susceptible to and/or under attack by neonicotinoid resistant insects which carry said plant virus, which method comprises applying to said crop, treating a plant propagation material of said crop with, and/or applying to said insects, a compound of formula I.

Examples of plant viruses that may be controlled according to this aspect of the invention include Sobemovirus, Caulimovirus (Caulimoviridae), Closterovirus (Closteroviridae), Sequivirus (Sequiviridae), Enamovirus (Luteoviridae), Luteovirus (Luteoviridae), Polerovirus (Luteoviridae), Umbravirus, Nanovirus (Nanoviridae), Cytorhabdovirus (Rhabdoviridae), Nucleorhabdovirus (Rhabdoviridae).

These viruses are spread preferably by insects which are one or more of as an example *Acyrthosiphum pisum, Aphis citricola, Aphis craccivora, Aphis fabae, Aphis frangulae, Aphis glycines, Aphis gossypii, Aphis nasturtii, Aphis pomi, Aphis spiraecola, Aulacorthum solani, Brachycaudus helichrysi, Brevicoryne brassicae, Diuraphis noxia, Dysaphis devecta, Dysaphis plantaginea, Eriosoma lanigerum, Hyalopterus pruni, Lipaphis erysimi, Macrosiphum avenae, Macrosiphum euphorbiae, Macrosiphum rosae, Myzus cerasi* F., *Myzus nicotianae, Myzus persicae, Nasonovia ribisnigri, Pemphigus bursarius, Phorodon humuli, Rhopalosiphum insertum* Wa, *Rhopalosiphum maidis* Fitch, *Rhopalosiphum padi* L., *Schizaphis graminum* Rond., *Sitobion avenae, Toxoptera aurantii, Toxoptera citricola, Phylloxera vitifoliae, Bemisia tabaci, Myzus persicae, Nilaparvata lugens, Aphis gossypii, Trialeurodes vaporariorum, Bactericera cockerelli.*

Methods of the invention as described herein may also involve a step of assessing whether insects are resistant to neonicotinoid insecticides and/or whether said insects carry a plant virus. This step will in general involve collecting a sample of insects from the area (e.g. crop, field, habitat) to be treated, before actually applying a compound of formula I, and testing (for example using any suitable phenotypic, biochemical or molecular biological technique applicable) for resistance/sensitivity and/or the presence or absence of a virus.

The term neonicotinoid insecticide as used herein refers to any insecticidal compound that acts at the insect nicotinic acetylcholine receptor, and in particular refers to those compounds classified as neonicotinoid insecticides according to Yamamoto (1996, Agrochem Jpn 68:14-15). Examples of neonicotinoid insecticides include those in Group 4A of the IRAC (insecticide resistance action committee, Crop Life) mode of action classification scheme, e.g. acetamiprid, clothianidin, dinotefuran, imidacloprid, nitenpyram, thiacloprid, and thiamethoxam, as well as any compound having the same mode of action.

By the terms "control" or "controlling" as applied to insects, it is meant that the targeted insects are repelled from or less attracted to the crops to be protected. Additionally, as applied to insects, the terms "control" or "controlling" may also refer to the inability, or reduced ability, of the insects to feed or lay eggs. These terms may further include that the targeted insects are killed.

Thus the method of the invention may involve the use of an amount of the active ingredient that is sufficient to repel insects (i.e a repellently effective amount of active ingredient), an amount of the active ingredient that is sufficient to stop insects feeding, or it may involve the use of an insecticidally effective amount of active ingredient (i.e. an amount sufficient to kill insects), or any combination of the above effects. Where the terms "control" or "controlling" are applied to viruses it is meant that the level of viral infection of a crop of useful plants is lower than would be observed in the absence of any application of a compound of formula I.

The terms "applying" and "application" are understood to mean direct application to the insect to be controlled, as well as indirect application to said insect, for example through application to the crop or plant on which the insect acts as pest, or to the locus of said crop or insect, or indeed through treatment of the plant propagation material of said crop of plant.

Thus a compound of formula I may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the plant propagation material, such as seed, before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

The methods of the invention are particularly applicable to the control of neonicotinoid resistant insects (and neonicotinoid resistance in insects) of the order Hemiptera, such as: *Acyrthosiphum pisum, Aphis citricola, Aphis craccivora, Aphis fabae, Aphis frangulae, Aphis glycines, Aphis gossypii, Aphis nasturtii, Aphis pomi, Aphis spiraecola, Aulacorthum solani, Brachycaudus helichrysi, Brevicoryne brassicae, Diuraphis noxia, Dysaphis devecta, Dysaphis plantaginea, Eriosoma lanigerum, Hyalopterus pruni, Lipaphis erysimi, Macrosiphum avenae, Macrosiphum euphorbiae, Macrosiphum rosae, Myzus cerasi* F., *Myzus nicotianae, Myzus persicae, Nasonovia ribisnigri, Pemphigus bursarius, Phorodon humuli, Rhopalosiphum insertum* Wa, *Rhopalosiphum maidis* Fitch, *Rhopalosiphum padi* L., *Schizaphis graminum* Rond., *Sitobion avenae, Toxoptera aurantii, Toxoptera citricola, Phylloxera vitifoliae, Acyrthosiphon dirhodum, Acyrthosiphon solani, Aphis forbesi, Aphis grossulariae, Aphis idaei, Aphis illinoisensis, Aphis*

*maidiradicis, Aphis ruborum, Aphis schneideri, Brachycaudus persicaecola, Cavariella aegopodii* Scop., *Cryptomyzus galeopsidis, Cryptomyzus ribis, Hyadaphis pseudobrassicae, Hyalopterus amygdali, Hyperomyzus pallidus, Macrosiphoniella sanborni, Metopolophium dirhodum, Myzus malisuctus, Myzus varians, Neotoxoptera* sp, *Nippolachnus piri* Mats., *Oregma lanigera* Zehnter, *Rhopalosiphum fitchii* Sand., *Rhopalosiphum nymphaeae, Rhopalosiphum sacchari* Ze, *Sappaphis piricola* Okam. +T, *Schizaphis piricola, Toxoptera theobromae* Sch, and *Phylloxera coccinea,*

*Aleurodicus dispersus, Aleurocanthus spiniferus, Aleurocanthus woglumi, Aleurodicus cocois, Aleurodicus destructor, Aleurolobus barodensis, Aleurothrixus floccosus, Bemisia tabaci, Bemisia argentifolli, Dialeurodes citri, Dialeurodes citrifolli, Parabemisia myricae, Trialeurodes packardi, Trialeurodes ricini, Trialeurodes vaporariorum, Trialeurodes variabilis,*

*Agonoscena targionii, Bactericera cockerelli, Cacopsylla pyri, Cacopsylla pyricola, Cacopsylla pyrisuga, Diaphorina citri, Glycaspis brimblecombei, Paratrioza cockerelli, Troza erytreae,*

*Amarasca biguttula biguttula, Amritodus atkinsoni, Cicadella viridis, Cicadulina mbila, Cofana spectra, Dalbulus maidis, Empoasca decedens, Empoasca biguttula, Empoasca fabae, Empoasca vitis, Empoasca papaya, Idioscopus clypealis, Jacobiasca lybica, Laodelphax striatellus, Myndus crudus, Nephotettix virescens, Nephotettix cincticeps, Nilaparvata lugens, Peregrinus maidis, Perkinsiella saccharicida, Perkinsiella vastatrix, Recilia dorsalis, Sogatella furcifera, Tarophagus Proserpina, Zygina flammigera,*

*Acanthocoris scabrator, Adelphocoris lineolatus, Amblypelta nitida, Bathycoelia thalassina, Blissus leucopterus, Clavigralla tomentosicollis, Edessa meditabunda, Eurydema pulchrum, Eurydema rugosum, Eurygaster Maura, Euschistus servus, Euschistus tristigmus, Euschistus heros Helopeltis antonii, Horcias nobilellus, Leptocorisa acuta, Lygus lineolaris, Lygus hesperus, Murgantia histrionic, Nesidiocoris tenuis, Nezara viridula, Oebalus insularis, Scotinophara coarctata,*

Specific examples of neonicotinoid resistant Hemiptera include *Bemisia tabaci, Myzus persicae, Nilaparvata lugens, Aphis gossypii, Trialeurodes vaporariorum, Bactericera cockerelli.*

Preferably, the insects are one or more of as an example *Acyrthosiphum pisum, Aphis citricola, Aphis craccivora, Aphis fabae, Aphis frangulae, Aphis glycines, Aphis gossypii, Aphis nasturtii, Aphis pomi, Aphis spiraecola, Aulacorthum solani, Brachycaudus helichrysi, Brevicoryne brassicae, Diuraphis noxia, Dysaphis devecta, Dysaphis plantaginea, Eriosoma lanigerum, Hyalopterus pruni, Lipaphis erysimi, Macrosiphum avenae, Macrosiphum euphorbiae, Macrosiphum rosae, Myzus cerasi* F., *Myzus nicotianae, Myzus persicae, Nasonovia ribisnigri, Pemphigus bursarius, Phorodon humuli, Rhopalosiphum insertum* Wa, *Rhopalosiphum maidis* Fitch, *Rhopalosiphum padi* L., *Schizaphis graminum* Rond., *Sitobion avenae, Toxoptera aurantii, Toxoptera citricola, Phylloxera vitifoliae, Bemisia tabaci, Myzus persicae, Nilaparvata lugens, Aphis gossypii, Trialeurodes vaporariorum, Bactericera cockerelli.*

More preferably, the insects are one or more of as an example *Bemisia tabaci, Myzus persicae, Nilaparvata lugens, Aphis gossypii, Trialeurodes vaporariorum, Bactericera cockerelli.*

Since the methods of the invention have the effect of controlling insect pest and or viral infestation in crops of useful plants, said methods may also be viewed as methods of improving and/or maintaining plant health in said crops or as methods of increasing/maintaining the well-being of a crop.

Crops of useful plants that may be protected according to the invention, and to which a compound of formula I may be applied in accordance with the invention, include: cereals, such as wheat, barley, rye, oats, rice, maize (fodder maize and sugar maize/sweet and field corn) or sorghum; beet, such as sugar or fodder beet; fruit, for example pomaceous fruit, stone fruit, tree nut or soft fruit, such as apples, pears, plums, peaches, bananas, almonds, walnuts, pistachios, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, marrow, cucumbers or melons; fibre plants, such as cotton, flax, hemp or jute; citrus fruit, such as oranges, lemons, clementines, grapefruit or tangerines; vegetables, such as spinach, lettuce, asparagus, cabbages, iceberg, carrots, onions, tomatoes, paprika, potatoes or bell peppers; Lauraceae, such as avocado, Cinnamonium or camphor; and also tobacco, nuts, coffee, eggplants, sugarcane, tea, pepper, grapevines, hops, the plantain family, latex plants, lawn, turf, fodder grass, and ornamentals, such as petunias, geranium/pelargoniums, pansies and impatiens; and shrubs, broad-leaved trees and evergreens, such as conifers. Crops of useful plants are to be understood as including those which are/have been made tolerant to herbicides or classes of herbicide (such as, for example, imidazolinones such as imazamox, as is the case with Clearfield® Rice) and/or insecticide or classes of insecticide, and/or which have acquired a so-called "output" trait (e.g. improved storage stability, higher nutritional value, improved yield etc.) by conventional plant-breeding or genetic engineering methods.

Thus useful plants include those where the plants are transgenic, or where the plants have inherited a trait as a consequence of the introduction at least one transgene in their lineage.

Table below lists key aphids (as an example of a family of Hemiptera) and crops they target.

| PEST | COMMON NAME | EXAMPLES OF CROPS |
|---|---|---|
| *Acyrthosiphum pisum* | Pea aphid | pea |
| *Aphis citricola* | Citrus aphid | citrus |
| *Aphis craccivora* | Cowpea aphid | vegetables, beans, sugarbeet |
| *Aphis fabae* | Black bean aphid | vegetables, beans, sugarbeet |
| *Aphis frangulae* | Breaking buckthorn aphid | cotton potato |
| *Aphis glycines* | Soybean aphid | soybean |
| *Aphis gossypii* | Cotton aphid | cotton, vegetables, citrus, potato |
| *Aphis nasturtii* | Buckthorn aphid | potato |
| *Aphis pomi* | Green apple aphid | apple |

-continued

| PEST | COMMON NAME | EXAMPLES OF CROPS |
|---|---|---|
| *Aphis spiraecola* | Green citurs aphis | apple, citrus, papaya |
| *Aulacorthum solani* | Foxglove aphid | citrus, sugar beet |
| *Brachycaudus helichrysi* | Plum aphid | peach, stone fruits |
| *Brevicoryne brassicae* | Cabbage aphid | *brassica* |
| *Diuraphis noxia* | Russion wheat aphid | cereals |
| *Dysaphis devecta* | Leaf-curling aphid | pome fruits |
| *Dysaphis plantaginea* | Rosy apple aphid | pome fruits, stone fruits |
| *Eriosoma lanigerum* | Wooly apple aphid | pome fruits, stone fruits |
| *Hyalopterus pruni* | Mealy plum aphid | stone fruits |
| *Lipaphis erysimi* | False cabbage aphid | *brassica* |
| *Macrosiphum avenae* | Grain aphid | cereals |
| *Macrosiphum euphorbiae* | Potato aphid | potato, sugar beet, vegetables |
| *Macrosiphum rosae* | Rose aphid | ornamentals |
| *Myzus cerasi* F. | Black cherry aphid | cherry, stone fruits |
| *Myzus nicotianae* | Tobacco aphid | tobacco |
| *Myzus persicae* | Peach aphid | peach, deciduous fruits, vegetables, sugarbeet, potato, cereals, sugarcane, maize, ornamentals |
| *Myzus persicae* | Green peach aphid | peach, deciduous fruits, vegetables, sugarbeet, potato, cereals, sugarcane, maize, ornamentals |
| *Nasonovia ribisnigri* | Lettuce aphid | vegetables |
| *Pemphigus bursarius* | Lettuce root aphid | vegetables |
| *Phorodon humuli* | Hop aphid | hops |
| *Rhopalosiphum insertum* Wa | Apple-grass aphid | Deciduous fruits, ornamentals |
| *Rhopalosiphum maidis* Fitch | Corn leaf aphid | Maize, cereals |
| *Rhopalosiphum padi* L. | Wheat aphid | Maize, cereals |
| *Schizaphis graminum* Rond. | Spring grain aphid | cereals |
| *Sitobion avenae* | Wheat aphid | cereals |
| *Toxoptera aurantii* | Citrus aphid | citrus |
| *Toxoptera citricola* | Black citrus aphid | citrus |
| *Phylloxera vitifoliae* | Grape Phylloxera | vine |

The term "plant propagation material" is understood to denote all the generative parts of the plant, such as seeds, transplants, young plants, which can be used for the multiplication of the latter and vegetative plant materials such as cuttings and tubers (for example, potatoes).

Accordingly, as used herein, part of a plant includes propagation material. There may be mentioned, e.g., the seeds (in the strict sense), roots, fruits, tubers, bulbs, rhizomes, parts of plants. Germinated plants and young plants, which are to be transplanted after germination or after emergence from the soil, may also be mentioned. These young plants may be protected before transplantation by a total or partial treatment by immersion.

Parts of plant and plant organs that grow at later point in time are any sections of a plant that develop from a plant propagation material, such as a seed. Parts of plant, plant organs, and plants can also benefit from the pest damage protection achieved by the application of the compound on to the plant propagation material. In an embodiment, certain parts of a plant and certain plant organs that grow at later point in time can also be considered as plant propagation material, which can themselves be applied (or treated) with the compound; and consequently, the plant, further parts of the plant and further plant organs that develop from the treated parts of plant and treated plant organs can also benefit from the pest damage protection achieved by the application of the compound on to the certain parts of plant and certain plant organs.

Methods for applying or treating pesticidal active ingredients on to plant propagation material, especially seeds, are known in the art, and include dressing, coating, pelleting and soaking application methods of the propagation material. It is preferred that the plant propagation material is a seed.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications). The seed may also be primed either before or after the treatment.

Even distribution of the compound and adherence thereof to the seeds is desired during propagation material treatment. Treatment could vary from a thin film (dressing) of a formulation containing the compound, for example, a mixture of active ingredient(s), on a plant propagation material, such as a seed, where the original size and/or shape are recognizable to an intermediary state (such as a coating) and then to a thicker film (such as pelleting with many layers of different materials (such as carriers, for example, clays; different formulations, such as of other active ingredients; polymers; and colourants) where the original shape and/or size of the seed is no longer recognisable into the controlled release material or applied between layers of materials, or both.

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the active ingredient is applied to the soil but would include any application practice that would target the seed during the planting process.

Preferably, the treatment occurs before sowing of the seed so that the sown seed has been pre-treated with the compound. In particular, seed coating or seed pelleting are preferred in the treatment of the compound. As a result of the treatment, the compound is adhered on to the seed and therefore available for pest control. The treated seeds can be stored, handled, sowed and tilled in the same manner as any other active ingredient treated seed.

In the compounds of the formula I, each alkyl moiety either alone or as part of a larger group is a straight or branched chain and is, for example, methyl, ethyl, n-propyl, n-butyl, iso-propyl, sec-butyl, iso-butyl, tert-butyl, n-pentyl, iso-pentyl and n-hexyl.

Alkoxy groups preferably have a preferred chain length of from 1 to 4 carbon atoms. Alkoxy is, for example, methoxy, ethoxy, propoxy, i-propoxy, n-butoxy, isobutoxy, sec-butoxy and tert-butoxy. Such groups can be part of a larger group such as alkoxyalkyl and alkoxyalkoxyalkyl. Alkoxyalkyl groups preferably have a chain length of 1 to 4 carbon atoms. Alkoxyalkyl is, for example, methoxymethyl, methoxyethyl, ethoxymethyl, ethoxyethyl, n-propoxymethyl, n-propoxyethyl or isopropoxymethyl.

Halogen is generally fluorine, chlorine, bromine or iodine. This also applies, correspondingly, to halogen in combination with other meanings, such as haloalkyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

The cycloalkyl groups preferably have from 3 to 6 ring carbon atoms, for example cyclopropyl, cyclobutyl, cyclopentyl and cyclohexyl. In these rings, a methylene group can be replaced by an oxygen and/or sulphur atom, which leads, for example, to oxetanyl, tetrahydrofuranyl, tetrahydropyranyl, furanyl, tetrahydro-thiofuranyl and tetrahydro-thiopyranyl rings.

Phenyl, also as part of a substituent such as benzyl, may be substituted, preferably by alkyl, haloalkyl or halogen groups. In this case, the substituents can be in ortho, meta and/or para position. The preferred substituent positions are the ortho and para positions to the ring attachment point.

The latentiating groups G are selected to allow its removal by one or a combination of biochemical, chemical or physical processes to afford compounds of formula I where G is hydrogen before, during or following application to the treated area or plants. Examples of these processes include enzymatic cleavage, chemical hydrolysis and photolysis. Compounds bearing such groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils.

Such latentiating groups are known in the art, for example, from WO08/071,405, WO09/074314, WO09/049,851, WO10/063,670 and WO10/066,780.

In particular, the latentiating group G is a group $-C(X^a)-R^a$ or $-C(X^b)-X^c-R^b$, and the meanings of $X^a$, $X^b$, and $X^c$ are independently of each other oxygen or sulfur; and $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyl$C_1$-$C_5$oxyalkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro, and $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, $C_2$-$C_8$dialkylamino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, $C_2$-$C_8$dialkylaminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, $C_3$-$C_6$-trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkyl-thio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$halo-alkoxy, halogen, cyano or nitro, heteroaryl or heteroaryl substituted by $C_1$-$C_3$ alkyl, $C_{1-3}$haloalkyl, $C_1$-$C_3$alkoxy, $C_1$-$C_3$haloalkoxy, halogen, cyano or nitro.

It is preferred that G is hydrogen, a metal, preferably an alkali metal or alkaline earth metal, or an ammonium or sulfonium group, where hydrogen is especially preferred. In particular, the latentiating group G is a group —C($X^a$)—$R^a$ or —C($X^b$)—$X^c$—$R^b$, and the meanings of $X^a$, $R^a$, $X^b$, $X^c$ and $R^b$ are as defined above.

It is preferred that G is hydrogen, a metal, preferably an alkali metal or alkaline earth metal, or an ammonium or sulfonium group, where hydrogen is especially preferred.

Depending on the nature of the substituents, compounds of formula I may exist in different isomeric forms. When G is hydrogen, for example, compounds of formula I may exist in different tautomeric forms:

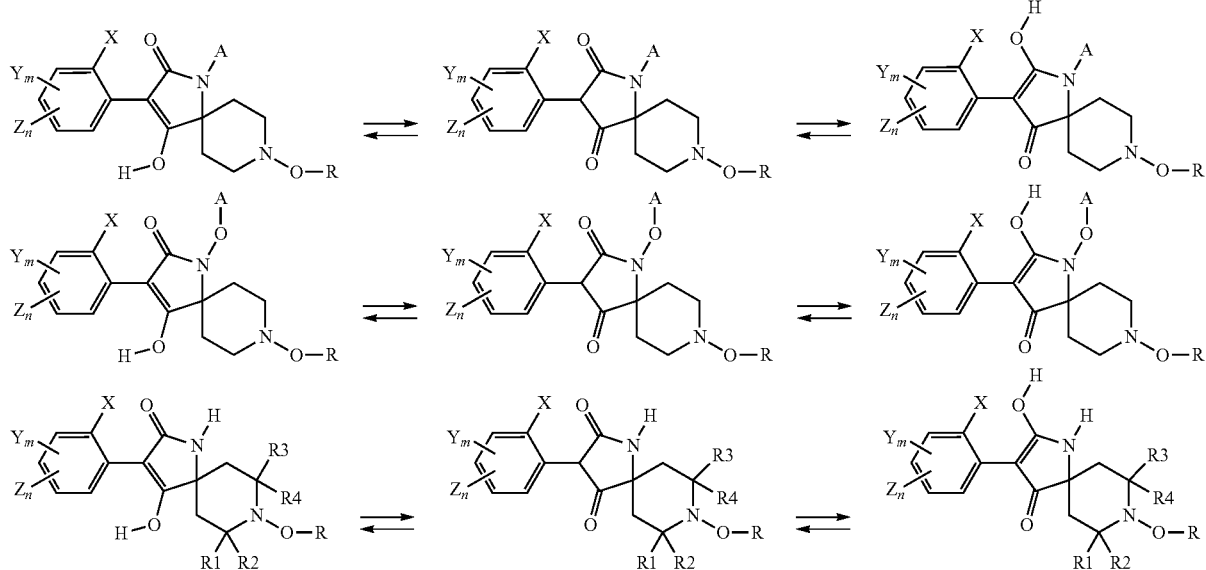

This invention covers all isomers and tautomers and mixtures thereof in all proportions. Also, when substituents contain double bonds, cis- and trans-isomers can exist. These isomers, too, are within the scope of the claimed compounds of the formula I.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, i-propylamine, the four butylamine isomers, n-amylamine, i-amylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-i-propylamine, di-n-butylamine, di-n-amylamine, di-i-amylamine, dihexylamine, diheptylamine, dioctylamine, ethanolamine, n-propanolamine, i-propanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-i-opropylamine, tri-n-butylamine, tri-i-butylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, i-propylamine and di-i-propylamine.

Preferred quaternary ammonium bases suitable for salt formation correspond, for example, to the formula [N($R_a R_b R_c R_d$)]OH, wherein $R_a$, $R_b$, $R_c$ and $R_d$ are each independently of the others hydrogen or $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula [S$R_e R_f R_g$]OH, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

The compounds of the invention may be made by a variety of methods as described in detail, for example, in WO09/049851, WO10/063,670 and WO10/066,780.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

Preferably, in the compounds of the formula I, the substituent R is hydrogen, $C_{1-6}$alkyl, $C_{1-6}$haloalkyl, $C_2$-$C_6$alkenyl, $C_3$-$C_6$alkynyl, benzyl or $C_{1-4}$alkoxy($C_{1-4}$) alkyl, in particular hydrogen, methyl, ethyl, trifluoromethyl, allyl, propargyl, benzyl, methoxymethyl, ethoxymethyl or methoxyethyl.

Preferably, X, Y and Z denote $C_1$-$C_4$alkyl, $C_3$-$C_6$cycloalkyl, $C_1$-$C_4$alkoxy or halogen, in particular methyl, ethyl, cyclopropyl, methoxy, fluoro, bromo or chloro, when m+n is 1-3, in particular, when m+n is 1-2.

Alternatively, Y and Z, independently of each other, denote $C_1$-$C_4$alkyl, $C_3$-$C_6$cycloalkyl, $C_1$-$C_4$alkoxy, halogen, phenyl or phenyl substituted by $C_{1-4}$alkyl or halogen, in particular methyl, ethyl, cyclopropyl, methoxy, fluoro, chloro, bromo, phenyl or phenyl substituted with halogen, in particular fluoro or chloro, in particular in 4-position, when m+n is 1-3, in particular, when m+n is 1-2.

In the compounds of the formula I, the substituent A is preferably $C_{1-6}$alkyl, $C_{1-6}$haloalkyl, $C_{3-6}$cycloalkyl, $C_{3-6}$cycloalkyl($C_{1-4}$)alkyl, or $C_{3-6}$cycloalkyl($C_{1-4}$)alkyl where in the cycloalkyl moiety a methylene group is replaced by O, S or $NR_0$, where $R_0$ is $C_{1-6}$alkyl or $C_{1-6}$alkoxy, or A is $C_{2-6}$alkenyl, $C_{3-6}$alkynyl, benzyl, $C_{1-4}$alkoxy($C_{1-4}$)alkyl, $C_{1-4}$alkoxy($C_{1-4}$)alkoxy($C_{1-4}$)alkyl, oxetanyl, tetrahydrofuranyl, tetrahydropyranyl or $C_{1-4}$alkylthio($C_{1-4}$)alkyl, in particular methyl, ethyl, isopropyl, trifluoromethyl, 2,2,2-trifluoroethyl, 2,2-difluoroethyl, 2-fluoroethyl, cyclopropyl, cyclobutyl, cyclopentyl, cyclohexyl, cyclopropylmethyl, cyclobutylmethyl, cyclopentylmethyl, cyclohexylmethyl, oxetan-3-ylmethyl, tetrahydrofuran-2-ylmethyl, tetrahydropyran-2-ylmethyl, tetrahydrofuran-3-ylmethyl, tetrahydropyran-3-ylmethyl, tetrahydropyran-4-ylmethyl, allyl, propargyl, benzyl, methoxymethyl, ethoxymethyl, methoxyethyl, methoxypropyl, methoxyethoxymethyl, methoxymethoxyethyl, oxetanyl-3-yl, tetrahydrofuran-2-yl, tetrahydropyran-2-yl, tetrahydrofuran-3-yl, tetrahydropyran-4-yl or methylthioethyl;

when Q is ii, A may also preferably be hydrogen, furanyl ($C_{1-4}$)alkyl, tetrahydro-thiofuranyl, tetrahydro-thiopyranyl or 1-($C_{1-4}$)alkoxy-piperidin-4-yl, in particular hydrogen, furan-2-ylmethyl, furan-3-ylmethyl, tetrahydro-thiopyran-4-ylmethyl or 1-methoxy-piperidin-4-yl.

In another preferred group of compounds of the formula (I), R is hydrogen, methyl, ethyl, trifluoromethyl, allyl, propargyl, benzyl, methoxymethyl, ethoxymethyl or methoxyethyl, X is methyl, ethyl, cyclopropyl, methoxy, fluoro, bromo or chloro, Y and Z, independently of each other, are methyl, ethyl, cyclopropyl, methoxy, fluoro, chloro, bromo, phenyl or phenyl substituted by halogen or $C_1$-$C_2$alkyl, G is hydrogen and A has the meanings assigned to it above.

In a particularly preferred group of compounds of the formula (I), R is methyl, ethyl, allyl, propargyl, methoxymethyl, X is methyl, ethyl, cyclopropyl, methoxy, fluoro, bromo or chloro, Y and Z, independently of each other, are methyl, ethyl, cyclopropyl, methoxy, fluoro, chloro, bromo, phenyl or phenyl substituted by halogen or $C_1$-$C_2$alkyl, G is hydrogen and A has the meanings assigned to it above.

Preferably, Q is i or ii, more preferably i.

In a more preferred group of compounds of the formula (I), R is methyl, ethyl, methoxymethyl, X is methyl, ethyl, cyclopropyl, methoxy, fluoro, bromo or chloro, Y and Z, independently of each other, are methyl, ethyl, cyclopropyl, methoxy, fluoro, chloro, bromo, phenyl or phenyl substituted by halogen or $C_1$-$C_2$alkyl, G is hydrogen and A is methyl, ethyl, isopropyl, trifluoromethyl, 2,2,2-trifluoroethyl, 2,2-difluoroethyl, 2-fluoroethyl, cyclopropyl, cyclobutyl, cyclopentyl, cyclohexyl, cyclopropylmethyl, cyclobutylmethyl, cyclopentylmethyl, cyclohexylmethyl, oxetan-3-ylmethyl, tetrahydrofuran-2-ylmethyl, tetrahydropyran-2-ylmethyl, tetrahydrofuran-3-ylmethyl, tetrahydropyran-3-ylmethyl, tetrahydropyran-4-ylmethyl, allyl, propargyl, benzyl, methoxymethyl, ethoxymethyl, methoxyethyl, methoxypropyl, methoxyethoxymethyl, methoxymethoxyethyl, oxetanyl-3-yl, tetrahydrofuran-2-yl, tetrahydropyran-2-yl, tetrahydrofuran-3-yl, tetrahydropyran-4-yl or methylthioethyl; and when Q is ii, A is also hydrogen, furan-2-ylmethyl, furan-3-ylmethyl, tetrahydro-thiopyran-4-ylmethyl or 1-methoxy-piperidin-4-yl.

Preferably, Q is i or iii, more preferably i.

It is preferred that when Q is iii, then $R_1$ to $R_4$ are hydrogen.

In a another preferred group of compounds of the formula (I), R is methyl, X is methyl or methoxy, Y and Z, independently of each other, are methyl, ethyl, methoxy, chloro or bromo, G is hydrogen, methoxycarbonyl or propenyloxycarbonyl, and A is methyl, ethyl, methoxymethyl, tetrahydrofuran-2-yl or tetrahydrofuran-3-yl, and when Q is ii, A is also hydrogen.

The compounds according to the following Tables below can be prepared according to the methods disclosed in the art mentioned above.

TABLE 1

This table discloses the 132 compounds T1.001 to T1.132 of the formula Ia:

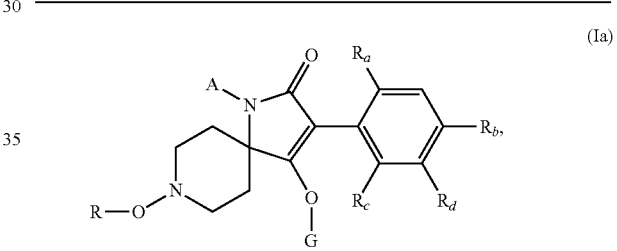

(Ia)

wherein R is $CH_3$, A is $CH_3$, G is hydrogen and $R_a$, $R_b$, $R_c$ and $R_d$ are as defined below:

| No. | $R_a$ | $R_b$ | $R_c$ | $R_d$ |
|---|---|---|---|---|
| T1.001 | Br | H | H | H |
| T1.002 | Cl | H | H | H |
| T1.003 | $CH_3$ | H | H | H |
| T1.004 | $CH_2CH_3$ | H | H | H |
| T1.005 | $OCH_3$ | H | H | H |
| T1.006 | Br | Cl | H | H |
| T1.007 | Cl | Br | H | H |
| T1.008 | Cl | Cl | H | H |
| T1.009 | Cl | $CH_3$ | H | H |
| T1.010 | $CH_3$ | Cl | H | H |
| T1.011 | $CH_3$ | $CH_3$ | H | H |
| T1.012 | Cl | H | Cl | H |
| T1.013 | Cl | H | $CH_3$ | H |
| T1.014 | Cl | H | $CH_2CH_3$ | H |
| T1.015 | Cl | H | $OCH_3$ | H |
| T1.016 | $CH_3$ | H | $CH_3$ | H |
| T1.017 | $CH_3$ | H | $CH_2CH_3$ | H |
| T1.018 | $CH_3$ | H | $OCH_3$ | H |
| T1.019 | $CH_2CH_3$ | H | $CH_2CH_3$ | H |
| T1.020 | $CH_2CH_3$ | H | $OCH_3$ | H |
| T1.021 | $OCH_3$ | H | $OCH_3$ | H |
| T1.022 | Br | H | H | Cl |
| T1.023 | Br | H | H | $CH_3$ |
| T1.024 | Br | H | H | 4-Cl—$C_6H_4$ |
| T1.025 | Cl | H | H | Cl |
| T1.026 | Cl | H | H | $CH_3$ |
| T1.027 | Cl | H | H | 4-Cl—$C_6H_4$ |
| T1.028 | $CH_3$ | H | H | Br |
| T1.029 | $CH_3$ | H | H | Cl |

TABLE 1-continued

This table discloses the 132 compounds T1.001 to T1.132 of the formula Ia:

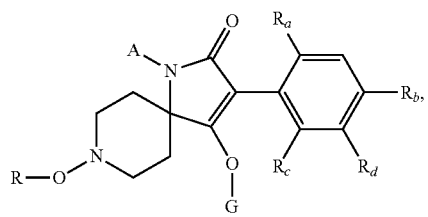

(Ia)

wherein R is CH$_3$, A is CH$_3$, G is hydrogen and R$_a$, R$_b$, R$_c$ and R$_d$ are as defined below:

| No. | R$_a$ | R$_b$ | R$_c$ | R$_d$ |
|---|---|---|---|---|
| T1.030 | CH$_3$ | H | H | CH$_3$ |
| T1.031 | CH$_3$ | H | H | C$_6$H$_5$ |
| T1.032 | CH$_3$ | H | H | 4-Cl—C$_6$H$_4$ |
| T1.033 | CH$_2$CH$_3$ | H | H | CH$_3$ |
| T1.034 | CH$_2$CH$_3$ | H | H | 4-Cl—C$_6$H$_4$ |
| T1.035 | OCH$_3$ | H | H | CH$_3$ |
| T1.036 | OCH$_3$ | H | H | 4-Cl—C$_6$H$_4$ |
| T1.037 | Cl | H | Cl | Br |
| T1.038 | CH$_3$ | H | CH$_3$ | Br |
| T1.039 | CH$_3$ | H | CH$_3$ | Cl |
| T1.040 | CH$_3$ | H | CH$_3$ | 4-Cl—C$_6$H$_4$ |
| T1.041 | Br | Cl | H | CH$_3$ |
| T1.042 | Br | CH$_3$ | H | CH$_3$ |
| T1.043 | Cl | Cl | H | Cl |
| T1.044 | Cl | Br | H | CH$_3$ |
| T1.045 | Cl | Cl | H | CH$_3$ |
| T1.046 | Cl | CH$_3$ | H | Cl |
| T1.047 | Cl | CH$_3$ | H | CH$_3$ |
| T1.048 | CH$_3$ | Br | H | CH$_3$ |
| T1.049 | CH$_3$ | Cl | H | CH$_3$ |
| T1.050 | CH$_3$ | CH$_3$ | H | CH$_3$ |
| T1.051 | CH$_3$ | CH$_3$ | H | 4-Cl—C$_6$H$_4$ |
| T1.052 | Br | Br | CH$_3$ | H |
| T1.053 | Br | Cl | CH$_3$ | H |
| T1.054 | Br | CH$_3$ | Br | H |
| T1.055 | Br | CH$_3$ | Cl | H |
| T1.056 | Cl | Br | CH$_3$ | H |
| T1.057 | Cl | Cl | Cl | H |
| T1.058 | Cl | Cl | CH$_3$ | H |
| T1.059 | Cl | CH$_3$ | Cl | H |
| T1.060 | Cl | CH$_3$ | CH$_2$CH$_3$ | H |
| T1.061 | Cl | CH$_3$ | OCH$_3$ | H |
| T1.062 | Cl | 4-Cl—C$_6$H$_4$ | Cl | H |
| T1.063 | Cl | 4-Cl—C$_6$H$_4$ | CH$_3$ | H |
| T1.064 | Cl | 4-Cl—C$_6$H$_4$ | CH$_2$CH$_3$ | H |
| T1.065 | Cl | 4-Cl—C$_6$H$_4$ | OCH$_3$ | H |
| T1.066 | CH$_3$ | Br | CH$_3$ | H |
| T1.067 | CH$_3$ | Cl | CH$_3$ | H |
| T1.068 | CH$_3$ | CH$_3$ | Br | H |
| T1.069 | CH$_3$ | CH$_3$ | Cl | H |
| T1.070 | CH$_3$ | CH$_3$ | CH$_3$ | H |
| T1.071 | CH$_3$ | CH$_3$ | CH$_2$CH$_3$ | H |
| T1.072 | CH$_3$ | CH$_3$ | OCH$_3$ | H |
| T1.073 | CH$_3$ | 4-Cl—C$_6$H$_4$ | CH$_3$ | H |
| T1.074 | CH$_3$ | 4-Cl—C$_6$H$_4$ | CH$_2$CH$_3$ | H |
| T1.075 | CH$_3$ | 4-Cl—C$_6$H$_4$ | OCH$_3$ | H |
| T1.076 | CH$_2$CH$_3$ | Br | Br | H |
| T1.077 | CH$_2$CH$_3$ | Br | Cl | H |
| T1.078 | CH$_2$CH$_3$ | Br | CH$_3$ | H |
| T1.079 | CH$_2$CH$_3$ | Br | CH$_2$CH$_3$ | H |
| T1.080 | CH$_2$CH$_3$ | Br | OCH$_3$ | H |
| T1.081 | CH$_2$CH$_3$ | Cl | Br | H |
| T1.082 | CH$_2$CH$_3$ | Cl | Cl | H |
| T1.083 | CH$_2$CH$_3$ | Cl | CH$_3$ | H |
| T1.084 | CH$_2$CH$_3$ | Cl | CH$_2$CH$_3$ | H |
| T1.085 | CH$_2$CH$_3$ | Cl | OCH$_3$ | H |
| T1.086 | CH$_2$CH$_3$ | CH$_3$ | Br | H |
| T1.087 | CH$_2$CH$_3$ | CH$_3$ | Cl | H |
| T1.088 | CH$_2$CH$_3$ | CH$_3$ | CH$_2$CH$_3$ | H |
| T1.089 | CH$_2$CH$_3$ | CH$_3$ | OCH$_3$ | H |
| T1.090 | CH$_2$CH$_3$ | CH$_2$CH$_3$ | CH$_3$ | H |
| T1.091 | CH$_2$CH$_3$ | CH$_2$CH$_3$ | CH$_2$CH$_3$ | H |
| T1.092 | CH$_2$CH$_3$ | 4-Cl—C$_6$H$_4$ | Br | H |
| T1.093 | CH$_2$CH$_3$ | 4-Cl—C$_6$H$_4$ | CH$_2$CH$_3$ | H |
| T1.094 | CH$_2$CH$_3$ | 4-Cl—C$_6$H$_4$ | OCH$_3$ | H |
| T1.095 | OCH$_3$ | Br | CH$_3$ | H |
| T1.096 | OCH$_3$ | Cl | CH$_3$ | H |
| T1.097 | OCH$_3$ | CH$_3$ | Br | H |
| T1.098 | OCH$_3$ | CH$_3$ | Cl | H |
| T1.099 | OCH$_3$ | CH$_3$ | OCH$_3$ | H |
| T1.100 | OCH$_3$ | 4-Cl—C$_6$H$_4$ | OCH$_3$ | H |
| T1.101 | CH$_3$ | CH$_3$ | CH$_3$ | F |
| T1.102 | CH$_3$ | CH$_3$ | CH$_3$ | Cl |
| T1.103 | CH$_3$ | CH$_3$ | CH$_3$ | Br |
| T1.104 | CH$_3$ | CH$_3$ | CH$_3$ | CH$_3$ |
| T1.105 | CH$_3$ | CH$_3$ | CH$_3$ | 4-Cl—C$_6$H$_4$ |
| T1.106 | Cl | CH$_3$ | CH$_3$ | CH$_3$ |
| T1.107 | CH$_3$ | Cl | CH$_3$ | CH$_3$ |
| T1.108 | CH$_3$ | CH$_3$ | Cl | CH$_3$ |
| T1.109 | CH$_2$CH$_3$ | CH$_3$ | CH$_3$ | CH$_3$ |
| T1.110 | OCH$_3$ | CH$_3$ | CH$_3$ | CH$_3$ |
| T1.111 | Cyclo-C3 | CH$_3$ | CH$_3$ | CH$_3$ |
| T1.112 | CH$_3$ | CH$_3$ | Cyclo-C3 | H |
| T1.113 | CH$_3$ | F | H | Br |
| T1.114 | CH$_3$ | CH$_3$ | H | Br |
| T1.115 | CH$_2$CH$_3$ | CH$_3$ | H | CH$_3$ |
| T1.116 | OCH$_3$ | CH$_3$ | H | CH$_3$ |
| T1.117 | Cyclo-C3 | CH$_3$ | H | CH$_3$ |
| T1.118 | CH$_2$CH$_3$ | Cl | H | CH$_3$ |
| T1.119 | OCH$_3$ | Cl | H | CH$_3$ |
| T1.120 | Cyclo-C3 | Cl | H | CH$_3$ |
| T1.121 | Cl | H | CH$_3$ | CH$_3$ |
| T1.122 | CH$_3$ | H | CH$_3$ | CH$_3$ |
| T1.123 | CH$_2$CH$_3$ | H | CH$_3$ | CH$_3$ |
| T1.124 | OCH$_3$ | H | CH$_3$ | CH$_3$ |
| T1.125 | Cyclo-C3 | H | CH$_3$ | CH$_3$ |
| T1.126 | F | H | Cl | CH$_3$ |
| T1.127 | Cl | H | F | CH$_3$ |
| T1.128 | H | CH$_3$ | CH$_3$ | CH$_3$ |
| T1.129 | Br | CH$_3$ | CH$_3$ | CH$_3$ |
| T1.130 | CH$_3$ | H | Cl | CH$_3$ |
| T1.131 | CH$_3$ | H | Br | CH$_3$ |
| T1.132 | Br | H | CH$_3$ | CH$_3$ |

Cyclo-C3 means cyclopropyl.

Table 2: This table discloses the 132 compounds T2.001 to T2.132 of the formula Ia, wherein R is CH$_3$, A is CH$_2$CH$_3$, G is hydrogen and R$_a$, R$_b$, R$_c$ and R$_d$ are as defined in Table 1.

Table 3: This table discloses the 132 compounds T3.001 to T3.132 of the formula Ia, wherein R is CH$_3$, A is n-C$_3$H$_7$, G is hydrogen and R$_a$, R$_b$, R$_c$ and R$_d$ are as defined in Table 1.

Table 4: This table discloses the 132 compounds T4.001 to T4.132 of the formula Ia, wherein R is CH$_3$, A is i-C$_3$H$_7$, G is hydrogen and R$_a$, R$_b$, R$_c$ and R$_d$ are as defined in Table 1.

Table 5: This table discloses the 132 compounds T5.001 to T5.132 of the formula Ia, wherein R is $CH_3$, A is n-$C_4H_9$, G is hydrogen and $R_a$, $R_b$, $R_c$ and $R_d$ are as defined in Table 1.

Table 6: This table discloses the 132 compounds T6.001 to T6.132 of the formula Ia, wherein R is $CH_3$, A is i-$C_4H_9$, G is hydrogen and $R_a$, $R_b$, $R_c$ and $R_d$ are as defined in Table 1.

Table 7: This table discloses the 132 compounds T7.001 to T7.132 of the formula Ia, wherein R is $CH_3$, A is t-$C_4H_9$, G is hydrogen and $R_a$, $R_b$, $R_c$ and $R_d$ are as defined in Table 1.

Table 8: This table discloses the 132 compounds T8.001 to T8.132 of the formula Ia, wherein R is $CH_3$, A is cyclopropyl, G is hydrogen and $R_a$, $R_b$, $R_c$ and $R_d$ are as defined in Table 1.

Table 9: This table discloses the 132 compounds T9.001 to T9.132 of the formula Ia, wherein R is $CH_3$, A is cyclopentyl, G is hydrogen and $R_a$, $R_b$, $R_c$ and $R_d$ are as defined in Table 1.

Table 10: This table discloses the 132 compounds T10.001 to T10.132 of the formula Ia, wherein R is $CH_3$, A is cyclohexyl, G is hydrogen and $R_a$, $R_b$, $R_c$ and $R_d$ are as defined in Table 1.

Table 11: This table discloses the 132 compounds T11.001 to T11.132 of the formula Ia, wherein R is $CH_3$, A is 2,2-$(CH_3)_2$-propyl, G is hydrogen and $R_a$, $R_b$, $R_c$ and $R_d$ are as defined in Table 1.

Table 12: This table discloses the 132 compounds T12.001 to T12.132 of the formula Ia, wherein R is $CH_3$, A is allyl, G is hydrogen and $R_a$, $R_b$, $R_c$ and $R_d$ are as defined in Table 1.

Table 13: This table discloses the 132 compounds T13.001 to T13.132 of the formula Ia, wherein R is $CH_3$, A is $CH_2$—CH=C$(CH_3)_2$, G is hydrogen and $R_a$, $R_b$, $R_c$ and $R_d$ are as defined in Table 1.

Table 14: This table discloses the 132 compounds T14.001 to T14.132 of the formula Ia, wherein R is $CH_3$, A is $CH_2$—CH=C$(Cl)_2$, G is hydrogen and $R_a$, $R_b$, $R_c$ and $R_d$ are as defined in Table 1.

Table 15: This table discloses the 132 compounds T15.001 to T15.132 of the formula Ia, wherein R is $CH_3$, A is propargyl, G is hydrogen and $R_a$, $R_b$, $R_c$ and $R_d$ are as defined in Table 1.

Table 16: This table discloses the 132 compounds T16.001 to T16.132 of the formula Ia, wherein R is $CH_3$, A is $CH_2$C≡$CCH_3$, G is hydrogen and $R_a$, $R_b$, $R_c$ and $R_d$ are as defined in Table 1.

Table 17: This table discloses the 132 compounds T17.001 to T17.132 of the formula Ia, wherein R is $CH_3$, A is $CH_2$-cyclopropyl, G is hydrogen and $R_a$, $R_b$, $R_c$ and $R_d$ are as defined in Table 1.

Table 18: This table discloses the 132 compounds T18.001 to T18.132 of the formula Ia, wherein R is $CH_3$, A is $CH_2CN$, G is hydrogen and $R_a$, $R_b$, $R_c$ and $R_d$ are as defined in Table 1.

Table 19: This table discloses the 132 compounds T19.001 to T19.132 of the formula Ia, wherein R is $CH_3$, A is $CH_2OCH_3$, G is hydrogen and $R_a$, $R_b$, $R_c$ and $R_d$ are as defined in Table 1.

Table 20: This table discloses the 132 compounds T20.001 to T20.132 of the formula Ia, wherein R is $CH_3$, A is $CH_2OCH_2CH_3$, G is hydrogen and $R_a$, $R_b$, $R_c$ and $R_d$ are as defined in Table 1.

Table 21: This table discloses the 132 compounds T21.001 to T21.132 of the formula Ia, wherein R is $CH_3$, A is $CH_2CH_2OCH_3$, G is hydrogen and $R_a$, $R_b$, $R_c$ and $R_d$ are as defined in Table 1.

Table 22: This table discloses the 132 compounds T22.001 to T22.132 of the formula Ia, wherein R is $CH_3$, A is $CH_2OCH_2CH_2OCH_3$, G is hydrogen and $R_a$, $R_b$, $R_c$ and $R_d$ are as defined in Table 1.

Table 23: This table discloses the 132 compounds T23.001 to T23.132 of the formula Ia, wherein R is $CH_3$, A is $CH_2CH_2OCH_2OCH_3$, G is hydrogen and $R_a$, $R_b$, $R_c$ and $R_d$ are as defined in Table 1.

Table 24: This table discloses the 132 compounds T24.001 to T24.132 of the formula Ia, wherein R is $CH_3$, A is oxetan-3-yl, G is hydrogen and $R_a$, $R_b$, $R_c$ and $R_d$ are as defined in Table 1.

Table 25: This table discloses the 132 compounds T25.001 to T25.132 of the formula Ia, wherein R is $CH_3$, A is tetrahydrofuran-2-yl, G is hydrogen and $R_a$, $R_b$, $R_c$ and $R_d$ are as defined in Table 1.

Table 26: This table discloses the 132 compounds T26.001 to T26.132 of the formula Ia, wherein R is $CH_3$, A is tetrahydrofuran-3-yl, G is hydrogen and $R_a$, $R_b$, $R_c$ and $R_d$ are as defined in Table 1.

Table 27: This table discloses the 132 compounds T27.001 to T27.132 of the formula Ia, wherein R is $CH_3$, A is tetrahydropyran-2-yl, G is hydrogen and $R_a$, $R_b$, $R_c$ and $R_d$ are as defined in Table 1.

Table 28: This table discloses the 132 compounds T28.001 to T28.132 of the formula Ia, wherein R is $CH_3$, A is tetrahydropyran-4-yl, G is hydrogen and $R_a$, $R_b$, $R_c$ and $R_d$ are as defined in Table 1.

Table 29: This table discloses the 132 compounds T29.001 to T29.132 of the formula Ia, wherein R is $CH_3$, A is $CH_2CH_2F$, G is hydrogen and $R_a$, $R_b$, $R_c$ and $R_d$ are as defined in Table 1.

Table 30: This table discloses the 132 compounds T30.001 to T30.132 of the formula Ia, wherein R is $CH_3$, A is $CH_2CHF_2$, G is hydrogen and $R_a$, $R_b$, $R_c$ and $R_d$ are as defined in Table 1.

Table 31: This table discloses the 132 compounds T31.001 to T31.132 of the formula Ia, wherein R is $CH_3$, A is $CH_2CF_3$, G is hydrogen and $R_a$, $R_b$, $R_c$ and $R_d$ are as defined in Table 1.

Table 32: This table discloses the 132 compounds T32.001 to T32.132 of the formula Ia, wherein R is $CH_3$, A is benzyl, G is hydrogen and $R_a$, $R_b$, $R_c$ and $R_d$ are as defined in Table 1.

Table 33: This table discloses the 132 compounds T33.001 to T33.132 of the formula Ia, wherein R is $CH_3$, A is C(O)—$CH_3$, G is hydrogen and $R_a$, $R_b$, $R_c$ and $R_d$ are as defined in Table 1.

Table 34: This table discloses the 132 compounds T34.001 to T34.132 of the formula Ia, wherein R is $CH_3$, A is C(O)—$OCH_3$, G is hydrogen and $R_a$, $R_b$, $R_c$ and $R_d$ are as defined in Table 1.

Table 35: This table discloses the 132 compounds T35.001 to T35.132 of the formula Ia, wherein R is $CH_3$, A is C(O)-cyclopropyl, G is hydrogen and $R_a$, $R_b$, $R_c$ and $R_d$ are as defined in Table 1.

Table 36: This table discloses the 132 compounds T36.001 to T36.132 of the formula Ia, wherein R is $CH_3$, A is C(O)—N$(CH_3)_2$, G is hydrogen and $R_a$, $R_b$, $R_c$ and $R_d$ are as defined in Table 1.

Table 37: This table discloses the 132 compounds T37.001 to T37.132 of the formula Ia, wherein R is $CH_3$, A is $C(O)-C_6H_5$, G is hydrogen and $R_a$, $R_b$, $R_c$ and $R_d$ are as defined in Table 1.

Table 38: This table discloses the 132 compounds T38.001 to T38.132 of the formula Ia, wherein R is $CH_3$, A is $SO_2CH_3$, G is hydrogen and $R_a$, $R_b$, $R_c$ and $R_d$ are as defined in Table 1.

Table 39: This table discloses the 132 compounds T39.001 to T39.132 of the formula Ia, wherein R is $CH_3$, A is $SO_2C_6H_5$, G is hydrogen and $R_a$, $R_b$, $R_c$ and $R_d$ are as defined in Table 1.

Table 40: This table discloses the 132 compounds T40.001 to T40.132 of the formula Ia, wherein R is hydrogen, A is $CH_3$, G is hydrogen and $R_a$, $R_b$, $R_c$ and $R_d$ are as defined in Table 1.

Table 41: This table discloses the 132 compounds T41.001 to T41.132 of the formula Ia, wherein R is hydrogen, A is $CH_2CH_3$, G is hydrogen and $R_a$, $R_b$, $R_c$ and $R_d$ are as defined in Table 1.

Table 42: This table discloses the 132 compounds T42.001 to T42.132 of the formula Ia, wherein R is hydrogen, A is $i\text{-}C_3H_7$, G is hydrogen and $R_a$, $R_b$, $R_c$ and $R_d$ are as defined in Table 1.

Table 43: This table discloses the 132 compounds T43.001 to T43.132 of the formula Ia, wherein R is hydrogen, A is cyclopropyl, G is hydrogen and $R_a$, $R_b$, $R_c$ and $R_d$ are as defined in Table 1.

Table 44: This table discloses the 132 compounds T44.001 to T44.132 of the formula Ia, wherein R is hydrogen, A is $CH_2$-cyclopropyl, G is hydrogen and $R_a$, $R_b$, $R_c$ and $R_d$ are as defined in Table 1.

Table 45: This table discloses the 132 compounds T45.001 to T45.132 of the formula Ia, wherein R is hydrogen, A is $CH_2OCH_3$, G is hydrogen and $R_a$, $R_b$, $R_c$ and $R_d$ are as defined in Table 1.

Table 46: This table discloses the 132 compounds T46.001 to T46.132 of the formula Ia, wherein R is hydrogen, A is $CH_2CH_2OCH_3$, G is hydrogen and $R_a$, $R_b$, $R_c$ and $R_d$ are as defined in Table 1.

Table 47: This table discloses the 132 compounds T47.001 to T47.132 of the formula Ia, wherein R is hydrogen, A is $CH_2OCH_2CH_2OCH_3$, G is hydrogen and $R_a$, $R_b$, $R_c$ and $R_d$ are as defined in Table 1.

Table 48: This table discloses the 132 compounds T48.001 to T48.132 of the formula Ia, wherein R is hydrogen, A is $CH_2CH_2OCH_2OCH_3$, G is hydrogen and $R_a$, $R_b$, $R_c$ and $R_d$ are as defined in Table 1.

Table 49: This table discloses the 132 compounds T49.001 to T49.132 of the formula Ia, wherein R is hydrogen, A is oxetan-3-yl, G is hydrogen and $R_a$, $R_b$, $R_c$ and $R_d$ are as defined in Table 1.

Table 50: This table discloses the 132 compounds T50.001 to T50.132 of the formula Ia, wherein R is hydrogen, A is $CH_2CHF_2$, G is hydrogen and $R_a$, $R_b$, $R_c$ and $R_d$ are as defined in Table 1.

Table 51: This table discloses the 132 compounds T51.001 to T51.132 of the formula Ia, wherein R is hydrogen, A is $CH_2CF_3$, G is hydrogen and $R_a$, $R_b$, $R_c$ and $R_d$ are as defined in Table 1.

Table 52: This table discloses the 132 compounds T52.001 to T52.132 of the formula Ia, wherein R is hydrogen, A is benzyl, G is hydrogen and $R_a$, $R_b$, $R_c$ and $R_d$ are as defined in Table 1.

Table 53: This table discloses the 132 compounds T53.001 to T53.132 of the formula Ia, wherein R is $CH_2CH_3$, A is $CH_3$, G is hydrogen and $R_a$, $R_b$, $R_c$ and $R_d$ are as defined in Table 1.

Table 54: This table discloses the 132 compounds T54.001 to T54.132 of the formula Ia, wherein R is $CH_2CH_3$, A is $CH_2CH_3$, G is hydrogen and $R_a$, $R_b$, $R_c$ and $R_d$ are as defined in Table 1.

Table 55: This table discloses the 132 compounds T55.001 to T55.132 of the formula Ia, wherein R is $CH_2CH_3$, A is $i\text{-}C_3H_7$, G is hydrogen and $R_a$, $R_b$, $R_c$ and $R_d$ are as defined in Table 1.

Table 56: This table discloses the 132 compounds T56.001 to T56.132 of the formula Ia, wherein R is $CH_2CH_3$, A is cyclopropyl, G is hydrogen and $R_a$, $R_b$, $R_c$ and $R_d$ are as defined in Table 1.

Table 57: This table discloses the 132 compounds T57.001 to T57.132 of the formula Ia, wherein R is $CH_2CH_3$, A is $CH_2$-cyclopropyl, G is hydrogen and $R_a$, $R_b$, $R_c$ and $R_d$ are as defined in Table 1.

Table 58: This table discloses the 132 compounds T58.001 to T58.132 of the formula Ia, wherein R is $CH_2CH_3$, A is $CH_2OCH_3$, G is hydrogen and $R_a$, $R_b$, $R_c$ and $R_d$ are as defined in Table 1.

Table 59: This table discloses the 132 compounds T59.001 to T59.132 of the formula Ia, wherein R is $CH_2CH_3$, A is $CH_2CH_2OCH_3$, G is hydrogen and $R_a$, $R_b$, $R_c$ and $R_d$ are as defined in Table 1.

Table 60: This table discloses the 132 compounds T60.001 to T60.132 of the formula Ia, wherein R is $CH_2CH_3$, A is $CH_2OCH_2CH_2OCH_3$, G is hydrogen and $R_a$, $R_b$, $R_c$ and $R_d$ are as defined in Table 1.

Table 61: This table discloses the 132 compounds T61.001 to T61.132 of the formula Ia, wherein R is $CH_2CH_3$, A is $CH_2CH_2OCH_2OCH_3$, G is hydrogen and $R_a$, $R_b$, $R_c$ and $R_d$ are as defined in Table 1.

Table 62: This table discloses the 132 compounds T62.001 to T62.132 of the formula Ia, wherein R is $CH_2CH_3$, A is oxetan-3-yl, G is hydrogen and $R_a$, $R_b$, $R_c$ and $R_d$ are as defined in Table 1.

Table 63: This table discloses the 132 compounds T63.001 to T63.132 of the formula Ia, wherein R is $CH_2CH_3$, A is $CH_2CHF_2$, G is hydrogen and $R_a$, $R_b$, $R_c$ and $R_d$ are as defined in Table 1.

Table 64: This table discloses the 132 compounds T64.001 to T64.132 of the formula Ia, wherein R is $CH_2CH_3$, A is $CH_2CF_3$, G is hydrogen and $R_a$, $R_b$, $R_c$ and $R_d$ are as defined in Table 1.

Table 65: This table discloses the 132 compounds T65.001 to T65.132 of the formula Ia, wherein R is $CH_2CH_3$, A is benzyl, G is hydrogen and $R_a$, $R_b$, $R_c$ and $R_d$ are as defined in Table 1.

Table 66: This table discloses the 132 compounds T66.001 to T66.132 of the formula Ia, wherein R is $CH_2OCH_3$, A is $CH_3$, G is hydrogen and $R_a$, $R_b$, $R_c$ and $R_d$ are as defined in Table 1.

Table 67: This table discloses the 132 compounds T67.001 to T67.132 of the formula Ia, wherein R is $CH_2OCH_3$, A is $CH_2CH_3$, G is hydrogen and $R_a$, $R_b$, $R_c$ and $R_d$ are as defined in Table 1.

Table 68: This table discloses the 132 compounds T68.001 to T68.132 of the formula Ia, wherein R is $CH_2OCH_3$, A is $i\text{-}C_3H_7$, G is hydrogen and $R_a$, $R_b$, $R_c$ and $R_d$ are as defined in Table 1.

Table 69: This table discloses the 132 compounds T69.001 to T69.132 of the formula Ia, wherein R is $CH_2OCH_3$, A is cyclopropyl, G is hydrogen and $R_a$, $R_b$, $R_c$ and $R_d$ are as defined in Table 1.

Table 70: This table discloses the 132 compounds T70.001 to T70.132 of the formula Ia, wherein R is $CH_2OCH_3$, A is $CH_2$-cyclopropyl, G is hydrogen and $R_a$, $R_b$, $R_c$ and $R_d$ are as defined in Table 1.

Table 71: This table discloses the 132 compounds T71.001 to T71.132 of the formula Ia, wherein R is $CH_2OCH_3$, A is $CH_2OCH_3$, G is hydrogen and $R_a$, $R_b$, $R_c$ and $R_d$ are as defined in Table 1.

Table 72: This table discloses the 132 compounds T72.001 to T72.132 of the formula Ia, wherein R is $CH_2OCH_3$, A is $CH_2CH_2OCH_3$, G is hydrogen and $R_a$, $R_b$, $R_c$ and $R_d$ are as defined in Table 1.

Table 73: This table discloses the 132 compounds T73.001 to T73.132 of the formula Ia, wherein R is $CH_2OCH_3$, A is $CH_2OCH_2CH_2OCH_3$, G is hydrogen and $R_a$, $R_b$, $R_c$ and $R_d$ are as defined in Table 1.

Table 74: This table discloses the 132 compounds T74.001 to T74.132 of the formula Ia, wherein R is $CH_2OCH_3$, A is $CH_2CH_2OCH_2OCH_3$, G is hydrogen and $R_a$, $R_b$, $R_c$ and $R_d$ are as defined in Table 1.

Table 75: This table discloses the 132 compounds T75.001 to T75.132 of the formula Ia, wherein R is $CH_2OCH_3$, A is oxetan-3-yl, G is hydrogen and $R_a$, $R_b$, $R_c$ and $R_d$ are as defined in Table 1.

Table 76: This table discloses the 132 compounds T76.001 to T76.132 of the formula Ia, wherein R is $CH_2OCH_3$, A is $CH_2CHF_2$, G is hydrogen and $R_a$, $R_b$, $R_c$ and $R_d$ are as defined in Table 1.

Table 77: This table discloses the 132 compounds T77.001 to T77.132 of the formula Ia, wherein R is $CH_2OCH_3$, A is $CH_2CF_3$, G is hydrogen and $R_a$, $R_b$, $R_c$ and $R_d$ are as defined in Table 1.

Table 78: This table discloses the 132 compounds T78.001 to T78.132 of the formula Ia, wherein R is $CH_2OCH_3$, A is benzyl, G is hydrogen and $R_a$, $R_b$, $R_c$ and $R_d$ are as defined in Table 1.

Table 79: This table discloses the 132 compounds T79.001 to T79.132 of the formula Ia, wherein R is $CH_2CH_2OCH_3$, A is $CH_3$, G is hydrogen and $R_a$, $R_b$, $R_c$ and $R_d$ are as defined in Table 1.

Table 80: This table discloses the 132 compounds T80.001 to T80.132 of the formula Ia, wherein R is $CH_2CH_2OCH_3$, A is $CH_2CH_3$, G is hydrogen and $R_a$, $R_b$, $R_c$ and $R_d$ are as defined in Table 1.

Table 81: This table discloses the 132 compounds T81.001 to T81.132 of the formula Ia, wherein R is $CH_2CH_2OCH_3$, A is i-$C_3H_7$, G is hydrogen and $R_a$, $R_b$, $R_c$ and $R_d$ are as defined in Table 1.

Table 82: This table discloses the 132 compounds T82.001 to T82.132 of the formula Ia, wherein R is $CH_2CH_2OCH_3$, A is cyclopropyl, G is hydrogen and $R_a$, $R_b$, $R_c$ and $R_d$ are as defined in Table 1.

Table 83: This table discloses the 132 compounds T83.001 to T83.132 of the formula Ia, wherein R is $CH_2CH_2OCH_3$, A is $CH_2$-cyclopropyl, G is hydrogen and $R_a$, $R_b$, $R_c$ and $R_d$ are as defined in Table 1.

Table 84: This table discloses the 132 compounds T84.001 to T84.132 of the formula Ia, wherein R is $CH_2CH_2OCH_3$, A is $CH_2OCH_3$, G is hydrogen and $R_a$, $R_b$, $R_c$ and $R_d$ are as defined in Table 1.

Table 85: This table discloses the 132 compounds T85.001 to T85.132 of the formula Ia, wherein R is $CH_2CH_2OCH_3$, A is $CH_2OCH_3$, G is hydrogen and $R_a$, $R_b$, $R_c$ and $R_d$ are as defined in Table 1.

Table 86: This table discloses the 132 compounds T86.001 to T86.132 of the formula Ia, wherein R is $CH_2CH_2OCH_3$, A is $CH_2OCH_2CH_2OCH_3$, G is hydrogen and $R_a$, $R_b$, $R_c$ and $R_d$ are as defined in Table 1.

Table 87: This table discloses the 132 compounds T87.001 to T87.132 of the formula Ia, wherein R is $CH_2CH_2OCH_3$, A is $CH_2CH_2OCH_2OCH_3$, G is hydrogen and $R_a$, $R_b$, $R_c$ and $R_d$ are as defined in Table 1.

Table 88: This table discloses the 132 compounds T88.001 to T88.132 of the formula Ia, wherein R is $CH_2CH_2OCH_3$, A is oxetan-3-yl, G is hydrogen and $R_a$, $R_b$, $R_c$ and $R_d$ are as defined in Table 1.

Table 89: This table discloses the 132 compounds T89.001 to T89.132 of the formula Ia, wherein R is $CH_2CH_2OCH_3$, A is $CH_2CHF_2$, G is hydrogen and $R_a$, $R_b$, $R_c$ and $R_d$ are as defined in Table 1.

Table 90: This table discloses the 132 compounds T90.001 to T90.132 of the formula Ia, wherein R is $CH_2CH_2OCH_3$, A is $CH_2CF_3$, G is hydrogen and $R_a$, $R_b$, $R_c$ and $R_d$ are as defined in Table 1.

Table 91: This table discloses the 132 compounds T91.001 to T91.132 of the formula Ia, wherein R is $CH_2CH_2OCH_3$, A is benzyl, G is hydrogen and $R_a$, $R_b$, $R_c$ and $R_d$ are as defined in Table 1.

Table 92: This table discloses the 132 compounds T92.001 to T92.132 of the formula Ia, wherein R is benzyl, A is $CH_3$, G is hydrogen and $R_a$, $R_b$, $R_c$ and $R_d$ are as defined in Table 1.

Table 93: This table discloses the 132 compounds T93.001 to T93.132 of the formula Ia, wherein R is benzyl, A is $CH_2CH_3$, G is hydrogen and $R_a$, $R_b$, $R_c$ and $R_d$ are as defined in Table 1.

Table 94: This table discloses the 132 compounds T94.001 to T94.132 of the formula Ia, wherein R is benzyl, A is i-$C_3H_7$, G is hydrogen and $R_a$, $R_b$, $R_c$ and $R_d$ are as defined in Table 1.

Table 95: This table discloses the 132 compounds T95.001 to T95.132 of the formula Ia, wherein R is benzyl, A is cyclopropyl, G is hydrogen and $R_a$, $R_b$, $R_c$ and $R_d$ are as defined in Table 1.

Table 96: This table discloses the 132 compounds T96.001 to T96.132 of the formula Ia, wherein R is benzyl, A is $CH_2$-cyclopropyl, G is hydrogen and $R_a$, $R_b$, $R_c$ and $R_d$ are as defined in Table 1.

Table 97: This table discloses the 132 compounds T97.001 to T97.132 of the formula Ia, wherein R is benzyl, A is $CH_2OCH_3$, G is hydrogen and $R_a$, $R_b$, $R_c$ and $R_d$ are as defined in Table 1.

Table 98: This table discloses the 132 compounds T98.001 to T98.132 of the formula Ia, wherein R is benzyl, A is $CH_2CH_2OCH_3$, G is hydrogen and $R_a$, $R_b$, $R_c$ and $R_d$ are as defined in Table 1.

Table 99: This table discloses the 132 compounds T99.001 to T99.132 of the formula Ia, wherein R is benzyl, A is $CH_2OCH_2CH_2OCH_3$, G is hydrogen and $R_a$, $R_b$, $R_c$ and $R_d$ are as defined in Table 1.

Table 100: This table discloses the 132 compounds T100.001 to T100.132 of the formula Ia, wherein R is benzyl, A is $CH_2CH_2OCH_2OCH_3$, G is hydrogen and $R_a$, $R_b$, $R_c$ and $R_d$ are as defined in Table 1.

Table 101: This table discloses the 132 compounds T101.001 to T101.132 of the formula Ia, wherein R is benzyl, A is oxetan-3-yl, G is hydrogen and $R_a$, $R_b$, $R_c$ and $R_d$ are as defined in Table 1.

Table 102: This table discloses the 132 compounds T102.001 to T102.132 of the formula Ia, wherein R is benzyl, A is CH$_2$CHF$_2$, G is hydrogen and R$_a$, R$_b$, R$_c$ and R$_d$ are as defined in Table 1.

Table 103: This table discloses the 132 compounds T103.001 to T103.132 of the formula Ia, wherein R is benzyl, A is CH$_2$CF$_3$, G is hydrogen and R$_a$, R$_b$, R$_c$ and R$_d$ are as defined in Table 1.

Table 104: This table discloses the 132 compounds T104.001 to T104.132 of the formula Ia, wherein R is benzyl, A is benzyl, G is hydrogen and R$_a$, R$_b$, R$_c$ and R$_d$ are as defined in Table 1.

Table 105: This table discloses the 132 compounds T105.001 to T105.132 of the formula Ia, wherein R is CH$_3$, A is methoxypropyl, G is hydrogen and R$_a$, R$_b$, R$_c$ and R$_d$ are as defined in Table 1.

Table 106: This table discloses the 132 compounds T106.001 to T106.132 of the formula Ia, wherein R is CH$_3$, A is oxetan-3-ylmethyl, G is hydrogen and R$_a$, R$_b$, R$_c$ and R$_d$ are as defined in Table 1.

Table 107: This table discloses the 132 compounds T107.001 to T107.132 of the formula Ia, wherein R is CH$_3$, A is tetrahydrofuran-2-ylmethyl, G is hydrogen and R$_a$, R$_b$, R$_c$ and R$_d$ are as defined in Table 1.

Table 108: This table discloses the 132 compounds T108.001 to T108.132 of the formula Ia, wherein R is CH$_3$, A is tetrahydrofuran-3-ylmethyl, G is hydrogen and R$_a$, R$_b$, R$_c$ and R$_d$ are as defined in Table 1.

Table 109: This table discloses the 132 compounds T109.001 to T109.132 of the formula Ia, wherein R is CH$_3$, A is tetrahydropyran-4-ylmethyl, G is hydrogen and R$_a$, R$_b$, R$_c$ and R$_d$ are as defined in Table 1.

Table 110: This table discloses the 132 compounds T110.001 to T110.132 of the formula Ia, wherein R is CH$_3$, A is methylthioethyl, G is hydrogen and R$_a$, R$_b$, R$_c$ and R$_d$ are as defined in Table 1.

Table 111: This table discloses the 132 compounds T111.001 to T111.132 of the formula Ia, wherein R is H, A is methoxypropyl, G is hydrogen and R$_a$, R$_b$, R$_c$ and R$_d$ are as defined in Table 1.

Table 112: This table discloses the 132 compounds T112.001 to T112.132 of the formula Ia, wherein R is CH$_2$CH$_3$, A is methoxypropyl, G is hydrogen and R$_a$, R$_b$, R$_c$ and R$_d$ are as defined in Table 1.

Table 113: This table discloses the 132 compounds T113.001 to T113.132 of the formula Ia, wherein R is CH$_2$CH$_2$OCH$_3$, A is methoxypropyl, G is hydrogen and R$_a$, R$_b$, R$_c$ and R$_d$ are as defined in Table 1.

Table 114: This table discloses the 132 compounds T114.001 to T114.132 of the formula Ia, wherein R is H, A is tetrahydrofuran-2-ylmethyl, G is hydrogen and R$_a$, R$_b$, R$_c$ and R$_d$ are as defined in Table 1.

Table 115: This table discloses the 132 compounds T115.001 to T115.132 of the formula Ia, wherein R is CH$_2$CH$_3$, A is tetrahydrofuran-2-ylmethyl, G is hydrogen and R$_a$, R$_b$, R$_c$ and R$_d$ are as defined in Table 1.

Table 116: This table discloses the 132 compounds T116.001 to T116.132 of the formula Ia, wherein R is CH$_2$CH$_2$OCH$_3$, A is tetrahydrofuran-2-ylmethyl, G is hydrogen and R$_a$, R$_b$, R$_c$ and R$_d$ are as defined in Table 1.

TABLE 1ii

This table discloses the 132 compounds T1ii.001 to T1ii.132 of the formula Ib:

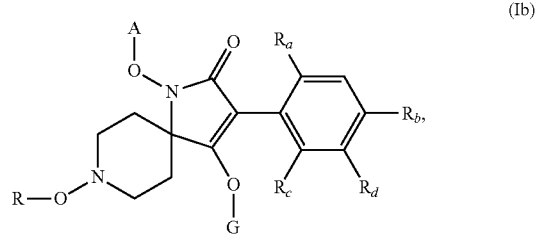

(Ib)

wherein R is CH$_3$, A is hydrogen, G is hydrogen and R$_a$, R$_b$, R$_c$ and R$_d$ are as defined below:

| No. | R$_a$ | R$_b$ | R$_c$ | R$_d$ |
|---|---|---|---|---|
| T1ii.001 | Br | H | H | H |
| T1ii.002 | Cl | H | H | H |
| T1ii.003 | CH$_3$ | H | H | H |
| T1ii.004 | CH$_2$CH$_3$ | H | H | H |
| T1ii.005 | OCH$_3$ | H | H | H |
| T1ii.006 | Br | Cl | H | H |
| T1ii.007 | Cl | Br | H | H |
| T1ii.008 | Cl | Cl | H | H |
| T1ii.009 | Cl | CH$_3$ | H | H |
| T1ii.010 | CH$_3$ | Cl | H | H |
| T1ii.011 | CH$_3$ | CH$_3$ | H | H |
| T1ii.012 | Cl | H | Cl | H |
| T1ii.013 | Cl | H | CH$_3$ | H |
| T1ii.014 | Cl | H | CH$_2$CH$_3$ | H |
| T1ii.015 | Cl | H | OCH$_3$ | H |
| T1ii.016 | CH$_3$ | H | CH$_3$ | H |
| T1ii.017 | CH$_3$ | H | CH$_2$CH$_3$ | H |
| T1ii.018 | CH$_3$ | H | OCH$_3$ | H |
| T1ii.019 | CH$_2$CH$_3$ | H | CH$_2$CH$_3$ | H |
| T1ii.020 | CH$_2$CH$_3$ | H | OCH$_3$ | H |
| T1ii.021 | OCH$_3$ | H | OCH$_3$ | H |
| T1ii.022 | Br | H | H | Cl |
| T1ii.023 | Br | H | H | CH$_3$ |
| T1ii.024 | Br | H | H | 4-Cl—C$_6$H$_4$ |
| T1ii.025 | Cl | H | H | Cl |
| T1ii.026 | Cl | H | H | CH$_3$ |
| T1ii.027 | Cl | H | H | 4-Cl—C$_6$H$_4$ |
| T1ii.028 | CH$_3$ | H | H | Br |
| T1ii.029 | CH$_3$ | H | H | Cl |
| T1ii.030 | CH$_3$ | H | H | CH$_3$ |
| T1ii.031 | CH$_3$ | H | H | C$_6$H$_5$ |
| T1ii.032 | CH$_3$ | H | H | 4-Cl—C$_6$H$_4$ |
| T1ii.033 | CH$_2$CH$_3$ | H | H | CH$_3$ |
| T1ii.034 | CH$_2$CH$_3$ | H | H | 4-Cl—C$_6$H$_4$ |
| T1ii.035 | OCH$_3$ | H | H | CH$_3$ |
| T1ii.036 | OCH$_3$ | H | H | 4-Cl—C$_6$H$_4$ |
| T1ii.037 | Cl | H | Cl | Br |
| T1ii.038 | CH$_3$ | H | CH$_3$ | Br |
| T1ii.039 | CH$_3$ | H | CH$_3$ | Cl |
| T1ii.040 | CH$_3$ | H | CH$_3$ | 4-Cl—C$_6$H$_4$ |
| T1ii.041 | Br | Cl | H | CH$_3$ |
| T1ii.042 | Br | CH$_3$ | H | CH$_3$ |
| T1ii.043 | Cl | Cl | H | Cl |
| T1ii.044 | Cl | Br | H | CH$_3$ |
| T1ii.045 | Cl | Cl | H | CH$_3$ |
| T1ii.046 | Cl | CH$_3$ | H | Cl |
| T1ii.047 | Cl | CH$_3$ | H | CH$_3$ |
| T1ii.048 | CH$_3$ | Br | H | CH$_3$ |
| T1ii.049 | CH$_3$ | Cl | H | CH$_3$ |
| T1ii.050 | CH$_3$ | CH$_3$ | H | CH$_3$ |
| T1ii.051 | CH$_3$ | CH$_3$ | H | 4-Cl—C$_6$H$_4$ |
| T1ii.052 | Br | Br | CH$_3$ | H |
| T1ii.053 | Br | Cl | CH$_3$ | H |
| T1ii.054 | Br | CH$_3$ | Br | H |
| T1ii.055 | Br | CH$_3$ | Cl | H |
| T1ii.056 | Cl | Br | CH$_3$ | H |
| T1ii.057 | Cl | Cl | Cl | H |
| T1ii.058 | Cl | Cl | CH$_3$ | H |
| T1ii.059 | Cl | CH$_3$ | Cl | H |

TABLE 1ii-continued

This table discloses the 132 compounds T1ii.001 to T1ii.132 of the formula Ib:

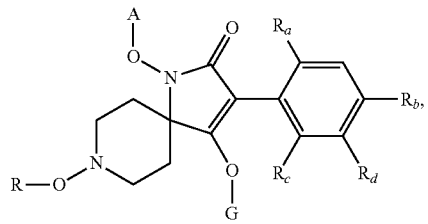

(Ib)

wherein R is CH$_3$, A is hydrogen, G is hydrogen and R$_a$, R$_b$, R$_c$ and R$_d$ are as defined below:

| No. | R$_a$ | R$_b$ | R$_c$ | R$_d$ |
|---|---|---|---|---|
| T1ii.060 | Cl | CH$_3$ | CH$_2$CH$_3$ | H |
| T1ii.061 | Cl | CH$_3$ | OCH$_3$ | H |
| T1ii.062 | Cl | 4-Cl—C$_6$H$_4$ | Cl | H |
| T1ii.063 | Cl | 4-Cl—C$_6$H$_4$ | CH$_3$ | H |
| T1ii.064 | Cl | 4-Cl—C$_6$H$_4$ | CH$_2$CH$_3$ | H |
| T1ii.065 | Cl | 4-Cl—C$_6$H$_4$ | OCH$_3$ | H |
| T1ii.066 | CH$_3$ | Br | CH$_3$ | H |
| T1ii.067 | CH$_3$ | Cl | CH$_3$ | H |
| T1ii.068 | CH$_3$ | CH$_3$ | Br | H |
| T1ii.069 | CH$_3$ | CH$_3$ | Cl | H |
| T1ii.070 | CH$_3$ | CH$_3$ | CH$_3$ | H |
| T1ii.071 | CH$_3$ | CH$_3$ | CH$_2$CH$_3$ | H |
| T1ii.072 | CH$_3$ | CH$_3$ | OCH$_3$ | H |
| T1ii.073 | CH$_3$ | 4-Cl—C$_6$H$_4$ | CH$_3$ | H |
| T1ii.074 | CH$_3$ | 4-Cl—C$_6$H$_4$ | CH$_2$CH$_3$ | H |
| T1ii.075 | CH$_3$ | 4-Cl—C$_6$H$_4$ | OCH$_3$ | H |
| T1ii.076 | CH$_2$CH$_3$ | Br | Br | H |
| T1ii.077 | CH$_2$CH$_3$ | Br | Cl | H |
| T1ii.078 | CH$_2$CH$_3$ | Br | CH$_3$ | H |
| T1ii.079 | CH$_2$CH$_3$ | Br | CH$_2$CH$_3$ | H |
| T1ii.080 | CH$_2$CH$_3$ | Br | OCH$_3$ | H |
| T1ii.081 | CH$_2$CH$_3$ | Cl | Br | H |
| T1ii.082 | CH$_2$CH$_3$ | Cl | Cl | H |
| T1ii.083 | CH$_2$CH$_3$ | Cl | CH$_3$ | H |
| T1ii.084 | CH$_2$CH$_3$ | Cl | CH$_2$CH$_3$ | H |
| T1ii.085 | CH$_2$CH$_3$ | Cl | OCH$_3$ | H |
| T1ii.086 | CH$_2$CH$_3$ | CH$_3$ | Br | H |
| T1ii.087 | CH$_2$CH$_3$ | CH$_3$ | Cl | H |
| T1ii.088 | CH$_2$CH$_3$ | CH$_3$ | CH$_2$CH$_3$ | H |
| T1ii.089 | CH$_2$CH$_3$ | CH$_3$ | OCH$_3$ | H |
| T1ii.090 | CH$_2$CH$_3$ | CH$_2$CH$_3$ | CH$_3$ | H |
| T1ii.091 | CH$_2$CH$_3$ | CH$_2$CH$_3$ | CH$_2$CH$_3$ | H |
| T1ii.092 | CH$_2$CH$_3$ | 4-Cl—C$_6$H$_4$ | Br | H |
| T1ii.093 | CH$_2$CH$_3$ | 4-Cl—C$_6$H$_4$ | CH$_2$CH$_3$ | H |
| T1ii.094 | CH$_2$CH$_3$ | 4-Cl—C$_6$H$_4$ | OCH$_3$ | H |
| T1ii.095 | OCH$_3$ | Br | CH$_3$ | H |
| T1ii.096 | OCH$_3$ | Cl | CH$_3$ | H |
| T1ii.097 | OCH$_3$ | CH$_3$ | Br | H |
| T1ii.098 | OCH$_3$ | CH$_3$ | Cl | H |
| T1ii.099 | OCH$_3$ | CH$_3$ | OCH$_3$ | H |
| T1ii.100 | OCH$_3$ | 4-Cl—C$_6$H$_4$ | OCH$_3$ | H |
| T1ii.101 | CH$_3$ | CH$_3$ | CH$_3$ | F |
| T1ii.102 | CH$_3$ | CH$_3$ | CH$_3$ | Cl |
| T1ii.103 | CH$_3$ | CH$_3$ | CH$_3$ | Br |
| T1ii.104 | CH$_3$ | CH$_3$ | CH$_3$ | CH$_3$ |
| T1ii.105 | CH$_3$ | CH$_3$ | CH$_3$ | 4-Cl—C$_6$H$_4$ |
| T1ii.106 | Cl | CH$_3$ | CH$_3$ | CH$_3$ |
| T1ii.107 | CH$_3$ | Cl | CH$_3$ | CH$_3$ |
| T1ii.108 | CH$_3$ | CH$_3$ | Cl | CH$_3$ |
| T1ii.109 | CH$_2$CH$_3$ | CH$_3$ | CH$_3$ | CH$_3$ |
| T1ii.110 | OCH$_3$ | CH$_3$ | CH$_3$ | CH$_3$ |
| T1ii.111 | Cyclo-C3 | CH$_3$ | CH$_3$ | CH$_3$ |
| T1ii.112 | CH$_3$ | CH$_3$ | Cyclo-C3 | H |
| T1ii.113 | CH$_3$ | F | H | Br |
| T1ii.114 | CH$_3$ | CH$_3$ | H | Br |
| T1ii.115 | CH$_2$CH$_3$ | CH$_3$ | H | CH$_3$ |
| T1ii.116 | OCH$_3$ | CH$_3$ | H | CH$_3$ |
| T1ii.117 | Cyclo-C3 | CH$_3$ | H | CH$_3$ |
| T1ii.118 | CH$_2$CH$_3$ | Cl | H | CH$_3$ |
| T1ii.119 | OCH$_3$ | Cl | H | CH$_3$ |
| T1ii.120 | Cyclo-C3 | Cl | H | CH$_3$ |
| T1ii.121 | Cl | H | CH$_3$ | CH$_3$ |
| T1ii.122 | CH$_3$ | H | CH$_3$ | CH$_3$ |
| T1ii.123 | CH$_2$CH$_3$ | H | CH$_3$ | CH$_3$ |
| T1ii.124 | OCH$_3$ | H | CH$_3$ | CH$_3$ |
| T1ii.125 | Cyclo-C3 | H | CH$_3$ | CH$_3$ |
| T1ii.126 | F | H | Cl | CH$_3$ |
| T1ii.127 | Cl | H | F | CH$_3$ |
| T1ii.128 | H | CH$_3$ | CH$_3$ | CH$_3$ |
| T1ii.129 | Br | CH$_3$ | CH$_3$ | CH$_3$ |
| T1ii.130 | CH$_3$ | H | Cl | CH$_3$ |
| T1ii.131 | CH$_3$ | H | Br | CH$_3$ |
| T1ii.132 | Br | H | CH$_3$ | CH$_3$ |

Cyclo-C3 means cyclopropyl.

Table 2ii: This table discloses the 132 compounds T2ii.001 to T2ii.132 of the formula Ib, wherein R is CH$_3$, A is CH$_3$, G is hydrogen and R$_a$, R$_b$, R$_c$ and R$_d$ are as defined in Table 1.

Table 3ii: This table discloses the 132 compounds T3ii.001 to T3ii.132 of the formula Ib, wherein R is CH$_3$, A is CH$_2$CH$_3$, G is hydrogen and R$_a$, R$_b$, R$_c$ and R$_d$ are as defined in Table 1.

Table 4ii: This table discloses the 132 compounds T4ii.001 to T4ii.132 of the formula Ib, wherein R is CH$_3$, A is n-C$_3$H$_7$, G is hydrogen and R$_a$, R$_b$, R$_c$ and R$_d$ are as defined in Table 1.

Table 5ii: This table discloses the 132 compounds T5ii.001 to T5ii.132 of the formula Ib, wherein R is CH$_3$, A is i-C$_3$H$_7$, G is hydrogen and R$_a$, R$_b$, R$_c$ and R$_d$ are as defined in Table 1.

Table 6ii: This table discloses the 132 compounds T6ii.001 to T6ii.132 of the formula Ib, wherein R is CH$_3$, A is n-C$_4$H$_9$, G is hydrogen and R$_a$, R$_b$, R$_c$ and R$_d$ are as defined in Table 1.

Table 7ii: This table discloses the 132 compounds T7ii.001 to T7ii.132 of the formula Ib, wherein R is CH$_3$, A is i-C$_4$H$_9$, G is hydrogen and R$_a$, R$_b$, R$_c$ and R$_d$ are as defined in Table 1.

Table 8ii: This table discloses the 132 compounds T8ii.001 to T8ii.132 of the formula Ib, wherein R is CH$_3$, A is t-C$_4$H$_9$, G is hydrogen and R$_a$, R$_b$, R$_c$ and R$_d$ are as defined in Table 1.

Table 9ii: This table discloses the 132 compounds T9ii.001 to T9ii.132 of the formula Ib, wherein R is CH$_3$, A is cyclopropyl, G is hydrogen and R$_a$, R$_b$, R$_c$ and R$_d$ are as defined in Table 1.

Table 10ii: This table discloses the 132 compounds T10ii.001 to T10ii.132 of the formula Ib, wherein R is CH$_3$, A is cyclopentyl, G is hydrogen and R$_a$, R$_b$, R$_c$ and R$_d$ are as defined in Table 1.

Table 11ii: This table discloses the 132 compounds T11ii.001 to T11ii.132 of the formula Ib, wherein R is $CH_3$, A is cyclohexyl, G is hydrogen and $R_a$, $R_b$, $R_c$ and $R_d$ are as defined in Table 1.

Table 12ii: This table discloses the 132 compounds T12ii.001 to T12ii.132 of the formula Ib, wherein R is $CH_3$, A is 2,2-$(CH_3)_2$-propyl, G is hydrogen and $R_a$, $R_b$, $R_c$ and $R_d$ are as defined in Table 1.

Table 13ii: This table discloses the 132 compounds T13ii.001 to T13ii.132 of the formula Ib, wherein R is $CH_3$, A is allyl, G is hydrogen and $R_a$, $R_b$, $R_c$ and $R_d$ are as defined in Table 1.

Table 14ii: This table discloses the 132 compounds T14ii.001 to T14ii.132 of the formula Ib, wherein R is $CH_3$, A is $CH_2$—CH=C$(CH_3)_2$, G is hydrogen and $R_a$, $R_b$, $R_c$ and $R_d$ are as defined in Table 1.

Table 15ii: This table discloses the 132 compounds T15ii.001 to T15ii.132 of the formula Ib, wherein R is $CH_3$, A is $CH_2$—CH=C$(Cl)_2$, G is hydrogen and $R_a$, $R_b$, $R_c$ and $R_d$ are as defined in Table 1.

Table 16ii: This table discloses the 132 compounds T16ii.001 to T16ii.132 of the formula Ib, wherein R is $CH_3$, A is propargyl, G is hydrogen and $R_a$, $R_b$, $R_c$ and $R_d$ are as defined in Table 1.

Table 17ii: This table discloses the 132 compounds T17ii.001 to T17ii.132 of the formula Ib, wherein R is $CH_3$, A is $CH_2C\equiv CCH_3$, G is hydrogen and $R_a$, $R_b$, $R_c$ and $R_d$ are as defined in Table 1.

Table 18ii: This table discloses the 132 compounds T18ii.001 to T18ii.132 of the formula Ib, wherein R is $CH_3$, A is $CH_2$-cyclopropyl, G is hydrogen and $R_a$, $R_b$, $R_c$ and $R_d$ are as defined in Table 1.

Table 19ii: This table discloses the 132 compounds T19ii.001 to T19ii.132 of the formula Ib, wherein R is $CH_3$, A is $CH_2CN$, G is hydrogen and $R_a$, $R_b$, $R_c$ and $R_d$ are as defined in Table 1.

Table 20ii: This table discloses the 132 compounds T20ii.001 to T20ii.132 of the formula Ib, wherein R is $CH_3$, A is $CH_2OCH_3$, G is hydrogen and $R_a$, $R_b$, $R_c$ and $R_d$ are as defined in Table 1.

Table 21ii: This table discloses the 132 compounds T21ii.001 to T21ii.132 of the formula Ib, wherein R is $CH_3$, A is $CH_2OCH_2CH_3$, G is hydrogen and $R_a$, $R_b$, $R_c$ and $R_d$ are as defined in Table 1.

Table 22ii: This table discloses the 132 compounds T22ii.001 to T22ii.132 of the formula Ib, wherein R is $CH_3$, A is $CH_2CH_2OCH_3$, G is hydrogen and $R_a$, $R_b$, $R_c$ and $R_d$ are as defined in Table 1.

Table 23ii: This table discloses the 132 compounds T23ii.001 to T23ii.132 of the formula Ib, wherein R is $CH_3$, A is $CH_2OCH_2CH_2OCH_3$, G is hydrogen and $R_a$, $R_b$, $R_c$ and $R_d$ are as defined in Table 1.

Table 24ii: This table discloses the 132 compounds T24ii.001 to T24ii.132 of the formula Ib, wherein R is $CH_3$, A is oxetan-3-yl, G is hydrogen and $R_a$, $R_b$, $R_c$ and $R_d$ are as defined in Table 1.

Table 25ii: This table discloses the 132 compounds T25ii.001 to T25ii.132 of the formula Ib, wherein R is $CH_3$, A is tetrahydrofuran-2-yl, G is hydrogen and $R_a$, $R_b$, $R_c$ and $R_d$ are as defined in Table 1.

Table 26ii: This table discloses the 132 compounds T26ii.001 to T26ii.132 of the formula Ib, wherein R is $CH_3$, A is tetrahydrofuran-3-yl, G is hydrogen and $R_a$, $R_b$, $R_c$ and $R_d$ are as defined in Table 1.

Table 27ii: This table discloses the 132 compounds T27ii.001 to T27ii.132 of the formula Ib, wherein R is $CH_3$, A is tetrahydropyran-2-yl, G is hydrogen and $R_a$, $R_b$, $R_c$ and $R_d$ are as defined in Table 1.

Table 28ii: This table discloses the 132 compounds T28ii.001 to T28ii.132 of the formula Ib, wherein R is $CH_3$, A is tetrahydropyran-4-yl, G is hydrogen and $R_a$, $R_b$, $R_c$ and $R_d$ are as defined in Table 1.

Table 29ii: This table discloses the 132 compounds T29ii.001 to T29ii.132 of the formula Ib, wherein R is $CH_3$, A is $CH_2CHF_2$, G is hydrogen and $R_a$, $R_b$, $R_c$ and $R_d$ are as defined in Table 1.

Table 30ii: This table discloses the 132 compounds T30ii.001 to T30ii.132 of the formula Ib, wherein R is $CH_3$, A is $CH_2C(O)$—$CH_3$, G is hydrogen and $R_a$, $R_b$, $R_c$ and $R_d$ are as defined in Table 1.

Table 31ii: This table discloses the 132 compounds T31ii.001 to T31ii.132 of the formula Ib, wherein R is $CH_3$, A is $CH_2C(O)$—$CH_2CH_3$, G is hydrogen and $R_a$, $R_b$, $R_c$ and $R_d$ are as defined in Table 1.

Table 32ii: This table discloses the 132 compounds T32ii.001 to T32ii.132 of the formula Ib, wherein R is $CH_3$, A is $CH(CH_3)C(O)$—$CH_3$, G is hydrogen and $R_a$, $R_b$, $R_c$ and $R_d$ are as defined in Table 1.

Table 33ii: This table discloses the 132 compounds T33ii.001 to T33ii.132 of the formula Ib, wherein R is $CH_3$, A is $C(CH_3)_2C(O)$—$CH_3$, G is hydrogen and $R_a$, $R_b$, $R_c$ and $R_d$ are as defined in Table 1.

Table 34ii: This table discloses the 132 compounds T34ii.001 to T34ii.132 of the formula Ib, wherein R is $CH_3$, A is benzyl, G is hydrogen and $R_a$, $R_b$, $R_c$ and $R_d$ are as defined in Table 1.

Table 35ii: This table discloses the 132 compounds T35ii.001 to T35ii.132 of the formula Ib, wherein R is $CH_3$, A is $C(O)$—$CH_3$, G is hydrogen and $R_a$, $R_b$, $R_c$ and $R_d$ are as defined in Table 1.

Table 36ii: This table discloses the 132 compounds T36ii.001 to T36ii.132 of the formula Ib, wherein R is $CH_3$, A is $C(O)$—$OCH_3$, G is hydrogen and $R_a$, $R_b$, $R_c$ and $R_d$ are as defined in Table 1.

Table 37ii: This table discloses the 132 compounds T37ii.001 to T37ii.132 of the formula Ib, wherein R is $CH_3$, A is $C(O)$-cyclopropyl, G is hydrogen and $R_a$, $R_b$, $R_c$ and $R_d$ are as defined in Table 1.

Table 38ii: This table discloses the 132 compounds T37ii.001 to T37ii.132 of the formula Ib, wherein R is $CH_3$, A is $C(O)$—$N(CH_3)_2$, G is hydrogen and $R_a$, $R_b$, $R_c$ and $R_d$ are as defined in Table 1.

Table 39ii: This table discloses the 132 compounds T39ii.001 to T39ii.132 of the formula Ib, wherein R is hydrogen, A is hydrogen, G is hydrogen and $R_a$, $R_b$, $R_c$ and $R_d$ are as defined in Table 1.

Table 40ii: This table discloses the 132 compounds T40ii.001 to T40ii.132 of the formula Ib, wherein R is hydrogen, A is $CH_3$, G is hydrogen and $R_a$, $R_b$, $R_c$ and $R_d$ are as defined in Table 1.

Table 41ii: This table discloses the 132 compounds T41ii.001 to T41ii.132 of the formula Ib, wherein R is hydrogen, A is $CH_2OCH_3$, G is hydrogen and $R_a$, $R_b$, $R_c$ and $R_d$ are as defined in Table 1.

Table 42ii: This table discloses the 132 compounds T42ii.001 to T42ii.132 of the formula Ib, wherein R is hydrogen, A is $CH_2CH_2OCH_3$, G is hydrogen and $R_a$, $R_b$, $R_c$ and $R_d$ are as defined in Table 1.

Table 43ii: This table discloses the 132 compounds T43ii.001 to T43ii.132 of the formula Ib, wherein R is hydrogen, A is propargyl, G is hydrogen and $R_a$, $R_b$, $R_c$ and $R_d$ are as defined in Table 1.

Table 44ii: This table discloses the 132 compounds T44ii.001 to T44ii.132 of the formula Ib, wherein R is $CH_2CH_3$, A is hydrogen, G is hydrogen and $R_a$, $R_b$, $R_c$ and $R_d$ are as defined in Table 1.

Table 45ii: This table discloses the 132 compounds T45ii.001 to T45ii.132 of the formula Ib, wherein R is $CH_2CH_3$, A is $CH_3$, G is hydrogen and $R_a$, $R_b$, $R_c$ and $R_d$ are as defined in Table 1.

Table 46ii: This table discloses the 132 compounds T46ii.001 to T46ii.132 of the formula Ib, wherein R is $CH_2CH_3$, A is $CH_2OCH_3$, G is hydrogen and $R_a$, $R_b$, $R_c$ and $R_d$ are as defined in Table 1.

Table 47ii: This table discloses the 132 compounds T47ii.001 to T47ii.132 of the formula Ib, wherein R is $CH_2CH_3$, A is $CH_2CH_2OCH_3$, G is hydrogen and $R_a$, $R_b$, $R_c$ and $R_d$ are as defined in Table 1.

Table 48ii: This table discloses the 132 compounds T48ii.001 to T48ii.132 of the formula Ib, wherein R is $CH_2CH_3$, A is propargyl, G is hydrogen and $R_a$, $R_b$, $R_c$ and $R_d$ are as defined in Table 1.

Table 49ii: This table discloses the 132 compounds T49ii.001 to T49ii.132 of the formula Ib, wherein R is $CH_2OCH_3$, A is hydrogen, G is hydrogen and $R_a$, $R_b$, $R_c$ and $R_d$ are as defined in Table 1.

Table 50ii: This table discloses the 132 compounds T50ii.001 to T50ii.132 of the formula Ib, wherein R is $CH_2OCH_3$, A is $CH_3$, G is hydrogen and $R_a$, $R_b$, $R_c$ and $R_d$ are as defined in Table 1.

Table 51ii: This table discloses the 132 compounds T51ii.001 to T51ii.132 of the formula Ib, wherein R is $CH_2OCH_3$, A is $CH_2OCH_3$, G is hydrogen and $R_a$, $R_b$, $R_c$ and $R_d$ are as defined in Table 1.

Table 52ii: This table discloses the 132 compounds T52ii.001 to T52ii.132 of the formula Ib, wherein R is $CH_2OCH_3$, A is $CH_2CH_2OCH_3$, G is hydrogen and $R_a$, $R_b$, $R_c$ and $R_d$ are as defined in Table 1.

Table 53ii: This table discloses the 132 compounds T53ii.001 to T53ii.132 of the formula Ib, wherein R is $CH_2OCH_3$, A is propargyl, G is hydrogen and $R_a$, $R_b$, $R_c$ and $R_d$ are as defined in Table 1.

Table 54ii: This table discloses the 132 compounds T54ii.001 to T54ii.132 of the formula Ib, wherein R is $CH_2CH_2OCH_3$, A is hydrogen, G is hydrogen and $R_a$, $R_b$, $R_c$ and $R_d$ are as defined in Table 1.

Table 55ii: This table discloses the 132 compounds T55ii.001 to T55ii.132 of the formula Ib, wherein R is $CH_2CH_2OCH_3$, A is $CH_3$, G is hydrogen and $R_a$, $R_b$, $R_c$ and $R_d$ are as defined in Table 1.

Table 56ii: This table discloses the 132 compounds T56ii.001 to T56ii.132 of the formula Ib, wherein R is $CH_2CH_2OCH_3$, A is $CH_2OCH_3$, G is hydrogen and $R_a$, $R_b$, $R_c$ and $R_d$ are as defined in Table 1.

Table 57ii: This table discloses the 132 compounds T57ii.001 to T57ii.132 of the formula Ib, wherein R is $CH_2CH_2OCH_3$, A is $CH_2CH_2OCH_3$, G is hydrogen and $R_a$, $R_b$, $R_c$ and $R_d$ are as defined in Table 1.

Table 58ii: This table discloses the 132 compounds T58ii.001 to T58ii.132 of the formula Ib, wherein R is $CH_2CH_2OCH_3$, A is propargyl, G is hydrogen and $R_a$, $R_b$, $R_c$ and $R_d$ are as defined in Table 1.

Table 59ii: This table discloses the 132 compounds T59ii.001 to T59ii.132 of the formula Ib, wherein R is benzyl, A is hydrogen, G is hydrogen and $R_a$, $R_b$, $R_c$ and $R_d$ are as defined in Table 1.

Table 60ii: This table discloses the 132 compounds T60ii.001 to T60ii.132 of the formula Ib, wherein R is benzyl, A is $CH_3$, G is hydrogen and $R_a$, $R_b$, $R_c$ and $R_d$ are as defined in Table 1.

Table 61ii: This table discloses the 132 compounds T61ii.001 to T61ii.132 of the formula Ib, wherein R is benzyl, A is $CH_2OCH_3$, G is hydrogen and $R_a$, $R_b$, $R_c$ and $R_d$ are as defined in Table 1.

Table 62ii: This table discloses the 132 compounds T62ii.001 to T62ii.132 of the formula Ib, wherein R is benzyl, A is $CH_2CH_2OCH_3$, G is hydrogen and $R_a$, $R_b$, $R_c$ and $R_d$ are as defined in Table 1.

Table 63ii: This table discloses the 132 compounds T63ii.001 to T63ii.132 of the formula Ib, wherein R is benzyl, A is propargyl, G is hydrogen and $R_a$, $R_b$, $R_c$ and $R_d$ are as defined in Table 1.

Table 64ii: This table discloses the 132 compounds T64ii.001 to T64ii.132 of the formula Ib, wherein R is $CH_3$, A is cyclobutyl, G is hydrogen and $R_a$, $R_b$, $R_c$ and $R_d$ are as defined in Table 1.

Table 65ii: This table discloses the 132 compounds T65ii.001 to T65ii.132 of the formula Ib, wherein R is $CH_3$, A is $CH_2CH_2CH_2OCH_3$, G is hydrogen and $R_a$, $R_b$, $R_c$ and $R_d$ are as defined in Table 1.

Table 66ii: This table discloses the 132 compounds T66ii.001 to T66ii.132 of the formula Ib, wherein R is $CH_3$, A is $CH_2CH_2O$(tetrahydrofuran-2-yl), G is hydrogen and $R_a$, $R_b$, $R_c$ and $R_d$ are as defined in Table 1.

Table 67ii: This table discloses the 132 compounds T67ii.001 to T67ii.132 of the formula Ib, wherein R is $CH_3$, A is $CH_2CH_2O$(tetrahydropyran-2-yl), G is hydrogen and $R_a$, $R_b$, $R_c$ and $R_d$ are as defined in Table 1.

Table 68ii: This table discloses the 132 compounds T68ii.001 to T68ii.132 of the formula Ib, wherein R is $CH_3$, A is $CH_2$(oxetan-3-yl), G is hydrogen and $R_a$, $R_b$, $R_c$ and $R_d$ are as defined in Table 1.

Table 69ii: This table discloses the 132 compounds T69ii.001 to T69ii.132 of the formula Ib, wherein R is $CH_3$, A is $CH_2$(3-methyl-oxetan-3-yl), G is hydrogen and $R_a$, $R_b$, $R_c$ and $R_d$ are as defined in Table 1.

Table 70ii: This table discloses the 132 compounds T70ii.001 to T70ii.132 of the formula Ib, wherein R is $CH_3$, A is $CH_2$(tetrahydrofuran-2-yl), G is hydrogen and $R_a$, $R_b$, $R_c$ and $R_d$ are as defined in Table 1.

Table 71ii: This table discloses the 132 compounds T71ii.001 to T71ii.132 of the formula Ib, wherein R is $CH_3$, A is $CH_2$(tetrahydrofuran-3-yl), G is hydrogen and $R_a$, $R_b$, $R_c$ and $R_d$ are as defined in Table 1.

Table 72ii: This table discloses the 132 compounds T72ii.001 to T72ii.132 of the formula Ib, wherein R is $CH_3$, A is $CH_2$(tetrahydropyran-2-yl), G is hydrogen and $R_a$, $R_b$, $R_c$ and $R_d$ are as defined in Table 1.

Table 73ii: This table discloses the 132 compounds T73ii.001 to T73ii.132 of the formula Ib, wherein R is $CH_3$, A is $CH_2$(tetrahydropyran-3-yl), G is hydrogen and $R_a$, $R_b$, $R_c$ and $R_d$ are as defined in Table 1.

Table 74ii: This table discloses the 132 compounds T74ii.001 to T74ii.132 of the formula Ib, wherein R is $CH_3$, A is $CH_2$(tetrahydropyran-4-yl), G is hydrogen and $R_a$, $R_b$, $R_c$ and $R_d$ are as defined in Table 1.

Table 75ii: This table discloses the 132 compounds T75ii.001 to T75ii.132 of the formula Ib, wherein R is hydrogen, A is $CH_2CH_3$, G is hydrogen and $R_a$, $R_b$, $R_c$ and $R_d$ are as defined in Table 1.

Table 76ii: This table discloses the 132 compounds T76ii.001 to T76ii.132 of the formula Ib, wherein R is hydrogen, A is allyl, G is hydrogen and $R_a$, $R_b$, $R_c$ and $R_d$ are as defined in Table 1.

Table 77ii: This table discloses the 132 compounds T77ii.001 to T77ii.132 of the formula Ib, wherein R is hydrogen, A is tetrahydrofuran-2-yl, G is hydrogen and $R_a$, $R_b$, $R_c$ and $R_d$ are as defined in Table 1.

Table 78ii: This table discloses the 132 compounds T78ii.001 to T78ii.132 of the formula Ib, wherein R is hydrogen, A is tetrahydropyran-2-yl, G is hydrogen and $R_a$, $R_b$, $R_c$ and $R_d$ are as defined in Table 1.

Table 79ii: This table discloses the 132 compounds T79ii.001 to T79ii.132 of the formula Ib, wherein R is $CH_2CH_3$, A is $CH_2CH_3$, G is hydrogen and $R_a$, $R_b$, $R_c$ and $R_d$ are as defined in Table 1.

Table 80ii: This table discloses the 132 compounds T80ii.001 to T80ii.132 of the formula Ib, wherein R is $CH_2CH_3$, A is allyl, G is hydrogen and $R_a$, $R_b$, $R_c$ and $R_d$ are as defined in Table 1.

Table 81ii: This table discloses the 132 compounds T81ii.001 to T81ii.132 of the formula Ib, wherein R is $CH_2CH_3$, A is tetrahydrofuran-2-yl, G is hydrogen and $R_a$, $R_b$, $R_c$ and $R_d$ are as defined in Table 1.

Table 82ii: This table discloses the 132 compounds T82ii.001 to T82ii.132 of the formula Ib, wherein R is $CH_2CH_3$, A is tetrahydropyran-2-yl, G is hydrogen and $R_a$, $R_b$, $R_c$ and $R_d$ are as defined in Table 1.

Table 83ii: This table discloses the 132 compounds T83ii.001 to T83ii.132 of the formula Ib, wherein R is $CH_2OCH_3$, A is $CH_2CH_3$, G is hydrogen and $R_a$, $R_b$, $R_c$ and $R_d$ are as defined in Table 1.

Table 84ii: This table discloses the 132 compounds T84ii.001 to T84ii.132 of the formula Ib, wherein R is $CH_2OCH_3$, A is allyl, G is hydrogen and $R_a$, $R_b$, $R_c$ and $R_d$ are as defined in Table 1.

Table 85ii: This table discloses the 132 compounds T85ii.001 to T85ii.132 of the formula Ib, wherein R is $CH_2OCH_3$, A is tetrahydrofuran-2-yl, G is hydrogen and $R_a$, $R_b$, $R_c$ and $R_d$ are as defined in Table 1.

Table 86ii: This table discloses the 132 compounds T86ii.001 to T86ii.132 of the formula Ib, wherein R is $CH_2OCH_3$, A is tetrahydropyran-2-yl, G is hydrogen and $R_a$, $R_b$, $R_c$ and $R_d$ are as defined in Table 1.

Table 87ii: This table discloses the 132 compounds T87ii.001 to T87ii.132 of the formula Ib, wherein R is $CH_2CH_2OCH_3$, A is $CH_2CH_3$, G is hydrogen and $R_a$, $R_b$, $R_c$ and $R_d$ are as defined in Table 1.

Table 88ii: This table discloses the 132 compounds T88ii.001 to T88ii.132 of the formula Ib, wherein R is $CH_2CH_2OCH_3$, A is allyl, G is hydrogen and $R_a$, $R_b$, $R_c$ and $R_d$ are as defined in Table 1.

Table 89ii: This table discloses the 132 compounds T89ii.001 to T89ii.132 of the formula Ib, wherein R is $CH_2CH_2OCH_3$, A is tetrahydrofuran-2-yl, G is hydrogen and $R_a$, $R_b$, $R_c$ and $R_d$ are as defined in Table 1.

Table 90ii: This table discloses the 132 compounds T90ii.001 to T90ii.132 of the formula Ib, wherein R is $CH_2CH_2OCH_3$, A is tetrahydropyran-2-yl, G is hydrogen and $R_a$, $R_b$, $R_c$ and $R_d$ are as defined in Table 1.

Table 91ii: This table discloses the 132 compounds T91ii.001 to T91ii.132 of the formula Ib, wherein R is $CH_3$, A is $CH_2$-cyclobutyl, G is hydrogen and $R_a$, $R_b$, $R_c$ and $R_d$ are as defined in Table 1.

Table 92ii: This table discloses the 132 compounds T92ii.001 to T92ii.132 of the formula Ib, wherein R is $CH_3$, A is $CH_2$-cyclopentyl, G is hydrogen and $R_a$, $R_b$, $R_c$ and $R_d$ are as defined in Table 1.

Table 93ii: This table discloses the 132 compounds T93ii.001 to T93ii.132 of the formula Ib, wherein R is $CH_3$, A is $CH_2$-cyclohexyl, G is hydrogen and $R_a$, $R_b$, $R_c$ and $R_d$ are as defined in Table 1.

Table 94ii: This table discloses the 132 compounds T94ii.001 to T94ii.132 of the formula Ib, wherein R is $CH_3$, A is $CH_2$(3-ethyl-oxetan-3-yl), G is hydrogen and $R_a$, $R_b$, $R_c$ and $R_d$ are as defined in Table 1.

Table 95ii: This table discloses the 132 compounds T95ii.001 to T95ii.132 of the formula Ib, wherein R is $CH_3$, A is $CH_2$(furan-2-yl), G is hydrogen and $R_a$, $R_b$, $R_c$ and $R_d$ are as defined in Table 1.

Table 96ii: This table discloses the 132 compounds T96ii.001 to T96ii.132 of the formula Ib, wherein R is $CH_3$, A is $CH_2$(furan-3-yl), G is hydrogen and $R_a$, $R_b$, $R_c$ and $R_d$ are as defined in Table 1.

Table 97ii: This table discloses the 132 compounds T97ii.001 to T97ii.132 of the formula Ib, wherein R is $CH_3$, A is $CH_2$(tetrahydro-thiopyran-4-yl), G is hydrogen and $R_a$, $R_b$, $R_c$ and $R_d$ are as defined in Table 1.

Table 98ii: This table discloses the 132 compounds T98ii.001 to T98ii.132 of the formula Ib, wherein R is $CH_3$, A is $C(O)$—$OCH_2CH_3$, G is hydrogen and $R_a$, $R_b$, $R_c$ and $R_d$ are as defined in Table 1.

Table 99ii: This table discloses the 132 compounds T99ii.001 to T99ii.132 of the formula Ib, wherein R is $CH_3$, A is $CH_2CH_2SCH_3$, G is hydrogen and $R_a$, $R_b$, $R_c$ and $R_d$ are as defined in Table 1.

Table 100ii: This table discloses the 132 compounds T100ii.001 to T100ii.132 of the formula Ib, wherein R is $CH_3$, A is $CH_2CH_2S(O)CH_3$, G is hydrogen and $R_a$, $R_b$, $R_c$ and $R_d$ are as defined in Table 1.

Table 101ii: This table discloses the 132 compounds T101ii.001 to T101ii.132 of the formula Ib, wherein R is $CH_3$, A is $CH_2CH_2S(O)_2CH_3$, G is hydrogen and $R_a$, $R_b$, $R_c$ and $R_d$ are as defined in Table 1.

Table 102ii: This table discloses the 132 compounds T102ii.001 to T102ii.132 of the formula Ib, wherein R is $CH_3$, A is 1-methoxy-piperidin-4-yl, G is hydrogen and $R_a$, $R_b$, $R_c$ and $R_d$ are as defined in Table 1.

TABLE 1iii

This table discloses the 105 compounds T1iii.001 to T1iii.105 of the formula Ic:

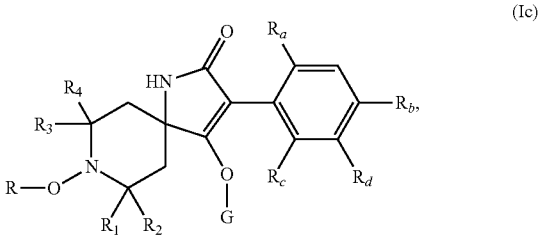

(Ic)

wherein R is $CH_3$, $R_1$, $R_2$, $R_3$ and $R_4$ are hydrogen, G is hydrogen and $R_a$, $R_b$, $R_c$ and $R_d$ are as defined below:

| No. | $R_a$ | $R_b$ | $R_c$ | $R_d$ |
|---|---|---|---|---|
| T1iii.001 | Br | H | H | H |
| T1iii.002 | Cl | H | H | H |
| T1iii.003 | $CH_3$ | H | H | H |
| T1iii.004 | $CH_2CH_3$ | H | H | H |
| T1iii.005 | $OCH_3$ | H | H | H |
| T1iii.006 | Br | Cl | H | H |
| T1iii.007 | Cl | Br | H | H |
| T1iii.008 | Cl | Cl | H | H |
| T1iii.009 | Cl | $CH_3$ | H | H |
| T1iii.010 | $CH_3$ | Cl | H | H |
| T1iii.011 | $CH_3$ | $CH_3$ | H | H |
| T1iii.012 | Cl | H | Cl | H |
| T1iii.013 | Cl | H | $CH_3$ | H |
| T1iii.014 | Cl | H | $CH_2CH_3$ | H |
| T1iii.015 | Cl | H | $OCH_3$ | H |
| T1iii.016 | $CH_3$ | H | $CH_3$ | H |
| T1iii.017 | $CH_3$ | H | $CH_2CH_3$ | H |
| T1iii.018 | $CH_3$ | H | $OCH_3$ | H |
| T1iii.019 | $CH_2CH_3$ | H | $CH_2CH_3$ | H |

TABLE 1iii-continued

This table discloses the 105 compounds T1iii.001 to T1iii.105 of the formula Ic:

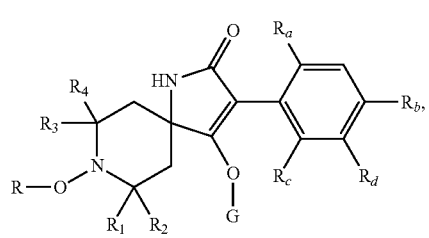

(Ic)

wherein R is CH$_3$, R$_1$, R$_2$, R$_3$ and R$_4$ are hydrogen, G is hydrogen and R$_a$, R$_b$, R$_c$ and R$_d$ are as defined below:

| No. | R$_a$ | R$_b$ | R$_c$ | R$_d$ |
|---|---|---|---|---|
| T1iii.020 | CH$_2$CH$_3$ | H | OCH$_3$ | H |
| T1iii.021 | OCH$_3$ | H | OCH$_3$ | H |
| T1iii.022 | Br | H | H | Cl |
| T1iii.023 | Br | H | H | CH$_3$ |
| T1iii.024 | Br | H | H | 4-Cl—C$_6$H$_4$ |
| T1iii.025 | Cl | H | H | Cl |
| T1iii.026 | Cl | H | H | CH$_3$ |
| T1iii.027 | Cl | H | H | 4-Cl—C$_6$H$_4$ |
| T1iii.028 | CH$_3$ | H | H | Br |
| T1iii.029 | CH$_3$ | H | H | Cl |
| T1iii.030 | CH$_3$ | H | H | CH$_3$ |
| T1iii.031 | CH$_3$ | H | H | C$_6$H$_5$ |
| T1iii.032 | CH$_3$ | H | H | 4-Cl—C$_6$H$_4$ |
| T1iii.033 | CH$_2$CH$_3$ | H | H | CH$_3$ |
| T1iii.034 | CH$_2$CH$_3$ | H | H | 4-Cl—C$_6$H$_4$ |
| T1iii.035 | OCH$_3$ | H | H | CH$_3$ |
| T1iii.036 | OCH$_3$ | H | H | 4-Cl—C$_6$H$_4$ |
| T1iii.037 | Cl | H | Cl | Br |
| T1iii.038 | CH$_3$ | H | CH$_3$ | Br |
| T1iii.039 | CH$_3$ | H | CH$_3$ | Cl |
| T1iii.040 | CH$_3$ | H | CH$_3$ | 4-Cl—C$_6$H$_4$ |
| T1iii.041 | Br | Cl | H | CH$_3$ |
| T1iii.042 | Br | CH$_3$ | H | CH$_3$ |
| T1iii.043 | Cl | Cl | H | Cl |
| T1iii.044 | Cl | Br | H | CH$_3$ |
| T1iii.045 | Cl | Cl | H | CH$_3$ |
| T1iii.046 | Cl | CH$_3$ | H | Cl |
| T1iii.047 | Cl | CH$_3$ | H | CH$_3$ |
| T1iii.048 | CH$_3$ | Br | H | CH$_3$ |
| T1iii.049 | CH$_3$ | Cl | H | CH$_3$ |
| T1iii.050 | CH$_3$ | CH$_3$ | H | CH$_3$ |
| T1iii.051 | CH$_3$ | CH$_3$ | H | 4-Cl—C$_6$H$_4$ |
| T1iii.052 | Br | Br | CH$_3$ | H |
| T1iii.053 | Br | Cl | CH$_3$ | H |
| T1iii.054 | Br | CH$_3$ | Br | H |
| T1iii.055 | Br | CH$_3$ | Cl | H |
| T1iii.056 | Cl | Br | CH$_3$ | H |
| T1iii.057 | Cl | Cl | Cl | H |
| T1iii.058 | Cl | Cl | CH$_3$ | H |
| T1iii.059 | Cl | CH$_3$ | Cl | H |
| T1iii.060 | Cl | CH$_3$ | CH$_2$CH$_3$ | H |
| T1iii.061 | Cl | CH$_3$ | OCH$_3$ | H |
| T1iii.062 | Cl | 4-Cl—C$_6$H$_4$ | Cl | H |
| T1iii.063 | Cl | 4-Cl—C$_6$H$_4$ | CH$_3$ | H |
| T1iii.064 | Cl | 4-Cl—C$_6$H$_4$ | CH$_2$CH$_3$ | H |
| T1iii.065 | Cl | 4-Cl—C$_6$H$_4$ | OCH$_3$ | H |
| T1iii.066 | CH$_3$ | Br | CH$_3$ | H |
| T1iii.067 | CH$_3$ | Cl | CH$_3$ | H |
| T1iii.068 | CH$_3$ | CH$_3$ | Br | H |
| T1iii.069 | CH$_3$ | CH$_3$ | Cl | H |
| T1iii.070 | CH$_3$ | CH$_3$ | CH$_3$ | H |
| T1iii.071 | CH$_3$ | CH$_3$ | CH$_2$CH$_3$ | H |
| T1iii.072 | CH$_3$ | CH$_3$ | OCH$_3$ | H |
| T1iii.073 | CH$_3$ | 4-Cl—C$_6$H$_4$ | CH$_3$ | H |
| T1iii.074 | CH$_3$ | 4-Cl—C$_6$H$_4$ | CH$_2$CH$_3$ | H |
| T1iii.075 | CH$_3$ | 4-Cl—C$_6$H$_4$ | OCH$_3$ | H |
| T1iii.076 | CH$_2$CH$_3$ | Br | Br | H |
| T1iii.077 | CH$_2$CH$_3$ | Br | Cl | H |
| T1iii.078 | CH$_2$CH$_3$ | Br | CH$_3$ | H |
| T1iii.079 | CH$_2$CH$_3$ | Br | CH$_2$CH$_3$ | H |

TABLE 1iii-continued

This table discloses the 105 compounds T1iii.001 to T1iii.105 of the formula Ic:

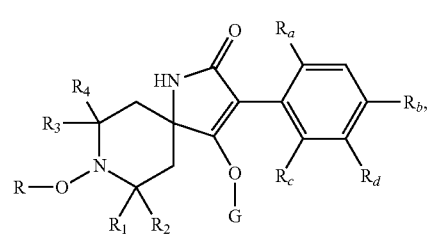

(Ic)

wherein R is CH$_3$, R$_1$, R$_2$, R$_3$ and R$_4$ are hydrogen, G is hydrogen and R$_a$, R$_b$, R$_c$ and R$_d$ are as defined below:

| No. | R$_a$ | R$_b$ | R$_c$ | R$_d$ |
|---|---|---|---|---|
| T1iii.080 | CH$_2$CH$_3$ | Br | OCH$_3$ | H |
| T1iii.081 | CH$_2$CH$_3$ | Cl | Br | H |
| T1iii.082 | CH$_2$CH$_3$ | Cl | Cl | H |
| T1iii.083 | CH$_2$CH$_3$ | Cl | CH$_3$ | H |
| T1iii.084 | CH$_2$CH$_3$ | Cl | CH$_2$CH$_3$ | H |
| T1iii.085 | CH$_2$CH$_3$ | Cl | OCH$_3$ | H |
| T1iii.086 | CH$_2$CH$_3$ | CH$_3$ | Br | H |
| T1iii.087 | CH$_2$CH$_3$ | CH$_3$ | Cl | H |
| T1iii.088 | CH$_2$CH$_3$ | CH$_3$ | CH$_2$CH$_3$ | H |
| T1iii.089 | CH$_2$CH$_3$ | CH$_3$ | OCH$_3$ | H |
| T1iii.090 | CH$_2$CH$_3$ | CH$_2$CH$_3$ | CH$_3$ | H |
| T1iii.091 | CH$_2$CH$_3$ | CH$_2$CH$_3$ | CH$_2$CH$_3$ | H |
| T1iii.092 | CH$_2$CH$_3$ | 4-Cl—C$_6$H$_4$ | Br | H |
| T1iii.093 | CH$_2$CH$_3$ | 4-Cl—C$_6$H$_4$ | CH$_2$CH$_3$ | H |
| T1iii.094 | CH$_2$CH$_3$ | 4-Cl—C$_6$H$_4$ | OCH$_3$ | H |
| T1iii.095 | OCH$_3$ | Br | CH$_3$ | H |
| T1iii.096 | OCH$_3$ | Cl | CH$_3$ | H |
| T1iii.097 | OCH$_3$ | CH$_3$ | Br | H |
| T1iii.098 | OCH$_3$ | CH$_3$ | Cl | H |
| T1iii.099 | OCH$_3$ | CH$_3$ | OCH$_3$ | H |
| T1iii.100 | OCH$_3$ | 4-Cl—C$_6$H$_4$ | OCH$_3$ | H |
| T1iii.101 | CH$_3$ | CH$_3$ | CH$_3$ | F |
| T1iii.102 | CH$_3$ | CH$_3$ | CH$_3$ | Cl |
| T1iii.103 | CH$_3$ | CH$_3$ | CH$_3$ | Br |
| T1iii.104 | CH$_3$ | CH$_3$ | CH$_3$ | CH$_3$ |
| T1iii.105 | CH$_3$ | CH$_3$ | CH$_3$ | 4-Cl—C$_6$H$_4$ |

Table 2iii: This table discloses the 105 compounds T2iii.001 to T2iii.105 of the formula Ic, wherein R is CH$_2$CH$_3$, R$_1$, R$_2$, R$_3$ and R$_4$ are hydrogen, G is hydrogen and R$_a$, R$_b$, R$_c$ and R$_d$ are as defined in Table 1.

Table 3iii: This table discloses the 105 compounds T3iii.001 to T3iii.105 of the formula Ic, wherein R is n-C$_3$H$_7$, R$_1$, R$_2$, R$_3$ and R$_4$ are hydrogen, G is hydrogen and R$_a$, R$_b$, R$_c$ and R$_d$ are as defined in Table 1.

Table 4iii: This table discloses the 105 compounds T4iii.001 to T4iii.105 of the formula Ic, wherein R is i-C$_3$H$_7$, R$_1$, R$_2$, R$_3$ and R$_4$ are hydrogen, G is hydrogen and R$_a$, R$_b$, R$_c$ and R$_d$ are as defined in Table 1.

Table 5iii: This table discloses the 105 compounds T5iii.001 to T5iii.105 of the formula Ic, wherein R is allyl, R$_1$, R$_2$, R$_3$ and R$_4$ are hydrogen, G is hydrogen and R$_a$, R$_b$, R$_c$ and R$_d$ are as defined in Table 1.

Table 6iii: This table discloses the 105 compounds T6iii.001 to T6iii.105 of the formula Ic, wherein R is benzyl, R$_1$, R$_2$, R$_3$ and R$_4$ are hydrogen, G is hydrogen and R$_a$, R$_b$, R$_c$ and R$_d$ are as defined in Table 1.

Table 7iii: This table discloses the 105 compounds T7iii.001 to T7iii.105 of the formula Ic, wherein R is C(=O)—CH$_3$, R$_1$, R$_2$, R$_3$ and R$_4$ are hydrogen, G is hydrogen and R$_a$, R$_b$, R$_c$ and R$_d$ are as defined in Table 1.

Table 8iii: This table discloses the 105 compounds T8iii.001 to T8iii.105 of the formula Ic, wherein R is C(=O)—CH$_2$CH$_3$, R$_1$, R$_2$, R$_3$ and R$_4$ are hydrogen, G is hydrogen and R$_a$, R$_b$, R$_c$ and R$_d$ are as defined in Table 1.

Table 9iii: This table discloses the 105 compounds T9iii.001 to T9iii.105 of the formula Ic, wherein R is C(=O)-n-$C_3H_7$, $R_1$, $R_2$, $R_3$ and $R_4$ are hydrogen, G is hydrogen and $R_a$, $R_b$, $R_c$ and $R_d$ are as defined in Table 1.

Table 10iii: This table discloses the 105 compounds T10iii.001 to T10iii.105 of the formula Ic, wherein R is C(=O)O—$CH_3$, $R_1$, $R_2$, $R_3$ and $R_4$ are hydrogen, G is hydrogen and $R_a$, $R_b$, $R_c$ and $R_d$ are as defined in Table 1.

Table 11iii: This table discloses the 105 compounds T11iii.001 to T11iii.105 of the formula Ic, wherein R is C(=O)O—$CH_2CH_3$, $R_1$, $R_2$, $R_3$ and $R_4$ are hydrogen, G is hydrogen and $R_a$, $R_b$, $R_c$ and $R_d$ are as defined in Table 1.

Table 12iii: This table discloses the 105 compounds T12iii.001 to T12iii.105 of the formula Ic, wherein R is C(=O)O-n-$C_3H_7$, $R_1$, $R_2$, $R_3$ and $R_4$ are hydrogen, G is hydrogen and $R_a$, $R_b$, $R_c$ and $R_d$ are as defined in Table 1.

Table 13iii: This table discloses the 105 compounds T13iii.001 to T13iii.105 of the formula Ic, wherein R is C(=O)NH—$CH_3$, $R_1$, $R_2$, $R_3$ and $R_4$ are hydrogen, G is hydrogen and $R_a$, $R_b$, $R_c$ and $R_d$ are as defined in Table 1.

Table 14iii: This table discloses the 105 compounds T14iii.001 to T14iii.105 of the formula Ic, wherein R is C(=O)NH—$CH_2CH_3$, $R_1$, $R_2$, $R_3$ and $R_4$ are hydrogen, G is hydrogen and $R_a$, $R_b$, $R_c$ and $R_d$ are as defined in Table 1.

Table 15iii: This table discloses the 105 compounds T15iii.001 to T15iii.105 of the formula Ic, wherein R is C(=O)NH-n-$C_3H_7$, $R_1$, $R_2$, $R_3$ and $R_4$ are hydrogen, G is hydrogen and $R_a$, $R_b$, $R_c$ and $R_d$ are as defined in Table 1.

Table 16iii: This table discloses the 105 compounds T16iii.001 to T16iii.105 of the formula Ic, wherein R is hydrogen, $R_1$, $R_2$, $R_3$ and $R_4$ are hydrogen, G is hydrogen and $R_a$, $R_b$, $R_c$ and $R_d$ are as defined in Table 1.

Table 17iii: This table discloses the 105 compounds T17iii.001 to T17iii.105 of the formula Ic, wherein R is $CH_2$—O—$CH_3$, $R_1$, $R_2$, $R_3$ and $R_4$ are hydrogen, G is hydrogen and $R_a$, $R_b$, $R_c$ and $R_d$ are as defined in Table 1.

Table 18iii: This table discloses the 105 compounds T18iii.001 to T18iii.105 of the formula Ic, wherein R is $CH_2$—O—$C_2H_5$, $R_1$, $R_2$, $R_3$ and $R_4$ are hydrogen, G is hydrogen and $R_a$, $R_b$, $R_c$ and $R_d$ are as defined in Table 1.

Table 19iii: This table discloses the 105 compounds T19iii.001 to T19iii.105 of the formula Ic, wherein R is $CH_2$—O—$C_2H_4$—O—$CH_3$, $R_1$, $R_2$, $R_3$ and $R_4$ are hydrogen, G is hydrogen and $R_a$, $R_b$, $R_c$ and $R_d$ are as defined in Table 1.

Table 20iii: This table discloses the 105 compounds T20iii.001 to T20iii.105 of the formula Ic, wherein R is hydrogen, $R_1$, $R_2$, $R_3$ and $R_4$ are $CH_3$, G is hydrogen and $R_a$, $R_b$, $R_c$ and $R_d$ are as defined in Table 1.

Table 21iii: This table discloses the 105 compounds T21iii.001 to T21iii.105 of the formula Ic, wherein R is $CH_3$, $R_1$, $R_2$, $R_3$ and $R_4$ are $CH_3$, G is hydrogen and $R_a$, $R_b$, $R_c$ and $R_d$ are as defined in Table 1.

Table 22iii: This table discloses the 105 compounds T22iii.001 to T22iii.105 of the formula Ic, wherein R is $C_2H_5$, $R_1$, $R_2$, $R_3$ and $R_4$ are $CH_3$, G is hydrogen and $R_a$, $R_b$, $R_c$ and $R_d$ are as defined in Table 1.

Agrochemically acceptable salts of the compounds of formula I are, for example, acid addition salts. Those salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halogen-substituted, $C_1$-$C_4$ alkanecarboxylic acids, for example formic acid, acetic acid or trifluoroacetic acid, unsaturated or saturated dicarboxylic acids, for example oxalic, malonic, succinic, maleic, fumaric or phthalic acid, hydroxycarboxylic acids, for example ascorbic, lactic, malic, tartaric or citric acid, or benzoic acid, or with organic sulfonic acids, such as unsubstituted or substituted, for example halogen-substituted, $C_1$-$C_4$ alkane- or aryl-sulfonic acids, for example methane- or p-toluene-sulfonic acid.

In order to apply an active ingredient to insects (in particular neonicotinoid resistant insects) and/or crops of useful plants as required by the methods of the invention said active ingredient may be used in pure form or, more typically, formulated into a composition which includes, in addition to said active ingredient, a suitable inert diluent or carrier and optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). SFAs include nonionic, cationic and/or anionic surfactants, as well as surfactant mixtures. Examples are suitable phosphates, such as salts of the phosphoric ester of a p-nonylphenol/(4-14) ethylene oxide adduct, or phospholipids. Further suitable phosphates are tris-esters of phosphoric acid with aliphatic or aromatic alcohols and/or bis-esters of alkyl phosphonic acids with aliphatic or aromatic alcohols, which are a high performance oil-type adjuvant. These tris-esters have been described, for example, in WO0147356, WO0056146, EP-A-0579052 or EP-A-1018299 or are commercially available under their chemical name. Preferred tris-esters of phosphoric acid for use in the new compositions are tris-(2-ethylhexyl)phosphate, tris-n-octyl phosphate and tris-butoxyethyl phosphate, where tris-(2-ethylhexyl)phosphate is most preferred. Suitable bis-ester of alkyl phosphonic acids are bis-(2-ethylhexyl)-(2-ethylhexyl)-phosphonate, bis-(2-ethyl hexyl)-(n-octyl)-phosphonate, dibutyl-butyl phosphonate and bis(2-ethylhexyl)-tripropylene-phosphonate, where bis-(2-ethylhexyl)-(n-octyl)-phosphonate is particularly preferred.

The compositions according to the invention can preferably additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil such as ADIGOR® and MERO®, olive oil or sunflower oil, emulsified vegetable oil, such as AMIGO® (Rhone-Poulenc Canada Inc.), alkyl esters of oils of vegetable origin, for example the methyl derivatives, or an oil of animal origin, such as fish oil or beef tallow.

A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

Also, alkoxylated fatty acids can be used as additives in the inventive compositions as well as polymethylsiloxane based additives, which have been described in WO08/037,373.

Thus in further embodiments according to any aspect of the invention mentioned hereinbefore, the active ingredient will be in the form of a composition additionally comprising an agriculturally acceptable carrier or diluent.

It is preferred that all compositions (both solid and liquid formulations) for use in the invention comprise, by weight, from 0.0001 to 95% (inclusive), more preferably from 1 to 85% (inclusive), for example from 5 to 60% (inclusive), of active ingredient. The composition is generally used in methods of the invention such that the active ingredient is applied at a concentration are from 0.1 to 1000 ppm, preferably from 0.1 to 500 ppm, of active ingredient. In particular, spray mixtures with active ingredient concentrations of 50, 100, 200, 300 or 500 ppm are used.

The rates of application (use) of a the compound vary, for example, according to type of use, type of crop, type of plant propagation material (if appropriate), but is such that the active ingredient is in an effective amount to provide the control (such as pest control) and can be determined by trials and routine experimentation known to one of ordinary skill in the art.

The rates of application per hectare are generally from 1 to 2000 g of active ingredient per hectare, especially from 10 to 1000 g/ha, preferably from 20 to 600 g/ha, more preferably from 12.5 to 500 g/ha, especially from 25 to 400 g/ha. Rates of application of 25, 50, 100, 150, 200, 250, 300, or 400 g of active ingredient per hectare are preferred. In the instance, the compound is treated on to the plant propagation material, the corresponding rates would apply.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula I.

Dustable powders (DP) may be prepared by mixing the active ingredient with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula I with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing the active ingredient with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of the active ingredient and one or more powdered solid diluents or carriers, or from pre-formed blank granules by absorbing the active ingredient (or a solution thereof, in a suitable agent) in a porous granular material (such as pumice, attapulgite clays, fuller's earth, kieselguhr, diatomaceous earths or ground corn cobs) or by adsorbing the active ingredient (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving the active ingredient in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving the active ingredient in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula I either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. The active ingredient is present initially in either the water or the solvent/SFA blend. Suitable solvents for use in MEs include those hereinbefore described for use in ECs or in EWs. A ME may be either an oil-in-water or a water-in-oil system (which system is present may be determined by conductivity measurements) and may be suitable for mixing water-soluble and oil-soluble pesticides in the same formulation. A ME is suitable for dilution into water, either remaining as a microemulsion or forming a conventional oil-in-water emulsion.

Suspension concentrates (SC) may comprise aqueous or non-aqueous suspensions of finely divided insoluble solid particles the active ingredient. SCs may be prepared by ball or bead milling the solid active ingredient in a suitable medium, optionally with one or more dispersing agents, to produce a fine particle suspension of the compound. One or more wetting agents may be included in the composition and a suspending agent may be included to reduce the rate at which the particles settle. Alternatively, the active ingredient may be dry milled and added to water, containing agents hereinbefore described, to produce the desired end product.

Aerosol formulations comprise the active ingredient and a suitable propellant (for example n-butane). Active ingredients may also be dissolved or dispersed in a suitable medium (for example water or a water miscible liquid, such as n-propanol) to provide compositions for use in non-pressurised, hand-actuated spray pumps.

The active ingredient may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains the active ingredient and, optionally, a carrier or diluent therefor. The polymeric shell may be produced by either an interfacial polycondensation reaction or by a coacervation procedure. The compositions may provide for controlled release of the compound of the active ingredient. Active ingredients may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of the active ingredient. Such additives include surface active agents, spray additives based on oils, for example certain mineral oils, natural plant oils (such as soy bean and rape seed oil) and/or modified plant oils (e.g. esterified plant oils), and blends of these with other bio-enhancing adjuvants (ingredients which may aid or modify the action of the active ingredient.

Preferred compositions for use in methods of the invention are composed in particular of the following constituents (throughout, percentages are by weight):

Emulsifiable Concentrates (EC):
active ingredient: 1 to 90%, preferably 5 to 20%
SFA: 1 to 30%, preferably 10 to 20%
solvent: 5 to 98%, preferably 70 to 85%

Dusts (DP):
active ingredient: 0.1 to 10%, preferably 0.1 to 1%
solid carrier/diluent: 99.9 to 90%, preferably 99.9 to 99%

Suspension Concentrates (SC):
active ingredient: 5 to 75%, preferably 10 to 50%
water: 94 to 24%, preferably 88 to 30%
SFA: 1 to 40%, preferably 2 to 30%

Wettable Powders (WP):
active ingredient: 0.5 to 90%, preferably 1 to 80%, more preferably 20 to 30%
SFA: 0.5 to 20%, preferably 1 to 15%
solid carrier: 5 to 99%, preferably 15 to 98%

Granules (GR, SG, WG):
active ingredient: 0.5 to 60%, preferably 5 to 60%, more preferably 50 to 60%
solid carrier/diluent: 99.5 to 40%, preferably 95 to 40%, more preferably 50 to 40%

A compound of formula I may be applied to a neonicotinoid resistant insect or crop of useful plants using any standard application method with which the skilled man is familiar, such as foliar spay or treatment of the plant propagation materials of the crop. Similarly, for methods of controlling insect resistance, neonicotinoid insecticides may be applied to an insect/crop/plant propagation material of useful plants using any known method of application. Further guidance may be found in the art, which includes for example, advice on application given on the labels of commercially available products. In another aspect of the invention, the neonicotinoid insecticide is applied to the plant propagation material (such as seeds, young plants, transplants etc.) of the respective crops followed by the foliar application of a compound of the formula (I) starting in the 3- to 5-leaf up to the fruit setting crop stage. It has been found, that beginning with the 3- to 5-leaf crop stage, when the level of insect control by the neonicotinoid insecticide starts to decrease, another boost in insect control can be achieved by the foliar application of a compound of the formula (I), which, surprisingly, is accompanied by pronounced crop enhancement effects such as an increase in the formation of fine roots, synchronisation of flowering, drought resistance and, in particular, an increase in yield.

Examples of typical formulations are provided below (throughout, percentages are by weight)

Example F1: Solutions

| | a) | b) | c) | d) |
|---|---|---|---|---|
| active ingredient | 80% | 10% | 5% | 95% |
| ethylene glycol monomethyl ether | 20% | — | — | — |
| polyethylene glycol (mol. wt 400) | — | 70% | — | — |
| N-methyl-2-pyrrolidone | — | 20% | — | — |
| epoxidised coconut oil | — | — | 1% | 5% |
| petroleum fraction (boiling range 160-190. degree.) | — | — | 94% | — |

These solutions are suitable for application in the form of micro-drops.

Example F2: Granules

| | a) | b) | c) | d) |
|---|---|---|---|---|
| active ingredient | 5% | 10% | 8% | 21% |
| Kaolin | 94% | — | 79% | 54% |
| Highly dispersed silicic acid | 1% | — | 13% | 7% |
| Attapulgite | — | 90% | — | 18% |

The active ingredient is dissolved in dichloromethane, the solution is sprayed onto the carrier, and the solvent is subsequently evaporated off in vacuo.

Example F3: Dusts

| | a) | b) |
|---|---|---|
| active ingredient | 2% | 5% |
| Highly dispersed silicic acid | 1% | 5% |
| Talcum | 97% | — |
| Kaolin | — | 90% |

Ready-for-use dusts are obtained by intimately mixing the carriers with the active ingredient.

| Example F4: Wettable powders | |
|---|---|
| active ingredient | 25% |
| Sodium sulphate | 5% |
| castor oil polyethylene glycol ether (36-37 mol of ethylene oxide) | 10% |
| silicone oil | 1% |
| Agridex | 2% |
| highly dispersed silicic acid | 10% |
| kaolin powder | 37% |
| sulfite spent lye powder | 5% |
| Ultravon W-300% (disodium salt of 1-benzyl-2 heptadecylbenzimidazole-X,X'-disulfonic acid) | 5% |

The active ingredient is mixed with the other formulation components and the mixture is ground in a suitable mill, affording wettable powders which can be diluted with water to give suspensions of the desired concentration.

| Example F5: Dusts | | |
|---|---|---|
| | a) | b) |
| active ingredient | 5% | 8% |
| Talcum | 95% | — |
| Kaolin | — | 92% |

Ready-for-use dusts are obtained by mixing the active ingredient with the carrier and grinding the mixture in a suitable mill.

| Example F6: Extruder granules | |
|---|---|
| active ingredient | 10% |
| Sodium lignosulfonate | 2% |
| Carboxymethylcellulose | 1% |
| Kaolin | 87% |

The active ingredient is mixed and ground with the other formulation components, and the mixture is subsequently moistened with water. The moist mixture is extruded and granulated and then the granules are dried in a stream of air.

| Example F7: Coated granules | |
|---|---|
| active ingredient | 3% |
| Polyethylene glycol (mol. wt. 200) | 3% |
| Kaolin | 94% |

The finely ground active ingredient is uniformly applied, in a mixer, to the kaolin moistened with polyethylene glycol. Non-dusty coated granules are obtained in this manner.

| Example F8: Suspension concentrate | |
|---|---|
| active ingredient | 40% |
| Ethylene glycol | 10% |
| Nonylphenol polyethylene glycol Ether (15 mol of ethylene oxide) | 6% |
| Sodium lignosulfonate | 10% |
| Carboxymethylcellulose | 1% |
| Aqueous formaldehyde solution (37%) | 0.2% |
| Aqueous silicone oil emulsion (75%) | 0.8% |
| Water | 32% |

The finely ground active ingredient is intimately mixed with the other formulation components giving a suspension concentrate from which suspensions of any desired concentration can be obtained by dilution with water.

| Example F9: Emulsifiable concentrates | | | |
|---|---|---|---|
| | a) | b) | c) |
| active ingredient | 25% | 40% | 50% |
| Calcium dodecylbenzenesulfonate | 5% | 8% | 6% |
| Castor oil polyethylene glycol ether (36 mol of ethylene oxide) | 5% | — | — |
| Tristyrylphenol polyethylene glycol ether (30 mol of ethylene oxide | — | 12% | 4% |
| Cyclohexanone | — | 15% | 20% |
| Xylene mixture | 65% | 25% | 20% |

Emulsions of any desired concentration can be produced from such concentrates by dilution with water.

| Example F10: Wettable powders | | | |
|---|---|---|---|
| | a) | b) | c) |
| active ingredient | 25% | 50% | 75% |
| Sodium lignosulfonate | 5% | 5% | — |
| Sodium laurylsulfate | 3% | — | 5% |
| Sodium diisobutylnapthalene-sulfonate | — | 6% | 10% |
| Octylphenol polyethylene glycol ether (7-8 mol of ethylene oxide) | — | 2% | — |
| Highly dispersed silicic acid | 5% | 10% | 10% |
| Kaolin | 62% | 27% | — |

The active ingredient is mixed with the other formulation components and the mixture is ground in a suitable mill, affording wettable powders which can be diluted with water to give suspensions of the desired concentration.

| Example F11: Emulsifiable concentrate | |
|---|---|
| active ingredient | 10% |
| Octylphenol polyethylene glycol ether (4-5 mol of ethylene oxide) | 3% |
| Calcium dodecylbenzenesulfonate | 3% |
| Castor oil polyglycol ether (36 mol of ethylene oxide) | 4% |
| Cyclohexanone | 30% |
| Xylene mixture | 50% |

Emulsions of any required concentration can be obtained from this concentrate by dilution with water.

Various aspects and embodiments of the present invention will now be illustrated in more detail by way of example. It will be appreciated that modification of detail may be made without departing from the scope of the invention.

EXAMPLE 1

Preparation of Carbonic acid ethyl ester 8-methoxy-1-methyl-2-oxo-3-(2,4,6-trimethyl-phenyl)-1,8-diaza-spiro[4.5]dec-3-en-4-yl ester (compound P1.2)

Step 1: Preparation of 4-hydroxy-8-methoxy-1-methyl-3-(2,4,6-trimethyl-phenyl)-1,8-diaza-spiro[4.5]dec-3-en-2-one (compound P2.2)

Two-Steps (Amide N-Alkylation and Cyclisation), One-Pot Procedure

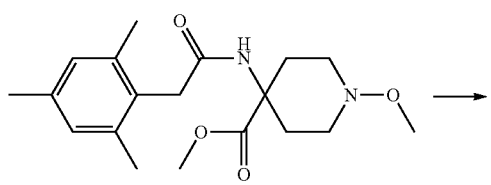

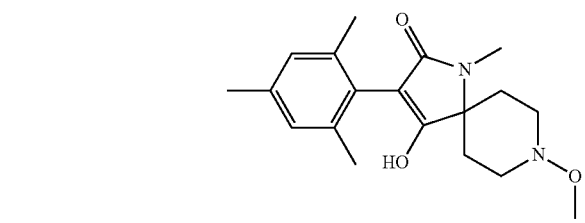

To a solution of 1-methoxy-4-[2-(2,4,6-trimethyl-phenyl)-acetylamino]-piperidine-4-carboxylic acid methyl ester [prepared according to WO09/049,851] (850 mg, 2.44 mmol) in dimethylformamide (20 ml) at 0° C. was added sodium hydride (122 mg, 55% w/w dispersion in mineral oil, 2.81 mmol) in two portions. The reaction mixture was stirred at 0° C. for one hour, treated with methyl iodide (0.175 ml, 398 mg, 2.81 mmol) dropwise, and further stirred at 0° C. for one hour and at room temperature for 3 hours. To the mixture recooled at 0° C. was added sodium methoxide (198 mg, 3.66 mmol) in one portion, and stirring continued at room temperature for 2 hours, at 40° C. for 30 minutes and after further addition of sodium methoxide (~20 mg) at 50° C. for 45 minutes. The reaction mixture was poured on iced aqueous ammonium chloride, acidified to pH 5-6 with an aqueous HCl solution and thoroughly extracted with ethyl acetate. The combined organic layers were washed with brine, dried over sodium sulfate and concentrated. The crude oily product was purified by chromatography on silica gel (ethyl acetate), and further triturated with cold diethyl ether, filtered and dried. Yield: 338 mg of 4-hydroxy-8-methoxy-1-methyl-3-(2,4,6-trimethyl-phenyl)-1,8-diaza-spiro[4.5]dec-3-en-2-one (compound P2.2) as a solid, mp 241-243° C.

$^1$H-NMR (CD$_3$OD): 1.44 (br m, 1H), 1.72 (br m, 1H), 2.10 (s, 6H), 2.25 (s, 3H), 2.33 (br m, 1H), 2.48 (br m, 1H), 2.89 (br signal, 3H), 3.20 (br m, 1H), 3.27-3.43 (br signals, total 3H), 3.54 (s, 3H), 6.89 (s, 2H).

LC/MS (ES+): 331 (M+H)$^+$, LC/MS (ES−): 329 (M−H)$^−$

Step 2: Preparation of carbonic acid ethyl ester 8-methoxy-1-methyl-2-oxo-3-(2,4,6-trimethyl-phenyl)-1,8-diaza-spiro[4.5]dec-3-en-4-yl ester (title compound P1.2)

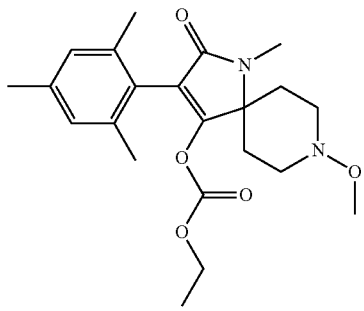

To a solution of 4-hydroxy-8-methoxy-1-methyl-3-(2,4,6-trimethyl-phenyl)-1,8-diaza-spiro[4.5]dec-3-en-2-one (238 mg, 0.72 mmol), triethylamine (0.15 ml, 109 mg, 1.08 mmol) and 4-dimethylaminopyridine (2 mg) in tetrahydrofuran (10 ml) at 0° C. was added ethyl chloroformate (0.075 ml, 85 mg, 0.79 mmol) dropwise. The suspension was stirred at 0° C. for one hour. The reaction mixture was diluted with ethyl acetate and water, the layers separated, the aqueous phase extracted with ethyl acetate, the combined organic phases washed with brine, dried over sodium sulfate and concentrated. The residue was purified by chromatography on silica gel (ethyl acetate/heptane 5:1). Yield: 145 mg of carbonic acid ethyl ester 8-methoxy-1-methyl-2-oxo-3-(2,4,6-trimethyl-phenyl)-1,8-diaza-spiro[4.5]dec-3-en-4-yl ester (title compound P1.2) as a white solid, mp 134-136° C.

$^1$H-NMR (CDCl$_3$): 1.05 (t, 3H), 1.59 (br m, 1H), 1.83 (br m, 1H), 2.15 (s, 6H), 2.25 (s, 3H), 2.36 (br m, 2H), 2.88 (br m, 1H), 2.95 (br s, 3H), 3.22 (br m, 1H), 3.38 (m, 2H), 3.55 (s, 3H), 3.98 (q, 2H), 6.84 (s, 2H).

LC/MS (ES+): 403 (M+H)$^+$

EXAMPLE 2

Preparation of 4-Hydroxy-8-methoxy-1-methyl-3-(2,4,6-trimethyl-phenyl)-1,8-diaza-spiro[4.5]dec-3-en-2-one (compound P2.2)

Step 1: Preparation of 4-benzyloxy-8-methoxy-3-(2,4,6-trimethyl-phenyl)-1,8-diaza-spiro[4.5]dec-3-en-2-one (compound P3.4)

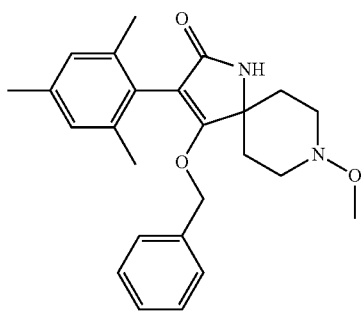

To a suspension of 4-hydroxy-8-methoxy-3-(2,4,6-trimethyl-phenyl)-1,8-diaza-spiro[4.5]dec-3-en-2-one [prepared according to WO09/049,851] (67.0 g, 211.7 mmol) in acetone (900 ml) was added potassium carbonate (35.1 g, 254.1 mmol), followed by benzyl bromide (35.3 ml, 50.7 g, 296.4 mmol) dropwise. The suspension was stirred at reflux for one hour, then poured on ice water and ethyl acetate. The resulting precipitate was filtered off, dissolved in methylene chloride, dried over sodium sulfate, concentrated and dried over phosphorus pentoxide under vacuum at 50° C. overnight to afford a first crop of product as a white solid (55.8 g). The layers of the mother liquor were separated, the aqueous phase extracted with ethyl acetate, the combined organic phases washed with brine, dried over sodium sulfate and concentrated. The residue was suspended in diethyl ether, filtered and dried to further deliver 22.6 g of product. Yield: 78.4 g of 4-benzyloxy-8-methoxy-3-(2,4,6-trimethyl-phenyl)-1,8-diaza-spiro[4.5]dec-3-en-2-one (compound P3.4) as a solid, mp 184-186° C.

$^1$H-NMR (CDCl$_3$): 1.66 (m, 2H), 2.11 (s, 6H), 2.28 (s, 3H), 2.33 (m, 2H), 2.47 (m, 2H), 3.45 (m, 2H), 3.55 (s, 3H), 4.68 (s, 2H), 6.13 (br s, 1H), 6.87 (s, 2H), 7.04 (m, 2H), 7.28 (m, 3H).

LC/MS (ES+): 407 (M+H)$^+$

Step 2: Preparation of 4-benzyloxy-8-methoxy-1-methyl-3-(2,4,6-trimethyl-phenyl)-1,8-diaza-spiro[4.5]dec-3-en-2-one (compound P3.5)

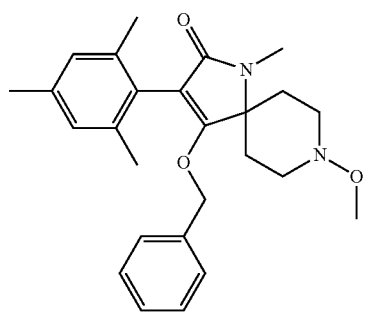

To a solution of 4-benzyloxy-8-methoxy-3-(2,4,6-trimethyl-phenyl)-1,8-diaza-spiro[4.5]dec-3-en-2-one (40.0 g, 98.4 mmol) in tetrahydrofuran (500 ml) at 0° C. was added a 1.0 M solution of lithium bis(trimethylsilyl)amide in tetrahydrofuran (108.3 ml, 108.3 mmol) dropwise over one hour. The mixture was stirred at 0° C. for 30 minutes and at room temperature for 30 minutes, then treated with methyl iodide (6.75 ml, 15.4 g, 108.2 mmol) dropwise at 0° C. over 10 minutes. Stirring was continued at room temperature overnight and the reaction mixture was quenched with cold saturated aqueous ammonium chloride. The layers were separated, the aqueous phase extracted twice with ethyl acetate, the combined organic phases washed with brine, dried over sodium sulfate and concentrated. The residue was suspended in diethyl ether, stirred for 30 minutes, filtered and dried. Yield: 28.6 g of 4-benzyloxy-8-methoxy-1-methyl-3-(2,4,6-trimethyl-phenyl)-1,8-diaza-spiro[4.5]dec-3-en-2-one (compound P3.5) as a solid, mp 139-141° C.

$^1$H-NMR (CDCl$_3$): 1.52 (br m, 1H), 1.74 (br m, 1H), 2.11 (br s, 6H), 2.28 (s, 3H), 2.34 (br m, 2H), 2.92 (br signal, 3H), 3.12 (br m, 1H), 3.30 (m, 3H), 3.52 (s, 3H), 4.67 (br signal, 2H), 6.85 (s, 2H), 7.04 (m, 2H), 7.28 (m, 3H).

LC/MS (ES+): 421 (M+H)$^+$

Step 3: Preparation of 4-hydroxy-8-methoxy-1-methyl-3-(2,4,6-trimethyl-phenyl)-1,8-diaza-spiro[4.5]dec-3-en-2-one (title compound P2.2)

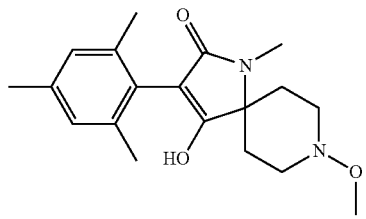

To a solution of 4-benzyloxy-8-methoxy-1-methyl-3-(2,4,6-trimethyl-phenyl)-1,8-diaza-spiro[4.5]dec-3-en-2-one (22.6 g, 53.7 mmol) in methanol (226 ml) and water (22.6 ml) in a Parr shaker type hydrogenator was added 5% Pd/C (22.6 g). After hydrogenation under 4 bars H$_2$ at 36° C. for 22 hours, the reaction mixture was filtered and concentrated. The residue was diluted with ethyl acetate and extracted with saturated aqueous sodium carbonate under ice cooling. The organic layer was discarded, the aqueous alkaline phase acidified with cooling to pH 5-6 with an aqueous HCl solution and thoroughly extracted with ethyl acetate. The combined organic layers were washed with brine, dried over sodium sulfate and concentrated. Yield: 13.0 g of 4-hydroxy-8-methoxy-1-methyl-3-(2,4,6-trimethyl-phenyl)-1,8-diaza-spiro[4.5]dec-3-en-2-one (title compound P2.2) as a solid, mp 239-241° C.

The spectral data were identical to those described above under preparation example 1, step 1.

EXAMPLE 3

Preparation of 1-Cyclopropylmethyl-4-hydroxy-8-methoxy-3-(2,4,6-trimethyl-phenyl)-1,8-diaza-spiro[4.5]dec-3-en-2-one (compound P2.8)

Step 1: Preparation of 4-benzyloxy-1-cyclopropyl-methyl-8-methoxy-3-(2,4,6-trimethyl-phenyl)-1,8-diaza-spiro[4.5]dec-3-en-2-one (compound P3.8)

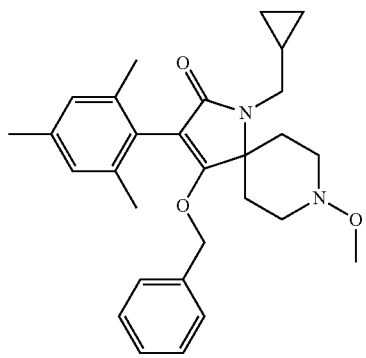

To a solution of 4-benzyloxy-8-methoxy-3-(2,4,6-trimethyl-phenyl)-1,8-diaza-spiro[4.5]dec-3-en-2-one (compound P3.4) (1.0 g, 2.46 mmol) in dioxane (40 ml) was added bromomethyl-cyclopropane (1.257 ml, 1.78 g, 13.16 mmol) and potassium tert-butoxide (1.50 g, 13.37 mmol). The reaction mixture was stirred at 100° C. for 5 days, then poured on water and extracted with ethyl acetate. The combined organic phases were washed with brine, dried over sodium sulfate and concentrated. The residue was suspended in ethyl acetate/heptane 1:5, stirred overnight, filtered and dried to afford a first crop of product as a white solid (350 mg). The mother liquor was concentrated, and the residue purified by chromatography on silica gel (dichloromethane/acetone 10:1) to further deliver 205 mg of product. Yield: 555 mg of 4-benzyloxy-1-cyclopropylmethyl-8-methoxy-3-(2,4,6-trimethyl-phenyl)-1,8-diaza-spiro[4.5]dec-3-en-2-one (compound P3.8) as a solid, mp 119-121° C.

$^1$H-NMR (CD$_3$OD): 0.34 (m, 2H), 0.52 (m, 2H), 1.10 (m, 1H), 1.48 (br m, 1H), 1.83 (br m, 1H), 2.11 (br s, 6H), 2.29 (s, 3H), 2.41 (br m, 1H), 2.60 (br m, 1H), 3.12 (br m, 1H), 3.23 (m, 2H), 3.24-3.41 (br signals, total 3H), 3.50 (s, 3H), 4.72 (br signal, 2H), 6.91 (s, 2H), 7.06 (m, 2H), 7.29 (m, 3H).

LC/MS (ES+): 461 (M+H)$^+$

Step 2: Preparation of 1-cyclopropylmethyl-4-hydroxy-8-methoxy-3-(2,4,6-trimethyl-phenyl)-1,8-diaza-spiro[4.5]dec-3-en-2-one (title compound P2.8)

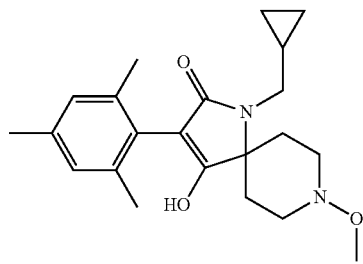

Debenzylation was conducted using an H-Cube® continuous-flow hydrogenator: 4-benzyloxy-1-cyclopropylmethyl-8-methoxy-3-(2,4,6-trimethyl-phenyl)-1,8-diaza-spiro[4.5]dec-3-en-2-one (546 mg, 1.34 mmol) was dissolved in methanol (47 ml) and this substrate solution (0.029 M) pumped twice through a 5% Pd/C filled cartridge at a flow-rate of 1 mL/min, a temperature of 35° C. and a pressure of 2-3 bars. The collected product solution was concentrated, and the residue purified by chromatography on silica gel (ethyl acetate/heptane 1:1). Yield: 215 mg of 1-cyclopropylmethyl-4-hydroxy-8-methoxy-3-(2,4,6-trimethyl-phenyl)-1,8-diaza-spiro[4.5]dec-3-en-2-one (title compound P2.8) as a white solid, mp 223-225° C.

$^1$H-NMR (CD$_3$OD): 0.34 (m, 2H), 0.52 (m, 2H), 1.11 (m, 1H), 1.43 (br m, 1H), 1.78 (br m, 1H), 2.11 (s, 6H), 2.25 (s, 3H), 2.41 (br m, 1H), 2.62 (br m, 1H), 3.23 (br signal, total 3H), 3.28-3.45 (br signals, total 3H), 3.55 (s, 3H), 6.90 (s, 2H).

LC/MS (ES+): 371 (M+H)$^+$, 369 (M−H)$^-$

EXAMPLE 4

Preparation of 4-Hydroxy-8-methoxy-1-methyl-3-(2,4,6-trimethyl-phenyl)-1,8-diaza-spiro[4.5]dec-3-en-2-one (compound P2.2)

Step 1: Preparation of 1-methoxy-4-methylamino-piperidine-4-carbonitrile (compound P5.1)

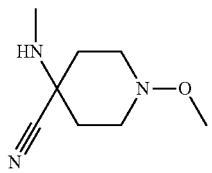

To a solution of 1-methoxy-piperidin-4-one [prepared according to Journal of Organic Chemistry (1961), 26, 1867-74] (100 g, 0.77 mol), aqueous methylamine (40 wt. % in H$_2$O, 86 ml) and methylamine hydrochloride (57.5 g, 0.85 mol) in water (700 ml) at 0° C. was added a solution of potassium cyanide (55.5 g, 0.85 mol) in water (150 ml) dropwise over one hour. The reaction mixture was stirred at room temperature for two days. Over the next five days, the mixture was further treated with methylamine hydrochloride (5×2.6 g, total 13.0 g), aqueous methylamine (5×4.3 ml, total 21.5 ml) and potassium cyanide (5×2.5 g, total 12.5 g), and stirring continued at room temperature until the reaction was judged complete by thin layer chromatography. The aqueous reaction mixture was extracted with dichloromethane (1×500 ml, and 4×200 ml), the combined organic phases dried over sodium sulfate and evaporated. Yield: 113.0 g of 1-methoxy-4-methylamino-piperidine-4-carbonitrile (compound P5.1) as a red liquid. This material was used without further purification in the next step.

$^1$H-NMR (CDCl$_3$): 1.36 (br s, 1H), 1.62-2.22 (br signals, total 4H), 2.51 (s, 3H), 2.63-3.41 (br signals, total 4H), 3.51 (s, 3H).

IR (CN): ν 2220 cm$^{-1}$. LC/MS (ES+): 170 (M+H)$^+$

Step 2: Preparation of N-(4-cyano-1-methoxy-piperidin-4-yl)-N-methyl-2-(2,4,6-trimethyl-phenyl)-acetamide (compound P4.1)

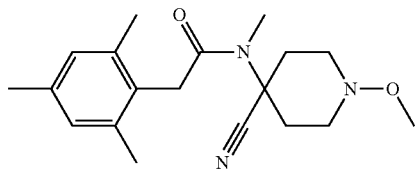

Method A: To a solution of 1-methoxy-4-methylamino-piperidine-4-carbonitrile (20.0 g, 118.2 mmol), triethylamine (24.6 ml, 17.9 g, 177.3 mmol) and 4-dimethylaminopyridine (DMAP, 0.1 g) in tetrahydrofuran (250 ml) at 0-5° C. was added a solution of (2,4,6-trimethyl-phenyl)-acetyl chloride (25.6 g, 130.0 mmol) in THF (25 ml) dropwise over 1.5 hour. The reaction mixture was stirred at room temperature for a total of three hours, during which it was further treated with (2,4,6-trimethyl-phenyl)-acetyl chloride (5.4 g)

and triethylamine (7 ml). The reaction mixture was diluted with ethyl acetate and water, the layers separated, the aqueous phase extracted twice with ethyl acetate, the combined organic phases washed twice with saturated aqueous sodium hydrogen carbonate and brine, dried over sodium sulfate and concentrated. The solid residue was suspended in diethyl ether (500 ml), stirred overnight at room temperature, filtered and dried. Yield: 27.5 g of N-(4-cyano-1-methoxy-piperidin-4-yl)-N-methyl-2-(2,4,6-trimethyl-phenyl)-acetamide (compound P4.1) as a white solid, mp 171-178° C. This material was used without further purification in the next step.

$^1$H-NMR (CDCl$_3$): 2.01 (br m, 1H), 2.11 (br m, 1H), 2.20 (s, 6H), 2.25 (s, 3H), 2.34 (br m, 1H), 2.57 (br m, 1H), 2.83 (br m, 1H), 3.12 (s, 3H), 3.20 (br m, 1H), 3.34 (br m, 2H), 3.50 (br s, 3H), 3.66 (s, 2H), 6.85 (s, 2H).

IR (CN): ν 2231 cm$^{-1}$. LC/MS (ES+): 330 (M+H)$^+$

Method B: To a solution of 1-methoxy-4-methylamino-piperidine-4-carbonitrile (20.0 g, 118.2 mmol) in pyridine (250 ml) was added (2,4,6-trimethyl-phenyl)-acetyl chloride (25.6 g, 130.0 mmol) dropwise at 0° C. The reaction mixture was stirred at 0° C. for one hour and at room temperature overnight, poured on ice water and acidified to pH 7 with an aqueous 2N HCl solution. The resulting thick precipitate was filtered, washed with cold water, dissolved in dichloromethane, dried over sodium sulfate and concentrated. The solid residue was suspended in hexane, stirred at room temperature, filtered and dried. Yield: 32.7 g of N-(4-cyano-1-methoxy-piperidin-4-yl)-N-methyl-2-(2,4,6-trimethyl-phenyl)-acetamide (compound P4.1) as a pale yellow solid, mp 175-177° C. The spectral data of this material were identical to those described above under preparation example 4, step 2, Method A.

Step 3: Preparation of 1-methoxy-4-{methyl-[2-(2,4,6-trimethyl-phenyl)-acetyl]-amino}-piperidine-4-carboxylic acid methyl ester (compound P4.2)

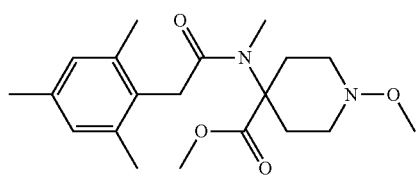

To a suspension of N-(4-cyano-1-methoxy-piperidin-4-yl)-N-methyl-2-(2,4,6-trimethyl-phenyl)-acetamide (106.0 g, 0.322 mol) in methanol (222 ml) at 15-20° C. was added concentrated sulfuric acid (85.7 ml, 157.8 g, 1.609 mol) dropwise over 75 minutes and the reaction mixture was stirred at room temperature for one hour. The mixture was poured on ice (1 kg), stirred for one hour, then neutralised carefully with 30% aqueous sodium hydroxide to pH 5-5.5 (external ice cooling). The thick pasty mixture was diluted with water (1000 ml) and filtered. The solid residue was washed with water and hexane, air-dried and further dried over phosphorus pentoxide under vacuum at 40° C. for two hours. In order to eliminate inorganic impurities (sodium sulfate!), the solid material was diluted with dichloromethane (600 ml), washed with water (2×300 ml), the aqueous phases extracted once with dichloromethane, the combined organic phases dried over sodium sulfate and evaporated. Yield: 85.4 g of 1-methoxy-4-{methyl-[2-(2,4,6-trimethyl-phenyl)-acetyl]-amino}-piperidine-4-carboxylic acid methyl ester (compound P4.2) as a white solid, mp 133-135° C.

$^1$H-NMR (CDCl$_3$): 1.92 (br m, 1H), 2.04 (br m, 1H), 2.16 (s, 6H), 2.23 (s, 3H), 2.27-2.49 (br m, 2H), 2.82 (br m, 2H), 3.14 (br m, 2H), 3.22 (br s, 3H), 3.52 (s, 3H), 3.62 (br s, 5H), 6.82 (s, 2H).

LC/MS (ES+): 363 (M+H)$^+$

Step 4: Preparation of 4-hydroxy-8-methoxy-1-methyl-3-(2,4,6-trimethyl-phenyl)-1,8-diaza-spiro[4.5]dec-3-en-2-one (title compound P2.2)

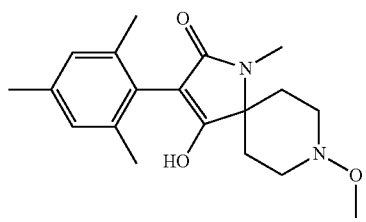

To a solution of 1-methoxy-4-{methyl-[2-(2,4,6-trimethyl-phenyl)-acetyl]-amino}-piperidine-4-carboxylic acid methyl ester (85.0 g, 234.5 mmol) in dimethylformamide (800 ml) at 0° C. was added sodium methoxide (38.0 g, 703.5 mmol) in four portions and stirring continued at 0° C. for 30 minutes, then at room temperature for 1 hour. The reaction mixture was poured on ice and saturated aqueous ammonium chloride, acidified to pH 5-6 with concentrated HCl and thoroughly extracted with ethyl acetate. The combined organic layers were washed with water and brine, dried over sodium sulfate, concentrated and the residue dried in vacuo. Yield: 72.7 g of 4-hydroxy-8-methoxy-1-methyl-3-(2,4,6-trimethyl-phenyl)-1,8-diaza-spiro[4.5]dec-3-en-2-one (title compound P2.2) as a solid.

The spectral data of this crude material were identical to those described above under preparation example 1, step 1.

EXAMPLE 5

Preparation of 4-Cyclopropylamino-1-methoxy-piperidine-4-carbonitrile (compound P5.2)

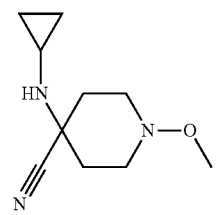

To a solution of cyclopropylamine (1.4 ml, 1.14 g, 20.0 mmol) in methanol (20 ml) at 0° C. was added 1N hydrochloric acid (20 ml, 20.0 mmol) dropwise and the mixture was stirred at room temperature for 30 minutes. 1-Methoxy-piperidin-4-one [prepared according to Journal of Organic Chemistry (1961), 26, 1867-74] (2.58 g, 20.0 mmol), followed 10 minutes later by potassium cyanide (1.3 g, 20.0 mmol) in water (10 ml) were then added dropwise at 0° C. The reaction mixture was warmed to room temperature and stirred overnight, diluted with water and diethyl ether, the layers separated and the aqueous phase thoroughly extracted with diethyl ether. The combined organic layers were washed with brine, dried over sodium sulfate and evaporated. Yield: 3.19 g of 4-cyclopropylamino-1-methoxy-piperidine-4-carbonitrile (title compound P5.2) as an oil. This material was used without further purification in the next step.

$^1$H-NMR (CDCl$_3$): 0.42 (br m, 2H), 0.56 (m, 2H), 1.57-2.30 (br signals, total 5H), 2.31 (m, 1H), 2.63-3.41 (br signals, total 4H), 3.51 (br s, 3H).

IR (CN): ν 2223 cm$^{-1}$. LC/MS (ES+): 196 (M+H)$^+$

EXAMPLE 6

Preparation of 1-Methoxy-4-methylamino-piperidine-4-carboxylic acid methyl ester (compound P5.4)

Step 1: Preparation of 8-methoxy-1-methyl-1,3,8-triaza-spiro[4.5]decane-2,4-dione (compound P5.6)

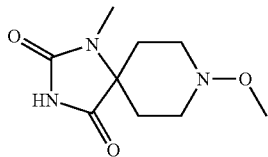

To a solution of 1-methoxy-4-methylamino-piperidine-4-carbonitrile (compound P5.1) (10.0 g, 59.09 mmol) in dichloromethane (180 ml) was added chlorosulfonyl isocyanate (5.14 ml, 8.36 g, 59.05 mmol) dropwise over 15 minutes at 20-30° C. The yellowish suspension was stirred at room temperature for 30 minutes and concentrated to generate a pale yellow solid. This material was dissolved in aqueous 1N hydrochloric acid (180 ml), heated at reflux for one hour, cooled to 0° C. and acidified to pH 5.5 with an aqueous 4N NaOH solution. The aqueous phase was extracted with ethyl acetate (4×), the combined organic layers were washed with brine, dried over sodium sulfate and concentrated. The residue was purified by chromatography on silica gel (ethyl acetate/heptane 1:1). Yield: 3.86 g of 8-methoxy-1-methyl-1,3,8-triaza-spiro[4.5]decane-2,4-dione (compound P5.6) as a solid.

$^1$H-NMR (CDCl$_3$): 1.33-2.41 (br signals, total 4H), 2.86 (br s, 3H), 3.09-3.42 (br signals, total 4H), 3.52 (br s, 3H), 7.76 (br s, 1H).

LC/MS (ES+): 214 (M+H)$^+$

Step 2: Preparation of 1-methoxy-4-methylamino-piperidine-4-carboxylic acid methyl ester (title compound P5.4)

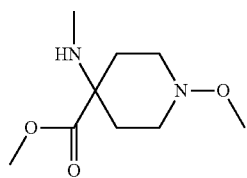

To a suspension of 8-methoxy-1-methyl-1,3,8-triaza-spiro[4.5]decane-2,4-dione (3.36 g, 15.76 mmol) in water (100 ml) was added sodium hydroxide (0.63 g, 15.75 mmol) and the mixture was heated in a microwave apparatus at 190° C. for 30 minutes, at 200° C. for one hour and further at 210° C. for one hour until judged complete by LC-MS analysis. The reaction mixture was acidified to pH 3 (ice cooling) with an aqueous HCl solution, concentrated in vacuo, the solid residue taken up in warm methanol (40° C.), filtered and the filtrate evaporated. The residue was dried over phosphorus pentoxide at 40° C. overnight. Yield: 2.08 g of 1-methoxy-4-methylamino-piperidine-4-carboxylic acid hydrochloride salt.

LC/MS (ES+): 189 (M+H)$^+$ of the free base.

To a suspension of 1-methoxy-4-methylamino-piperidine-4-carboxylic acid hydrochloride salt (2.08 g, 9.26 mmol) in methanol (20 ml) at 0-5° C. was added thionyl chloride (2.41 ml, 3.97 g, 33.40 mmol) and the reaction mixture was heated at reflux for 7 days. After cooling, the mixture was concentrated, the residue diluted with ice water and neutralised with aqueous sodium bicarbonate. The aqueous phase was extracted with ethyl acetate (4×), the combined organic layers washed with brine, dried over sodium sulfate and concentrated. The residue was purified by chromatography on silica gel (gradient ethyl acetate→ethyl acetate/methanol 20:1). Yield: 76 mg of 1-methoxy-4-methylamino-piperidine-4-carboxylic acid methyl ester (title compound P5.4) as an oil.

$^1$H-NMR (CDCl$_3$): 1.46-2.33 (br signals, total 5H), 2.22 (br s, 3H), 2.51-3.31 (br signals, total 4H), 3.51 (s, 3H), 3.72 (br s, 3H).

IR (COOMe): ν 1726 cm$^{-1}$. LC/MS (ES+): 203 (M+H)$^+$

EXAMPLE 7

Preparation of 3-(2-Chloro-4,5-dimethyl-phenyl)-4-hydroxy-8-methoxy-1-methyl-1,8-diaza-spiro[4.5]dec-3-en-2-one (compound P2.26)

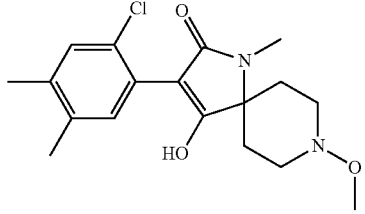

To a solution of 2-(2-chloro-4,5-dimethyl-phenyl)-N-(4-cyano-1-methoxy-piperidin-4-yl)-N-methyl-acetamide (compound P4.27) (1.15 g, 3.29 mmol) in methanol (~3 ml) at 10° C. was added concentrated sulfuric acid (0.876 ml, 16.43 mmol) dropwise and the reaction mixture was stirred at room temperature overnight. After further treatment with concentrated sulfuric acid (0.876 ml, 16.43 mmol) and stirring at 80° C. overnight, additional concentrated sulfuric acid (0.876 ml, 16.43 mmol) was added and stirring continued at 90° C. over another night. The mixture was poured on ice, neutralised carefully with 30% aqueous sodium hydroxide to pH 5-6, the resulting precipitate filtered and dried to afford a first crop of product as a beige solid (225 mg). The mother liquor was concentrated, and the residue purified by chromatography on silica gel (ethyl acetate) to further deliver 462 mg of product as a yellowish solid. Yield: 687 mg of 3-(2-chloro-4,5-dimethyl-phenyl)-4-hydroxy-8-methoxy-1-methyl-1,8-diaza-spiro[4.5]dec-3-en-2-one (title compound P2.26) as a solid, mp 191-192° C.

$^1$H-NMR (CD$_3$Cl$_3$): 1.49-2.57 (br signals, total 4H), 2.20 (s, 3H), 2.21 (s, 3H), 2.79-3.46 (br signals, total 4H), 3.00 (br s, 3H), 3.52 (br s, 3H), 4.40 (br s, 1H), 6.87 (s, 1H), 7.16 (s, 1H).

LC/MS (ES+): 351/353 (M+H)$^+$

EXAMPLE 8

Alternative preparation of 4-Hydroxy-8-methoxy-1-methyl-3-(2,4,6-trimethyl-phenyl)-1,8-diaza-spiro[4.5]dec-3-en-2-one (compound P2.2)

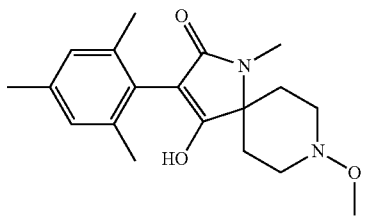

To a solution of 4-hydroxy-8-methoxy-3-(2,4,6-trimethyl-phenyl)-1,8-diaza-spiro[4.5]dec-3-en-2-one [starting material (SM) prepared according to WO09/049,851] (500 mg, 1.58 mmol) in tetrahydrofuran (20 ml) at 0° C. was added a 1.0 M lithium bis(trimethylsilyl)amide solution in hexanes (3.32 ml, 3.32 mmol) dropwise over 15 minutes. The mixture was stirred one hour at 0° C., treated with methyl iodide (0.099 ml, 225 mg, 1.59 mmol) dropwise over 10 minutes, and further stirred at 0° C. for 30 minutes and at room temperature for one hour. The reaction mixture was quenched over cold saturated aqueous ammonium chloride and extracted with tert-butyl methyl ether (3×), the combined organic phases washed with brine, dried over sodium sulfate and concentrated. The residue (210 mg) was suspended in hexane, stirred at room temperature for 10 minutes, filtered and dried. Yield: 171 mg of a clean mixture of starting material (SM) and 4-hydroxy-8-methoxy-1-methyl-3-(2,4,6-trimethyl-phenyl)-1,8-diaza-spiro[4.5]dec-3-en-2-one (title compound P2.2) as a beige solid. $^1$H-NMR and LC-MS analysis of the crude material indicated a ~1:2.5 ratio of this mixture SM/compound P2.2.

$^1$H-NMR (CD$_3$OD, selected signals only): 6.86 (s, 2H, H$_{arom}$ SM), 6.89 (s, 2H, H$_{arom}$ compound P2.2); both signals in a ratio 1:2.6.

LC/MS (ES+): 317 (M+H)$^+$; R$_t$=1.40 min for SM. LC/MS (ES+): 331 (M+H)$^+$; R$_t$=1.46 min for compound P2.2. Both signals in a ratio 1:2.5 considering UV peak areas at 220 nm.

EXAMPLE 9

Preparation of 2,2-Dimethyl-propionic acid 8-methoxy-1-methyl-2-oxo-3-(2,4,6-trimethyl-phenyl)-1,8-diaza-spiro[4.5]dec-3-en-4-yl ester (compound P1.31)

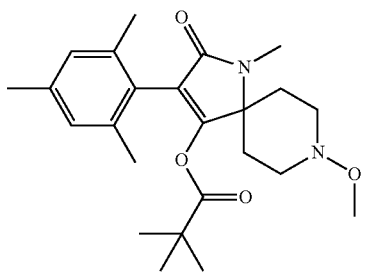

To a solution of 4-hydroxy-8-methoxy-1-methyl-3-(2,4,6-trimethyl-phenyl)-1,8-diaza-spiro[4.5]dec-3-en-2-one (compound P2.2) (350 mg, 1.06 mmol) and triethylamine (0.221 ml, 160.7 mg, 1.59 mmol) in tetrahydrofuran (10 ml) at 0° C. was added pivaloyl chloride (0.143 ml, 140.1 mg, 1.16 mmol) dropwise. The suspension was stirred at 0° C. for two hours. The reaction mixture was diluted with ethyl acetate and water, the layers separated, the aqueous phase extracted with ethyl acetate, the combined organic phases washed with brine, dried over sodium sulfate and concentrated. The residue was purified by chromatography on silica gel (ethyl acetate). Yield: 344 mg of 2,2-dimethyl-propionic acid 8-methoxy-1-methyl-2-oxo-3-(2,4,6-trimethyl-phenyl)-1,8-diaza-spiro[4.5]dec-3-en-4-yl ester (compound P1.31) as a colorless gum.

$^1$H-NMR (CDCl$_3$): 1.02 (br s, 9H), 1.46-2.51 (br signals, total 4H), 2.14 (s, 6H), 2.23 (s, 3H), 2.70-3.46 (br signals, total 4H), 2.95 (br s, 3H), 3.54 (s, 3H), 6.82 (s, 2H).

LC/MS (ES+): 415 (M+H)$^+$

EXAMPLE 10

Preparation of 4-{[2-(2,5-Dimethyl-phenyl)-acetyl]-methyl-amino}-1-methoxy-piperidine-4-carboxylic acid methyl ester (compound P4.46)

Step 1: Preparation of 1-methoxy-4-methylamino-piperidine-4-carboxylic acid (compound P5.7)

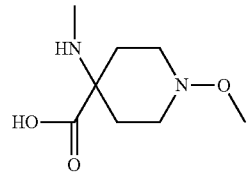

1-Methoxy-4-methylamino-piperidine-4-carbonitrile (compound P5.1) (3.0 g, 17.73 mmol) was added in two portions to concentrated sulfuric acid (30 ml) at 0° C. After stirring for 20 minutes, a yellow solution was obtained which was kept at room temperature overnight. The reaction mixture was carefully diluted with ice water (60 ml), heated at reflux for 4 hours, then poured on ice (50 g) and neutralised with 25% aqueous ammonia under cooling to pH 7-8. The reaction mixture was evaporated and the white solid residue triturated with warm (40° C.) methanol (3×50 ml), filtered and the combined methanol phases concentrated. The residue was treated with toluene (3×50 ml) to remove water azeotropically until constant weight, then triturated with tetrahydrofuran, filtered and dried. Yield: 2.30 g of 1-methoxy-4-methylamino-piperidine-4-carboxylic acid (compound P5.7) as a white solid, mp>250° C.

$^1$H-NMR (D$_2$O): 1.73 (m, 1H), 2.02 (m, 2H), 2.32 (m, 1H), 2.54 (appar. d, 3H), 2.69 (m, 1H), 2.99 (m, 1H), 3.18 (m, 1H), 3.33 (m, 1H), 3.49 (appar. d, 3H). The spectral data are suggesting two major conformers in a 1:1 ratio.

LC/MS (ES+): 189 (M+H)$^+$

Step 2: Preparation of 1-methoxy-4-methylamino-piperidine-4-carboxylic acid methyl ester (compound P5.4)

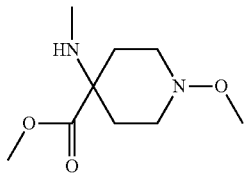

To a suspension of 1-methoxy-4-methylamino-piperidine-4-carboxylic acid (2.0 g, 10.63 mmol) in methanol (50 ml) at 0-10° C. was added thionyl chloride (2.29 ml, 3.76 g, 31.57 mmol) and the reaction mixture was heated at reflux overnight. After cooling, the mixture was concentrated, the residue diluted with ice water (20 ml) and neutralised with aqueous sodium bicarbonate. The aqueous phase was extracted with ethyl acetate (4×25 ml) and dichloromethane (4×50 ml), the combined organic layers washed with aqueous sodium bicarbonate (15 ml) and brine (15 ml), dried over sodium sulfate and concentrated. Yield: 0.76 g of 1-methoxy-4-methylamino-piperidine-4-carboxylic acid methyl ester (compound P5.4) as a viscous, orange oil. The spectral data of this crude material were identical to those described above under preparation example 6, step 2.

LC/MS (ES+): 203 (M+H)$^+$

Step 3: Preparation of 4-{[2-(2,5-dimethyl-phenyl)-acetyl]-methyl-amino}-1-methoxy-piperidine-4-carboxylic acid methyl ester (title compound P4.46)

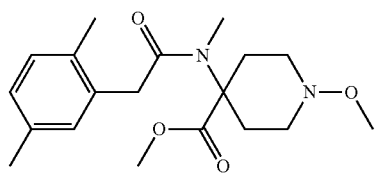 [SMILES: COC(=O)C1(N(C)C(=O)Cc2cc(C)ccc2C)CCN(OC)CC1]

To a solution of 1-methoxy-4-methylamino-piperidine-4-carboxylic acid methyl ester (200 mg, 0.99 mmol) in pyridine (5 ml) was added (2,5-dimethyl-phenyl)-acetyl chloride (240 mg, 1.31 mmol) dropwise at 0° C. The reaction mixture was stirred at 0° C. for one hour and at room temperature for 6 hours, poured on ice water, acidified to pH 7 with an aqueous 2N HCl solution and diluted with ethyl acetate (50 ml). The layers were separated, the aqueous phase extracted with ethyl acetate (3×25 ml), the combined organic phases washed with water (3×15 ml) and brine, dried over sodium sulfate and concentrated. The residue was purified by chromatography on silica gel (cyclohexane/ethyl acetate 2:1). Yield: 170 mg of 4-{[2-(2,5-dimethyl-phenyl)-acetyl]-methyl-amino}-1-methoxy-piperidine-4-carboxylic acid methyl ester (title compound P4.46) as a colorless gum.

$^1$H-NMR (CD$_3$OD): 1.99 (br m, 2H), 2.17 (s, 3H), 2.26 (s, 3H), 2.36 (br m, 2H), 2.79 (br m, 1H), 2.93 (br m, 1H), 3.06 (appar. d, 3H), 3.21 (br m, 2H), 3.50 (s, 3H), 3.67 (s, 3H), 3.68 (br s, 2H), 6.91 (br s, 1H), 6.95 (d, 1H), 7.04 (d, 1H).

LC/MS (ES+): 349 (M+H)$^+$

Compounds of the formula I from Table P1, compounds of the formula II from Table P2 and intermediates listed in Tables P3, P4 and P5 can be prepared by analogous procedures. Either one of the following LC-MS methods was used to characterize the compounds:

Method A

MS: ZQ Mass Spectrometer from Waters (Single quadrupole mass spectrometer); Ionisation method: Electrospray; Polarity: positive/negative ions; Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400; Mass range: 150 to 1000 or 100 to 900 Da.

LC: HP 1100 HPLC from Agilent: solvent degasser, quaternary pump (ZCQ)/binary pump (ZDQ), heated column compartment and diode-array detector. Column: Phenomenex Gemini C18, 3 µm particle size, 110 Angström, 30×3 mm, Temp: 60° C.; DAD Wavelength range (nm): 200 to 500; Solvent gradient: A=water+0.05% v/v HCOOH, B=Acetonitril/Methanol (4:1, v/v)+0.04% v/v HCOOH.

| Time (min) | A % | B % | Flow (ml/min) |
| --- | --- | --- | --- |
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method B

MS: ZMD Mass Spectrometer from Waters (Single quadrupole mass spectrometer); Ionisation method: Electrospray; Polarity: positive/negative ions; Capillary (kV) 3.80, Cone (V) 30.00, Extractor (V) 3.00, Source Temperature (° C.) 150, Desolvation Temperature (° C.) 350, Cone Gas Flow (L/Hr) OFF, Desolvation Gas Flow (L/Hr) 600; Mass range: 150 to 1000 (100 to 1500 for LowMass) or 100 to 900 Da.

LC: HP 1100 HPLC from Agilent: solvent degasser, binary pump, heated column compartment and diode-array detector. Column: Phenomenex Gemini C18, 3 µm particle size, 110 Angstöm, 30×3 mm, Temp: 60° C.; DAD Wavelength range (nm): 200 to 500; Solvent gradient: A=water+0.05% v/v HCOOH, B=Acetonitril/Methanol (4:1, v:v)+0.04% v/v HCOOH.

| Time (min) | A % | B % | Flow (ml/min) |
| --- | --- | --- | --- |
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

The characteristic values obtained for each compound were the retention time ("R$_t$", recorded in minutes) and the molecular ion as listed in Table P1, Table P2, Table P3, Table P4 and in Table P5.

TABLE P1

Physical data of compounds of formula I:

| Compound No. | Structures | Melting Point | MS/NMR |
|---|---|---|---|
| P1.1 | 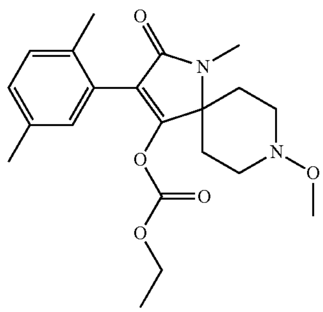 [SMILES: CCOC(=O)OC1=C(c2cc(C)ccc2C)C(=O)N(C)C12CCN(OC)CC2] | 96-110° C. | LC/MS: 389 (M + H)+<br>$R_t$ = 1.82 min |
| P1.2 | EXAMPLE 1, step 2 | 134-136° C. | LC/MS: 403 (M + H)+<br>$R_t$ = 1.81 min |
| P1.3 | 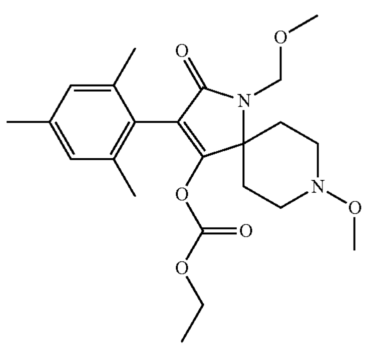 | gum | $^1$H-NMR (CD$_3$OD, selected signals only):<br>1.03 (t, 3H, OCH$_2$CH$_3$), 2.14 (s, 6H, mesityl CH$_3$), 2.26 (s, 3H, mesityl CH$_3$), 3.34 (br s, 3H, CH$_2$OCH$_3$), 3.55 (s, 3H, NOCH$_3$), 4.01 (q, 2H, OCH$_2$CH$_3$), 6.89 (s, 2H, H$_{arom}$). |
| P1.4 | 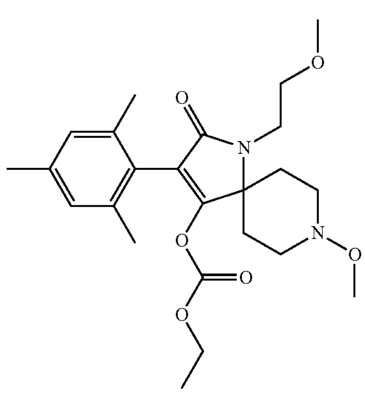 | solid | LC/MS: 447 (M + H)+<br>$R_t$ = 1.94 min |

TABLE P1-continued

Physical data of compounds of formula I:

| Compound No. | Structures | Melting Point | MS/NMR |
|---|---|---|---|
| P1.5 | 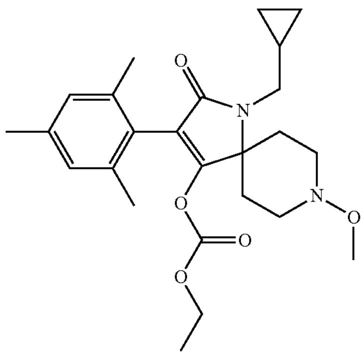 | gum | ¹H-NMR (CD₃OD): 0.38 (m, 2H), 0.55 (m, 2H), 1.02 (t, 3H), 1.15 (m, 1H), 1.54 (br m, 1H), 1.88 (br m, 1H), 2.13 (s, 6H), 2.25 (s, 3H), 2.48 (br m, 1H), 2.66 (br m, 1H), 2.83 (br m, 1H), 3.18 (br m, 1H), 3.30 (br m, 2H), 3.41 (br m, 2H), 3.55 (s, 3H), 4.00 (q, 2H), 6.87 (s, 2H). LC/MS (ES+): 443 (M + H)⁺; R$_t$ = 2.06 min |
| P1.6 | 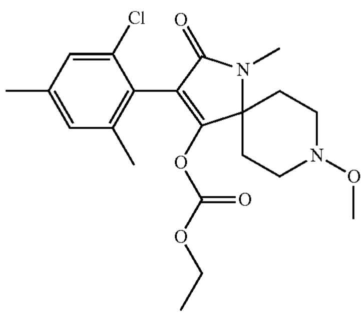 | 164-167° C. | LC/MS: 423/425 (M + H)⁺ R$_t$ = 1.82 min |
| P1.7 | 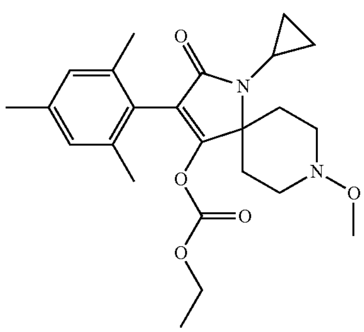 | gum | LC/MS: 429 (M + H)⁺ R$_t$ = 1.93 min |
| P1.8 | 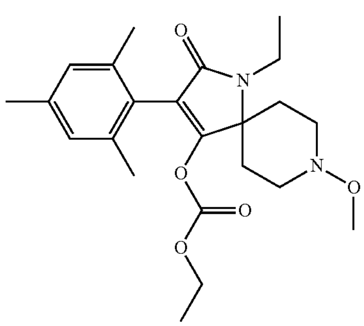 | 101-103° C. | LC/MS: 417 (M + H)⁺ R$_t$ = 1.91 min |

TABLE P1-continued

Physical data of compounds of formula I:

| Compound No. | Structures | Melting Point | MS/NMR |
|---|---|---|---|
| P1.9 | 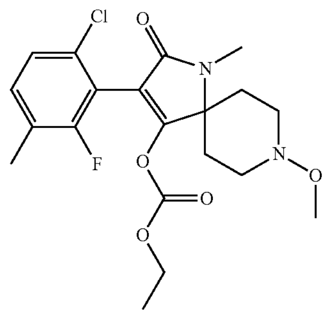 | solid | LC/MS: 427/429 (M + H)⁺<br>$R_t$ = 1.75 min |
| P1.10 | 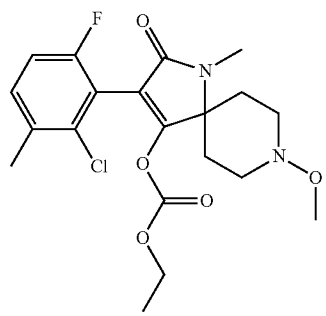 [SMILES: CCOC(=O)OC1=C(c2c(F)ccc(C)c2Cl)C(=O)N(C)C12CCN(OC)CC2] | 47-50° C. | LC/MS: 427/429 (M + H)⁺<br>$R_t$ = 1.73 min |
| P1.11 | 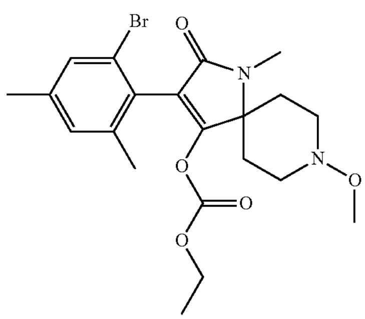 | 163-167° C. | LC/MS: 467/469 (M + H)⁺<br>$R_t$ = 1.83 min |
| P1.12 | 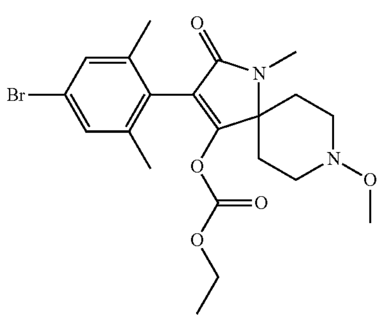 | 126-127° C. | LC/MS: 467/469 (M + H)⁺<br>$R_t$ = 1.89 min |

TABLE P1-continued

Physical data of compounds of formula I:

| Compound No. | Structures | Melting Point | MS/NMR |
|---|---|---|---|
| P1.13 | 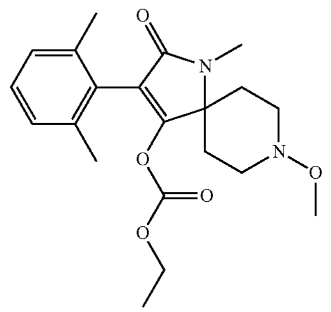 [SMILES: CCOC(=O)OC1=C(c2c(C)cccc2C)C(=O)N(C)C12CCN(OC)CC2] | 106-109° C. | LC/MS: 389 (M + H)⁺ R_t = 1.74 min |
| P1.14 | 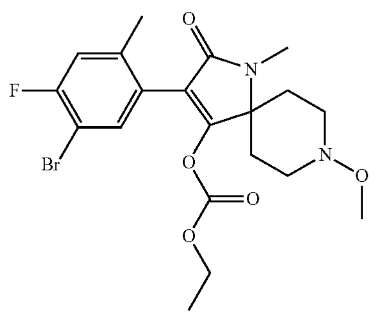 [SMILES: CCOC(=O)OC1=C(c2cc(Br)c(F)cc2C)C(=O)N(C)C12CCN(OC)CC2] | gum | LC/MS: 471/473 (M + H)⁺ R_t = 1.81 min |
| P1.15 | 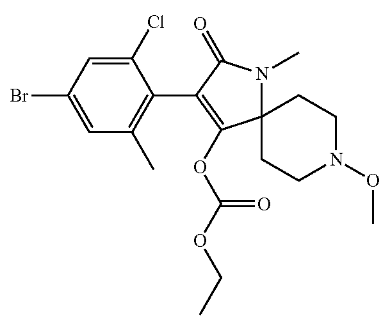 | 87-89° C. | LC/MS: 473/475/477 (M + H)⁺ R_t = 1.80 min |
| P1.16 | 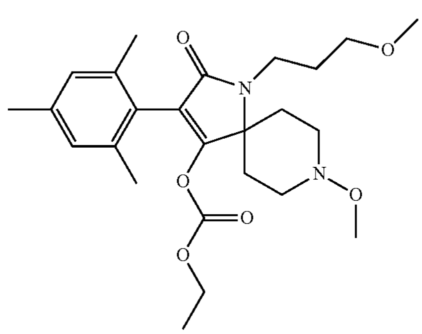 | gum | LC/MS: 461 (M + H)⁺ R_t = 1.91 min |

TABLE P1-continued

Physical data of compounds of formula I:

| Compound No. | Structures | Melting Point | MS/NMR |
|---|---|---|---|
| P1.17 | 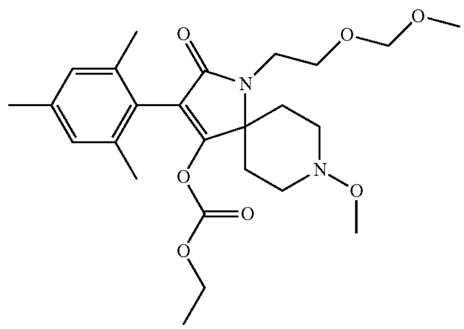 | gum | LC/MS: 477 (M + H)$^+$<br>R$_t$ = 1.89 min |
| P1.18 | 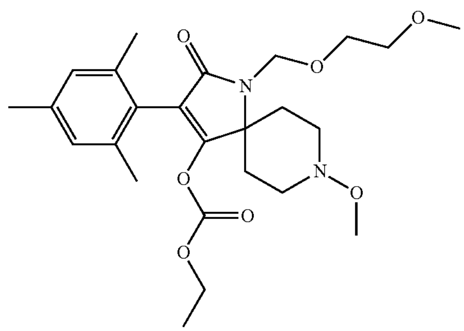 | gum | LC/MS: 477 (M + H)$^+$<br>R$_t$ = 1.91 min |
| P1.19 | 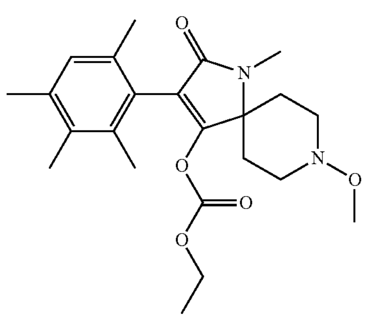 | solid | LC/MS: 417 (M + H)$^+$<br>R$_t$ = 1.86 min |
| P1.20 | 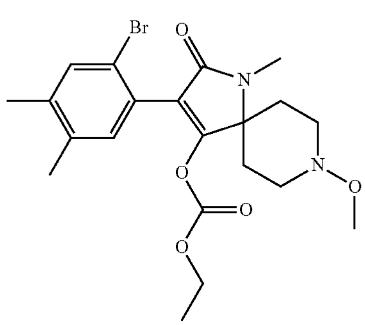 | 158-159° C. | $^1$H-NMR (CDCl$_3$, selected signals only):<br>1.16 (t, 3H, OCH$_2$CH$_3$), 2.20 (s, 3H, phenyl CH$_3$), 2.22 (s, 3H, phenyl CH$_3$), 2.94 (br s, 3H, N—CH$_3$; overlapping signal with piperidinyl Hs), 3.56 (s, 3H, NOCH$_3$), 4.09 (q, 2H, OCH$_2$CH$_3$), 7.07 (s, 1H, H$_{arom}$), 7.35 (s, 1H, H$_{arom}$). |

TABLE P1-continued

Physical data of compounds of formula I:

| Compound No. | Structures | Melting Point | MS/NMR |
|---|---|---|---|
| P1.21 | 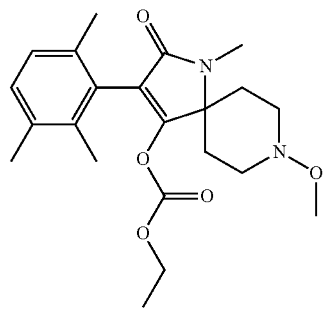 [SMILES: CCOC(=O)OC1=C(c2c(C)ccc(C)c2C)C(=O)N(C)C12CCN(OC)CC2] | gum | LC/MS: 403 (M + H)$^+$ $R_t$ = 1.81 min |
| P1.22 | 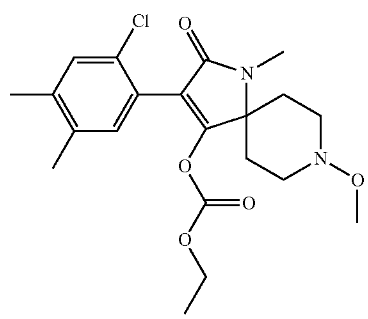 | 149-150° C. | LC/MS: 423/425 (M + H)$^+$ $R_t$ = 1.91 min |
| P1.23 | 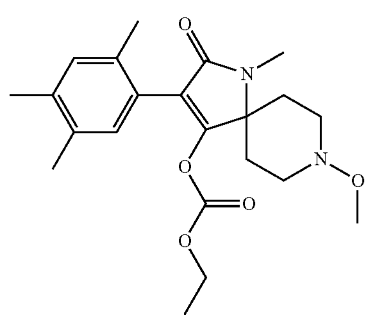 | gum | LC/MS: 403 (M + H)$^+$ $R_t$ = 1.83 min |
| P1.24 | 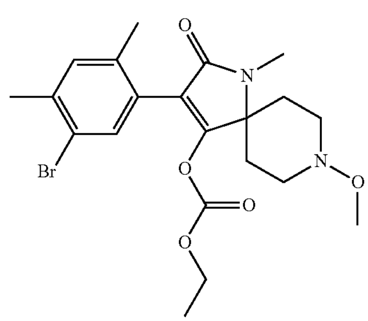 | solid | LC/MS: 467/469 (M + H)$^+$ $R_t$ = 1.88 min |

TABLE P1-continued

Physical data of compounds of formula I:

| Compound No. | Structures | Melting Point | MS/NMR |
|---|---|---|---|
| P1.25 | 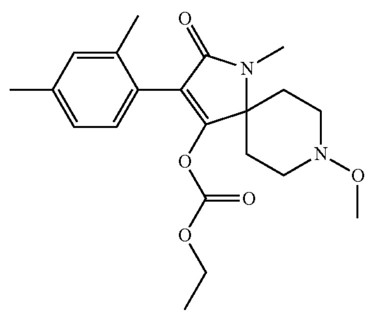 | solid | LC/MS: 389 (M + H)+<br>R$_t$ = 1.77 min |
| P1.26 | 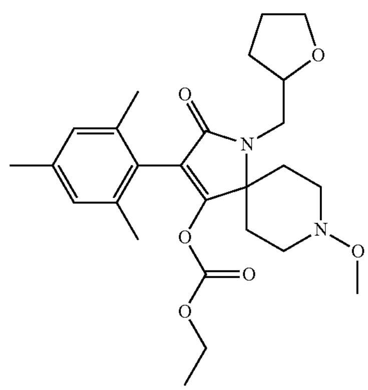 | gum | LC/MS: 473 (M + H)+<br>R$_t$ = 1.96 min |
| P1.27 | 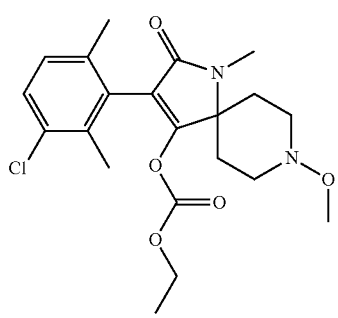 [SMILES: CCOC(=O)OC1=C(c2c(C)ccc(Cl)c2C)C(=O)N(C)C12CCN(OC)CC2] | gum | LC/MS: 423/425 (M + H)+<br>R$_t$ = 1.84 min |
| P1.28 | 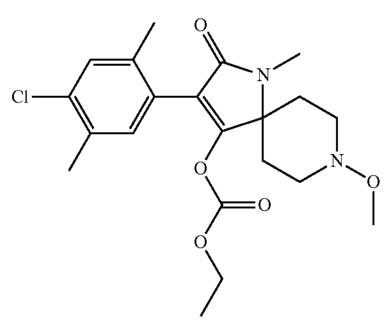 [SMILES: CCOC(=O)OC1=C(c2cc(C)c(Cl)cc2C)C(=O)N(C)C12CCN(OC)CC2] | gum | LC/MS: 423/425 (M + H)+<br>R$_t$ = 1.86 min |

TABLE P1-continued

Physical data of compounds of formula I:

| Compound No. | Structures | Melting Point | MS/NMR |
|---|---|---|---|
| P1.29 | 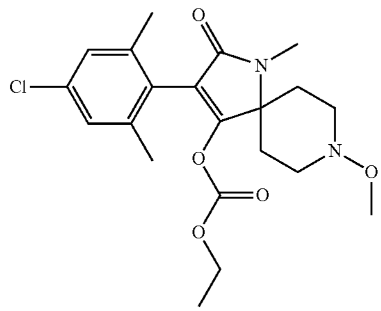 [SMILES: CCOC(=O)OC1=C(c2c(C)cc(Cl)cc2C)C(=O)N(C)C12CCN(OC)CC2] | 130-132° C. | LC/MS: 423/425 $(M + H)^+$<br>$R_t$ = 1.86 min |
| P1.30 | 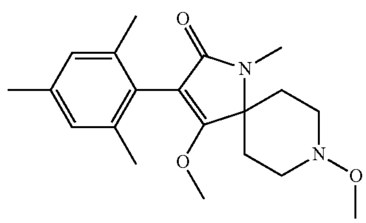 | | LC/MS: 345 $(M + H)^+$<br>$R_t$ = 1.77 min |
| P1.31<br>EXAMPLE 9 | | gum | LC/MS: 415 $(M + H)^+$<br>$R_t$ = 2.00 min |

TABLE P2

Physical data of compounds of formula II:

| Compound No. | Structures | Melting Point | MS/NMR |
|---|---|---|---|
| P2.1 | 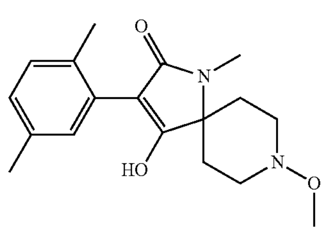 [SMILES: CON1CCC2(CC1)C(O)=C(c1cc(C)ccc1C)C(=O)N2C] | 121-123° C. | LC/MS: 317 $(M + H)^+$<br>$R_t$ = 1.49 min |

TABLE P2-continued

Physical data of compounds of formula II:

| Compound No. | Structures | Melting Point | MS/NMR |
|---|---|---|---|
| P2.2 | (structure) EXAMPLE 1, step 1; EXAMPLE 2, step 3; EXAMPLE 4, step 4 | 241-243° C. | LC/MS: 331 (M + H)$^+$ R$_t$ = 1.44 min |
| P2.3 | (structure) | solid | $^1$H-NMR (400 MHz, CDCl$_3$): 1.75 (m, 2H), 2.31 (m, 2H), 2.48 (m, 2H), 3.47 (m, 2H), 3.58 (s, 3H), 3.93 (m, 2H), 5.90 (m, 1H), 6.30 (br s, 1H), 7.25-7.32 (m, 2H), 7.40 (m, 1H). |
| P2.4 | (structure) | solid | $^1$H-NMR (400 MHz, CDCl$_3$, selected signals only): 3.57 (s, 3H, NOCH$_3$), 5.85 (m, 1H, CHF$_2$), 6.52 (br s, 1H), 7.27-7.35 (m, 2H, H$_{arom}$), 7.49 (d, 1H, H$_{arom}$). |
| P2.5 | (structure) | solid | $^1$H-NMR (400 MHz, CDCl$_3$, selected signals only): 2.18 (s, 3H, phenyl CH$_3$), 2.31 (s, 3H, phenyl CH$_3$), 3.39 (s, 3H, NOCH$_3$), 5.78 (m, 1H, CHF$_2$), 6.19 (br s, 1H), 7.00 (s, 1H, H$_{arom}$), 7.08 (d, 1H, H$_{arom}$), 7.12 (d, 1H, H$_{arom}$). |
| P2.6 | (structure) | 205-207° C. | LC/MS: 361 (M + H)$^+$ R$_t$ = 1.47 min |

TABLE P2-continued

Physical data of compounds of formula II:

| Compound No. | Structures | Melting Point | MS/NMR |
|---|---|---|---|
| P2.7 | 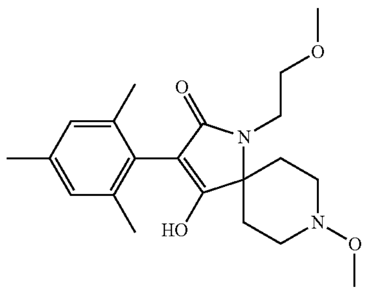 | solid | LC/MS: 375 (M + H)$^+$<br>R$_t$ = 1.58 min |
| P2.8<br>EXAMPLE 3, step 2 | | 223-225° C. | LC/MS: 371 (M + H)$^+$<br>R$_t$ = 1.76 min |
| P2.9 | 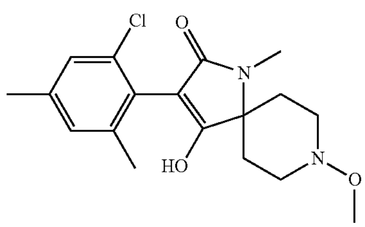 | >240° C. | LC/MS: 351/353 (M + H)$^+$<br>R$_t$ = 1.48 min |
| P2.10 | 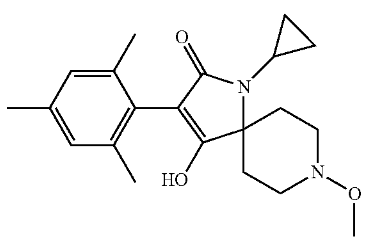 | 208-211° C. | LC/MS: 357 (M + H)$^+$<br>R$_t$ = 1.61 min |
| P2.11 | 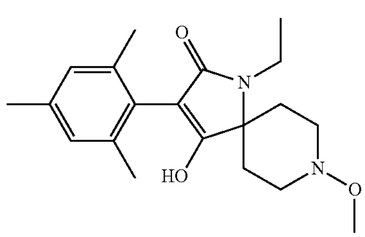 | 218-221° C. | LC/MS: 345 (M + H)$^+$<br>R$_t$ = 1.58 min |
| P2.12 | 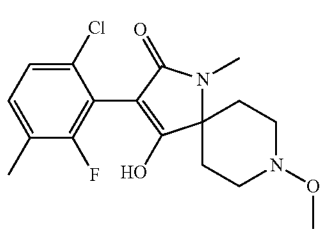 [SMILES: CON1CCC2(CC1)C(O)=C(c1c(Cl)ccc(C)c1F)C(=O)N2C] | solid | LC/MS: 355/357 (M + H)$^+$<br>R$_t$ = 1.52 min |

TABLE P2-continued
Physical data of compounds of formula II:
| Compound No. | Structures | Melting Point | MS/NMR |
|---|---|---|---|
| P2.13 | 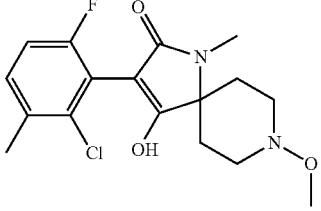 | 54-57° C. | LC/MS: 355/357 (M + H)+<br>R$_t$ = 1.49 min |
| P2.14 | 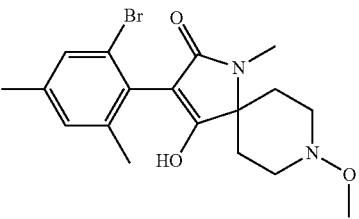 | solid | LC/MS: 395/397 (M + H)+<br>R$_t$ = 1.48 min |
| P2.15 | 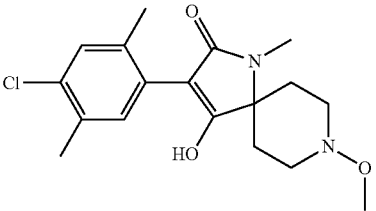 [SMILES: CON1CCC2(CC1)C(O)=C(c1cc(C)c(Cl)cc1C)C(=O)N2C] | 191-195° C. | LC/MS: 351/353 (M + H)+<br>R$_t$ = 1.58 min |
| P2.16 | 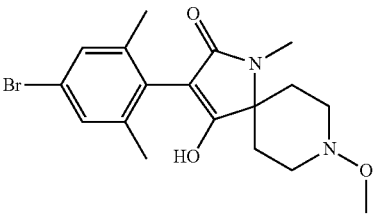 | 234-235° C. | LC/MS: 395/397 (M + H)+<br>R$_t$ = 1.54 min |
| P2.17 | 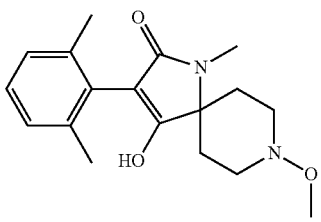 [SMILES: CON1CCC2(CC1)C(O)=C(c1c(C)cccc1C)C(=O)N2C] | 202-204° C. | LC/MS: 317 (M + H)+<br>R$_t$ = 1.36 min |
| P2.18 | 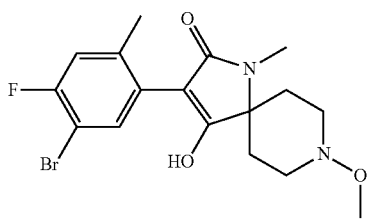 [SMILES: CON1CCC2(CC1)C(O)=C(c1cc(Br)c(F)cc1C)C(=O)N2C] | gum | LC/MS: 399/401 (M + H)+<br>R$_t$ = 1.54 min |

TABLE P2-continued

Physical data of compounds of formula II:

| Compound No. | Structures | Melting Point | MS/NMR |
|---|---|---|---|
| P2.19 | 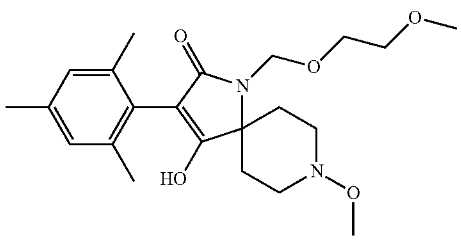 | 80-82° C. | $^1$H-NMR (CD$_3$OD, selected signals only): 2.12 (s, 6H, mesityl CH$_3$), 2.27 (s, 3H, mesityl CH$_3$), 3.37 (s, 3H, CH$_2$CH$_2$OCH$_3$), 3.47 (t, 2H, CH$_2$CH$_2$OMe), 3.55 (s, 3H, NOCH$_3$), 3.65 (t, 2H, CH$_2$CH$_2$OMe), 6.91 (s, 2H, H$_{arom}$). |
| P2.20 | 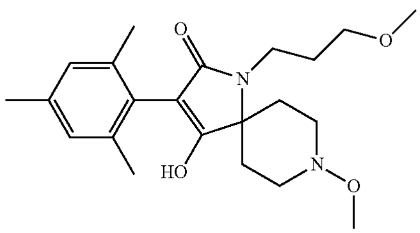 | 79-81° C. | LC/MS: 389 (M + H)$^+$ R$_t$ = 1.62 min |
| P2.21 | 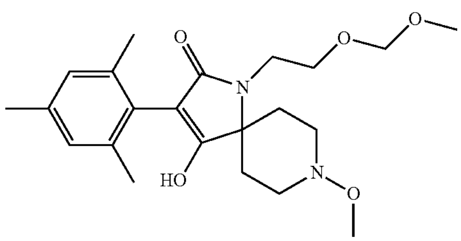 | 181-183° C. | LC/MS: 405 (M + H)$^+$ R$_t$ = 1.60 min |
| P2.22 | 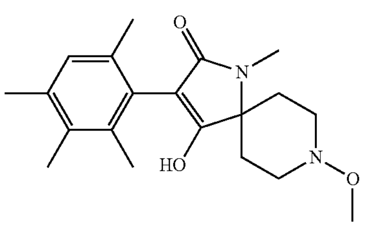 | solid | LC/MS: 345 (M + H)$^+$ R$_t$ = 1.55 min |
| P2.23 | 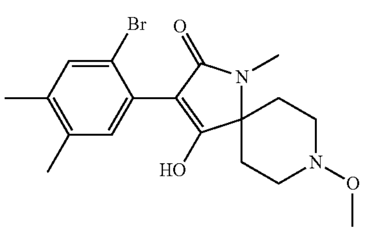 | 191-193° C. | LC/MS: 395/397 (M + H)$^+$ R$_t$ = 1.59 min |
| P2.24 | 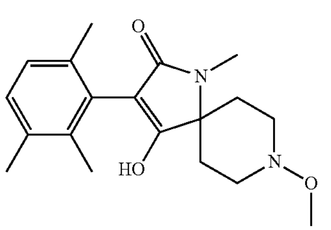 [SMILES: CON1CCC2(CC1)C(O)=C(c1c(C)ccc(C)c1C)C(=O)N2C] | 192-194° C. | LC/MS: 331 (M + H)$^+$ R$_t$ = 1.41 min |

TABLE P2-continued

Physical data of compounds of formula II:

| Compound No. | Structures | Melting Point | MS/NMR |
|---|---|---|---|
| P2.25 | 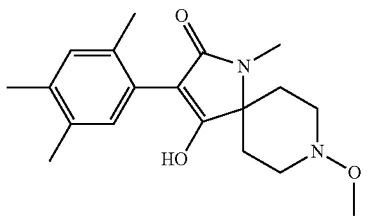 | 183-186° C. | LC/MS: 331 (M + H)+<br>R$_t$ = 1.56 min |
| P2.26 | EXAMPLE 7 | 191-192° C. | LC/MS: 351/353 (M + H)+<br>R$_t$ = 1.60 min |
| P2.27 | 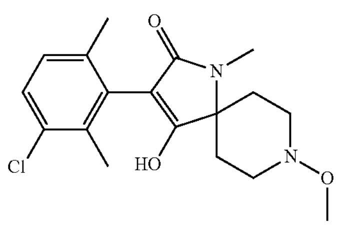 [SMILES: CON1CCC2(CC1)C(O)=C(c1c(C)ccc(Cl)c1C)C(=O)N2C] | 138-142° C. | LC/MS: 351/353 (M + H)+<br>R$_t$ = 1.49 min |
| P2.28 | 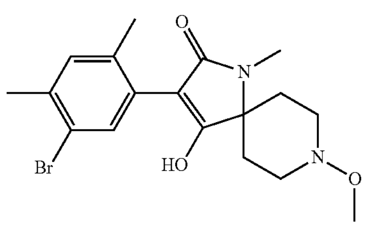 | 182-183° C. | LC/MS: 395/397 (M + H)+<br>R$_t$ = 1.62 min |
| P2.29 | 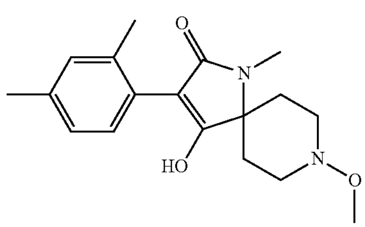 | solid | LC/MS: 317 (M + H)+<br>R$_t$ = 1.47 min |
| P2.30 | 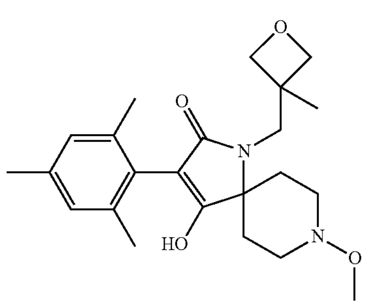 | 180-182° C. | LC/MS: 401 (M + H)+<br>R$_t$ = 1.50 min |

TABLE P2-continued

Physical data of compounds of formula II:

| Compound No. | Structures | Melting Point | MS/NMR |
|---|---|---|---|
| P2.31 | 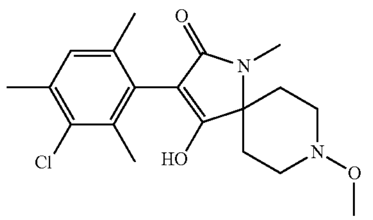 | gum | LC/MS: 365/367 (M + H)$^+$<br>$R_t$ = 1.59 min |
| P2.32 | 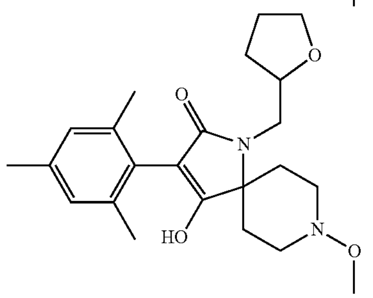 | 211-213° C. | LC/MS: 401 (M + H)$^+$<br>$R_t$ = 1.60 min |
| P2.33 | 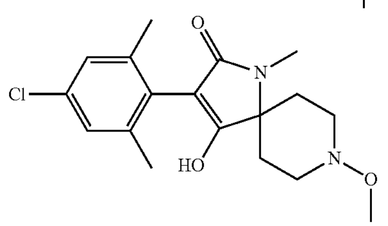 | solid | LC/MS: 351/353 (M + H)$^+$<br>$R_t$ = 1.50 min |
| P2.34 | 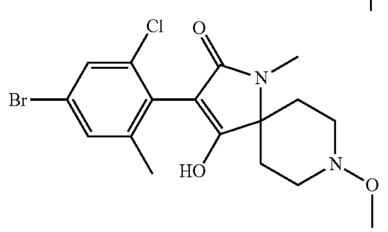 | >200° C. | LC/MS:<br>415/417/419 (M + H)$^+$<br>$R_t$ = 1.54 min |

Intermediates of the formula XIII or XIV from Table P3 can be prepared by analogous procedures.

TABLE P3

Physical data of intermediates of formula XIII or XIV:

| Compound No. | Structures | Melting Point | MS/NMR |
|---|---|---|---|
| P3.1 | 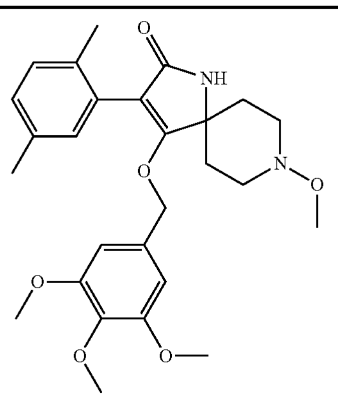 | 128-131° C. | Described in WO09/049851 |

TABLE P3-continued
Physical data of intermediates of formula XIII or XIV:
| Compound No. | Structures | Melting Point | MS/NMR |
|---|---|---|---|
| P3.2 | 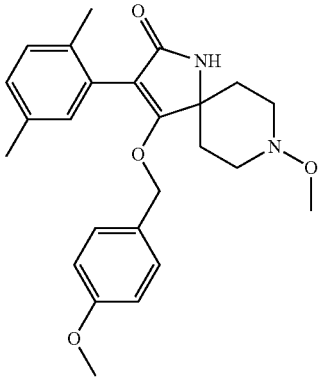 [SMILES: COc1ccc(COC2=C(c3cc(C)ccc3C)C(=O)NC23CCN(OC)CC3)cc1] | 180-183° C. | Described in WO09/049851 |
| P3.3 | 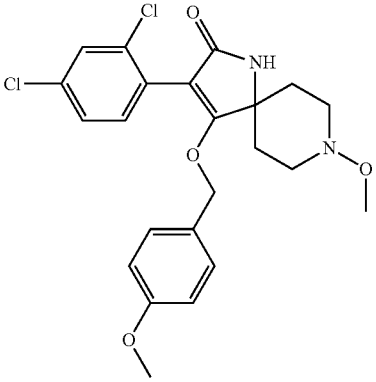 [SMILES: COc1ccc(COC2=C(c3ccc(Cl)cc3Cl)C(=O)NC23CCN(OC)CC3)cc1] | 111-113° C. | Described in WO09/049851 |
| P3.4 | 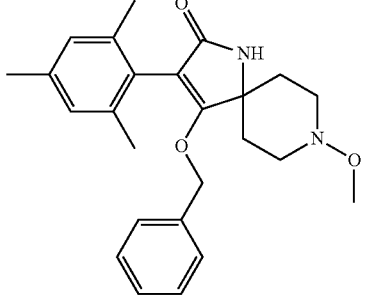<br>EXAMPLE 2, step 1 | 184-186° C. | LC/MS: 407 (M + H)$^+$<br>$R_t$ = 2.02 min |
| P3.5 | 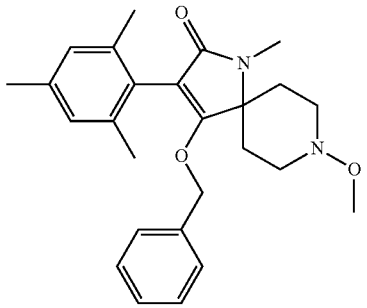<br>EXAMPLE 2, step 2 | 139-141° C. | LC/MS: 421 (M + H)$^+$<br>$R_t$ = 2.04 min |

TABLE P3-continued

Physical data of intermediates of formula XIII or XIV:

| Compound No. | Structures | Melting Point | MS/NMR |
|---|---|---|---|
| P3.6 | 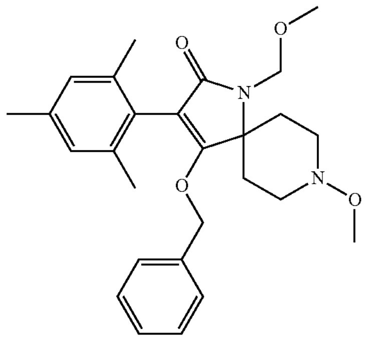 | solid | LC/MS: 451 (M + H)$^+$<br>R$_t$ = 2.08 min |
| P3.7 | 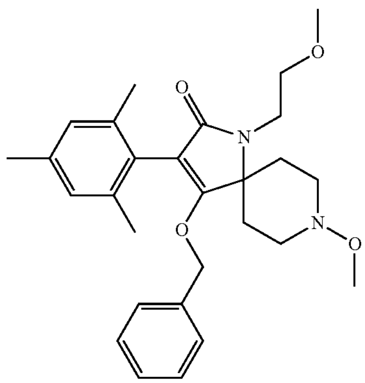 | solid | LC/MS: 465 (M + H)$^+$<br>R$_t$ = 2.05 min |
| P3.8 | <br>EXAMPLE 3, step 1 | 119-121° C. | LC/MS: 461 (M + H)$^+$<br>R$_t$ = 2.19 min |
| P3.9 | 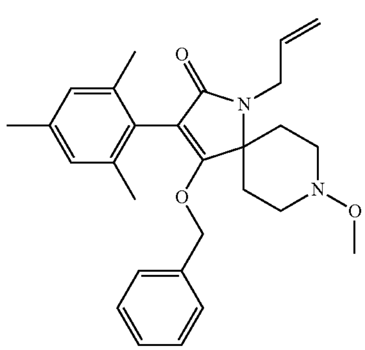 | 134-136° C. | LC/MS: 447 (M + H)$^+$<br>R$_t$ = 2.14 min |

TABLE P3-continued

Physical data of intermediates of formula XIII or XIV:

| Compound No. | Structures | Melting Point | MS/NMR |
|---|---|---|---|
| P3.10 | 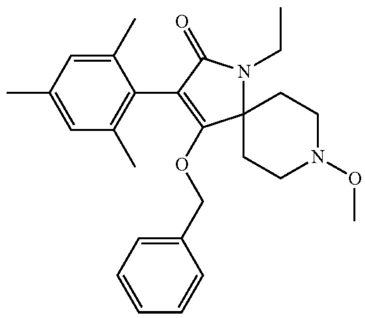 | solid | LC/MS: 435 (M + H)$^+$<br>R$_t$ = 2.07 min |
| P3.11 | 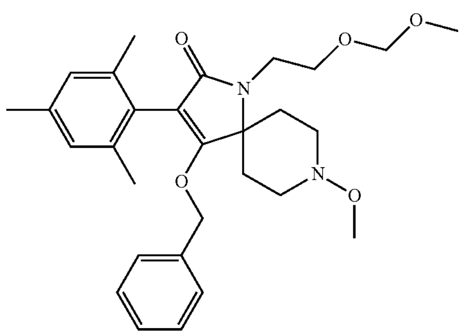 | 90-92° C. | LC/MS: 495 (M + H)$^+$<br>R$_t$ = 2.06 min |
| P3.12 | 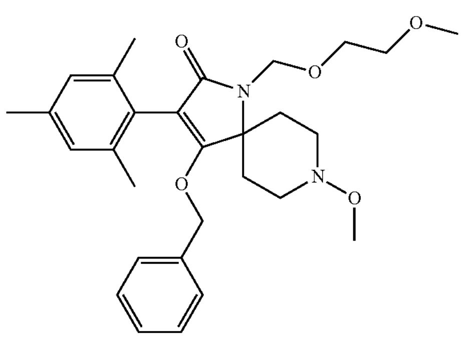 | 68-70° C. | LC/MS: 495 (M + H)$^+$<br>R$_t$ = 2.05 min |
| P3.13 | 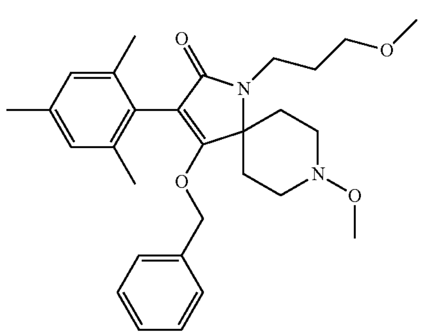 | solid | LC/MS: 479 (M + H)$^+$<br>R$_t$ = 2.07 min |

TABLE P3-continued

Physical data of intermediates of formula XIII or XIV:

| Compound No. | Structures | Melting Point | MS/NMR |
|---|---|---|---|
| P3.14 | 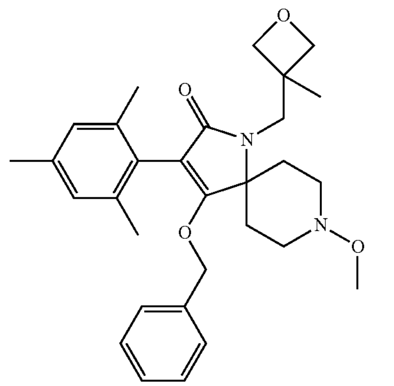 | | LC/MS: 491 (M + H)+<br>R$_t$ = 2.04 min |

Intermediates of the formula IV or XI from Table P4 can be prepared by analogous procedures.

TABLE P4

Physical data of intermediates of formula IV or XI:

| Compound No. | Structures | Melting Point | MS/NMR |
|---|---|---|---|
| P4.1 | EXAMPLE 4, step 2 | 175-177° C. | LC/MS: 330 (M + H)+<br>R$_t$ = 1.78 min |
| P4.2 | EXAMPLE 4, step 3 | 133-135° C. | LC/MS: 363 (M + H)+<br>R$_t$ = 1.79 min |
| P4.3 | 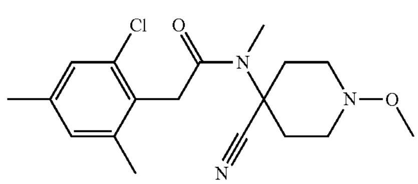 | | LC/MS: 350/352 (M + H)+<br>R$_t$ = 1.78 min |
| P4.4 | 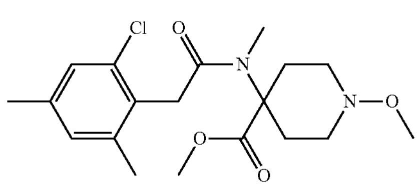 | | LC/MS: 383/385 (M + H)+<br>R$_t$ = 1.79 min |

TABLE P4-continued

Physical data of intermediates of formula IV or XI:

| Compound No. | Structures | Melting Point | MS/NMR |
|---|---|---|---|
| P4.5 | 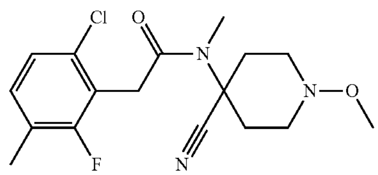 [SMILES: CON1CCC(C#N)(N(C)C(=O)Cc2c(Cl)ccc(C)c2F)CC1] | | LC/MS: 354/356 (M + H)+<br>$R_t$ = 1.71 min |
| P4.6 | 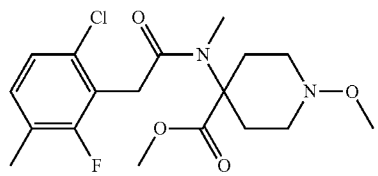 [SMILES: COC(=O)C1(N(C)C(=O)Cc2c(Cl)ccc(C)c2F)CCN(OC)CC1] | | LC/MS: 387/389 (M + H)+<br>$R_t$ = 1.73 min |
| P4.7 | 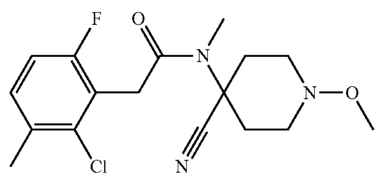 | | LC/MS: 354/356 (M + H)+<br>$R_t$ = 1.70 min |
| P4.8 | 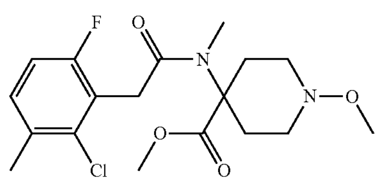 | | LC/MS: 387/389 (M + H)+<br>$R_t$ = 1.71 min |
| P4.9 | 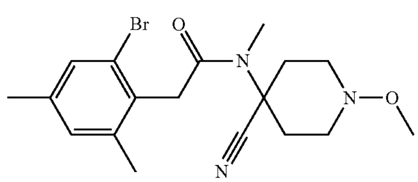 | | LC/MS: 394/396 (M + H)+<br>$R_t$ = 1.78 min |
| P4.10 | 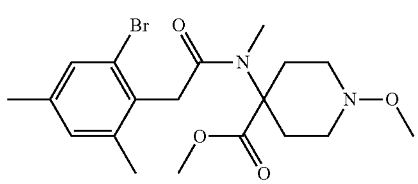 | | LC/MS: 427/429 (M + H)+<br>$R_t$ = 1.81 min |
| P4.11 | 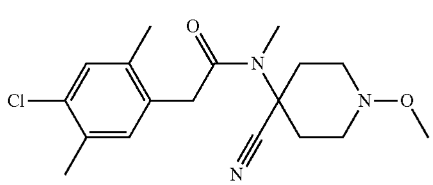 [SMILES: CON1CCC(C#N)(N(C)C(=O)Cc2cc(C)c(Cl)cc2C)CC1] | | LC/MS: 350/352 (M + H)+<br>$R_t$ = 1.78 min |
| P4.12 | 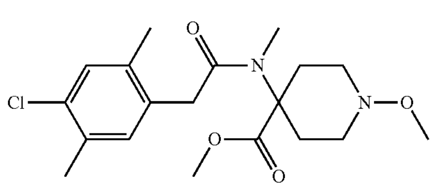 [SMILES: COC(=O)C1(N(C)C(=O)Cc2cc(C)c(Cl)cc2C)CCN(OC)CC1] | | LC/MS: 383/385 (M + H)+<br>$R_t$ = 1.78 min |

TABLE P4-continued

Physical data of intermediates of formula IV or XI:

| Compound No. | Structures | Melting Point | MS/NMR |
|---|---|---|---|
| P4.13 | 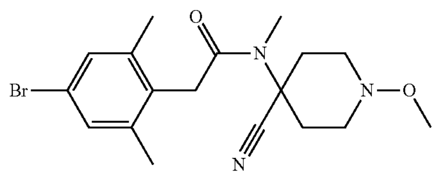 | solid | LC/MS: 394/396 (M + H)$^+$<br>R$_t$ = 1.78 min |
| P4.14 | 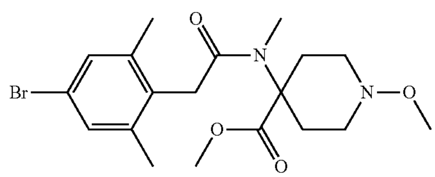 [SMILES: COC(=O)C1(N(C)C(=O)Cc2c(C)cc(Br)cc2C)CCN(OC)CC1] | solid | LC/MS: 427/429 (M + H)$^+$<br>R$_t$ = 1.80 min |
| P4.15 | 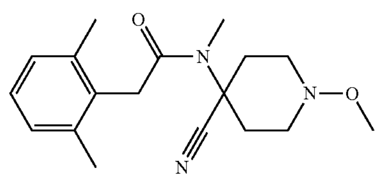 [SMILES: CON1CCC(C#N)(N(C)C(=O)Cc2c(C)cccc2C)CC1] | 171-174° C. | LC/MS: 316 (M + H)$^+$<br>R$_t$ = 1.64 min |
| P4.16 | 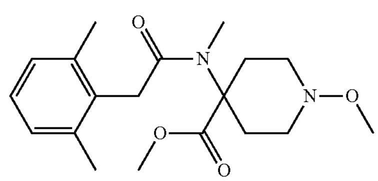 [SMILES: COC(=O)C1(N(C)C(=O)Cc2c(C)cccc2C)CCN(OC)CC1] | 139-141° C. | LC/MS: 349 (M + H)$^+$<br>R$_t$ = 1.64 min |
| P4.17 | 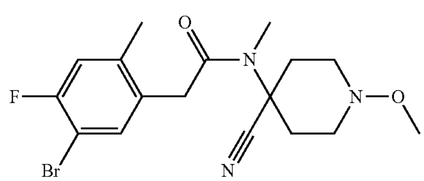 [SMILES: CON1CCC(C#N)(N(C)C(=O)Cc2cc(Br)c(F)cc2C)CC1] | gum | LC/MS: 398/400 (M + H)$^+$<br>R$_t$ = 1.71 min |
| P4.18 | 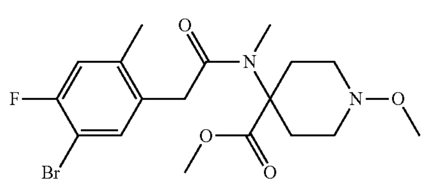 [SMILES: COC(=O)C1(N(C)C(=O)Cc2cc(Br)c(F)cc2C)CCN(OC)CC1] | solid | LC/MS: 431/433 (M + H)$^+$<br>R$_t$ = 1.75 min |
| P4.19 | 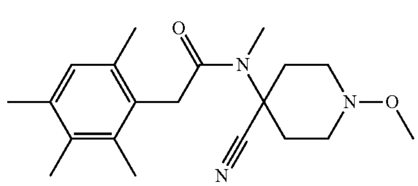 | | $^1$H-NMR (CDCl$_3$, selected signals only):<br>3.15 (s, 3H, N—CH$_3$), 3.50 (br s, 3H, NOCH$_3$), 3.75 (s, 2H, PhCH$_2$CO), 6.89 (s, 1H, H$_{arom}$). |
| P4.20 | 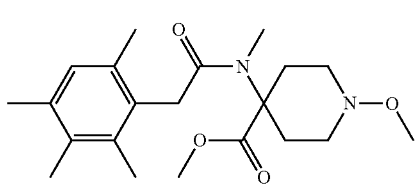 | | LC/MS: 377 (M + H)$^+$<br>R$_t$ = 1.81 min |

TABLE P4-continued

Physical data of intermediates of formula IV or XI:

| Compound No. | Structures | Melting Point | MS/NMR |
|---|---|---|---|
| P4.21 | 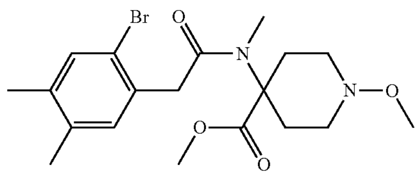 | gum | LC/MS: 427/429 (M + H)+<br>$R_t$ = 1.82 min |
| P4.22 | 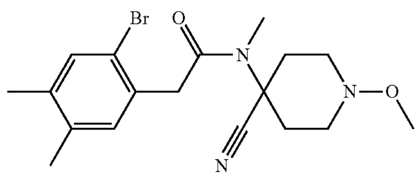 | 123-126° C. | LC/MS: 394/396 (M + H)+<br>$R_t$ = 1.82 min |
| P4.23 | 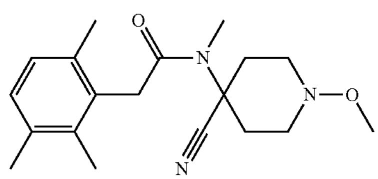 [SMILES: CON1CCC(C#N)(N(C)C(=O)Cc2c(C)ccc(C)c2C)CC1] | | $^1$H-NMR (CDCl$_3$, selected signals only):<br>2.13 (s, 3H, phenyl CH$_3$),<br>2.22 (s, 3H, phenyl CH$_3$),<br>2.25 (s, 3H, phenyl CH$_3$),<br>3.14 (s, 3H, N—CH$_3$), 3.51 (br s, 3H, NOCH$_3$), 3.73 (s, 2H, PhCH$_2$CO). |
| P4.24 | 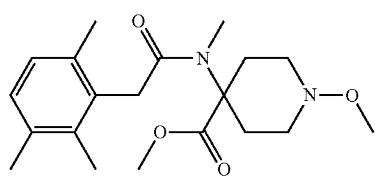 [SMILES: COC(=O)C1(N(C)C(=O)Cc2c(C)ccc(C)c2C)CCN(OC)CC1] | | $^1$H-NMR (CDCl$_3$, selected signals only):<br>3.52 (br s, 3H, NOCH$_3$). |
| P4.25 | 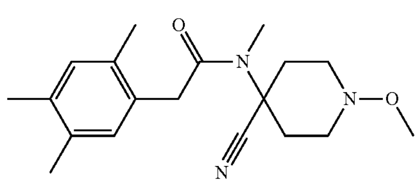 | | LC/MS: 330 (M + H)+<br>$R_t$ = 1.78 min |
| P4.26 | 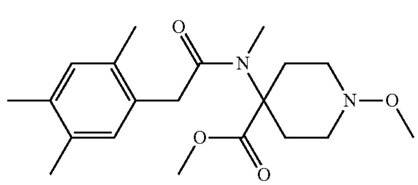 | | LC/MS: 363 (M + H)+<br>$R_t$ = 1.77 min |
| P4.27 | 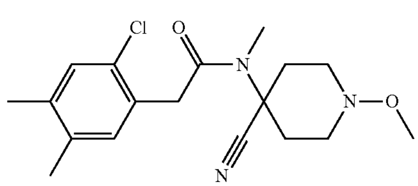 | solid | LC/MS: 350/352 (M + H)+<br>$R_t$ = 1.54 min |
| P4.28 | 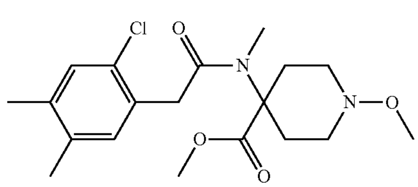 | | |

TABLE P4-continued

Physical data of intermediates of formula IV or XI:

| Compound No. | Structures | Melting Point | MS/NMR |
|---|---|---|---|
| P4.29 | 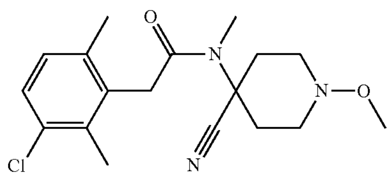 [SMILES: CON1CCC(C#N)(N(C)C(=O)Cc2c(C)ccc(Cl)c2C)CC1] | | |
| P4.30 | 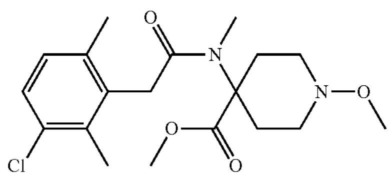 [SMILES: COC(=O)C1(N(C)C(=O)Cc2c(C)ccc(Cl)c2C)CCN(OC)CC1] | | |
| P4.31 | 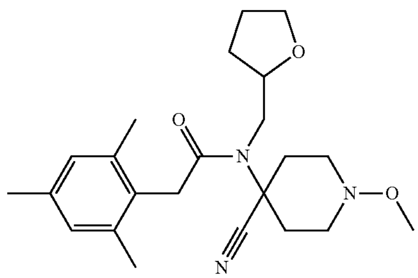 | 134-136° C. | LC/MS: 400 (M + H)⁺<br>$R_t$ = 1.87 min |
| P4.32 | 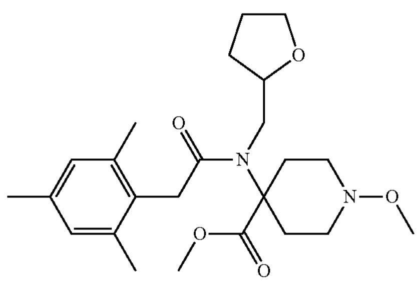 | 132-134° C. | LC/MS: 433 (M + H)⁺<br>$R_t$ = 1.87 min |
| P4.33 | 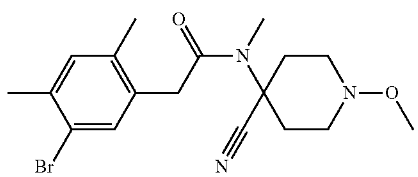 | 144-146° C. | LC/MS: 394/396 (M + H)⁺<br>$R_t$ = 1.82 min |
| P4.34 | 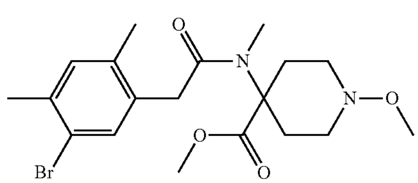 | gum | LC/MS: 427/429 (M + H)⁺<br>$R_t$ = 1.84 min |
| P4.35 | 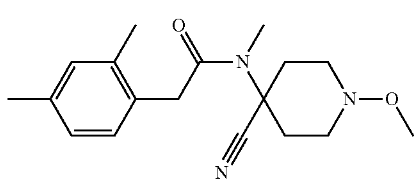 | solid | LC/MS: 316 (M + H)⁺<br>$R_t$ = 1.66 min |

TABLE P4-continued

Physical data of intermediates of formula IV or XI:

| Compound No. | Structures | Melting Point | MS/NMR |
|---|---|---|---|
| P4.36 | 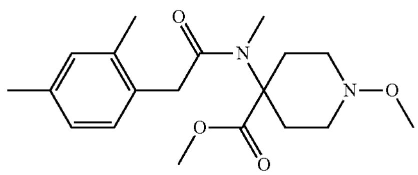 | solid | LC/MS: 349 (M + H)+<br>R$_t$ = 1.67 min |
| P4.37 | 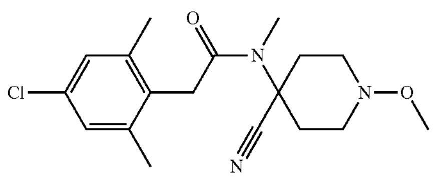 | 188-192° C. | LC/MS: 350/352 (M + H)+<br>R$_t$ = 1.75 min |
| P4.38 | 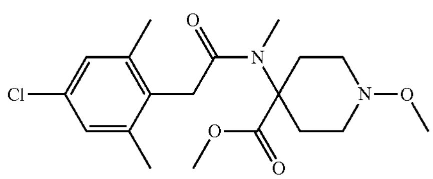 [SMILES: COC(=O)C1(N(C)C(=O)Cc2c(C)cc(Cl)cc2C)CCN(OC)CC1] | 150-152° C. | LC/MS: 383/385 (M + H)+<br>R$_t$ = 1.77 min |
| P4.39 | 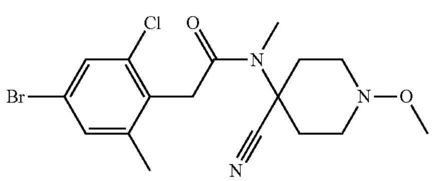 [SMILES: CON1CCC(C#N)(N(C)C(=O)Cc2c(C)cc(Br)cc2Cl)CC1] | solid | LC/MS: 414/416/418 (M + H)+<br>R$_t$ = 1.78 min |
| P4.40 | 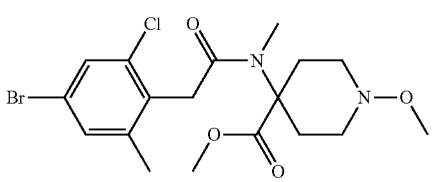 [SMILES: COC(=O)C1(N(C)C(=O)Cc2c(C)cc(Br)cc2Cl)CCN(OC)CC1] | gum | LC/MS: 447/449/451 (M + H)+<br>R$_t$ = 1.82 min |
| P4.41 | 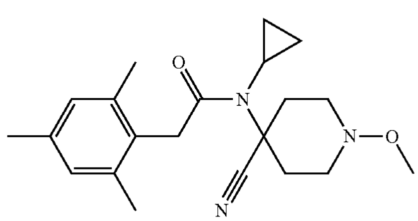 | | LC/MS: 356 (M + H)+<br>R$_t$ = 1.87 min |
| P4.42 | 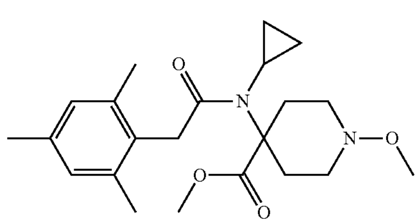 | | LC/MS: 389 (M + H)+<br>R$_t$ = 1.89 min |

TABLE P4-continued

Physical data of intermediates of formula IV or XI:

| Compound No. | Structures | Melting Point | MS/NMR |
|---|---|---|---|
| P4.43 | 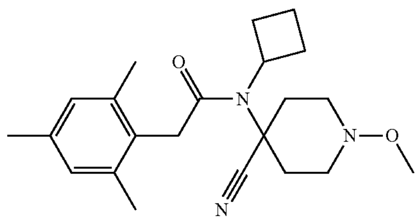 | gum | LC/MS: 370 (M + H)$^+$<br>R$_t$ = 1.99 min |
| P4.44 | 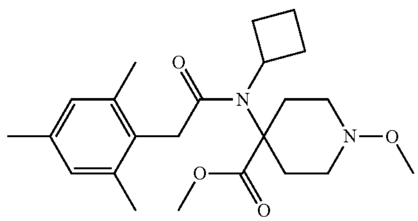 | | |
| P4.45 | 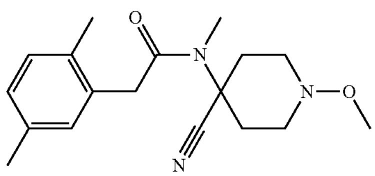 | | |
| P4.46 | EXAMPLE 10, step 3 | gum | LC/MS: 349 (M + H)$^+$<br>R$_t$ = 1.66 min |

Intermediates of the formula V, VII, VIII or IX from Table P5 can be prepared by analogous procedures.

TABLE P5

Physical data of intermediates of formula V, VII, VIII or IX:

| Compound No. | Structures | Melting Point | MS/NMR/IR |
|---|---|---|---|
| P5.1 | EXAMPLE 4, step 1 | liquid | $^1$H-NMR (CDCl$_3$):<br>1.36 (br s, 1H), 1.62-2.22 (br signals, total 4H), 2.51 (s, 3H), 2.63-3.41 (br signals, total 4H), 3.51 (s, 3H).<br>LC/MS (ES+):<br>170 (M + H)$^+$; R$_t$ = 0.25 min |
| P5.2 | EXAMPLE 5 | | LC/MS: 196 (M + H)$^+$<br>R$_t$ = 1.14 min<br>IR (CN): ν 2223 cm$^{-1}$ |

TABLE P5-continued

Physical data of intermediates of formula V, VII, VIII or IX:

| Compound No. | Structures | Melting Point | MS/NMR/IR |
|---|---|---|---|
| P5.3 | (tetrahydrofuran-2-ylmethyl-amino piperidine-4-carbonitrile, N-methoxy) | oil | LC/MS: 240 (M + H)$^+$<br>$R_t$ = 1.18 min |
| P5.4 | (methyl ester, HN-methyl, N-methoxy piperidine)<br>EXAMPLE 6, step 2<br>EXAMPLE 10, step 2 | oil | $^1$H-NMR (CDCl$_3$):<br>1.46-2.33 (br signals, total 5H), 2.22 (br s, 3H), 2.51-3.31 (br signals, total 4H), 3.51 (s, 3H), 3.72 (br s, 3H).<br>LC/MS (ES+):<br>203 (M + H)$^+$; $R_t$ = 0.20 min |
| P5.5 | (cyclobutylmethyl-amino piperidine-4-carbonitrile, N-methoxy) | | LC/MS: 210 (M + H)$^+$<br>$R_t$ = 1.10 min<br>IR (CN): ν 2222 cm$^{-1}$ |
| P5.6 | (spirohydantoin, N-methyl, N-methoxy piperidine)<br>EXAMPLE 6, step 1 | solid | LC/MS: 214 (M + H)$^+$<br>$R_t$ = 0.75 min |
| P5.7 | (HO-C(=O), HN-methyl, N-methoxy piperidine)<br>EXAMPLE 10, step 1 | >250° C. | $^1$H-NMR (D$_2$O):<br>1.73 (m, 1H), 2.02 (m, 2H), 2.32 (m, 1H), 2.54 (appar. d, 3H), 2.69 (m, 1H), 2.99 (m, 1H), 3.18 (m, 1H), 3.33 (m, 1H), 3.49 (appar. d, 3H).<br>LC/MS (ES+):<br>189 (M + H)$^+$; $R_t$ = 0.21 min |

EXAMPLE 11

Preparation of Carbonic acid 3-(2,5-dimethyl-phenyl)-8-methoxy-1-methoxy-methoxy-2-oxo-1,8-diaza-spiro[4.5]dec-3-en-4-yl ester ethyl ester (compound P1ii.2)

Step 1: Preparation of 1-methoxy-piperidin-4-one oxime

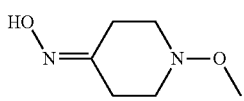

To a solution of 1-methoxy-piperidin-4-one [prepared according to Journal of Organic Chemistry (1961), 26, 1867-74] (258 g, 2.0 mol) and triethylamine (305.2 ml, 221.9 g, 4.4 mol) in methanol (3000 ml) was added hydroxylamine hydrochloride (277.6 g, 4.0 mol), and the reaction mixture heated at reflux for 1.5 hours. The solvent was evaporated, the residue diluted with diethyl ether and the suspension filtered. The filtrate was washed with water and brine, dried over sodium sulfate and concentrated. Yield: 286.25 g of 1-methoxy-piperidin-4-one oxime as a colorless, viscous oil. This material was used without further purification in the next step.

$^1$H-NMR (CDCl$_3$): 2.2-3.45 (br signals, total 8H), 3.55 (s, 3H), 8.65 (br s, 1H).

LC/MS (ES+): 145 (M+H)$^+$

Step 2: Preparation of 4-hydroxyamino-1-methoxy-piperidine-4-carbonitrile (compound P4ii.1)

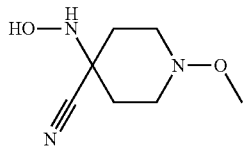

To a suspension of 1-methoxy-piperidin-4-one oxime (240 g, 1.66 mol) and potassium dihydrogen phosphate (792.9 g, 5.83 mol) in water (200 ml) at 0-5° C. was added a solution of potassium cyanide (195.1 g, 3.0 mol) in water (200 ml) draperies (caution!). The reaction mixture was stirred at room temperature overnight (stoppered flask), treated with another portion of potassium dihydrogen phosphate (79.3 g, 0.58 mol) and further stirred at room temperature over another night. The mixture was flushed with nitrogen, the semi-solid removed by filtration and dissolved in ethyl acetate. The aqueous layer was extracted twice with ethyl acetate, all organic layers combined, washed with water and brine, dried over sodium sulfate and concentrated. The residue was triturated with cold diethyl ether, filtered and dried. Yield: 230.8 g of 4-hydroxyamino-1-methoxy-piperidine-4-carbonitrile as a tan solid, mp 130-131° C.

$^1$H-NMR (CDCl$_3$): 1.55-2.35 (br signals, total 4H), 2.60-3.45 (br signals, total 4H), 3.52 (s, 3H), 5.19 (br s, 1H), 5.42 (br s, 1H).

IR (CN): ν 2227.8 cm$^{-1}$. LC/MS (ES+): 172 (M+H)$^+$

Step 3: Preparation of 4-hydroxyamino-1-methoxy-piperidine-4-carboxylic acid methyl ester (compound 4ii.2)

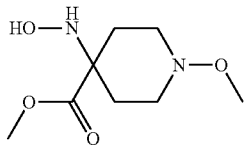

To a suspension of 4-hydroxyamino-1-methoxy-piperidine-4-carbonitrile (230 g, 1.34 mol) in dichloromethane (2400 ml) at room temperature was added concentrated sulfuric acid (358 ml, 658.8 g, 6.72 mol) dropwise, and the reaction mixture was stirred at 40° C. for one hour. Methanol (925.1 ml, 731.7 g, 22.8 mol) was added at 40° C. dropwise, and the mixture stirred at 40° C. for 4 hours. The dichloromethane was distilled off allowing to heat the reaction mixture at 60° C. for 24 hours. The reaction mixture was poured on ice (3 kg) and neutralized by careful addition of concentrated aqueous sodium hydroxide first, followed by saturated aqueous sodium hydrogen carbonate. The aqueous phase was saturated with sodium chloride, extracted with ter-butyl methyl ether (10×300 ml), the combined organic layers washed with brine, dried over sodium sulfate and concentrated to afford a first crop of product (163.8 g). Further extraction of the aqueous layer with ethyl acetate delivered another 35 g of crude product. Yield: 198.8 g of 4-hydroxyamino-1-methoxy-piperidine-4-carboxylic acid methyl ester as a red-brown, viscous oil. This material was used without further purification in the next step.

$^1$H-NMR (CDCl$_3$): 1.50-2.40 (br signals, total 4H), 2.76 (br m, 2H), 3.01-3.32 (br m, 2H), 3.52 (s, 3H), 3.76 (s, 3H), 5.58 (br s, 2H).

IR (COOMe): ν 1731.3 cm$^{-1}$. LC/MS (ES+): 205 (M+H)$^+$

Step 4: Preparation of 4-{[2-(2,5-dimethyl-phenyl)-acetyl]-hydroxy-amino}-1-methoxy-piperidine-4-carboxylic acid methyl ester (compound P3ii.1)

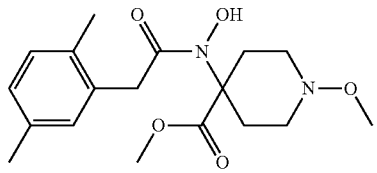 [SMILES: COC(=O)C1(N(O)C(=O)Cc2cc(C)ccc2C)CCN(OC)CC1]

To a solution of 4-hydroxyamino-1-methoxy-piperidine-4-carboxylic acid methyl ester (50 g, 244.8 mmol) in tetrahydrofuran (500 ml) at 0° C. was added sodium hydrogen carbonate (34.96 g, 416.2 mmol), followed by a solution of (2,5-dimethyl-phenyl)-acetyl chloride [prepared by treatment (2,5-dimethyl-phenyl)-acetic acid with oxalyl chloride in dichloromethane under standard conditions] (44.72 g, 244.8 mmol) in tetrahydrofuran (500 ml) dropwise. The reaction mixture was stirred at 0° C. for one hour and at room temperature for two hours. The solvent was evaporated, the residue diluted with water and ethyl acetate and the layers separated. The aqueous phase was extracted with ethyl acetate (6×250 ml), the combined organic layers washed with an aqueous sodium hydrogen carbonate solution and brine, dried over sodium sulfate and concentrated. The crude product was triturated with a cold diethyl ether/hexane 1:1 solution, filtered and dried to afford 36.4 g as a white solid. The mother liquor was concentrated and purified by chromatography on silica gel (ethyl acetate/hexane 1:1) to further afford 4.2 g of product. Yield: 40.6 g of 4-{[2-(2,5-dimethyl-phenyl)-acetyl]-hydroxy-amino}-1-methoxy-piperidine-4-carboxylic acid methyl ester (compound P3ii.1), mp 137-139° C.

$^1$H-NMR (CDCl$_3$): 1.99-3.32 (br signals, total 8H), 2.23 (s, 3H), 2.29 (s, 3H), 3.53 (s, 3H), 3.72 (s, 3H), 3.83 (s, 2H), 6.43 (br s, 1H), 6.98 (d, 1H), 6.99 (s, 1H), 7.06 (d, 1H).

LC/MS (ES+): 351 (M+H)$^+$

Step 5: Preparation of 3-(2,5-dimethyl-phenyl)-4-hydroxy-8-methoxy-1-methoxymethoxy-1,8-diazaspiro[4.5]dec-3-en-2-one (compound P2ii.2)

Two-Steps (Hydroxamic Acid O-Alkylation and Cyclisation), One-Pot Procedure

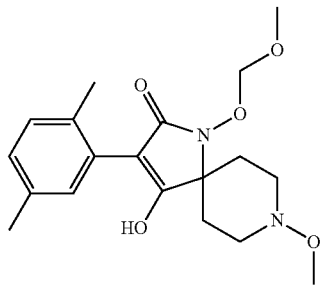 [SMILES: COCON1C(=O)C(c2cc(C)ccc2C)=C(O)C12CCN(OC)CC2]

To a solution of 4-{[2-(2,5-dimethyl-phenyl)-acetyl]-hydroxy-amino}-1-methoxy-piperidine-4-carboxylic acid methyl ester (35 g, 100.0 mmol) in dimethylformamide (300 ml) at 0° C. was added sodium hydride (5.02 g, 55% w/w dispersion in mineral oil, 115.0 mmol) in 5 portions. The reaction mixture was stirred at 0° C. for 30 minutes, treated with chloromethyl methyl ether (8.96 ml, 9.5 g, 118.0 mmol) dropwise, and further stirred at 0° C. for one hour and at room temperature for 1.5 hours. To the mixture recooled at 0° C. was added sodium methoxide (8.1 g, 150 mmol) in one portion, and stirring continued at room temperature for 2.5 hours. The reaction mixture was poured on ice water (500 ml), acidified to pH 5-6 with an aqueous HCl solution and thoroughly extracted with ethyl acetate. The combined organic layers were washed with brine, dried over sodium sulfate and concentrated. The crude oily product was triturated with a cold diethyl ether/hexane 1:1 solution, filtered and dried to afford 15.8 g as a white solid. The mother liquor was concentrated and purified by chromatography on silica gel (ethyl acetate/hexane 2:1) to further afford 2.1 g of product. Yield: 17.9 g of 3-(2,5-dimethyl-phenyl)-4-hydroxy-8-methoxy-1-methoxymethoxy-1,8-diaza-spiro[4.5]dec-3-en-2-one (compound P2ii.2), mp 136-138° C.

$^1$H-NMR (CDCl$_3$): 1.44-2.72 (br signals, total 4H), 2.27 (s, 3H), 2.30 (s, 3H), 2.78-3.48 (br signals, total 4H), 3.59 (s, 3H), 3.64 (s, 3H), 4.41 (s, 1H), 5.12 (br m, 2H), 6.76 (s, 1H), 7.02 (d, 1H), 7.10 (d, 1H) (mixture of keto-enol tautomers, signals of major diketo-form isomer shown).

LC/MS (ES+): 363 (M+H)$^+$, LC/MS (ES−): 361 (M−H)$^−$

Step 6: Preparation of carbonic acid 3-(2,5-dimethyl-phenyl)-8-methoxy-1-methoxy-methoxy-2-oxo-1,8-diaza-spiro[4.5]dec-3-en-4-yl ester ethyl ester (title compound P1ii.2)

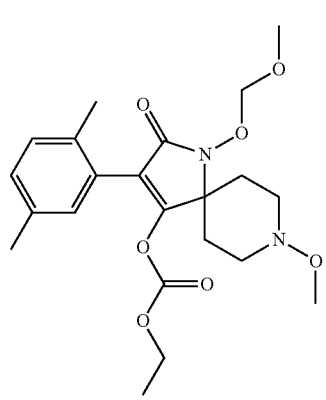 [SMILES: CCOC(=O)OC1=C(c2cc(C)ccc2C)C(=O)N(OCOC)C12CCN(OC)CC2]

To a solution of 3-(2,5-dimethyl-phenyl)-4-hydroxy-8-methoxy-1-methoxymethoxy-1,8-diaza-spiro[4.5]dec-3-en-2-one (9.0 g, 24.83 mmol), triethylamine (6.9 ml, 5.0 g, 49.66 mmol) and 4-dimethylaminopyridine (100 mg, 0.82 mmol) in tetrahydrofuran (250 ml) at 0° C. was added a solution of ethyl chloroformate (3.09 ml, 3.5 g, 32.28 mmol) in tetrahydrofuran (20 ml) dropwise. The suspension was stirred at 0° C. for one hour, and at room temperature for one hour. The reaction mixture was evaporated, diluted with ethyl acetate and filtered to remove salts. The filtrate was washed with a saturated aqueous sodium hydrogen carbonate solution (2×100 ml) and brine, dried over sodium sulfate and concentrated. The oily residue was purified by chromatography on silica gel (ethyl acetate/hexane 1:1). Yield: 9.63 g of carbonic acid 3-(2,5-dimethyl-phenyl)-8-methoxy-1-methoxy-methoxy-2-oxo-1,8-diaza-spiro[4.5]dec-3-en-4-yl ester ethyl ester (title compound P1ii.2) as a white solid, mp 109-111° C.

$^1$H-NMR (CDCl$_3$): 1.06 (t, 3H), 1.75-2.05 (br m, 2H), 2.20 (s, 3H), 2.28 (s, 3H), 2.47 (br m, 2H), 2.89 (br m, 1H), 3.15-3.45 (br m, 3H), 3.59 (s, 3H), 3.64 (s, 3H), 3.99 (q, 2H), 5.07 (br s, 2H), 6.96 (s, 1H), 7.03 (d, 1H), 7.09 (d, 1H).

LC/MS (ES+): 435 (M+H)$^+$

EXAMPLE 12

Preparation of 4-Hydroxy-8-methoxy-1-prop-2-ynyloxy-3-(2,4,6-trimethyl-phenyl)-1,8-diaza-spiro[4.5]dec-3-en-2-one (compound P2ii.8)

Stepwise Hydroxamic Acid O-Alkylation and Cyclisation

Step 1: Preparation of 1-methoxy-4-{prop-2-ynyloxy-[2-(2,4,6-trimethyl-phenyl)-acetyl]-amino}-piperidine-4-carboxylic acid methyl ester (compound P3ii.4)

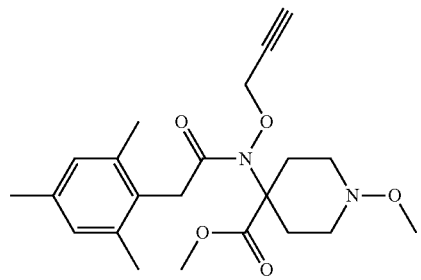

To a solution of 4-{hydroxy-[2-(2,4,6-trimethyl-phenyl)-acetyl]-amino}-1-methoxy-piperidine-4-carboxylic acid methyl ester (compound P3ii.3 obtained in analogy to preparation example 11, step 4) (500 mg, 1.37 mmol) in tetrahydrofuran (3 ml) at 0° C. was added sodium hydride (66 mg, 55% w/w dispersion in mineral oil, 1.51 mmol) in 2 portions. The reaction mixture was stirred at 0° C. for one hour, treated with propargyl bromide (202 mg, 1.65 mmol) dropwise, and further stirred at room temperature overnight. The reaction mixture was evaporated, diluted with ethyl acetate and filtered to remove salts. The filtrate was washed twice with brine, dried over sodium sulfate and concentrated. The oily residue was purified by chromatography on silica gel (ethyl acetate/hexane 1:2). Yield: 321 mg of 1-methoxy-4-{prop-2-ynyloxy-[2-(2,4,6-trimethyl-phenyl)-acetyl]-amino}-piperidine-4-carboxylic acid methyl ester (compound P3ii.4) as a colorless gum.

$^1$H-NMR (CDCl$_3$): 1.90-3.34 (br signals, total 8H), 2.21 (s, 6H), 2.24 (s, 3H), 2.68 (t, 1H), 3.53 (s, 3H), 3.68 (s, 3H), 3.77 (d, 1H), 4.03 (m, 1H), 4.65-4.89 (br m, 2H), 6.84 (s, 2H).

LC/MS (ES+): 403 (M+H)$^+$

Step 2: Preparation of 4-hydroxy-8-methoxy-1-prop-2-ynyloxy-3-(2,4,6-trimethyl-phenyl)-1,8-diaza-spiro[4.5]dec-3-en-2-one (title compound P2ii.8)

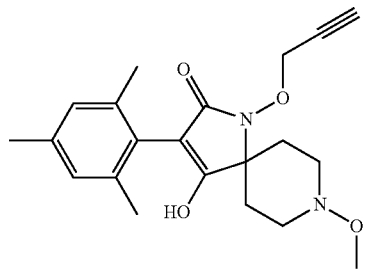

To a solution of 1-methoxy-4-{prop-2-ynyloxy-[2-(2,4,6-trimethyl-phenyl)-acetyl]-amino}-piperidine-4-carboxylic acid methyl ester (150 mg, 0.41 mmol) in dimethylformamide (2 ml) at 0° C. was added sodium methoxide (33 mg, 0.62 mmol) in one portion and stirring continued at room temperature for 4 hours. The reaction mixture was poured on ice water, acidified to pH 5-6 with an aqueous HCl solution, saturated with sodium chloride and thoroughly extracted with ethyl acetate. The combined organic layers were washed with brine, dried over sodium sulfate and concentrated. The residue was purified by chromatography on silica gel (ethyl acetate/hexane 2:1). Yield: 14 mg of 4-hydroxy-8-methoxy-1-prop-2-ynyloxy-3-(2,4,6-trimethyl-phenyl)-1,8-diaza-spiro[4.5]dec-3-en-2-one (title compound P2ii.8) as a tan solid.

$^1$H-NMR (CD$_3$OD): 1.97-2.08 (m, 2H), 2.10 (s, 6H), 2.25 (s, 3H), 2.23-2.32 (m, 2H), 3.04 (br s, 1H), 3.20 (m, 2H), 3.38 (m, 2H), 3.54 (s, 3H), 4.76 (br s, 2H), 6.89 (s, 2H).

LC/MS (ES+): 371 (M+H)$^+$

EXAMPLE 13

Preparation of Carbonic acid ethyl ester 8-methoxy-2-oxo-1-(tetrahydro-furan-2-yloxy)-3-(2,4,6-trimethyl-phenyl)-1,8-diaza-spiro[4.5]dec-3-en-4-yl ester (compound P1ii.9)

Step 1: Preparation of carbonic acid ethyl ester 1-hydroxy-8-methoxy-2-oxo-3-(2,4,6-trimethyl-phenyl)-1,8-diaza-spiro[4.5]dec-3-en-4-yl ester (compound P1ii.11)

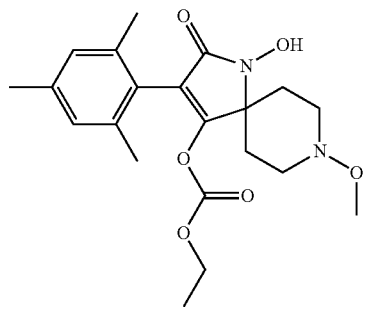

To a solution of carbonic acid ethyl ester 8-methoxy-1-methoxymethoxy-2-oxo-3-(2,4,6-trimethyl-phenyl)-1,8-diaza-spiro[4.5]dec-3-en-4-yl ester (compound P1ii.7 obtained in analogy to preparation example 11, step 6) (1.0 g, 2.23 mmol) in bromotrimethylsilane (4.33 ml, 5.12 g, 33.44 mmol) under argon atmosphere was added 3 Å molecular sieves (0.5 g) and the reaction mixture was stirred at 75° C. overnight. The mixture was diluted with dichloromethane, filtered, the filtrate evaporated, the residue triturated with cold diethyl ether, filtered and dried. The crude product was purified by chromatography on silica gel (gradient dichloromethane→dichloromethane/methanol 20:1→10:1). Yield: 580 mg of carbonic acid ethyl ester 1-hydroxy-8-methoxy-2-oxo-3-(2,4,6-trimethyl-phenyl)-1,8-diaza-spiro[4.5]dec-3-en-4-yl ester (compound P1ii.11) as a white solid, mp 154-155° C.

$^1$H-NMR (CD$_3$OD): 1.03 (t, 3H), 2.03 (br m, 2H), 2.13 (s, 6H), 2.22 (br m, 2H), 2.25 (s, 3H), 2.94 (br m, 1H), 3.28 (br m, 2H), 3.44 (br m, 1H), 3.54 (s, 3H), 4.00 (q, 2H), 6.87 (s, 2H).

LC/MS (ES+): 405 (M+H)$^+$

Step 2: Preparation of carbonic acid ethyl ester 8-methoxy-2-oxo-1-(tetrahydro-furan-2-yloxy)-3-(2,4,6-trimethyl-phenyl)-1,8-diaza-spiro[4.5]dec-3-en-4-yl ester (title compound P1ii.9)

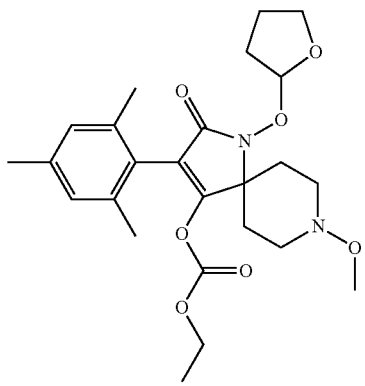

To a solution of carbonic acid ethyl ester 1-hydroxy-8-methoxy-2-oxo-3-(2,4,6-trimethyl-phenyl)-1,8-diaza-spiro[4.5]dec-3-en-4-yl ester (150 mg, 0.37 mmol) in dichloromethane (3 ml) under argon atmosphere was added 2,3-dihydro-furan (56 μl, 52 mg, 0.74 mmol) and a catalytic amount of p-toluenesulfonic acid monohydrate (2 mg). The reaction mixture was stirred at room temperature for 4 hours, diluted with dichloromethane, washed twice with brine, dried over sodium sulfate and concentrated. The residue was purified by chromatography on silica gel (ethyl acetate/hexane 2:1). Yield: 114 mg of carbonic acid ethyl ester 8-methoxy-2-oxo-1-(tetrahydro-furan-2-yloxy)-3-(2,4,6-trimethyl-phenyl)-1,8-diaza-spiro[4.5]dec-3-en-4-yl ester (title compound P1ii.9) as a colorless gum.

$^1$H-NMR (CD$_3$OD): 1.02 (t, 3H), 1.70-2.22 (br signals, total 6H), 2.12 (s, 3H), 2.13 (s, 3H), 2.25 (s, 3H), 2.31-2.68 (br m, 2H), 2.86 (br m, 1H), 3.20 (br m, 1H), 3.39 (br m, 2H), 3.54 (s, 3H), 3.96 (m, 1H), 4.00 (q, 2H), 4.18 (q, 1H), 5.62 (br s, 1H), 6.88 (s, 2H).

LC/MS (ES+): 475 (M+H)$^+$

EXAMPLE 14

Preparation of 1,4-Dihydroxy-8-methoxy-3-(2,4,6-trimethyl-phenyl)-1,8-diaza-spiro[4.5]dec-3-en-2-one (compound P2ii.4)

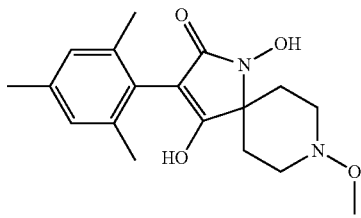

To a solution of 4-hydroxy-8-methoxy-1-methoxymethoxy-3-(2,4,6-trimethyl-phenyl)-1,8-diaza-spiro[4.5]dec-3-en-2-one (compound P2ii.6 obtained in analogy to preparation example 11, step 5) (500 mg, 1.33 mmol) in dichloromethane (10 ml) under argon atmosphere at 0° C. was added 3 Å molecular sieves (0.5 g), followed by bromotrimethylsilane (1.72 ml, 2.03 g, 13.28 mmol) dropwise and the reaction mixture was stirred at 0° C. for one hour and at room temperature for 48 hours. The mixture was poured on cold water, the water layer saturated with sodium chloride and thoroughly extracted with dichloromethane. The combined organic layers were washed with brine, dried over sodium sulfate and concentrated. The residue was purified by chromatography on silica gel (ethyl acetate). Yield: 40 mg of 1,4-dihydroxy-8-methoxy-3-(2,4,6-trimethyl-phenyl)-1,8-diaza-spiro[4.5]dec-3-en-2-one (title compound P2ii.4) as a white solid, mp 152-154° C.

$^1$H-NMR (CDCl$_3$): 1.82-2.58 (br signals, total 4H), 2.12 (s, 6H), 2.27 (s, 3H), 2.93-3.46 (br signals, total 4H), 3.57 (br s, 3H), 6.89 (s, 2H), 9.97 (br s, 1H).

LC/MS (ES+): 333 (M+H)$^+$

EXAMPLE 15

Preparation of Carbonic acid ethyl ester 8-methoxy-1-methoxycarbonyloxy-2-oxo-3-(2,4,6-trimethyl-phenyl)-1,8-diaza-spiro[4.5]dec-3-en-4-yl ester (compound P1ii.13)

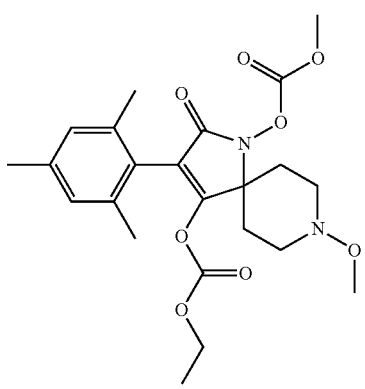

To a solution of carbonic acid ethyl ester 1-hydroxy-8-methoxy-2-oxo-3-(2,4,6-trimethyl-phenyl)-1,8-diaza-spiro[4.5]dec-3-en-4-yl ester (preparation example 13, step 1; compound P1ii.11) (140 mg, 0.33 mmol), triethylamine (93 µl, 68 mg, 0.67 mmol) and 4-dimethylaminopyridine (2 mg) in tetrahydrofuran (3 ml) at 0° C. was added a solution of methyl chloroformate (33 µl, 41 mg, 0.43 mmol) in tetrahydrofuran (2 ml) dropwise. The suspension was stirred at 0° C. for one hour, and at room temperature for one hour. The reaction mixture was evaporated, diluted with ethyl acetate and filtered to remove salts. The filtrate was washed with a saturated aqueous sodium hydrogen carbonate solution (2×15 ml) and brine, dried over sodium sulfate and concentrated. The oily residue was purified by chromatography on silica gel (ethyl acetate/hexane 1:2). Yield: 30 mg of carbonic acid ethyl ester 8-methoxy-1-methoxycarbonyloxy-2-oxo-3-(2,4,6-trimethyl-phenyl)-1,8-diaza-spiro[4.5] dec-3-en-4-yl ester (title compound P1ii.13) as a colorless gum.

$^1$H-NMR (CDCl$_3$): 1.06 (t, 3H), 2.16 (s, 6H), 2.20 (m, 4H), 2.25 (s, 3H), 2.75-3.16 (br m, total 2H), 3.34 (br m, 2H), 3.55 (s, 3H), 3.96 (s, 3H), 3.99 (q, 2H), 6.85 (s, 2H).

LC/MS (ES+): 463 (M+H)$^+$

EXAMPLE 16

Alternative preparation of 4-{[2-(2,5-Dimethyl-phenyl)-acetyl]-hydroxy-amino}-1-methoxy-piperidine-4-carboxylic acid methyl ester (compound P3ii.1)

Step 1: Preparation of N-(4-cyano-1-methoxy-piperidin-4-yl)-2-(2,5-dimethyl-phenyl)-N-hydroxy-acetamide (compound P3ii.2)

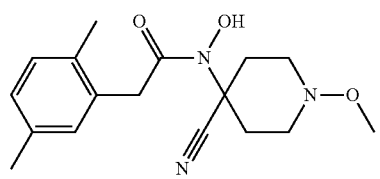 [SMILES: CON1CCC(C#N)(N(O)C(=O)Cc2cc(C)ccc2C)CC1]

To a solution of 4-hydroxyamino-1-methoxy-piperidine-4-carbonitrile (preparation example 11, step 2) (4.0 g, 23.4 mmol) and sodium hydrogen carbonate (3.0 g, 35.7 mmol) in ethyl acetate (35 ml) and water (25 ml) at 0° C. was added a solution of (2,5-dimethyl-phenyl)-acetyl chloride (4.2 g, 23.0 mmol) in ethyl acetate (35 ml) dropwise over one hour. The reaction mixture was stirred at 0° C. for one hour and at room temperature for two hours. The layers of the biphasic system were separated, the aqueous phase extracted with ethyl acetate (3×), the combined organic layers washed with brine, dried over sodium sulfate and concentrated. The oily residue was purified by chromatography on silica gel (gradient ethyl acetate/hexane 1:2→1:1→2:1). Yield: 1.55 g of N-(4-cyano-1-methoxy-piperidin-4-yl)-2-(2,5-dimethyl-phenyl)-N-hydroxy-acetamide (compound P3ii.2) as a white solid, mp 153-156° C.

$^1$H-NMR (CDCl$_3$): 2.11 (br m, 2H), 2.21 (s, 3H), 2.28 (s, 3H), 2.56 (br m, 2H), 2.77 (br m, 1H), 3.10 (br m, 2H), 3.31 (br m, 1H), 3.50 (s, 3H), 3.77 (s, 2H), 6.83 (br s, 1H), 6.97 (s, 1H), 6.98 (d, 1H), 7.06 (d, 1H).

IR (CN): v 2238.0 cm$^{-1}$. LC/MS (ES+): 318 (M+H)$^+$

Step 2: Preparation of 4-{[2-(2,5-dimethyl-phenyl)-acetyl]-hydroxy-amino}-1-methoxy-piperidine-4-carboxylic acid methyl ester (title compound P3ii.1)

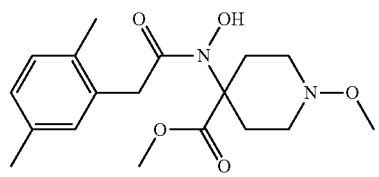

To a solution of N-(4-cyano-1-methoxy-piperidin-4-yl)-2-(2,5-dimethyl-phenyl)-N-hydroxy-acetamide (1.5 g, 4.73 mmol) in methanol (15 ml) at 0° C. was added concentrated sulfuric acid (1.26 ml, 2.3 g, 23.64 mmol) slowly dropwise and the reaction mixture was stirred at reflux for 40 hours. The mixture was poured on ice (50 g), neutralized carefully with a saturated aqueous sodium hydrogen carbonate solution and extracted with ethyl acetate (5×). The combined organic layers were washed with brine, dried over sodium sulfate and concentrated. The oily residue was purified by chromatography on silica gel (ethyl acetate/hexane 2:1) to afford 136 mg of an off-white solid. This material was triturated with a tert-butyl methyl ether/hexane 1:4 solution (2-3 ml), filtered and dried. Yield: 82 mg of 4-{[2-(2,5-dimethyl-phenyl)-acetyl]-hydroxy-amino}-1-methoxy-piperidine-4-carboxylic acid methyl ester (title compound P3ii.1) as a white solid, mp 140-142° C.

The spectral data were identical to those described above under preparation example 11, step 4.

EXAMPLE 17

Preparation of 4-Hydroxy-8-methoxy-1-(tetrahydro-furan-2-yloxy)-3-(2,4,6-trimethyl-phenyl)-1,8-diaza-spiro[4.5]dec-3-en-2-one (compound P2ii.18)

Stepwise Hydroxamic Acid O-Tetrahydrofuranylation and Cyclisation

Step 1: Preparation of 1-methoxy-4-{(tetrahydro-furan-2-yloxy)-[2-(2,4,6-trimethyl-phenyl)-acetyl]-amino}-piperidine-4-carboxylic acid methyl ester (compound P3ii.6)

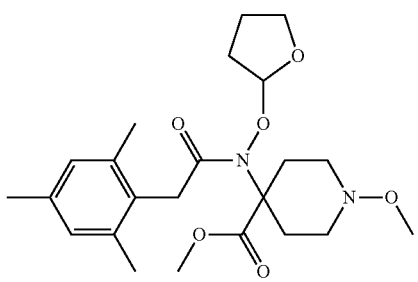

To a solution of 4-{hydroxy-[2-(2,4,6-trimethyl-phenyl)-acetyl]-amino}-1-methoxy-piperidine-4-carboxylic acid methyl ester (compound P3ii.3 obtained in analogy to preparation example 11, step 4) (70 g, 192.1 mmol) in dichloromethane (1500 ml) under argon atmosphere was added 2,3-dihydro-furan (29.1 ml, 26.9 g, 384.1 mmol) and a catalytic amount of p-toluenesulfonic acid monohydrate (1.94 g, 19.2 mmol). The reaction mixture was stirred at reflux for 7 hours, filtered and concentrated. The residue was triturated with hexane, filtered and the solid dried in vacuo. Yield: 70.0 g of 1-methoxy-4-{(tetrahydro-furan-2-yloxy)-[2-(2,4,6-trimethyl-phenyl)-acetyl]-amino}-piperidine-4-carboxylic acid methyl ester (compound P3ii.6) as a solid, mp 107-109° C. This material was used without further purification in the next step.

$^1$H-NMR (CD$_3$OD): 1.79-2.36 (br signals, total 6H), 2.15 (br s, 6H), 2.21 (s, 3H), 2.42 (m, 1H), 2.65 (m, 1H), 2.80 (m, 1H), 3.10 (m, 1H), 3.26 (br m, 2H), 3.53 (s, 3H), 3.63 (s, 3H), 3.77 (m, 1H), 4.01 (m, 1H), 4.10 (m, 2H), 5.68 (br m, 1H), 6.80 (s, 2H).

LC/MS (ES+): 435 (M+H)$^+$

Step 2: Preparation of 4-hydroxy-8-methoxy-1-(tetrahydro-furan-2-yloxy)-3-(2,4,6-trimethyl-phenyl)-1,8-diaza-spiro[4.5]dec-3-en-2-one (title compound P2ii.18)

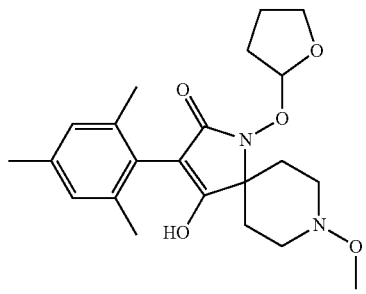

To a solution of 1-methoxy-4-{(tetrahydro-furan-2-yloxy)-[2-(2,4,6-trimethyl-phenyl)-acetyl]-amino}-piperidine-4-carboxylic acid methyl ester (70 g, 161.1 mmol) in dimethylformamide (350 ml) at 10° C. was added sodium methoxide (26.9 g, 483.3 mmol) in four portions and stirring continued at 10° C. for 30 minutes, then at room temperature for 2 hours. The reaction mixture was poured on cold saturated aqueous ammonium chloride and thoroughly extracted with ethyl acetate (6×100 ml). The combined organic layers were washed with brine, dried over sodium sulfate, concentrated and dried in vacuo. The residue was triturated with hexane, filtered and the solid dried. Yield: 51.0 g of 4-hydroxy-8-methoxy-1-(tetrahydro-furan-2-yloxy)-3-(2,4,6-trimethyl-phenyl)-1,8-diaza-spiro[4.5]dec-3-en-2-one (title compound P2ii.18) as a tan solid, mp 144-146° C.

$^1$H-NMR (CD$_3$OD): 1.75-2.19 (br signals, total 6H), 2.11 (s, 6H), 2.24 (s, 3H), 2.28-2.55 (m, 2H), 3.13-3.30 (m, 2H), 3.30-3.48 (m, 2H), 3.54 (s, 3H), 3.92 (m, 1H), 4.17 (m, 1H), 5.58 (m, 1H), 6.87 (s, 2H).

LC/MS (ES+): 403 (M+H)$^+$

EXAMPLE 18

Preparation of 1-Cyclohexyloxy-4-hydroxy-8-methoxy-3-(2,4,6-trimethyl-phenyl)-1,8-diaza-spiro[4.5]dec-3-en-2-one (compound P2ii.26)

Stepwise Hydroxamic Acid O-Alkylation Via Mitsunobu and Cyclisation

Step 1: Preparation of 4-{cyclohexyloxy-[2-(2,4,6-trimethyl-phenyl)-acetyl]-amino}-1-methoxy-piperidine-4-carboxylic acid methyl ester (compound P3ii.8)

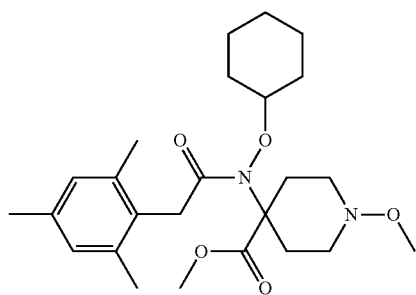

To a solution of triphenylphosphine (0.81 g, 3.09 mmol) in THF (20 ml) at 0° C. was added diisopropyl azodicarboxylate (0.64 ml, 0.66 g, 3.10 mmol) dropwise and the resulting precipitate was stirred at 0° C. for 30 minutes. 4-{Hydroxy-[2-(2,4,6-trimethyl-phenyl)-acetyl]-amino}-1-methoxy-piperidine-4-carboxylic acid methyl ester (compound P3ii.3 obtained in analogy to preparation example 11, step 4) (1.0 g, 2.74 mmol) was further added in one portion, followed by a solution of cyclohexanol (0.33 ml, 0.31 g, 3.10 mmol) in THF (2 ml) dropwise at 0° C. The reaction mixture was stirred at room temperature for two hours and concentrated in vacuo. The residue was purified by chromatography on silica gel (ethyl acetate/cyclohexane 1:3). Yield: 690 mg of 4-{cyclohexyloxy-[2-(2,4,6-trimethyl-phenyl)-acetyl]-amino}-1-methoxy-piperidine-4-carboxylic acid methyl ester (compound P3ii.8) as a colorless gum.

$^1$H-NMR (CD$_3$OD): 1.17-1.59 (br signals, total 7H), 1.68 (m, 1H), 1.91 (m, 2H), 2.03 (m, 1H), 2.17 (br s, 6H), 2.21 (s, 3H), 2.32 (m, 2H), 2.44 (m, 1H), 2.69 (m, 1H), 3.09 (m, 1H), 3.25 (m, 2H), 3.51 (s, 3H), 3.61 (s, 3H), 3.69 (m, 1H), 3.92-4.12 (m, 2H), 6.80 (s, 2H).

LC/MS (ES+): 447 (M+H)$^+$

Step 2: Preparation of 1-cyclohexyloxy-4-hydroxy-8-methoxy-3-(2,4,6-trimethyl-phenyl)-1,8-diaza-spiro[4.5]dec-3-en-2-one (title compound P2ii.26)

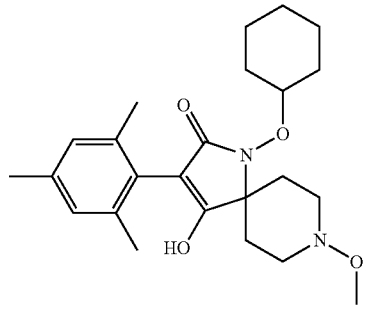

To a solution of 4-{cyclohexyloxy-[2-(2,4,6-trimethyl-phenyl)-acetyl]-amino}-1-methoxy-piperidine-4-carboxylic acid methyl ester (600 mg, 1.34 mmol) in dimethylformamide (10 ml) at 0° C. was added sodium methoxide (217 mg, 4.02 mmol) in one portion and the mixture was stirred at room temperature overnight. The reaction mixture was poured on cold saturated aqueous ammonium chloride and thoroughly extracted with ethyl acetate (4×25 ml). The combined organic layers were washed with water and brine, dried over sodium sulfate and concentrated. The residue was purified by chromatography on silica gel (ethyl acetate/cyclohexane 1:1). Yield: 329 mg of 1-cyclohexyloxy-4-hydroxy-8-methoxy-3-(2,4,6-trimethyl-phenyl)-1,8-diaza-spiro[4.5]dec-3-en-2-one (title compound P2ii.26) as a slight tan foam. Trituration with hexane gave a white solid, mp 115-118° C.

$^1$H-NMR (CD$_3$OD): 1.20-1.38 (m, 3H), 1.47 (m, 2H), 1.58 (m, 1H), 1.85 (m, 4H), 2.06 (m, 2H), 2.11 (s, 6H), 2.25 (s, 3H), 2.39 (m, 2H), 3.12-3.29 (m, 2H), 3.30-3.48 (m, 2H), 3.55 (s, 3H), 3.98 (m, 1H), 6.90 (s, 2H).

LC/MS (ES+): 415 (M+H)$^+$.

EXAMPLE 19

Preparation of 1-Methoxy-4-{(1-methoxy-piperidin-4-yloxy)-[2-(2,4,6-trimethyl-phenyl)-acetyl]-amino}-piperidine-4-carboxylic acid methyl ester (compound P3ii.26)

Step 1: Preparation of 1-methoxy-piperidin-4-ol

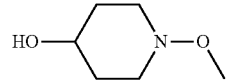

To a solution of 1-methoxy-piperidin-4-one [prepared according to Journal of Organic Chemistry (1961), 26, 1867-74] (15.0 g, 116.1 mmol) in ethanol (430 ml) was added sodium borohydride 96% (2.29 g, 58.1 mmol) in portions. The reaction mixture was stirred at room temperature for 5 hours, evaporated to half of its volume, poured on cold saturated aqueous ammonium chloride and thoroughly extracted with ethyl acetate. The combined organic layers were washed with brine, dried over sodium sulfate and concentrated. The residue was purified by chromatography on silica gel (ethyl acetate).

Yield: 10.9 g of 1-methoxy-piperidin-4-ol as a liquid.

$^1$H-NMR (CDCl$_3$): 1.46-2.06 (br signals, total 5H), 2.34-3.40 (br signals, total 4H), 3.53 (s, 3H), 3.59-3.96 (br signals, total 1H).

LC/MS (ES+): 132 (M+H)$^+$

Step 2: Preparation of 1-methoxy-4-{(1-methoxy-piperidin-4-yloxy)-[2-(2,4,6-trimethyl-phenyl)-acetyl]-amino}-piperidine-4-carboxylic acid methyl ester (title compound P3ii.26)

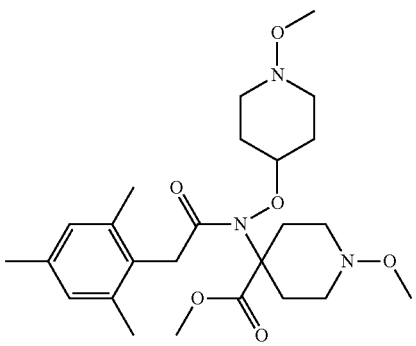

To a solution of triphenylphosphine (1.11 g, 4.23 mmol) in THF (20 ml) at 0° C. was added diisopropyl azodicarboxylate (0.83 ml, 0.85 g, 4.24 mmol) dropwise and the resulting precipitate was stirred at 0° C. for 30 minutes. 4-{Hydroxy-[2-(2,4,6-trimethyl-phenyl)-acetyl]-amino}-1-methoxy-piperidine-4-carboxylic acid methyl ester (compound P3ii.3 obtained in analogy to preparation example 11, step 4) (1.3 g, 3.57 mmol) was further added in one portion, followed by a solution of 1-methoxy-piperidin-4-ol (0.53 g, 4.04 mmol) in THF (6 ml) dropwise at 0° C. The reaction mixture was stirred at room temperature for two hours and concentrated in vacuo. The residue was triturated with hexane and filtered to remove part of the insoluble triphenylphosphine oxide. The filtrate was evaporated and the residue purified by chromatography on silica gel (gradient ethyl acetate/heptane 3:7→ethyl acetate). Yield: 861 mg of pure 1-methoxy-4-{(1-methoxy-piperidin-4-yloxy)-[2-(2,4,6-trimethyl-phenyl)-acetyl]-amino}-piperidine-4-carboxylic acid methyl ester (title compound P3ii.26) as a colorless gum, followed by a second fraction of compound P3ii.26 (701 mg) slightly contaminated with triphenylphosphine oxide.

¹H-NMR (CD₃OD, selected signals only): 2.19 (s, 6H, mesityl CH₃), 2.23 (s, 3H, mesityl CH₃), 3.52 (br s, 3H, NOCH₃), 3.54 (br s, 3H, NOCH₃), 3.65 (s, 3H, COOCH₃), 6.82 (s, 2H, mesityl H$_{arom}$).

LC/MS (ES+): 478 (M+H)⁺

EXAMPLE 20

Preparation of Carbonic acid 3-(4-chloro-2,6-dimethyl-phenyl)-1-ethoxycarbonyloxy-8-methoxy-2-oxo-1,8-diaza-spiro[4.5]dec-3-en-4-yl ester ethyl ester (compound P1ii.115)

Step 1: Preparation of 4-{[2-(4-chloro-2,6-dimethyl-phenyl)-acetyl]-hydroxy-amino}-1-methoxy-piperidine-4-carboxylic acid methyl ester (compound P3ii.34)

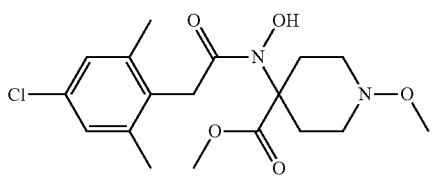 [SMILES: COC(=O)C1(N(O)C(=O)Cc2c(C)cc(Cl)cc2C)CCN(OC)CC1]

To a solution of (4-chloro-2,6-dimethyl-phenyl)-acetyl chloride (2.90 g, 13.4 mmol) in THF (25 ml) was added sodium hydrogen carbonate (1.90 g, 22.7 mmol) at 0° C., followed by 4-hydroxyamino-1-methoxy-piperidine-4-carboxylic acid methyl ester (preparation example 11, step 3; compound P4ii.2) (2.73 g, 13.4 mmol) dissolved in THF (25 ml) dropwise. The reaction mixture was stirred at 0° C. for 30 minutes, then further 30 minutes at room temperature. After completion of the reaction indicated by TLC and LC/MS, the reaction mixture was filtered and the residue (NaCl) washed with THF. The filtrate was concentrated to dryness and stirred several times with little amounts of an ether/hexane mixture (1:1) to remove side products. Finally, the compound was washed with ether to yield pure 4-{[2-(4-chloro-2,6-dimethyl-phenyl)-acetyl]-hydroxy-amino}-1-methoxy-piperidine-4-carboxylic acid methyl ester (compound P3ii.34) as white solid.

Yield: 3.7 g, mp 228-231° C.

¹H-NMR (DMSO-d₆): 1.77-1.91 (br m, 1H), 1.91-2.05 (br m, 1H), 2.13 (s, 6H), 2.30-2.42 (br m, 1H), 2.45-2.55 (br m, 1H; covered by DMSO solvent peak), 2.62-2.80 (br m, 2H), 3.05-3.21 (br m, 2H), 3.40 (s, 3H), 3.55 (s, 3H), 3.70-3.85 (br m, 2H), 7.05 (s, 2H).

LC/MS (ES+): 385/387 (M+H)⁺

Step 2: Preparation of 3-(4-chloro-2,6-dimethyl-phenyl)-1,4-dihydroxy-8-methoxy-1,8-diaza-spiro[4.5]dec-3-en-2-one (compound P2ii.103)

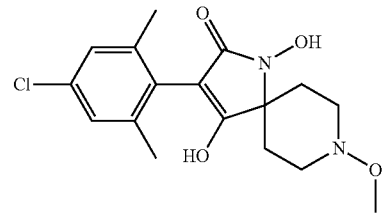

To a suspension of 4-{[2-(4-chloro-2,6-dimethyl-phenyl)-acetyl]-hydroxy-amino}-1-methoxy-piperidine-4-carboxylic acid methyl ester (0.40 g, 1.04 mmol) in dimethylformamide (3 ml) at 0° C. was added potassium tert-butoxide (0.35 g, 3.12 mmol) in portions. After completion of the addition, stirring was continued at 0° C. for 30 minutes and at room temperature overnight. The reaction mixture was poured into cold water (0° C.), the pH adjusted to ca 5.5 by adding 1 N HCl and then thoroughly extracted with ethyl acetate (three times). The combined organic layers were washed with water and brine, dried over sodium sulfate and concentrated. The resulting crude material was purified by column chromatography on silica gel (gradient ethyl acetate/cyclohexane 1:1→ethyl acetate). Yield: 0.14 g of 3-(4-chloro-2,6-dimethyl-phenyl)-1,4-dihydroxy-8-methoxy-1,8-diaza-spiro[4.5]dec-3-en-2-one (compound P2ii.103) as a white solid.

¹H-NMR (CD₃OD): 1.95-2.10 (br m, 2H), 2.15-2.30 (br m, 2H), 2.18 (s, 6H), 3.20-3.50 (br m, total 4H), 3.55 (s, 3H), 7.14 (s, 2H).

LC/MS (ES+): 353/355 (M+H)⁺

Step 3: Preparation of carbonic acid 3-(4-chloro-2,6-dimethyl-phenyl)-1-ethoxycarbonyloxy-8-methoxy-2-oxo-1,8-diaza-spiro[4.5]dec-3-en-4-yl ester ethyl ester (title compound P1ii.115)

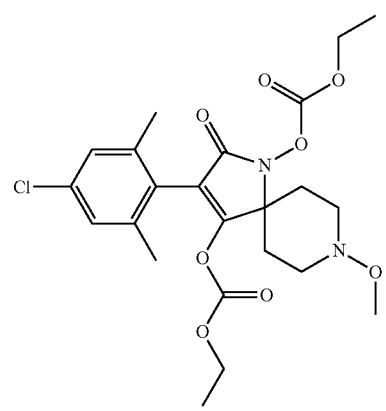 [SMILES: CCOC(=O)OC1=C(c2c(C)cc(Cl)cc2C)C(=O)N(OC(=O)OCC)C12CCN(OC)CC2]

To a solution of 3-(4-chloro-2,6-dimethyl-phenyl)-1,4-dihydroxy-8-methoxy-1,8-diaza-spiro[4.5]dec-3-en-2-one (140 mg, 0.40 mmol) and triethylamine (0.1 ml, 72 mg, 0.71 mmol) in THF (3 ml) at 0° C. was added a solution of ethyl chloroformate (0.05 ml, 52 mg, 0.48 mmol) dissolved in THF (2 ml) dropwise. The suspension was stirred at 0° C. for 30 minutes. Then the reaction mixture was poured into cold (0° C.) water and thoroughly extracted three times with ethyl acetate. The combined organic layers were washed with water and brine, dried over sodium sulfate and concentrated. The raw material was purified by column chromatography on silica gel (ethyl acetate/cyclohexane 1:4). Yield: 70 mg of carbonic acid 3-(4-chloro-2,6-dimethyl-phenyl)-1-ethoxycarbonyloxy-8-methoxy-2-oxo-1,8-diaza-spiro[4.5]dec-3-en-4-yl ester ethyl ester (title compound P1ii.115) as a colorless gum.

$^1$H-NMR (CDCl$_3$): 1.09 (t, 3H), 1.39 (t, 3H), 2.08-2.30 (br m, 4H), 2.19 (s, 6H), 2.70-3.13 (br m, total 2H), 3.20-3.42 (br m, 2H), 3.55 (s, 3H), 4.03 (q, 2H), 4.38 (br q, 2H), 7.05 (s, 2H).
LC/MS (ES+): 497/499 (M+H)$^+$

EXAMPLE 21

Preparation of Cyclopropanecarboxylic acid 3-(2,5-dimethyl-phenyl)-8-methoxy-1-methoxymethoxy-2-oxo-1,8-diaza-spiro[4.5]dec-3-en-4-yl ester (compound P1ii.4)

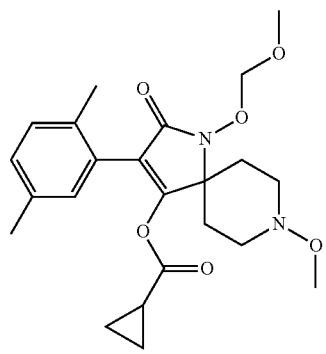 [SMILES: COCON1C(=O)C(c2cc(C)ccc2C)=C(OC(=O)C2CC2)C12CCN(OC)CC2]

To a solution of 3-(2,5-dimethyl-phenyl)-4-hydroxy-8-methoxy-1-methoxymethoxy-1,8-diaza-spiro[4.5]dec-3-en-2-one (compound P2ii.2) (200 mg, 0.55 mmol), triethylamine (0.153 ml, 111 mg, 1.10 mmol) and a catalytic amount of 4-dimethylaminopyridine in tetrahydrofuran (6 ml) at 0° C. was added cyclopropanecarboxylic acid chloride (0.066 ml, 75 mg, 0.72 mmol) dropwise. The suspension was stirred at 0° C. for 10 minutes, and at room temperature for one hour. The reaction mixture was evaporated, diluted with ethyl acetate and filtered to remove salts. The filtrate was washed with a saturated aqueous sodium hydrogen carbonate solution and brine, dried over sodium sulfate and concentrated. The residue was purified by chromatography on silica gel (ethyl acetate/hexane 1:2) to afford 200 mg of an oily product. This material was triturated with diethyl ether, filtered and dried. Yield: 190 mg of cyclopropanecarboxylic acid 3-(2,5-dimethyl-phenyl)-8-methoxy-1-methoxymethoxy-2-oxo-1,8-diaza-spiro[4.5]dec-3-en-4-yl ester (title compound P1ii.4) as a white solid, mp 114-116° C.

$^1$H-NMR (CDCl$_3$): 0.75-0.92 (br m, 4H), 1.63 (br m, 1H), 1.72-2.03 (br m, 2H), 2.19 (s, 3H), 2.28 (s, 3H), 2.47 (br m, 2H), 2.88 (br m, 1H), 3.16-3.45 (br m, 3H), 3.56 (s, 3H), 3.64 (s, 3H), 5.07 (br s, 2H), 6.91 (s, 1H), 7.02 (d, 1H), 7.08 (d, 1H).
LC/MS (ES+): 431 (M+H)$^+$

EXAMPLE 22

Preparation of Carbonic acid ethyl ester 1-(2-methanesulfinyl-ethoxy)-8-methoxy-2-oxo-3-(2,4,6-trimethyl-phenyl)-1,8-diaza-spiro[4.5]dec-3-en-4-yl ester (compound P1ii.111)

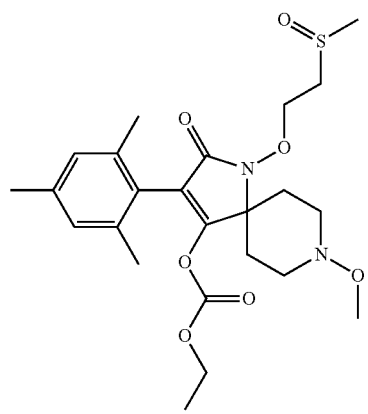

To a solution of carbonic acid ethyl ester 8-methoxy-1-(2-methylsulfanyl-ethoxy)-2-oxo-3-(2,4,6-trimethyl-phenyl)-1,8-diaza-spiro[4.5]dec-3-en-4-yl ester (compound P1ii.110) (400 mg, 0.84 mmol) in dichloromethane (10 ml) at 0° C. was added 3-chloroperbenzoic acid (210 mg, MCPBA ~70%, 0.85 mmol). The reaction mixture was stirred at room temperature overnight, then poured on saturated aqueous sodium metabisulfite and the layers separated. The aqueous phase was extracted with dichloromethane (3×), the combined organic layers were washed with water and brine, dried over sodium sulfate and concentrated. The residue was purified by chromatography on silica gel (ethyl acetate/methanol 20:1). Yield: 220 mg of carbonic acid ethyl ester 1-(2-methanesulfinyl-ethoxy)-8-methoxy-2-oxo-3-(2,4,6-trimethyl-phenyl)-1,8-diaza-spiro[4.5]dec-3-en-4-yl ester (title compound P1ii.111) as a colorless gum.

$^1$H-NMR (CD$_3$OD): 1.03 (t, 3H), 2.05 (br m, 2H), 2.13 (s, 3H), 2.14 (s, 3H), 2.26 (s, 3H), 2.33 (m, 2H), 2.75 (s, 3H), 2.96 (br m, 1H), 3.09-3.46 (br m, total 5H), 3.55 (s, 3H), 4.01 (q, 2H), 4.59 (m, 2H), 6.89 (s, 2H).
LC/MS (ES+): 495 (M+H)$^+$

EXAMPLE 23

Preparation of 2-(4-Chloro-2,6-dimethyl-phenyl)-N-(4-cyano-1-methoxy-piperidin-4-yl)-N-ethoxy-acetamide (compound P3ii.49)

Step 1: Preparation of 1-methoxy-piperidin-4-one O-ethyl-oxime

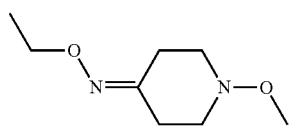

Obtained from 1-methoxy-piperidin-4-one (20 g, 154.85 mmol), triethylamine (47.4 ml, 34.5 g, 340.66 mmol) and O-ethyl-hydroxylamine hydrochloride (30.2 g, 309.69 mmol) in methanol (300 ml) according to procedure 'EXAMPLE 11, Step 1'. Yield: 22.02 g of 1-methoxy-piperidin-4-one O-ethyl-oxime as a colorless, viscous liquid. This material was used without further purification in the next step.

$^1$H-NMR (CDCl$_3$): 1.25 (t, 3H), 2.20-3.40 (br signals, total 8H), 3.55 (s, 3H), 4.07 (q, 2H).

LC/MS (ES+): 173 (M+H)$^+$

Step 2: Preparation of 4-ethoxyamino-1-methoxy-piperidine-4-carbonitrile (compound P4ii.3)

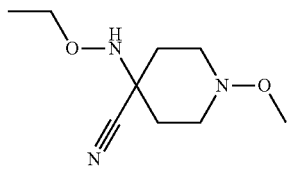

Obtained from 1-methoxy-piperidin-4-one O-ethyl-oxime (10 g, 58.06 mmol), potassium dihydrogen phosphate (31.6 g, 232.20 mmol) in water (50 ml) at 0-5° C. to which was added a solution of potassium cyanide (6.81 g, 104.58 mmol) in water (50 ml) according to procedure 'EXAMPLE 11, Step 2'. The reaction mixture was stirred at room temperature for 2 days [treated in between with another portion of potassium dihydrogen phosphate (7.9 g) and potassium cyanide (1.9 g)] and at 40° C. for 4 days [again treated in between with another portion of potassium dihydrogen phosphate (7.9 g) and potassium cyanide (1.9 g)]. The mixture was flushed with nitrogen, the aqueous layer saturated with sodium chloride and extracted with diethyl ether (4×150 ml). The combined organic layers were washed with brine, dried over sodium sulfate and concentrated. The residue was purified by chromatography on silica gel (ethyl acetate/cyclohexane 1:2). Yield: 5.1 g of 4-ethoxyamino-1-methoxy-piperidine-4-carbonitrile (compound P4ii.3) as a pale yellow oil.

$^1$H-NMR (CDCl$_3$): 1.19 (t, 3H), 1.59-2.29 (br signals, total 4H), 2.64-3.43 (br signals, total 4H), 3.52 (s, 3H), 3.80 (q, 2H), 5.37 (br s, 1H).

IR (CN): ν 2235.3 cm$^{-1}$. LC/MS (ES+): 200 (M+H)$^+$

Step 3: Preparation of 2-(4-chloro-2,6-dimethyl-phenyl)-N-(4-cyano-1-methoxy-piperidin-4-yl)-N-ethoxy-acetamide (title compound P3ii.49)

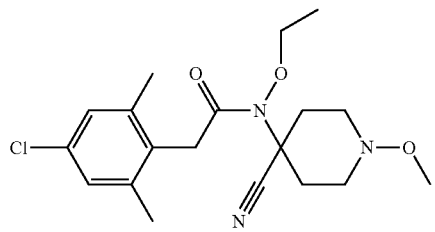 [SMILES: CCON(C(=O)Cc1c(C)cc(Cl)cc1C)C1(C#N)CCN(OC)CC1]

To a solution of 4-ethoxyamino-1-methoxy-piperidine-4-carbonitrile (2.0 g, 10.04 mmol), triethylamine (3.49 ml, 2.54 g, 25.09 mmol) and a catalytic amount of 4-dimethylaminopyridine in tetrahydrofuran (10 ml) at 0° C. was added a solution of (4-chloro-2,6-dimethyl-phenyl)-acetyl chloride (2.18 g, 10.04 mmol) in tetrahydrofuran (1 ml) dropwise. The suspension was stirred at 0° C. for 15 minutes, and at room temperature overnight. The reaction mixture was evaporated, diluted with ethyl acetate and water, and the layers separated. The aqueous phase was extracted with ethyl acetate, the combined organic layers washed with brine, dried over sodium sulfate and concentrated. The crude material was triturated with diisopropyl ether, filtered and the filtrate concentrated. The oily residue was purified by chromatography on silica gel (ethyl acetate/hexane 1:1).

Yield: 1.53 g of 2-(4-chloro-2,6-dimethyl-phenyl)-N-(4-cyano-1-methoxy-piperidin-4-yl)-N-ethoxy-acetamide (title compound P3ii.49) as a colorless oil, which solidified upon standing, mp 100-103° C.

$^1$H-NMR (CDCl$_3$): 1.36 (t, 3H), 2.00-3.44 (br signals, total 8H), 2.24 (s, 6H), 3.51 (br s, 3H), 3.63 (br d, 1H), 4.04 (br d, 1H), 4.13 (br q, 2H), 7.04 (s, 2H).

IR (CN): ν 2243.4 cm$^{-1}$. LC/MS (ES+): 380/382 (M+H)$^+$

EXAMPLE 24

Preparation of 3-(4'-Chloro-3,5-dimethyl-biphenyl-4-yl)-4-hydroxy-8-methoxy-1-methoxymethoxy-1,8-diaza-spiro[4.5]dec-3-en-2-one (compound P2ii.15)

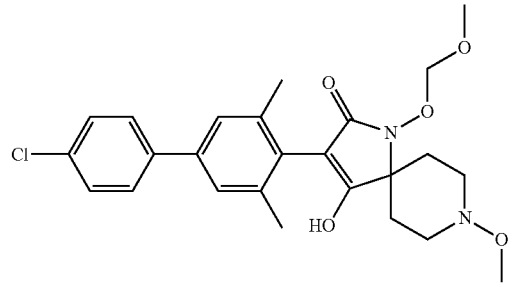 [SMILES: COCON1C(=O)C(c2c(C)cc(-c3ccc(Cl)cc3)cc2C)=C(O)C12CCN(OC)CC2]

To a suspension of 3-(4-bromo-2,6-dimethyl-phenyl)-4-hydroxy-8-methoxy-1-methoxymethoxy-1,8-diaza-spiro[4.5]dec-3-en-2-one (compound P2ii.14) (500 mg, 1.13 mmol) in dimethoxyethane (22 ml) under nitrogen atmosphere was added tetrakis(triphenylphosphine)palladium(0) (65 mg, 0.056 mmol) and the mixture stirred at room temperature for 15 minutes. After further addition of water (4.3 ml), 4-chlorophenylboronic acid (213 mg, 1.36 mmol) and sodium carbonate (410 mg, 3.87 mmol), the mixture was heated at reflux for 3 hours. The reaction mixture was acidified at room temperature with 1N hydrochloric acid and extracted with ethyl acetate (3×). The combined organic layers were washed with brine, dried over sodium sulfate and concentrated. The residue was purified by chromatography on silica gel (ethyl acetate/heptane 5:3) to afford 150 mg of an gummy product. This material was triturated with methanol, filtered and dried.

Yield: 90 mg of 3-(4'-chloro-3,5-dimethyl-biphenyl-4-yl)-4-hydroxy-8-methoxy-1-methoxymethoxy-1,8-diaza-spiro[4.5]dec-3-en-2-one (compound P2ii.15) as a white solid, mp 128° C. (dec).

$^1$H-NMR (CDCl$_3$, selected signals only): 2.27 (br s, 6H, mesityl CH$_3$), 3.60 (br s, 3H, OCH$_3$), 3.62 (br s, 3H, OCH$_3$), 5.05 (s, 2H, OCH$_2$OCH$_3$), 7.26 (s, 2H, H$_{arom}$), 7.39 (d, 2H, H$_{arom}$), 7.49 (d, 2H, H$_{arom}$).

LC/MS (ES+): 473/475 (M+H)$^+$

EXAMPLE 25

Alternative preparation of 4-Hydroxyamino-1-methoxy-piperidine-4-carboxylic acid methyl ester (compound P4ii.2)

Step 1: Preparation of 4-hydroxyamino-1-methoxy-piperidine-4-carboxylic acid (compound P4ii.4)

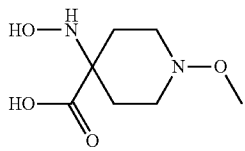

4-Hydroxyamino-1-methoxy-piperidine-4-carbonitrile (compound P4ii.1) (1.5 g, 8.76 mmol) was added in two portions to concentrated sulfuric acid (15 ml) at 0° C. After stirring for 20 minutes, a yellow solution was obtained which was kept at room temperature for two days. The reaction mixture was diluted with ice water (30 ml), heated at reflux for 4 hours, then poured on ice (25 g) and neutralised with 25% aqueous ammonia under cooling to pH 7-8. The reaction mixture was evaporated and the white solid residue triturated with warm (40° C.) methanol (3×50 ml), filtered and the combined methanol phases concentrated. The residue was treated with toluene (3×50 ml) to remove water azeotropically until constant weight, then triturated with tetrahydrofuran, filtered and dried. Yield: 1.58 g of 4-hydroxyamino-1-methoxy-piperidine-4-carboxylic acid (compound P4ii.4) as a white solid, mp 180° C. (dec).

$^1$H-NMR (CD$_3$OD): 1.54-2.29 (br signals, total 4H), 2.82 (br m, 2H), 3.07-3.26 (br signals, total 2H), 3.49 (s, 3H).

LC/MS (ES+): 191 (M+H)$^+$

Step 2: Preparation of 4-hydroxyamino-1-methoxy-piperidine-4-carboxylic acid methyl ester (title compound P4ii.2)

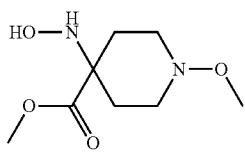

To a suspension of 4-hydroxyamino-1-methoxy-piperidine-4-carboxylic acid (1.0 g, 5.26 mmol) in methanol (25 ml) at 0-10° C. was added thionyl chloride (1.14 ml, 1.88 g, 15.77 mmol) and the reaction mixture was heated at reflux for 48 hours. After cooling, the mixture was concentrated, the residue diluted with ice water (20 ml) and neutralised with aqueous sodium bicarbonate. The aqueous phase was extracted with diethyl ether (3×25 ml), the combined organic layers washed with aqueous sodium bicarbonate and brine, dried over sodium sulfate and concentrated. Yield: 0.53 g of 4-hydroxyamino-1-methoxy-piperidine-4-carboxylic acid methyl ester (title compound P4ii.2) as a viscous, yellowish oil. This material was identical to the compound described above under preparation 'EXAMPLE 11, Step 3'.

LC/MS (ES+): 205 (M+H)$^+$

Compounds of the formula I from Table P1ii, compounds from Table P2ii and intermediates listed in Tables P3ii and P4ii can be prepared by analogous procedures. Either one of the following LC-MS methods was used to characterize the compounds:

Method A

MS: ZQ Mass Spectrometer from Waters (Single quadrupole mass spectrometer); Ionisation method: Electrospray; Polarity: positive/negative ions; Capillary (kV) 3.00, Cone (V) 30.00, Extractor (V) 2.00, Source Temperature (° C.) 100, Desolvation Temperature (° C.) 250, Cone Gas Flow (L/Hr) 50, Desolvation Gas Flow (L/Hr) 400; Mass range: 150 to 1000 or 100 to 900 Da.

LC: HP 1100 HPLC from Agilent: solvent degasser, quaternary pump (ZCQ)/binary pump (ZDQ), heated column compartment and diode-array detector. Column: Phenomenex Gemini C18, 3 µm particle size, 110 Angström, 30×3 mm, Temp: 60° C.; DAD Wavelength range (nm): 200 to 500; Solvent gradient: A=water+0.05% v/v HCOOH, B=Acetonitril/Methanol (4:1, v/v)+0.04% v/v HCOOH.

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method B

MS: ZMD Mass Spectrometer from Waters (Single quadrupole mass spectrometer); Ionisation method: Electrospray; Polarity: positive/negative ions; Capillary (kV) 3.80, Cone (V) 30.00, Extractor (V) 3.00, Source Temperature (° C.) 150, Desolvation Temperature (° C.) 350, Cone Gas Flow (L/Hr) OFF, Desolvation Gas Flow (L/Hr) 600; Mass range: 150 to 1000 (100 to 1500 for LowMass) or 100 to 900 Da.

LC: HP 1100 HPLC from Agilent: solvent degasser, binary pump, heated column compartment and diode-array detector. Column: Phenomenex Gemini C18, 3 µm particle size, 110 Angstöm, 30×3 mm, Temp: 60° C.; DAD Wavelength range (nm): 200 to 500; Solvent gradient: A=water+ 0.05% v/v HCOOH, B=Acetonitril/Methanol (4:1, v:v)+ 0.04% v/v HCOOH.

| Time (min) | A % | B % | Flow (ml/min) |
|---|---|---|---|
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

The characteristic values obtained for each compound were the retention time ("R$_t$", recorded in minutes) and the molecular ion as listed in Table P1ii, Table P2ii, Table P3ii and in Table P4ii.

TABLE P1ii

*Physical data of compounds of formula I:*

| Compound No. | Structures | Melting Point | MS/NMR |
|---|---|---|---|
| P1ii.1 | 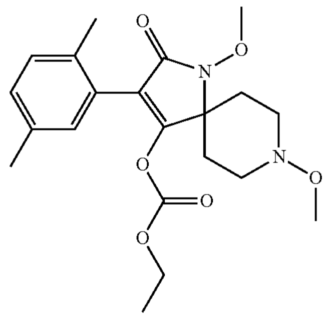 [SMILES: CCOC(=O)OC1=C(c2cc(C)ccc2C)C(=O)N(OC)C12CCN(OC)CC2] | gum | LC/MS: 405 (M + H)$^+$<br>R$_t$ = 1.88 min |
| P1ii.2 | EXAMPLE 11, step 6 | 109-111° C. | LC/MS: 435 (M + H)$^+$<br>R$_t$ = 1.90 min |
| P1ii.3 | 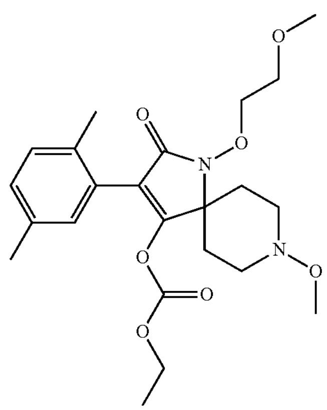 [SMILES: CCOC(=O)OC1=C(c2cc(C)ccc2C)C(=O)N(OCCOC)C12CCN(OC)CC2] | gum | LC/MS: 449 (M + H)$^+$<br>R$_t$ = 1.91 min |
| P1ii.4 | EXAMPLE 21 | 114-116° C. | LC/MS: 431 (M + H)$^+$<br>R$_t$ = 1.87 min |

TABLE P1ii-continued

Physical data of compounds of formula I:

| Compound No. | Structures | Melting Point | MS/NMR |
|---|---|---|---|
| P1ii.5 | 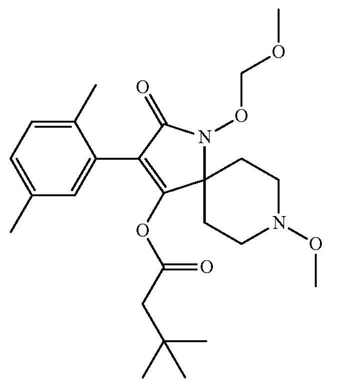 [SMILES: COCON1C(=O)C(c2cc(C)ccc2C)=C(OC(=O)CC(C)(C)C)C12CCN(OC)CC2] | 93-95° C. | LC/MS: 461 (M + H)+<br>$R_t$ = 2.12 min |
| P1ii.6 | 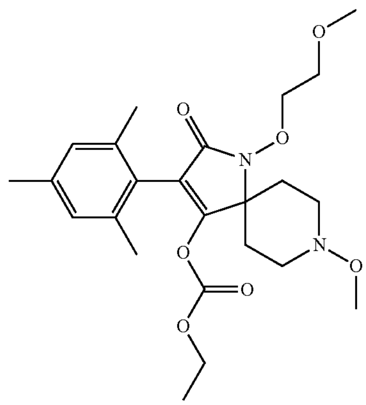 | gum | LC/MS: 463 (M + H)+<br>$R_t$ = 1.95 min |
| P1ii.7 | 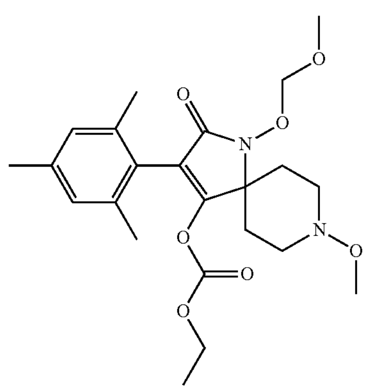 | 109-111° C. | LC/MS: 449 (M + H)+<br>$R_t$ = 1.95 min |
| P1ii.8 | 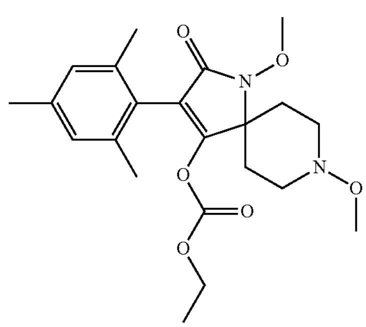 | 96-97° C. | LC/MS: 419 (M + H)+<br>$R_t$ = 1.91 min |

TABLE P1ii-continued

Physical data of compounds of formula I:

| Compound No. | Structures | Melting Point | MS/NMR |
|---|---|---|---|
| P1ii.9 | EXAMPLE 13, step 2 | 100-102° C. | LC/MS: 475 (M + H)$^+$<br>R$_t$ = 1.97 min |
| P1ii.10 | 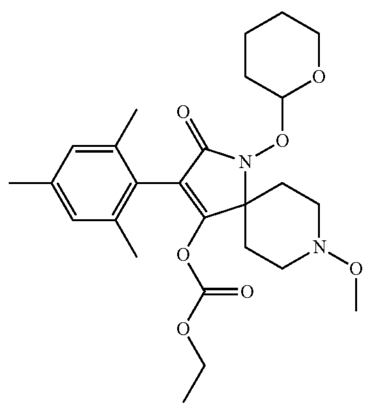 | 130-132° C. | LC/MS: 489 (M + H)$^+$<br>R$_t$ = 2.05 min |
| P1ii.11 | EXAMPLE 13, step 1 | 154-155° C. | LC/MS: 405 (M + H)$^+$<br>R$_t$ = 1.79 min |
| P1ii.12 | 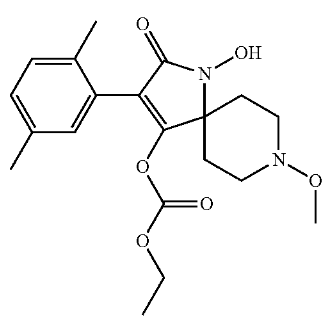 [SMILES: CCOC(=O)OC1=C(c2cc(C)ccc2C)C(=O)N(O)C12CCN(OC)CC2] | 78-81° C. | LC/MS: 391 (M + H)$^+$<br>R$_t$ = 1.67 min |

TABLE P1ii-continued

Physical data of compounds of formula I:

| Compound No. | Structures | Melting Point | MS/NMR |
|---|---|---|---|
| P1ii.13 | EXAMPLE 15 | gum | LC/MS: 463 (M + H)+<br>$R_t$ = 1.98 min |
| P1ii.14 | 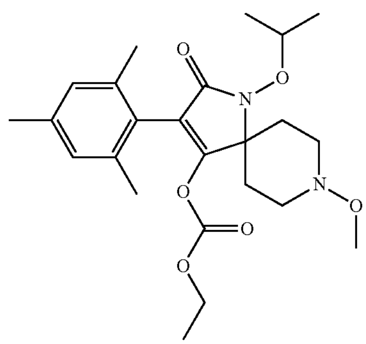 | gum | LC/MS: 447 (M + H)+<br>$R_t$ = 2.07 min |
| P1ii.15 | 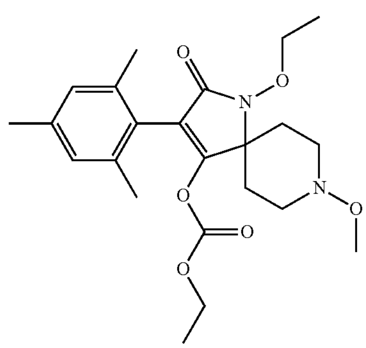 | 84-86° C. | LC/MS: 433 (M + H)+<br>$R_t$ = 1.98 min |
| P1ii.16 | 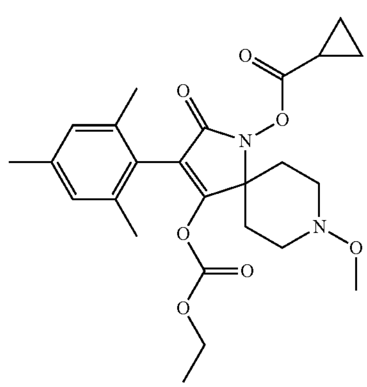 [SMILES: CCOC(=O)OC1=C(c2c(C)cc(C)cc2C)C(=O)N(OC(=O)C2CC2)C12CCN(OC)CC2] | gum | LC/MS: 473 (M + H)+<br>$R_t$ = 2.03 min |

TABLE P1ii-continued

Physical data of compounds of formula I:

| Compound No. | Structures | Melting Point | MS/NMR |
|---|---|---|---|
| P1ii.17 | 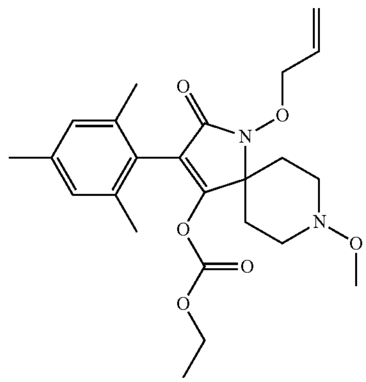 | gum | LC/MS: 445 (M + H)⁺<br>$R_t$ = 2.04 min |
| P1ii.18 | 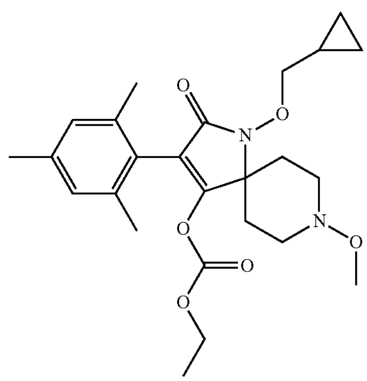 [SMILES: CCOC(=O)OC1=C(c2c(C)cc(C)cc2C)C(=O)N(OCC2CC2)C12CCN(OC)CC2] | gum | LC/MS: 459 (M + H)⁺<br>$R_t$ = 2.09 min |
| P1ii.19 | 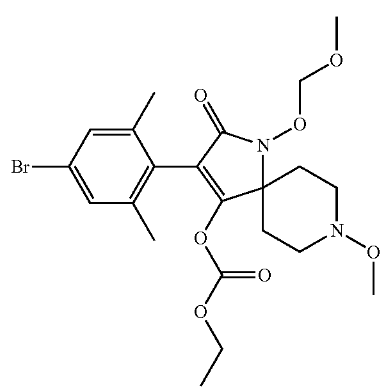 [SMILES: CCOC(=O)OC1=C(c2c(C)cc(Br)cc2C)C(=O)N(OCOC)C12CCN(OC)CC2] | 83-85° C. | LC/MS: 513/515 (M + H)⁺<br>$R_t$ = 2.03 min |
| P1ii.20 | 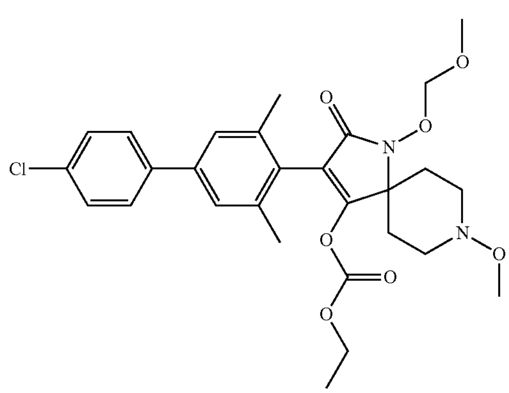 [SMILES: CCOC(=O)OC1=C(c2c(C)cc(-c3ccc(Cl)cc3)cc2C)C(=O)N(OCOC)C12CCN(OC)CC2] | 110-113° C. | LC/MS: 545/547 (M + H)⁺<br>$R_t$ = 2.20 min |

TABLE P1ii-continued

Physical data of compounds of formula I:

| Compound No. | Structures | Melting Point | MS/NMR |
|---|---|---|---|
| P1ii.21 | 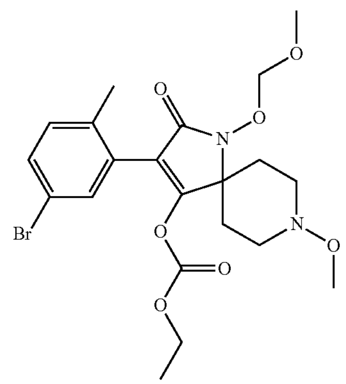 | 118-121° C. | LC/MS: 499/501 (M + H)$^+$<br>$R_t$ = 1.96 min |
| P1ii.22 | 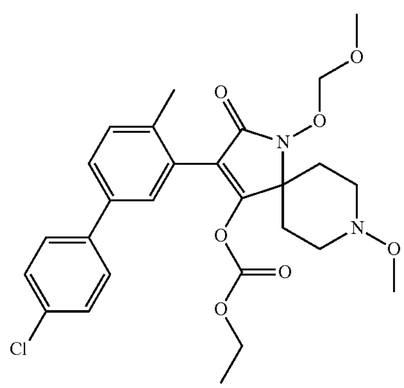 [SMILES: CCOC(=O)OC1=C(c2cc(-c3ccc(Cl)cc3)ccc2C)C(=O)N(OCOC)C12CCN(OC)CC2] | gum | LC/MS: 531/533 (M + H)$^+$<br>$R_t$ = 2.15 min |
| P1ii.23 | 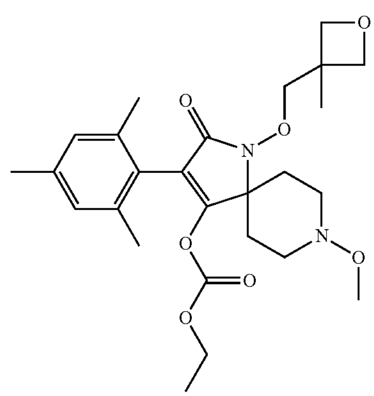 [SMILES: CCOC(=O)OC1=C(c2c(C)cc(C)cc2C)C(=O)N(OCC2(C)COC2)C12CCN(OC)CC2] | 132-134° C. | LC/MS: 489 (M + H)$^+$<br>$R_t$ = 1.99 min |
| P1ii.24 | 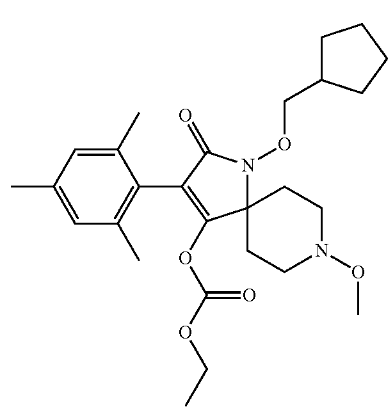 [SMILES: CCOC(=O)OC1=C(c2c(C)cc(C)cc2C)C(=O)N(OCC2CCCC2)C12CCN(OC)CC2] | 53-55° C. | LC/MS: 489 (M + H)$^+$<br>$R_t$ = 2.04 min |

TABLE P1ii-continued

Physical data of compounds of formula I:

| Compound No. | Structures | Melting Point | MS/NMR |
|---|---|---|---|
| P1ii.25 | 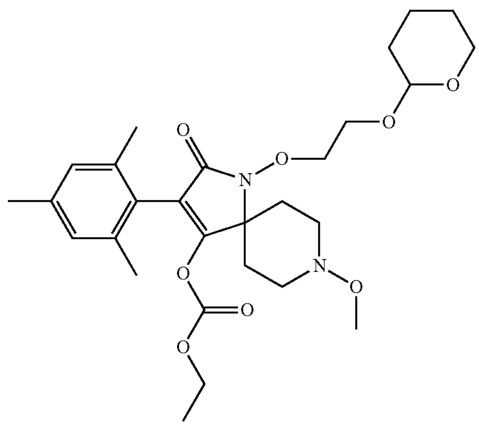 [SMILES: CCOC(=O)OC1=C(c2c(C)cc(C)cc2C)C(=O)N(OCCOC2CCCCO2)C12CCN(OC)CC2] | gum | LC/MS: 533 (M + H)+<br>$R_t$ = 2.12 min |
| P1ii.26 | 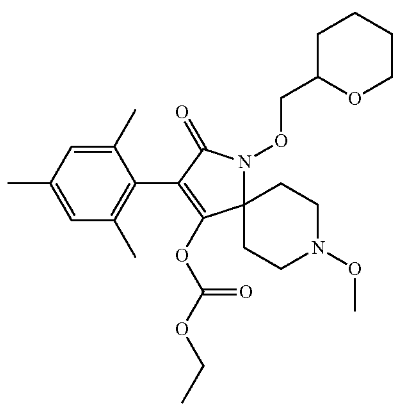 [SMILES: CCOC(=O)OC1=C(c2c(C)cc(C)cc2C)C(=O)N(OCC2CCCCO2)C12CCN(OC)CC2] | 74-76° C. | LC/MS: 503 (M + H)+<br>$R_t$ = 2.10 min |
| P1ii.27 | 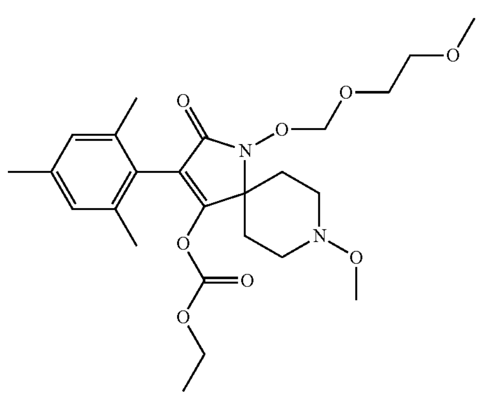 | 57-59° C. | LC/MS: 493 (M + H)+<br>$R_t$ = 1.96 min |

TABLE P1ii-continued

Physical data of compounds of formula I:

| Compound No. | Structures | Melting Point | MS/NMR |
|---|---|---|---|
| P1ii.28 | 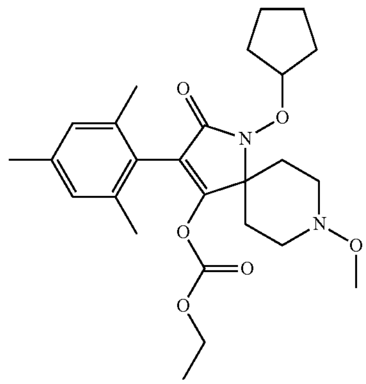 | gum | LC/MS: 473 (M + H)+<br>$R_t$ = 2.17 min |
| P1ii.29 | 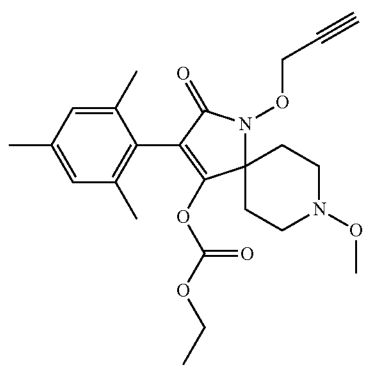 [SMILES: C#CCON1C(=O)C(c2c(C)cc(C)cc2C)=C(OC(=O)OCC)C12CCN(OC)CC2] | gum | LC/MS: 443 (M + H)+<br>$R_t$ = 1.99 min |
| P1ii.30 | 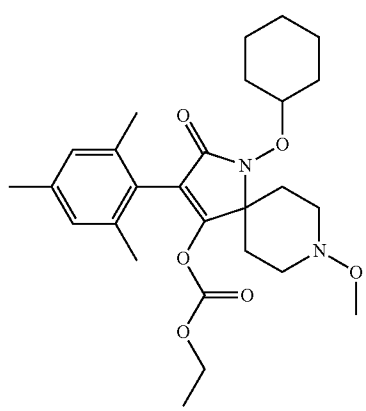 | gum | LC/MS: 487 (M + H)+<br>$R_t$ = 2.19 min |
| P1ii.31 | 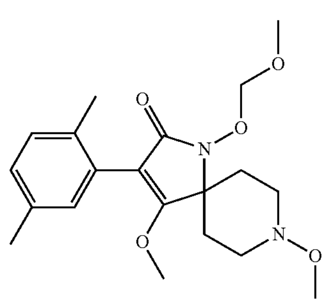 [SMILES: COCON1C(=O)C(c2cc(C)ccc2C)=C(OC)C12CCN(OC)CC2] | 91-93° C. | LC/MS: 377 (M + H)+<br>$R_t$ = 1.79 min |

TABLE P1ii-continued

Physical data of compounds of formula I:

| Compound No. | Structures | Melting Point | MS/NMR |
|---|---|---|---|
| P1ii.32 | 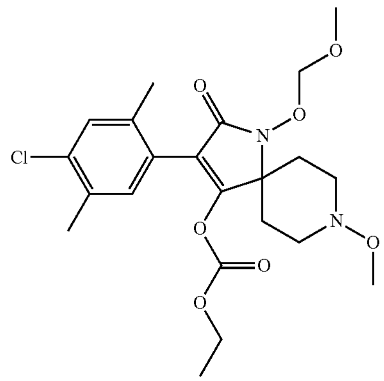 [SMILES: CCOC(=O)OC1=C(c2cc(C)c(Cl)cc2C)C(=O)N(OCOC)C12CCN(OC)CC2] | gum | LC/MS: 469/471 (M + H)$^+$<br>R$_t$ = 1.94 min |
| P1ii.33 | 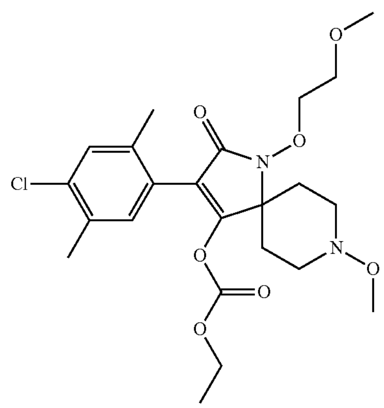 [SMILES: CCOC(=O)OC1=C(c2cc(C)c(Cl)cc2C)C(=O)N(OCCOC)C12CCN(OC)CC2] | gum | LC/MS: 483/485 (M + H)$^+$<br>R$_t$ = 1.93 min |
| P1ii.34 | 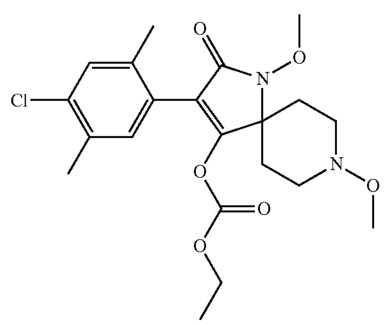 [SMILES: CCOC(=O)OC1=C(c2cc(C)c(Cl)cc2C)C(=O)N(OC)C12CCN(OC)CC2] | gum | LC/MS: 439/441 (M + H)$^+$<br>R$_t$ = 1.91 min |
| P1ii.35 | 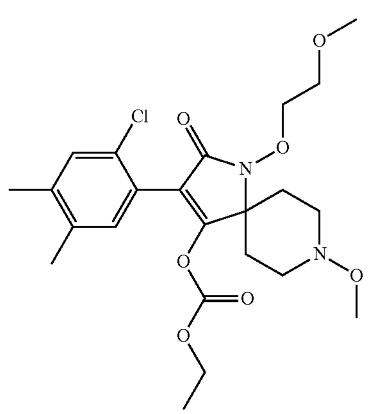 | solid | LC/MS: 483/485 (M + H)$^+$<br>R$_t$ = 1.87 min |

TABLE P1ii-continued

Physical data of compounds of formula I:

| Compound No. | Structures | Melting Point | MS/NMR |
|---|---|---|---|
| P1ii.36 | 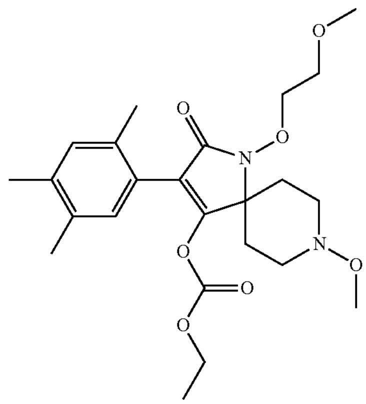 | gum | LC/MS: 463 (M + H)+ <br> $R_t$ = 1.91 min |
| P1ii.37 | 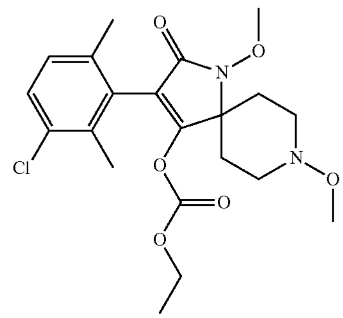 [SMILES: CCOC(=O)OC1=C(c2c(C)ccc(Cl)c2C)C(=O)N(OC)C12CCN(OC)CC2] | gum | LC/MS: 439/441 (M + H)+ <br> $R_t$ = 1.91 min |
| P1ii.38 | 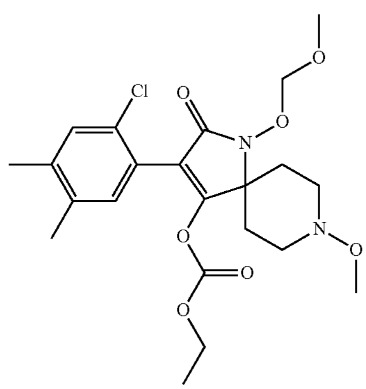 | solid | LC/MS: 469/471 (M + H)+ <br> $R_t$ = 1.90 min |
| P1ii.39 | 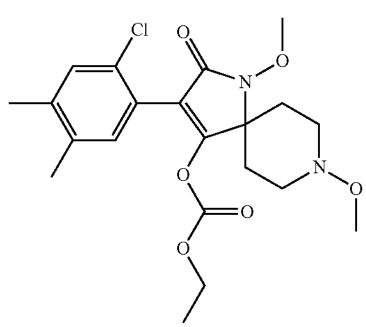 | gum | LC/MS: 439/441 (M + H)+ <br> $R_t$ = 1.84 min |

TABLE P1ii-continued

Physical data of compounds of formula I:

| Compound No. | Structures | Melting Point | MS/NMR |
|---|---|---|---|
| P1ii.40 | 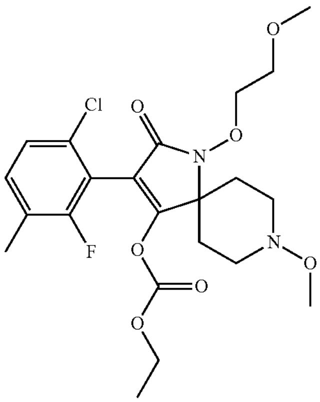 | gum | LC/MS: 487/489 (M + H)+<br>$R_t$ = 1.84 min |
| P1ii.41 | 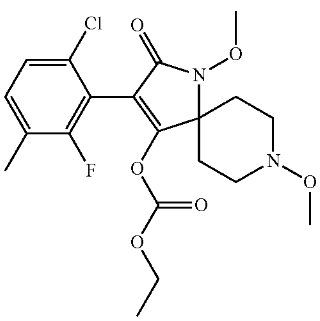 [SMILES: CCOC(=O)OC1=C(c2c(Cl)ccc(C)c2F)C(=O)N(OC)C12CCN(OC)CC2] | solid | LC/MS: 443/445 (M + H)+<br>$R_t$ = 1.82 min |
| P1ii.42 | 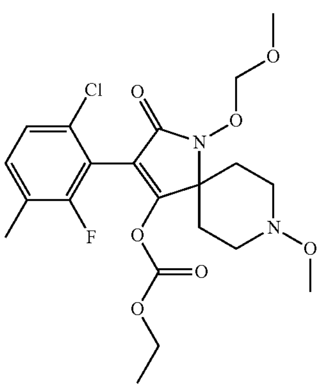 [SMILES: CCOC(=O)OC1=C(c2c(Cl)ccc(C)c2F)C(=O)N(OCOC)C12CCN(OC)CC2] | 119-123° C. | LC/MS: 473/475 (M + H)+<br>$R_t$ = 1.85 min |
| P1ii.43 | 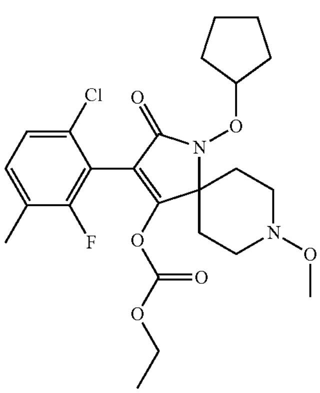 | 135-137° C. | LC/MS: 499/501 (M + H)+<br>$R_t$ = 1.89 min |

TABLE P1ii-continued

Physical data of compounds of formula I:

| Compound No. | Structures | Melting Point | MS/NMR |
|---|---|---|---|
| P1ii.44 | 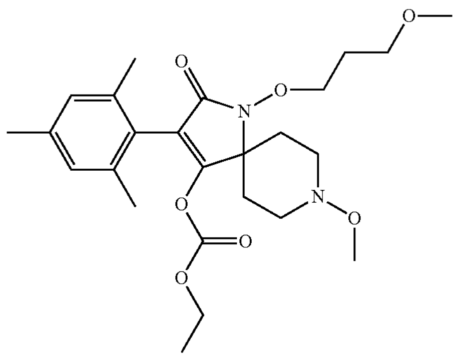 | 122-125° C. | LC/MS: 477 (M + H)+<br>$R_t$ = 1.97 min |
| P1ii.45 | 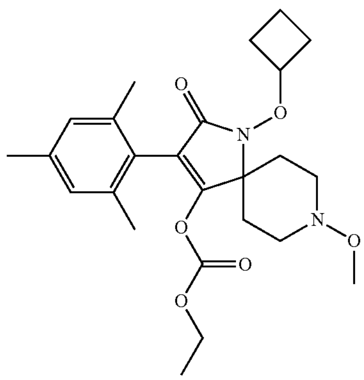 | gum | LC/MS: 459 (M + H)+<br>$R_t$ = 2.07 min |
| P1ii.46 | 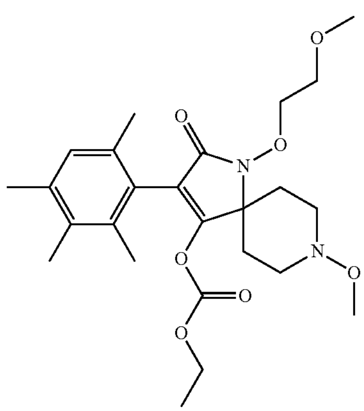 | gum | LC/MS: 477 (M + H)+<br>$R_t$ = 1.95 min |
| P1ii.47 | 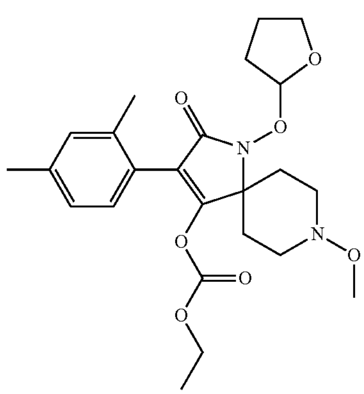 | gum | LC/MS: 461 (M + H)+<br>$R_t$ = 1.92 min |

TABLE P1ii-continued

Physical data of compounds of formula I:

| Compound No. | Structures | Melting Point | MS/NMR |
|---|---|---|---|
| P1ii.48 | 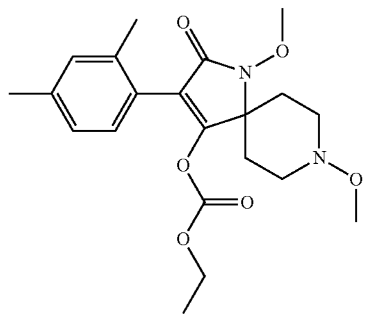 | gum | LC/MS: 405 (M + H)$^+$<br>R$_t$ = 1.83 min |
| P1ii.49 | 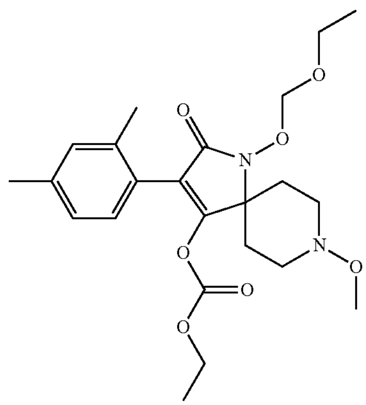 [SMILES: CCOCON1C(=O)C(c2ccc(C)cc2C)=C(OC(=O)OCC)C12CCN(OC)CC2] | powder | LC/MS: 449 (M + H)$^+$<br>R$_t$ = 1.95 min |
| P1ii.50 | 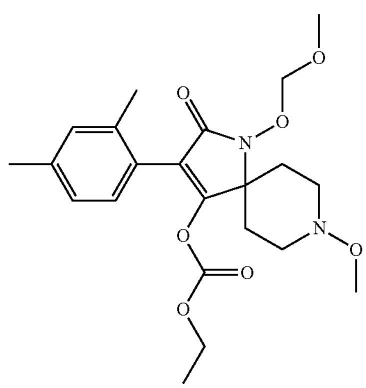 | 128-130° C. | LC/MS: 435 (M + H)$^+$<br>R$_t$ = 1.87 min |
| P1ii.51 | 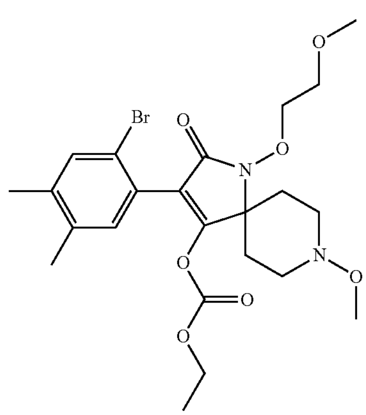 | gum | $^1$H-NMR (CDCl$_3$):<br>1.17 (t, 3H), 2.02-2.31 (br m, total 4H), 2.20 (s, 3H), 2.22 (s, 3H), 2.91-3.47 (br m, total 4H), 3.43 (s, 3H), 3.56 (s, 3H), 3.72 (br m, 2H), 4.08 (q, 2H), 4.35 (br m, 2H), 7.06 (s, 1H), 7.35 (s, 1H). |

TABLE P1ii-continued

Physical data of compounds of formula I:

| Compound No. | Structures | Melting Point | MS/NMR |
|---|---|---|---|
| P1ii.52 | 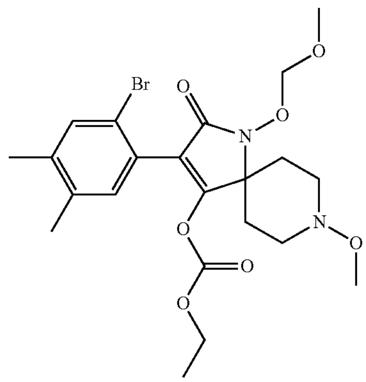 | gum | LC/MS: 513/515 (M + H)$^+$<br>$R_t$ = 1.92 min |
| P1ii.53 | 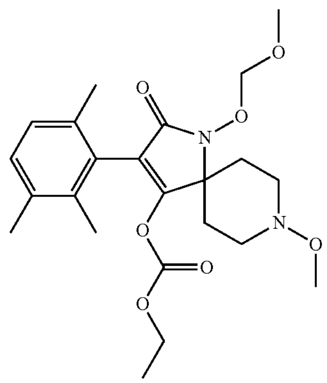 | gum | LC/MS: 449 (M + H)$^+$<br>$R_t$ = 1.90 min |
| P1ii.54 | 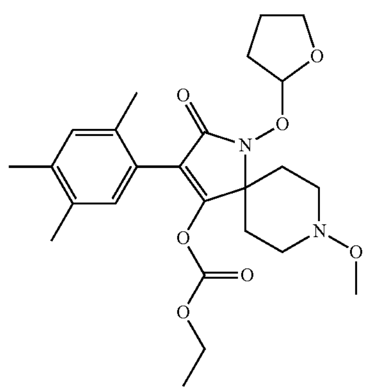 | gum | LC/MS: 475 (M + H)$^+$<br>$R_t$ = 1.96 min |
| P1ii.55 | 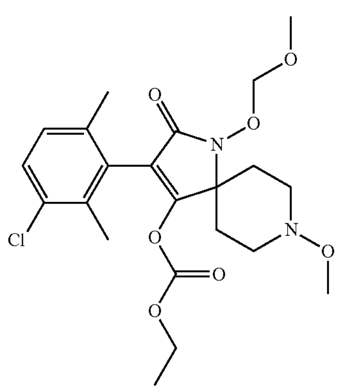 [SMILES: CCOC(=O)OC1=C(c2c(C)ccc(Cl)c2C)C(=O)N(OCOC)C12CCN(OC)CC2] | gum | LC/MS: 469/471 (M + H)$^+$<br>$R_t$ = 1.96 min |

TABLE P1ii-continued

Physical data of compounds of formula I:

| Compound No. | Structures | Melting Point | MS/NMR |
|---|---|---|---|
| P1ii.56 | 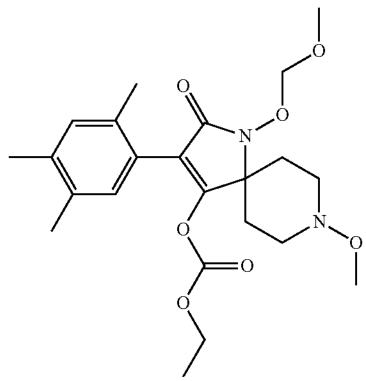 | gum | LC/MS: 449 (M + H)+<br>R$_t$ = 1.88 min |
| P1ii.57 | 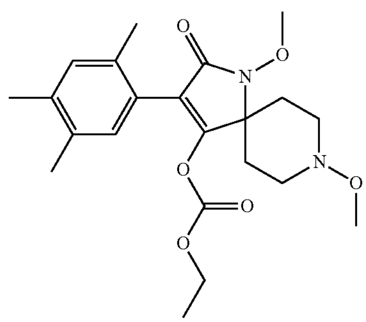 | gum | LC/MS: 419 (M + H)+<br>R$_t$ = 1.90 min |
| P1ii.58 | 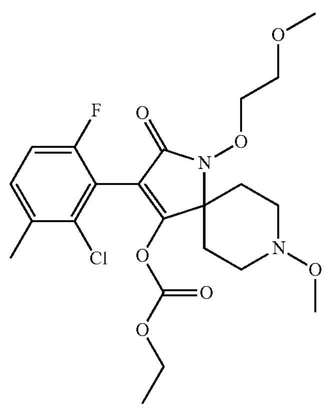 [SMILES: CCOC(=O)OC1=C(c2c(F)ccc(C)c2Cl)C(=O)N(OCCOC)C12CCN(OC)CC2] | gum | LC/MS: 487/489 (M + H)+<br>R$_t$ = 1.84 min |
| P1ii.59 | 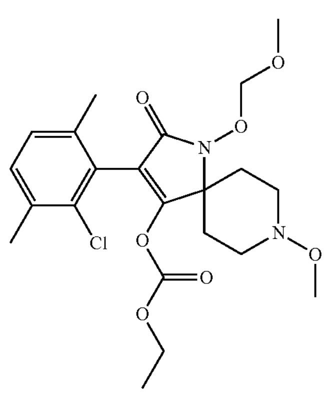 | gum | LC/MS: 469/471 (M + H)+<br>R$_t$ = 1.87 min |

TABLE P1ii-continued

Physical data of compounds of formula I:

| Compound No. | Structures | Melting Point | MS/NMR |
|---|---|---|---|
| P1ii.60 | 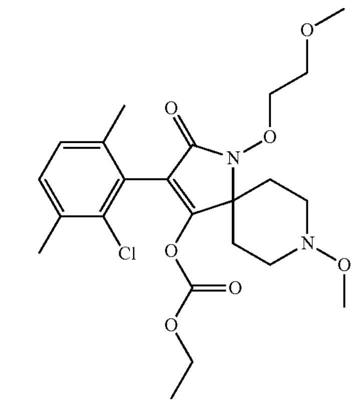 | gum | LC/MS: 483/485 (M + H)+<br>$R_t$ = 1.86 min |
| P1ii.61 | 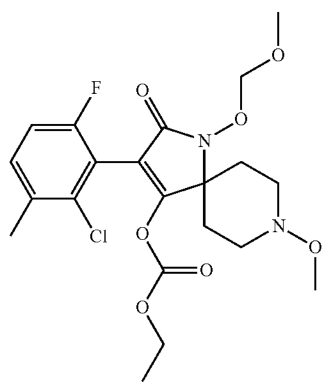 | 116-119° C. | LC/MS: 473/475 (M + H)+<br>$R_t$ = 1.80 min |
| P1ii.62 | 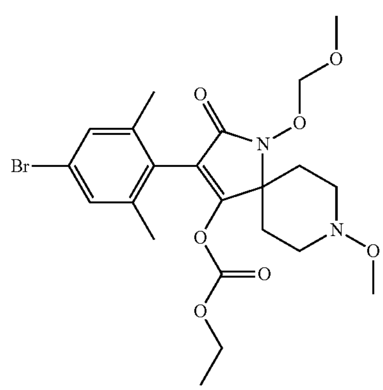 [SMILES: CCOC(=O)OC1=C(c2c(C)cc(Br)cc2C)C(=O)N(OCOC)C12CCN(OC)CC2] | gum | LC/MS: 513/515 (M + H)+<br>$R_t$ = 2.01 min |
| P1ii.63 | 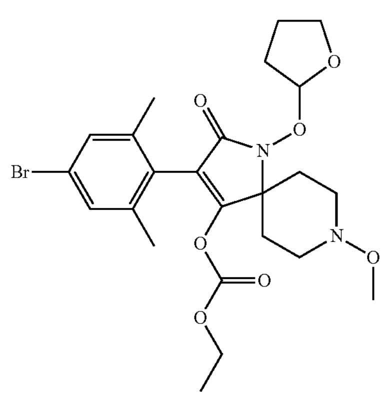 | gum | LC/MS: 539/541 (M + H)+<br>$R_t$ = 2.01 min |

TABLE P1ii-continued

Physical data of compounds of formula I:

| Compound No. | Structures | Melting Point | MS/NMR |
|---|---|---|---|
| P1ii.64 | 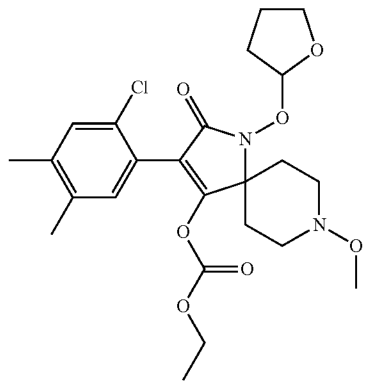 | gum | LC/MS: 495/497 (M + H)$^+$<br>$R_t$ = 1.95 min |
| P1ii.65 | 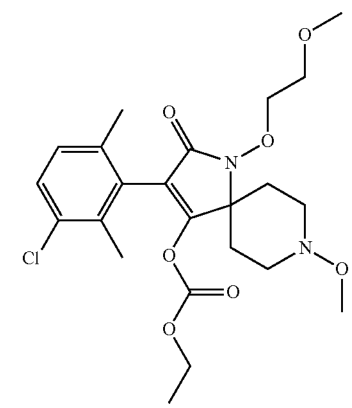 [SMILES: CCOC(=O)OC1=C(c2c(C)ccc(Cl)c2C)C(=O)N(OCCOC)C12CCN(OC)CC2] | gum | LC/MS: 483/485 (M + H)$^+$<br>$R_t$ = 1.94 min |
| P1ii.66 | 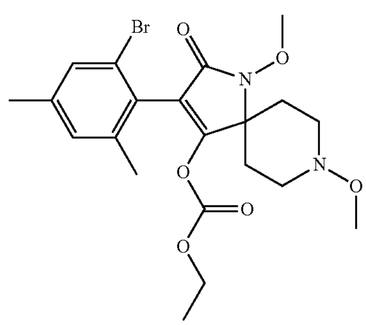 | 90-94° C. | LC/MS: 483/485 (M + H)$^+$<br>$R_t$ = 1.89 min |
| P1ii.67 | 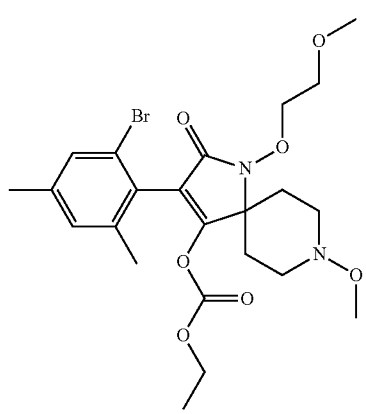 | gum | LC/MS: 527/529 (M + H)$^+$<br>$R_t$ = 1.92 min |

TABLE P1ii-continued

Physical data of compounds of formula I:

| Compound No. | Structures | Melting Point | MS/NMR |
|---|---|---|---|
| P1ii.68 | 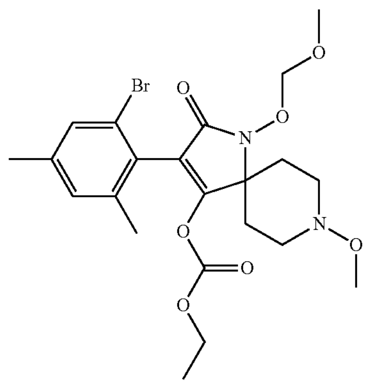 | gum | LC/MS: 513/515 (M + H)+<br>$R_t$ = 1.91 min |
| P1ii.69 | 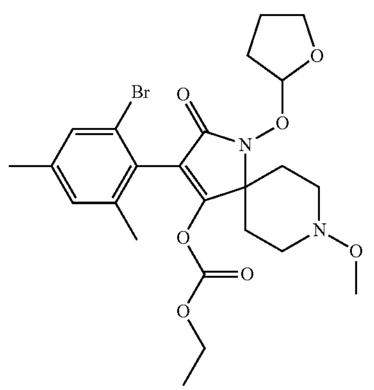 | gum | LC/MS: 539/541 (M + H)+<br>$R_t$ = 1.97 min |
| P1ii.70 | 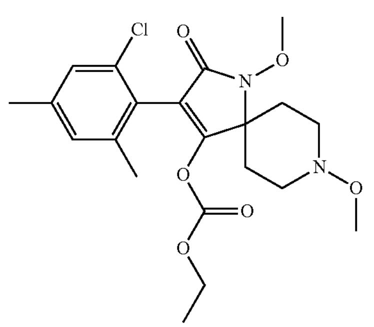 | gum | LC/MS: 439/441 (M + H)+<br>$R_t$ = 1.88 min |
| P1ii.71 | 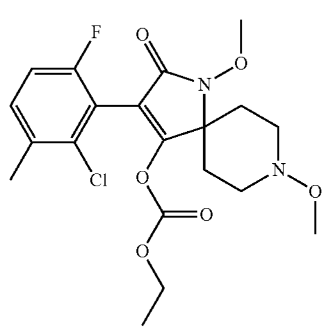 [SMILES: CCOC(=O)OC1=C(c2c(F)ccc(C)c2Cl)C(=O)N(OC)C12CCN(OC)CC2] | gum | LC/MS: 443/445 (M + H)+<br>$R_t$ = 1.79 min |

TABLE P1ii-continued

Physical data of compounds of formula I:

| Compound No. | Structures | Melting Point | MS/NMR |
|---|---|---|---|
| P1ii.72 | 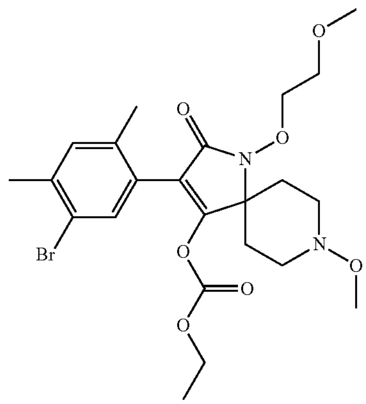 | gum | LC/MS: 527/529 (M + H)$^+$<br>R$_t$ = 1.97 min |
| P1ii.73 | 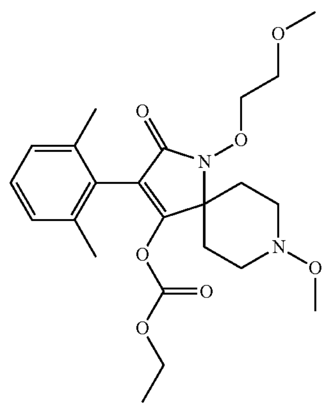 [SMILES: CCOC(=O)OC1=C(c2c(C)cccc2C)C(=O)N(OCCOC)C12CCN(OC)CC2] | gum | LC/MS: 449 (M + H)$^+$<br>R$_t$ = 1.84 min |
| P1ii.74 | 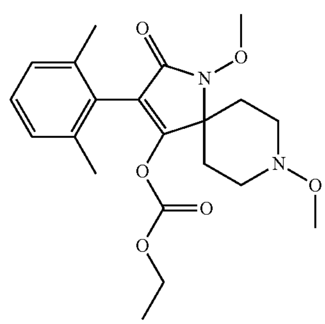 [SMILES: CCOC(=O)OC1=C(c2c(C)cccc2C)C(=O)N(OC)C12CCN(OC)CC2] | gum | LC/MS: 405 (M + H)$^+$<br>R$_t$ = 1.81 min |
| P1ii.75 | 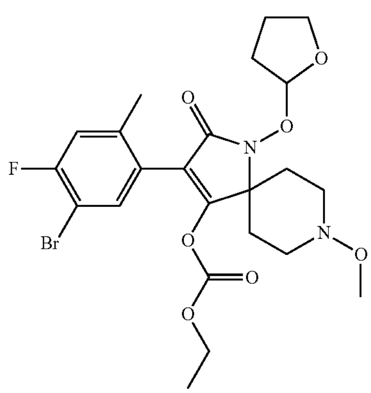 [SMILES: CCOC(=O)OC1=C(c2cc(Br)c(F)cc2C)C(=O)N(OC2CCCO2)C12CCN(OC)CC2] | gum | LC/MS: 543/545 (M + H)$^+$<br>R$_t$ = 1.97 min |

TABLE P1ii-continued

Physical data of compounds of formula I:

| Compound No. | Structures | Melting Point | MS/NMR |
|---|---|---|---|
| P1ii.76 | 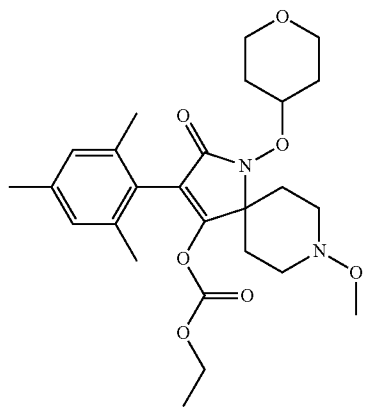 | gum | LC/MS: 489 (M + H)+<br>$R_t$ = 1.93 min |
| P1ii.77 | 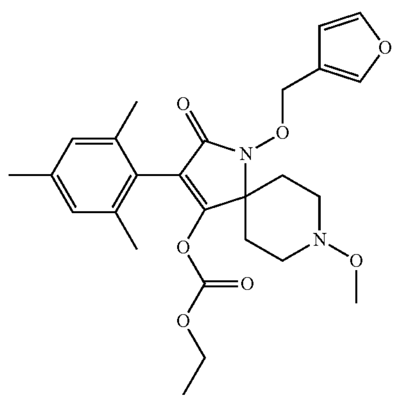 [SMILES: CCOC(=O)OC1=C(c2c(C)cc(C)cc2C)C(=O)N(OCc2ccoc2)C12CCN(OC)CC2] | gum | LC/MS: 485 (M + H)+<br>$R_t$ = 2.02 min |
| P1ii.78 | 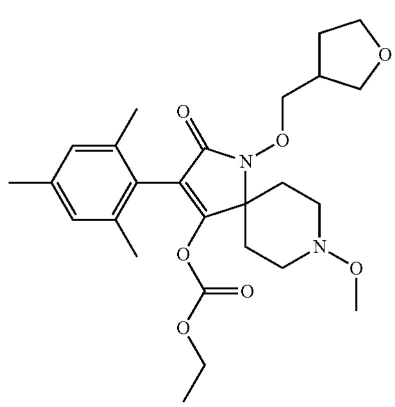 [SMILES: CCOC(=O)OC1=C(c2c(C)cc(C)cc2C)C(=O)N(OCC2CCOC2)C12CCN(OC)CC2] | gum | LC/MS: 489 (M + H)+<br>$R_t$ = 1.95 min |

TABLE P1ii-continued

Physical data of compounds of formula I:

| Compound No. | Structures | Melting Point | MS/NMR |
|---|---|---|---|
| P1ii.79 | 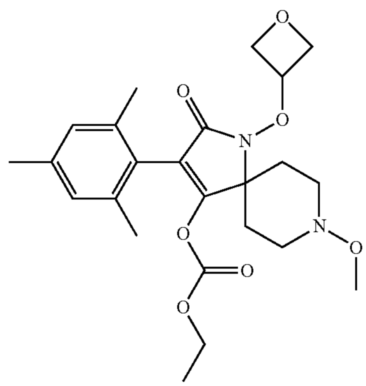 | gum | LC/MS: 461 (M + H)+<br>$R_t$ = 1.87 min |
| P1ii.80 | 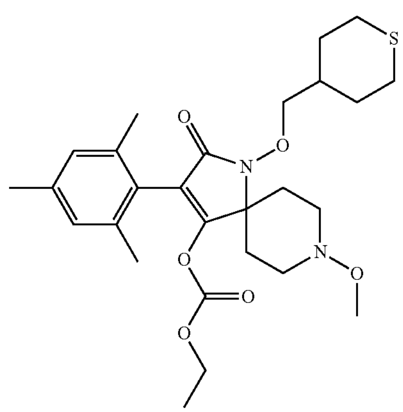 [SMILES: CCOC(=O)OC1=C(c2c(C)cc(C)cc2C)C(=O)N(OCC2CCSCC2)C12CCN(OC)CC2] | gum | LC/MS: 519 (M + H)+<br>$R_t$ = 2.14 min |
| P1ii.81 | 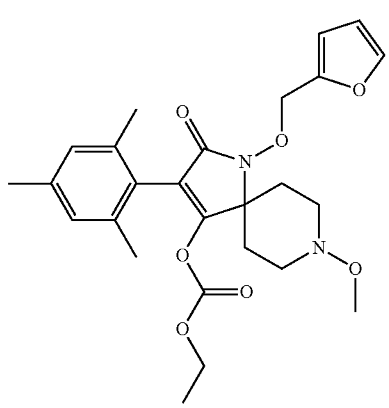 [SMILES: CCOC(=O)OC1=C(c2c(C)cc(C)cc2C)C(=O)N(OCc2ccco2)C12CCN(OC)CC2] | gum | LC/MS: 485 (M + H)+<br>$R_t$ = 2.03 min |

TABLE P1ii-continued

Physical data of compounds of formula I:

| Compound No. | Structures | Melting Point | MS/NMR |
| --- | --- | --- | --- |
| P1ii.82 | 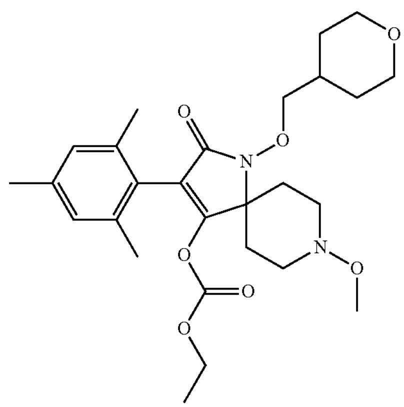 [SMILES: CCOC(=O)OC1=C(c2c(C)cc(C)cc2C)C(=O)N(OCC2CCOCC2)C12CCN(OC)CC2] | gum | LC/MS: 503 (M + H)+<br>$R_t$ = 1.98 min |
| P1ii.83 | 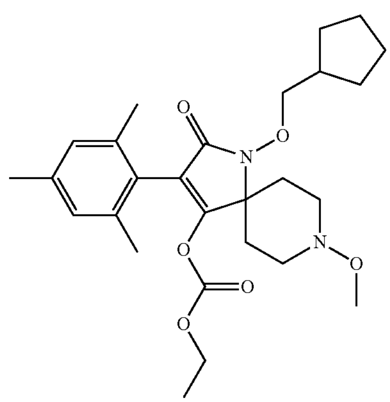 [SMILES: CCOC(=O)OC1=C(c2c(C)cc(C)cc2C)C(=O)N(OCC2CCCC2)C12CCN(OC)CC2] | gum | LC/MS: 487 (M + H)+<br>$R_t$ = 2.23 min |
| P1ii.84 | 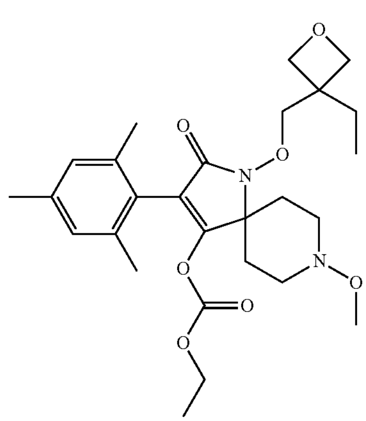 [SMILES: CCOC(=O)OC1=C(c2c(C)cc(C)cc2C)C(=O)N(OCC2(CC)COC2)C12CCN(OC)CC2] | 105-107° C. | LC/MS: 503 (M + H)+<br>$R_t$ = 2.03 min |

TABLE P1ii-continued

Physical data of compounds of formula I:

| Compound No. | Structures | Melting Point | MS/NMR |
|---|---|---|---|
| P1ii.85 | 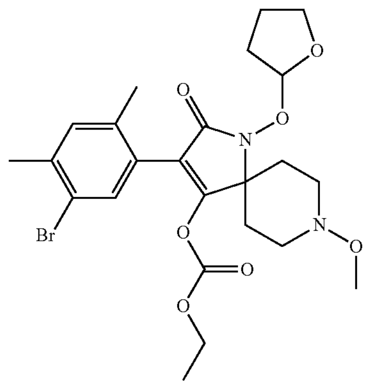 | gum | LC/MS: 539/541 (M + H)$^+$<br>R$_t$ = 2.03 min |
| P1ii.86 | 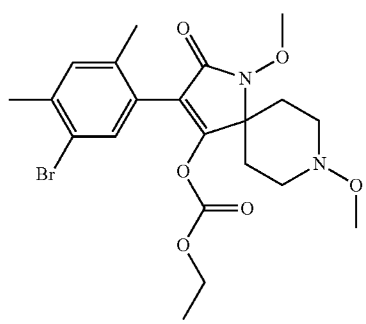 | gum | LC/MS: 483/485 (M + H)$^+$<br>R$_t$ = 1.94 min |
| P1ii.87 | 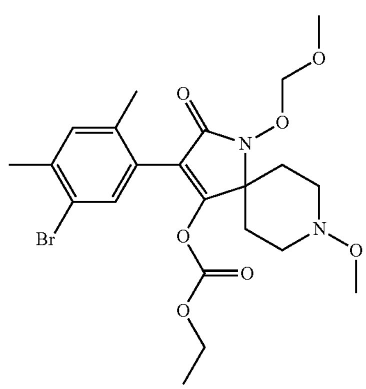 | gum | LC/MS: 513/515 (M + H)$^+$<br>R$_t$ = 1.95 min |
| P1ii.88 | 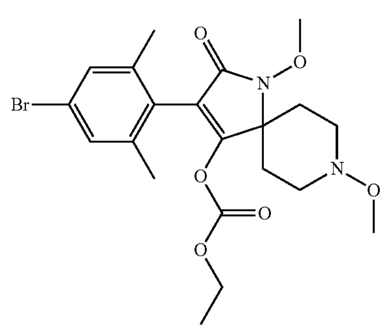 [SMILES: CCOC(=O)OC1=C(c2c(C)cc(Br)cc2C)C(=O)N(OC)C12CCN(OC)CC2] | 113-116° C. | LC/MS: 483/485 (M + H)$^+$<br>R$_t$ = 1.96 min |

TABLE P1ii-continued

Physical data of compounds of formula I:

| Compound No. | Structures | Melting Point | MS/NMR |
|---|---|---|---|
| P1ii.89 | 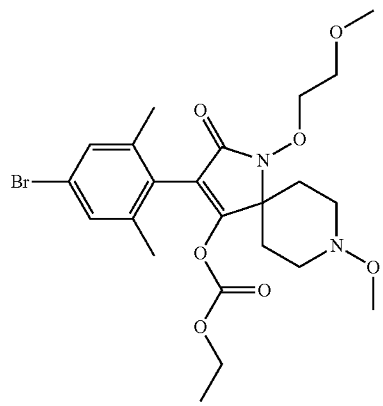 | gum | LC/MS: 527/529 (M + H)+<br>$R_t$ = 1.98 min |
| P1ii.90 | 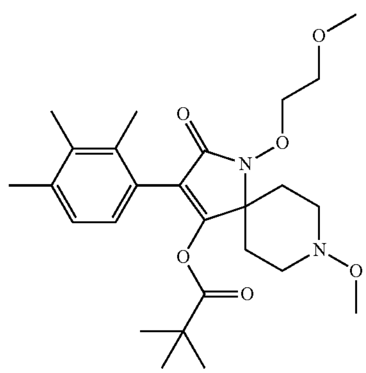 | gum | LC/MS: 475 (M + H)+<br>$R_t$ = 2.05 min |
| P1ii.91 | 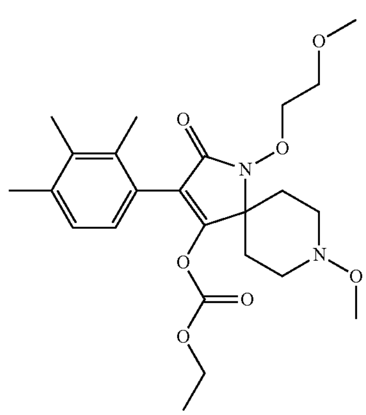 | gum | LC/MS: 463 (M + H)+<br>$R_t$ = 1.89 min |

TABLE P1ii-continued

Physical data of compounds of formula I:

| Compound No. | Structures | Melting Point | MS/NMR |
|---|---|---|---|
| P1ii.92 | 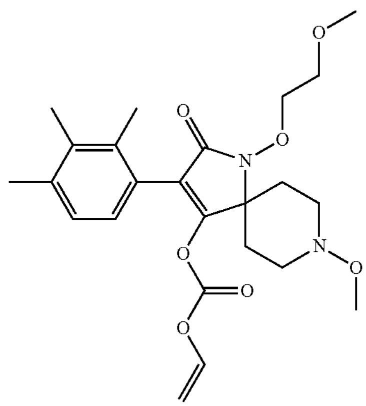 | solid | LC/MS: 461 (M + H)+<br>$R_t$ = 1.95 min |
| P1ii.93 | 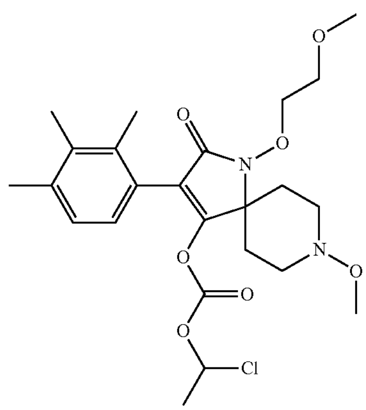 | gum | LC/MS: 497/499 (M + H)+<br>$R_t$ = 1.97 min |
| P1ii.94 | 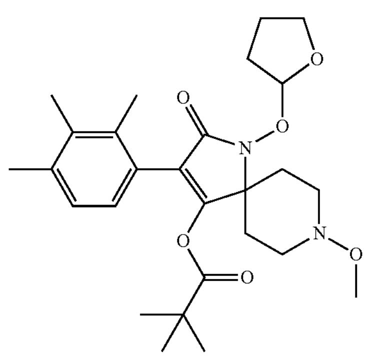 | gum | LC/MS: 487 (M + H)+<br>$R_t$ = 2.12 min |
| P1ii.95 | 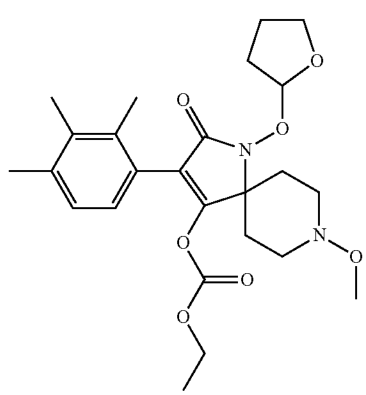 | gum | LC/MS: 475 (M + H)+<br>$R_t$ = 1.95 min |

TABLE P1ii-continued

Physical data of compounds of formula I:

| Compound No. | Structures | Melting Point | MS/NMR |
|---|---|---|---|
| P1ii.96 | 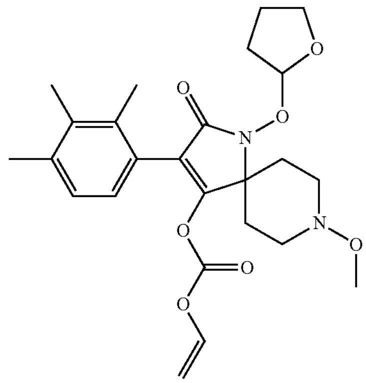 | gum | LC/MS: 473 (M + H)+<br>$R_t$ = 2.00 min |
| P1ii.97 | 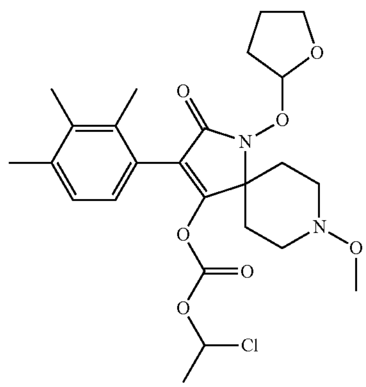 | gum | LC/MS: 509/511 (M + H)+<br>$R_t$ = 2.02 min |
| P1ii.98 | 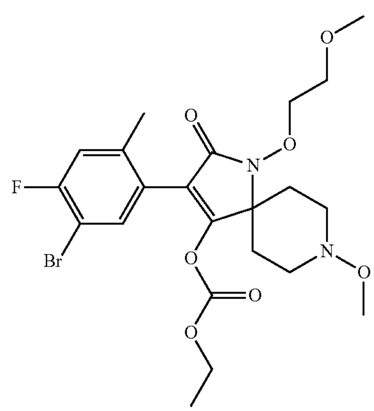 [SMILES: CCOC(=O)OC1=C(c2cc(Br)c(F)cc2C)C(=O)N(OCCOC)C12CCN(OC)CC2] | gum | LC/MS: 531/533 (M + H)+<br>$R_t$ = 1.92 min |
| P1ii.99 | 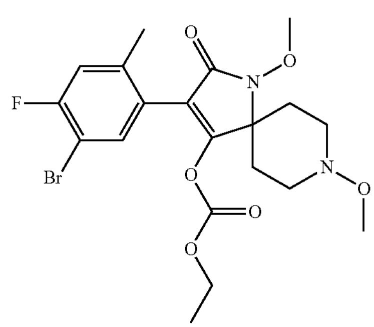 [SMILES: CCOC(=O)OC1=C(c2cc(Br)c(F)cc2C)C(=O)N(OC)C12CCN(OC)CC2] | gum | LC/MS: 487/489 (M + H)+<br>$R_t$ = 1.93 min |

TABLE P1ii-continued

Physical data of compounds of formula I:

| Compound No. | Structures | Melting Point | MS/NMR |
|---|---|---|---|
| P1ii.100 | 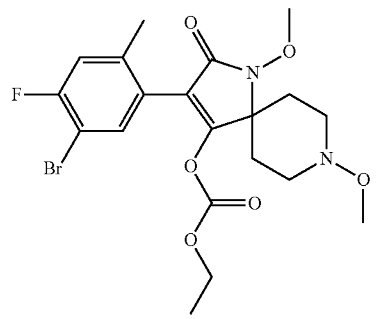 | gum | LC/MS: 517/519 (M + H)+<br>$R_t$ = 1.94 min |
| P1ii.101 | 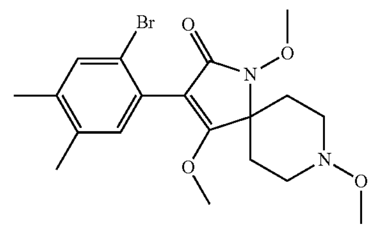 | gum | LC/MS: 425/427 (M + H)+<br>$R_t$ = 1.83 min |
| P1ii.102 | 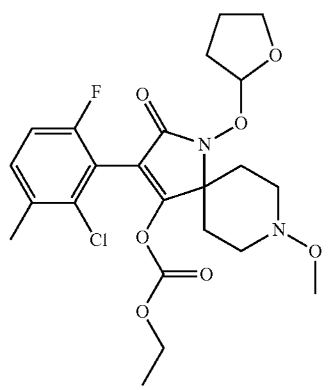 [SMILES: CCOC(=O)OC1=C(c2c(F)ccc(C)c2Cl)C(=O)N(OC2CCCO2)C12CCN(OC)CC2] | 134-138° C. | LC/MS: 499/501 (M + H)+<br>$R_t$ = 1.90 min |
| P1ii.103 | 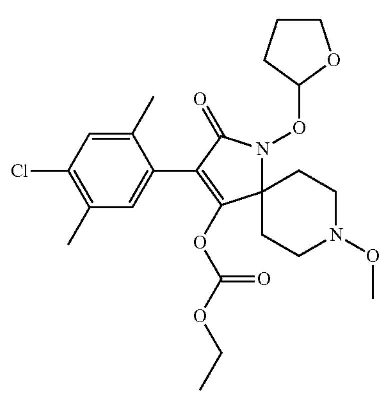 [SMILES: CCOC(=O)OC1=C(c2cc(C)c(Cl)cc2C)C(=O)N(OC2CCCO2)C12CCN(OC)CC2] | gum | LC/MS: 495/497 (M + H)+<br>$R_t$ = 2.03 min |

TABLE P1ii-continued

Physical data of compounds of formula I:

| Compound No. | Structures | Melting Point | MS/NMR |
| --- | --- | --- | --- |
| P1ii.104 | 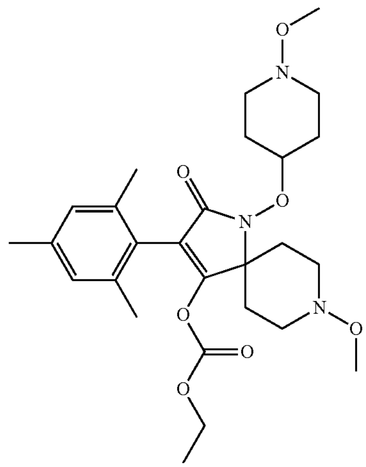 | gum | LC/MS: 518 (M + H)+<br>$R_t$ = 1.97 min |
| P1ii.105 | 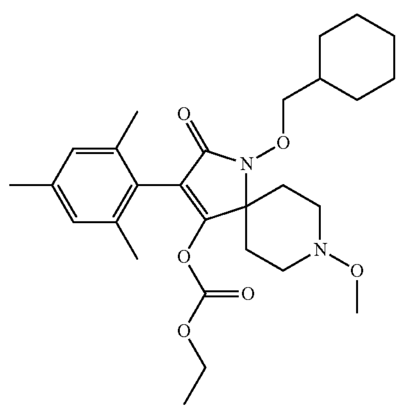 [SMILES: CCOC(=O)OC1=C(c2c(C)cc(C)cc2C)C(=O)N(OCC2CCCCC2)C12CCN(OC)CC2] | gum | LC/MS: 501 (M + H)+<br>$R_t$ = 2.26 min |
| P1ii.106 | 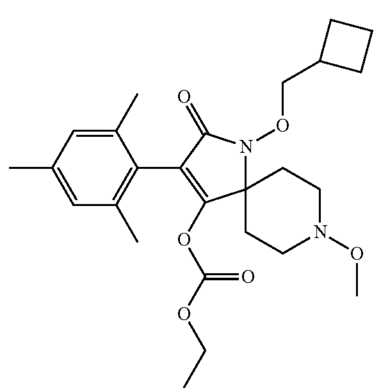 [SMILES: CCOC(=O)OC1=C(c2c(C)cc(C)cc2C)C(=O)N(OCC2CCC2)C12CCN(OC)CC2] | gum | LC/MS: 473 (M + H)+<br>$R_t$ = 2.15 min |

TABLE P1ii-continued

Physical data of compounds of formula I:

| Compound No. | Structures | Melting Point | MS/NMR |
|---|---|---|---|
| P1ii.107 | 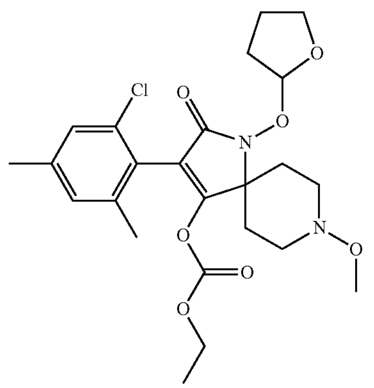 | gum | LC/MS: 495/497 (M + H)⁺<br>$R_t$ = 1.95 min |
| P1ii.108 | 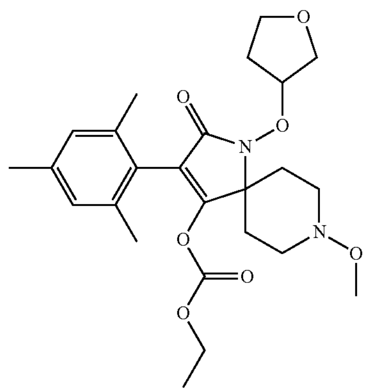 | gum | LC/MS: 475 (M + H)⁺<br>$R_t$ = 1.94 min |
| P1ii.109 | 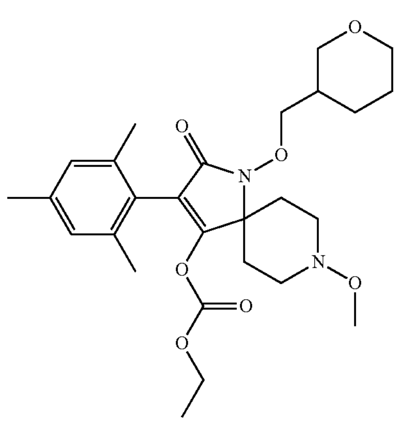 [SMILES: CCOC(=O)OC1=C(c2c(C)cc(C)cc2C)C(=O)N(OCC2CCCOC2)C12CCN(OC)CC2] | gum | LC/MS: 503 (M + H)⁺<br>$R_t$ = 2.04 min |

TABLE P1ii-continued

Physical data of compounds of formula I:

| Compound No. | Structures | Melting Point | MS/NMR |
|---|---|---|---|
| P1ii.110 | | gum | LC/MS: 479 (M + H)$^+$<br>$R_t$ = 2.03 min |
| P1ii.111<br>EXAMPLE 22 | | gum | LC/MS: 495 (M + H)$^+$<br>$R_t$ = 1.74 min |
| P1ii.112 | | | |

TABLE P1ii-continued

Physical data of compounds of formula I:

| Compound No. | Structures | Melting Point | MS/NMR |
|---|---|---|---|
| P1ii.113 | 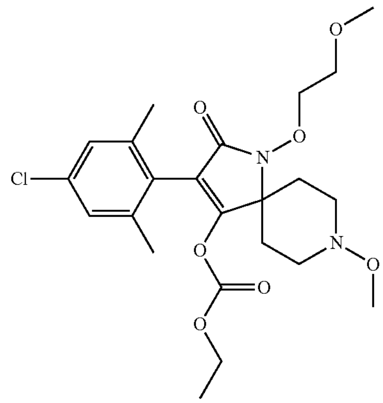 [SMILES: CCOC(=O)OC1=C(c2c(C)cc(Cl)cc2C)C(=O)N(OCCOC)C12CCN(OC)CC2] | gum | LC/MS: 483/485 (M + H)$^+$<br>$R_t$ = 1.94 min |
| P1ii.114 | 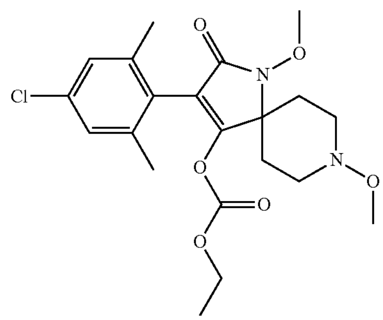 [SMILES: CCOC(=O)OC1=C(c2c(C)cc(Cl)cc2C)C(=O)N(OC)C12CCN(OC)CC2] | 122-125° C. | LC/MS: 439/441 (M + H)$^+$<br>$R_t$ = 1.92 min |
| P1ii.115 | EXAMPLE 20, step 3 | gum | LC/MS: 497/499 (M + H)$^+$<br>$R_t$ = 2.02 min |
| P1ii.116 | 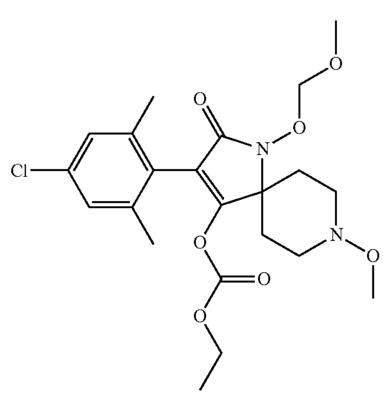 [SMILES: CCOC(=O)OC1=C(c2c(C)cc(Cl)cc2C)C(=O)N(OCOC)C12CCN(OC)CC2] | gum | LC/MS: 469/471 (M + H)$^+$<br>$R_t$ = 1.97 min |

TABLE P1ii-continued

Physical data of compounds of formula I:

| Compound No. | Structures | Melting Point | MS/NMR |
|---|---|---|---|
| P1ii.117 | 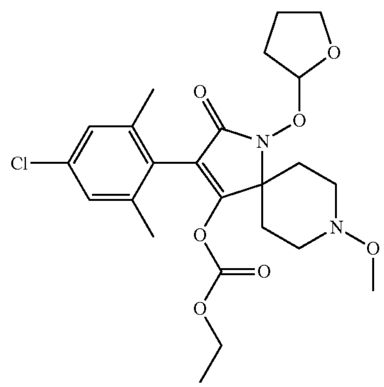 [SMILES: CCOC(=O)OC1=C(c2c(C)cc(Cl)cc2C)C(=O)N(OC2CCCO2)C12CCN(OC)CC2] | gum | LC/MS: 495/497 (M + H)$^+$<br>R$_t$ = 2.02 min |

TABLE P2ii

Physical data of compounds of formula II

| Compound No. | Structures | Melting Point | MS/NMR |
|---|---|---|---|
| P2ii.1 | 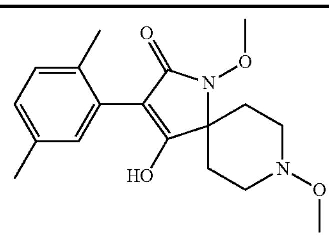 | gum | LC/MS: 333 (M + H)$^+$<br>R$_t$ = 1.54 min |
| P2ii.2 | EXAMPLE 11, step 5 | 136–138° C. | LC/MS: 363 (M + H)$^+$<br>R$_t$ = 1.55 min |
| P2ii.3 | 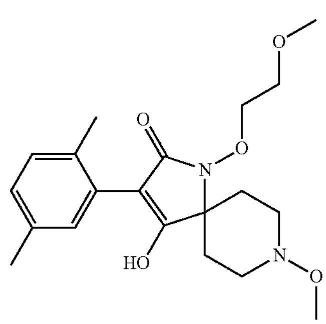 [SMILES: COCCON1C(=O)C(c2cc(C)ccc2C)=C(O)C12CCN(OC)CC2] | gum | LC/MS: 377 (M + H)$^+$<br>R$_t$ = 1.58 min |

TABLE P2ii-continued

Physical data of compounds of formula II

| Compound No. | Structures | Melting Point | MS/NMR |
|---|---|---|---|
| P2ii.4 | EXAMPLE 14 | 152-154° C. | LC/MS: 333 (M + H)+<br>R$_t$ = 1.40 min |
| P2ii.5 | 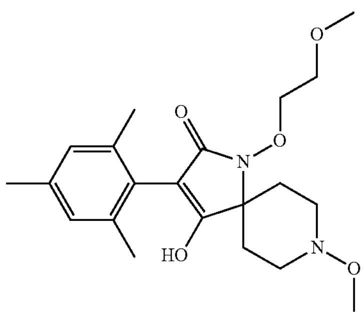 | 139-142° C. | LC/MS: 391 (M + H)+<br>R$_t$ = 1.61 min |
| P2ii.6 | 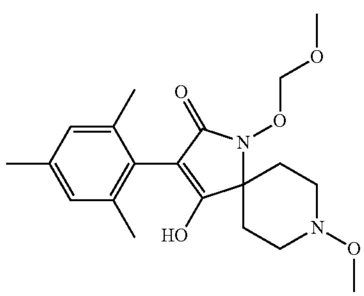 | 163-165° C. | LC/MS: 377 (M + H)+<br>R$_t$ = 1.64 min |
| P2ii.7 | 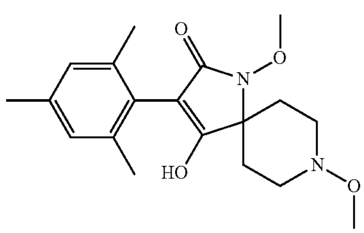 | 70° C. (dec) | LC/MS: 347 (M + H)+<br>R$_t$ = 1.60 min |
| P2ii.8 | EXAMPLE 12, step 2 | 167-169° C. | LC/MS: 371 (M + H)+<br>R$_t$ = 1.66 min |

TABLE P2ii-continued

Physical data of compounds of formula II

| Compound No. | Structures | Melting Point | MS/NMR |
|---|---|---|---|
| P2ii.9 | 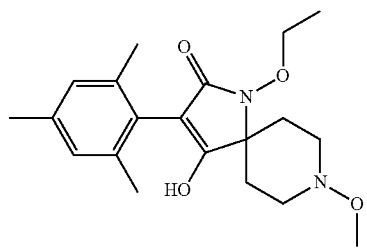 | 168-170° C. | LC/MS: 361 (M + H)+<br>R$_t$ = 1.67 min |
| P2ii.10 | 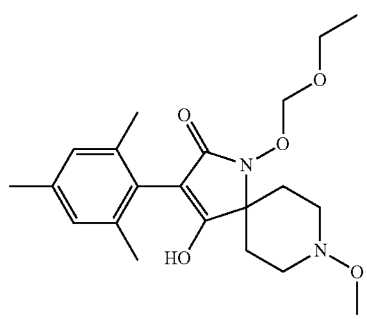 [SMILES: CCOCON1C(=O)C(c2c(C)cc(C)cc2C)=C(O)C12CCN(OC)CC2] | gum | LC/MS: 391 (M + H)+<br>R$_t$ = 1.71 min |
| P2ii.11 | 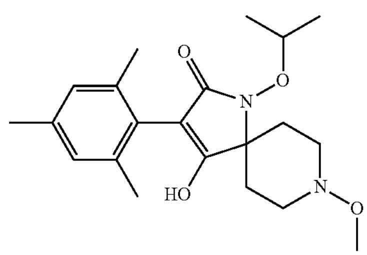 | 153-156° C. | LC/MS: 375 (M + H)+<br>R$_t$ = 1.78 min |
| P2ii.12 | 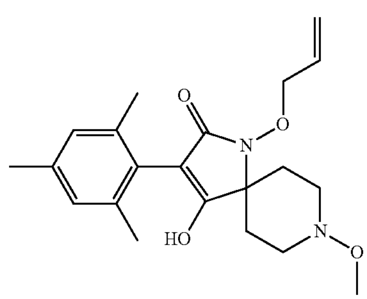 | 162-164° C. | LC/MS: 373 (M + H)+<br>R$_t$ = 1.73 min |
| P2ii.13 | 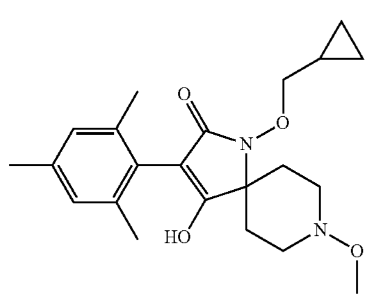 [SMILES: CON1CCC2(CC1)C(O)=C(c1c(C)cc(C)cc1C)C(=O)N2OCC1CC1] | 150-153° C. | LC/MS: 387 (M + H)+<br>R$_t$ = 1.81 min |

TABLE P2ii-continued
Physical data of compounds of formula II
| Compound No. | Structures | Melting Point | MS/NMR |
|---|---|---|---|
| P2ii.14 | 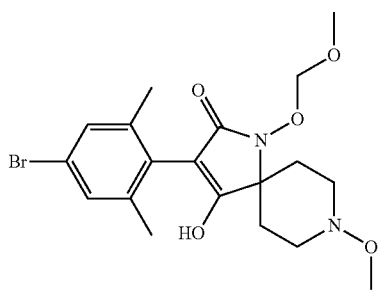 | 190-191° C. | LC/MS: 441/443 (M + H)$^+$<br>$R_t$ = 1.62 min |
| P2ii.15 | 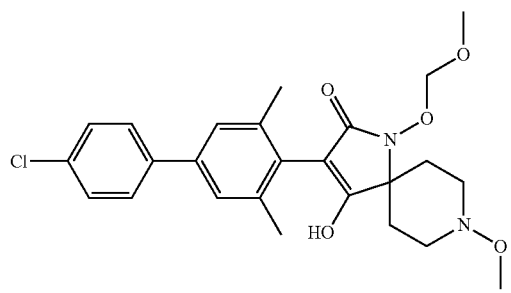 [SMILES: COCON1C(=O)C(c2c(C)cc(-c3ccc(Cl)cc3)cc2C)=C(O)C12CCN(OC)CC2]<br>EXAMPLE 24 | 128° C. (dec) | LC/MS: 473/475 (M + H)$^+$<br>$R_t$ = 1.97 min |
| P2ii.16 | 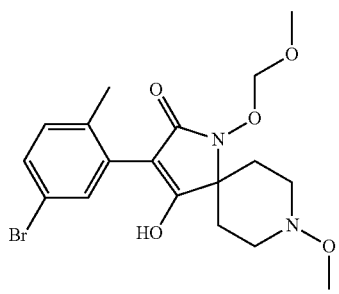 [SMILES: COCON1C(=O)C(c2cc(Br)ccc2C)=C(O)C12CCN(OC)CC2] | gum | LC/MS: 427/429 (M + H)$^+$<br>$R_t$ = 1.63 min |
| P2ii.17 | 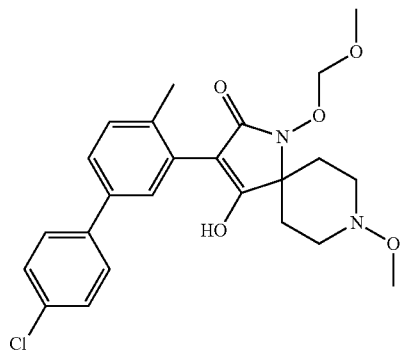 [SMILES: COCON1C(=O)C(c2cc(-c3ccc(Cl)cc3)ccc2C)=C(O)C12CCN(OC)CC2] | 68-71° C. | LC/MS: 459/461 (M + H)$^+$<br>$R_t$ = 1.93 min |

TABLE P2ii-continued
Physical data of compounds of formula II
| Compound No. | Structures | Melting Point | MS/NMR |
|---|---|---|---|
| P2ii.18 | 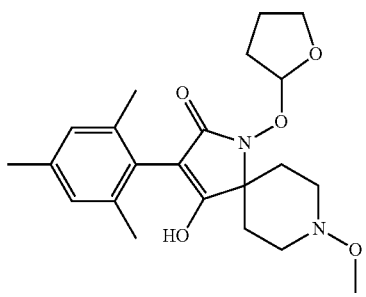<br>EXAMPLE 17, step 2 | 144-146° C. | LC/MS: 403 (M + H)$^+$<br>R$_t$ = 1.66 min |
| P2ii.19 | 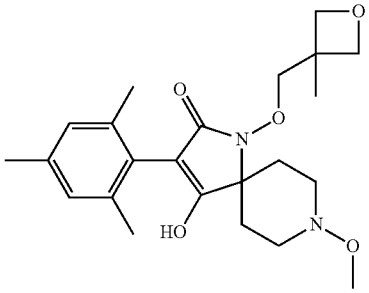 [SMILES: CON1CCC2(CC1)C(O)=C(c1c(C)cc(C)cc1C)C(=O)N2OCC1(C)COC1] | 108-111° C. | LC/MS: 417 (M + H)$^+$<br>R$_t$ = 1.68 min |
| P2ii.20 | 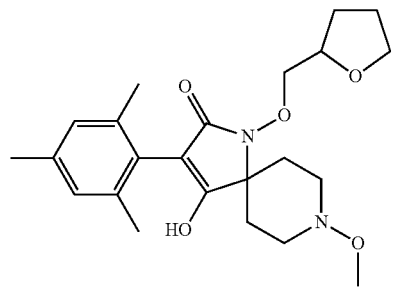 [SMILES: CON1CCC2(CC1)C(O)=C(c1c(C)cc(C)cc1C)C(=O)N2OCC1CCCO1] | gum | LC/MS: 417 (M + H)$^+$<br>R$_t$ = 1.72 min |
| P2ii.21 | 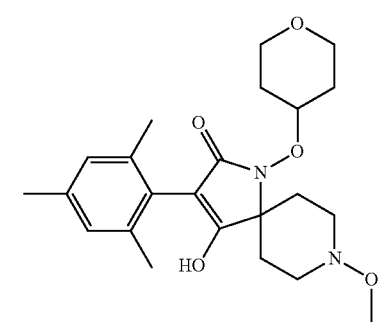 | 124-126° C. | LC/MS: 417 (M + H)$^+$<br>R$_t$ = 1.62 min |

TABLE P2ii-continued
Physical data of compounds of formula II
| Compound No. | Structures | Melting Point | MS/NMR |
|---|---|---|---|
| P2ii.22 | 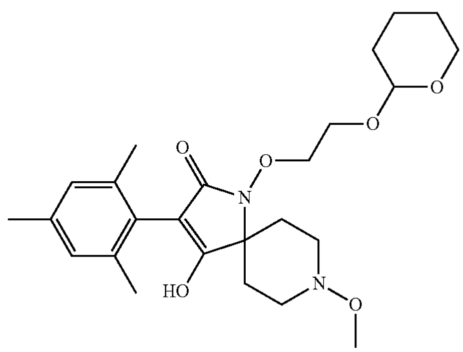 [SMILES: CON1CCC2(CC1)C(O)=C(c1c(C)cc(C)cc1C)C(=O)N2OCCOC1CCCCO1] | 135-137° C. | LC/MS: 461 (M + H)$^+$<br>R$_t$ = 1.87 min |
| P2ii.23 | 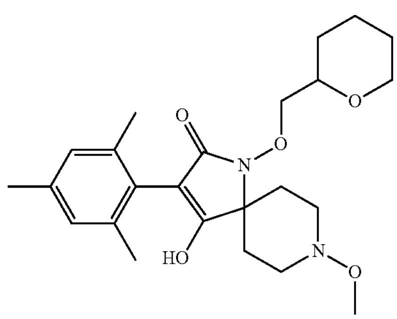 [SMILES: CON1CCC2(CC1)C(O)=C(c1c(C)cc(C)cc1C)C(=O)N2OCC1CCCCO1] | 90-93° C. | LC/MS: 431 (M + H)$^+$<br>R$_t$ = 1.81 min |
| P2ii.24 | 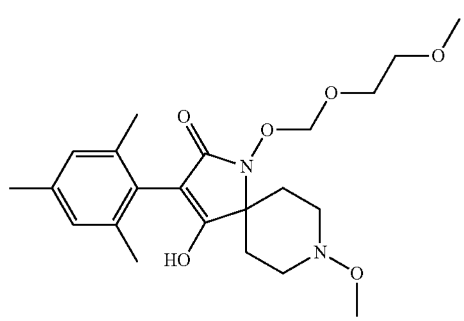 | 98-100° C. | LC/MS: 421 (M + H)$^+$<br>R$_t$ = 1.62 min |
| P2ii.25 | 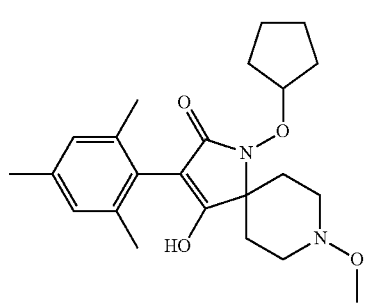 | 144-147° C. | LC/MS: 401 (M + H)$^+$<br>R$_t$ = 1.92 min |

TABLE P2ii-continued

Physical data of compounds of formula II

| Compound No. | Structures | Melting Point | MS/NMR |
|---|---|---|---|
| P2ii.26 | EXAMPLE 18, step 2 | 115-118° C. | LC/MS: 415 (M + H)+<br>R$_t$ = 1.98 min |
| P2ii.27 | 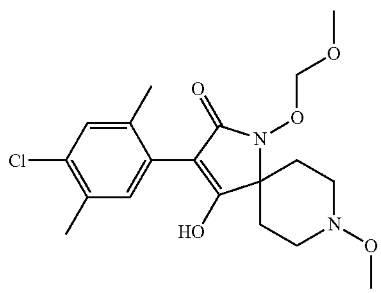 [SMILES: COCON1C(=O)C(c2cc(C)c(Cl)cc2C)=C(O)C12CCN(OC)CC2] | 139-143° C. | LC/MS: 397/399 (M + H)+<br>R$_t$ = 1.67 min |
| P2ii.28 | 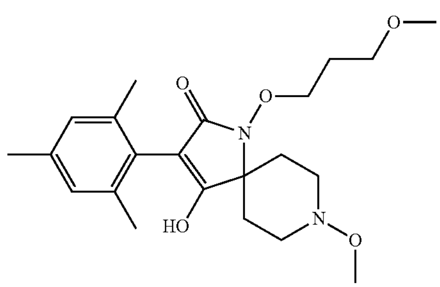 | 128-130° C. | LC/MS: 405 (M + H)+<br>R$_t$ = 1.69 min |
| P2ii.29 | 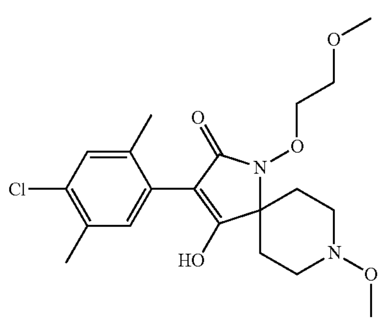 [SMILES: COCCON1C(=O)C(c2cc(C)c(Cl)cc2C)=C(O)C12CCN(OC)CC2] | 49-54° C. | LC/MS: 411/413 (M + H)+<br>R$_t$ = 1.68 min |
| P2ii.30 | 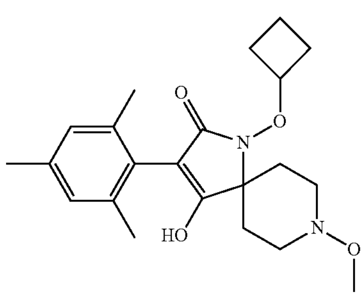 | gum | LC/MS: 387 (M + H)+<br>R$_t$ = 1.82 min |

TABLE P2ii-continued

Physical data of compounds of formula II

| Compound No. | Structures | Melting Point | MS/NMR |
|---|---|---|---|
| P2ii.31 | 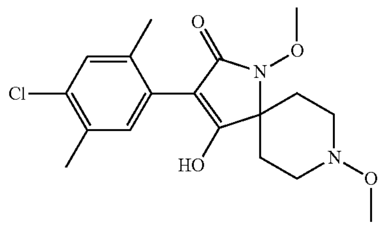 [SMILES: CON1CCC2(CC1)C(O)=C(c1cc(C)c(Cl)cc1C)C(=O)N2OC] | 92-95° C. | LC/MS: 367/369 (M + H)+<br>R$_t$ = 1.64 min |
| P2ii.32 | 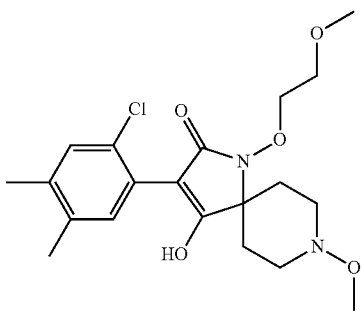 | solid | LC/MS: 411/413 (M + H)+<br>R$_t$ = 1.66 min |
| P2ii.33 | 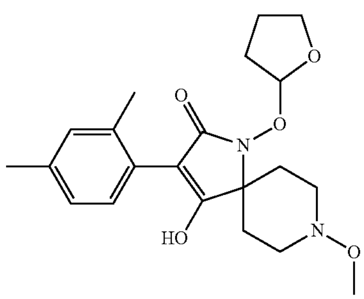 | solid | LC/MS: 389 (M + H)+<br>R$_t$ = 1.63 min |
| P2ii.34 | 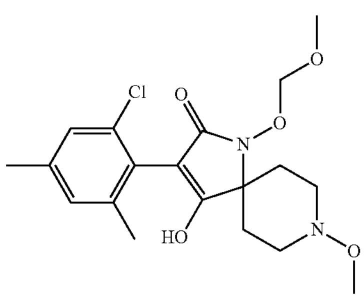 | 79-82° C. | LC/MS: 397/399 (M + H)+<br>R$_t$ = 1.55 min |
| P2ii.35 | 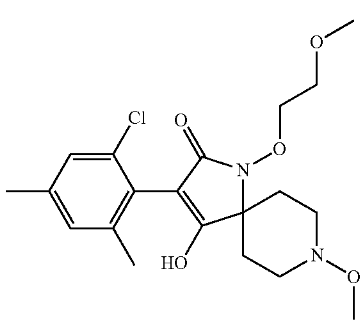 | 161-163° C. | LC/MS: 411/413 (M + H)+<br>R$_t$ = 1.55 min |

TABLE P2ii-continued
Physical data of compounds of formula II
| Compound No. | Structures | Melting Point | MS/NMR |
|---|---|---|---|
| P2ii.36 | 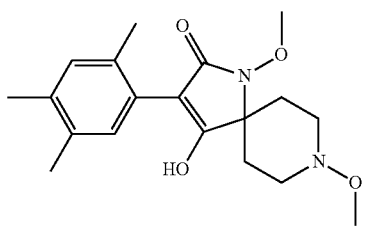 | gum | LC/MS: 347 (M + H)+<br>R_t = 1.59 min |
| P2ii.37 | 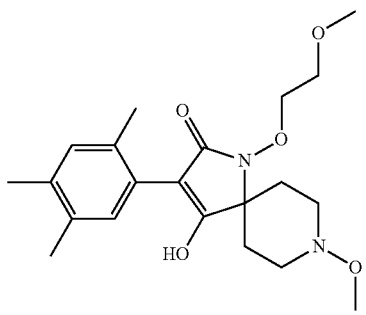 | gum | LC/MS: 391 (M + H)+<br>R_t = 1.65 min |
| P2ii.38 | 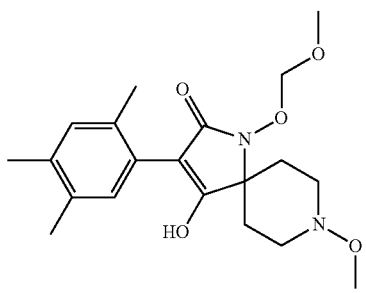 | gum | LC/MS: 377 (M + H)+<br>R_t = 1.60 min |
| P2ii.39 | 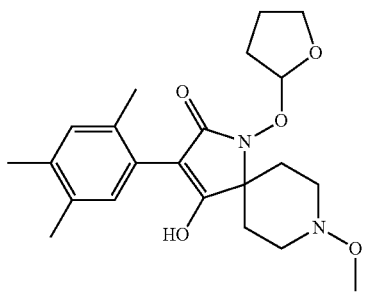 | gum | LC/MS: 403 (M + H)+<br>R_t = 1.72 min |
| P2ii.40 | 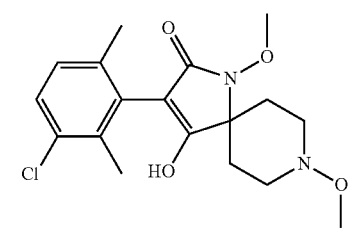 [SMILES: CON1CCC2(CC1)C(O)=C(c1c(C)ccc(Cl)c1C)C(=O)N2OC] | gum | LC/MS: 367/369 (M + H)+<br>R_t = 1.58 min |

TABLE P2ii-continued

Physical data of compounds of formula II

| Compound No. | Structures | Melting Point | MS/NMR |
|---|---|---|---|
| P2ii.41 | 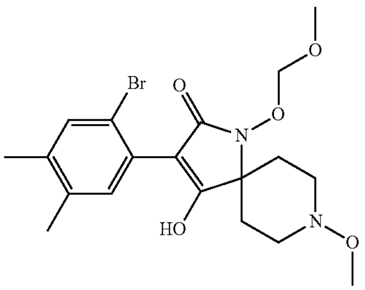 | solid | LC/MS: 441/443 (M + H)$^+$<br>R$_t$ = 1.64 min |
| P2ii.42 | 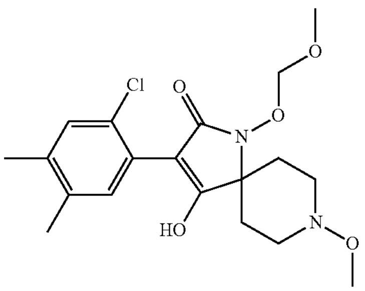 | solid | LC/MS: 395/397 (M − H)$^−$<br>R$_t$ = 1.64 min |
| P2ii.43 | 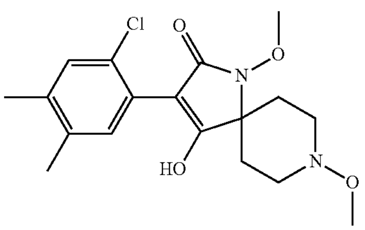 | solid | LC/MS: 367/369 (M + H)$^+$<br>R$_t$ = 1.64 min |
| P2ii.44 | 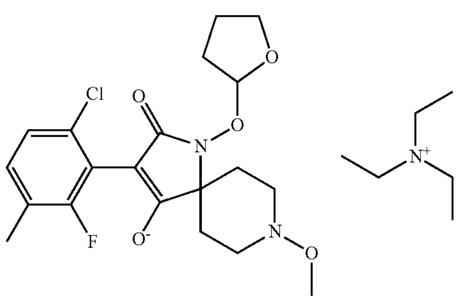 | gum | $^1$H-NMR (CD$_3$OD, selected signals only): 1.29 (t, 9H, N(CH$_2$CH$_3$)$_3$), 2.23 (d, $^4$J(H, F) = 1.9 Hz, 3H, mesityl CH$_3$), 3.17 (q, 6H, N(CH$_2$CH$_3$)$_3$), 3.54 (s, 3H, NOCH$_3$), 5.62 (br m, 1H, tetrahydrofuranyl CH). |
| P2ii.45 | 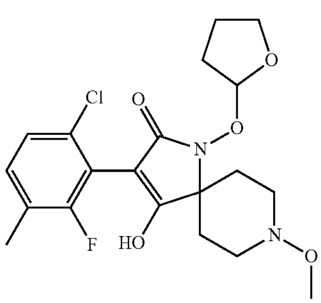 [SMILES: CON1CCC2(CC1)C(O)=C(c1c(Cl)ccc(C)c1F)C(=O)N2OC1CCCO1] | solid | LC/MS: 427/429 (M + H)$^+$<br>R$_t$ = 1.62 min |

TABLE P2ii-continued

Physical data of compounds of formula II

| Compound No. | Structures | Melting Point | MS/NMR |
|---|---|---|---|
| P2ii.46 | 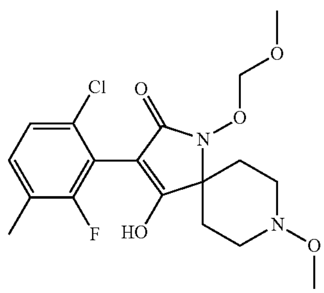 [SMILES: COCON1C(=O)C(c2c(Cl)ccc(C)c2F)=C(O)C12CCN(OC)CC2] | solid | LC/MS: 401/403 (M + H)$^+$<br>R$_t$ = 1.54 min |
| P2ii.47 | 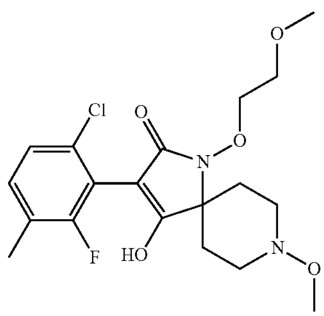 [SMILES: COCCON1C(=O)C(c2c(Cl)ccc(C)c2F)=C(O)C12CCN(OC)CC2] | gum | LC/MS: 415/417 (M + H)$^+$<br>R$_t$ = 1.57 min |
| P2ii.48 | 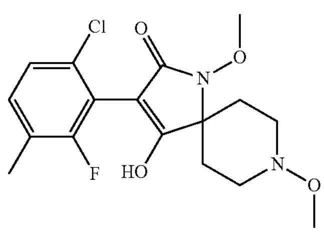 [SMILES: CON1CCC2(CC1)C(O)=C(c1c(Cl)ccc(C)c1F)C(=O)N2OC] | solid | LC/MS: 371/373 (M + H)$^+$<br>R$_t$ = 1.55 min |
| P2ii.49 | 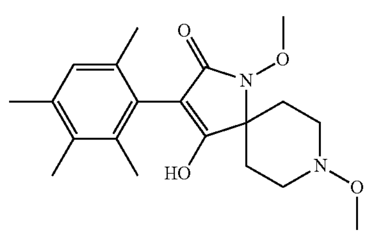 | gum | LC/MS: 361 (M + H)$^+$<br>R$_t$ = 1.63 min |
| P2ii.50 | 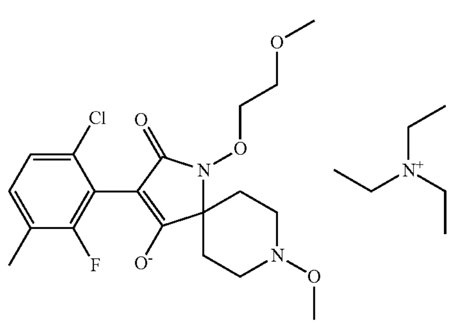 | gum | $^1$H-NMR (CD$_3$OD, selected signals only): 1.29 (t, 9H, N(CH$_2$CH$_3$)$_3$), 2.22 (d, $^4$J(H, F) = 2.2 Hz, 3H, mesityl CH$_3$), 3.17 (q, 6H, N(CH$_2$CH$_3$)$_3$), 3.39 (s, 3H, CH$_2$CH$_2$OCH$_3$), 3.54 (s, 3H, NOCH$_3$). |

TABLE P2ii-continued

Physical data of compounds of formula II

| Compound No. | Structures | Melting Point | MS/NMR |
|---|---|---|---|
| P2ii.51 | 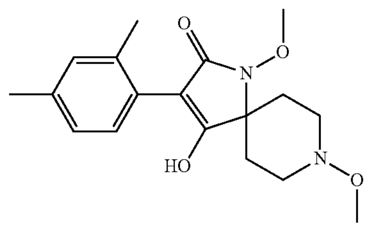 | powder | LC/MS: 333 (M + H)+<br>R$_t$ = 1.53 min |
| P2ii.52 | 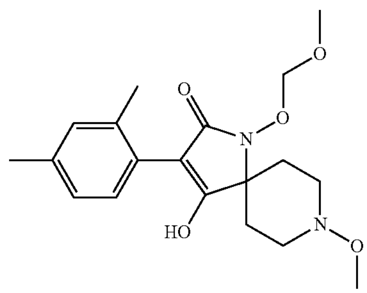 | 133-136° C. | |
| P2ii.53 | 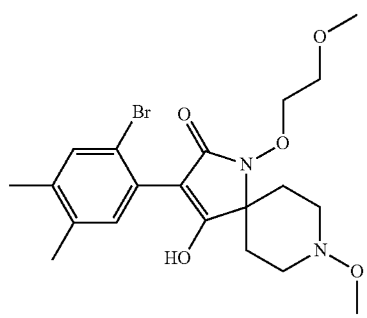 | solid | LC/MS: 455/457 (M + H)+<br>R$_t$ = 1.67 min |
| P2ii.54 | 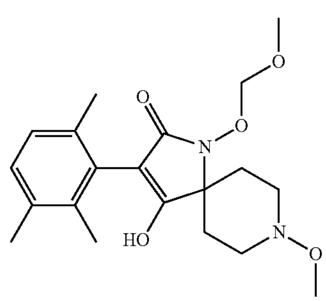 | gum | LC/MS: 377 (M + H)+<br>R$_t$ = 1.57 min |
| P2ii.55 | 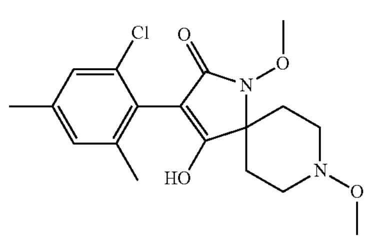 | 176-180° C. | LC/MS: 367/369 (M + H)+<br>R$_t$ = 1.55 min |

TABLE P2ii-continued

Physical data of compounds of formula II

| Compound No. | Structures | Melting Point | MS/NMR |
|---|---|---|---|
| P2ii.56 | 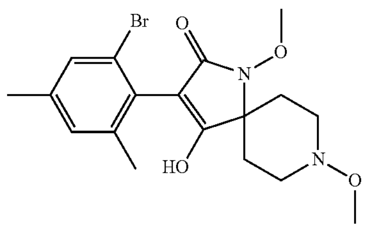 | 185-190° C. | LC/MS: 411/413 (M + H)⁺<br>$R_t$ = 1.56 min |
| P2ii.57 | 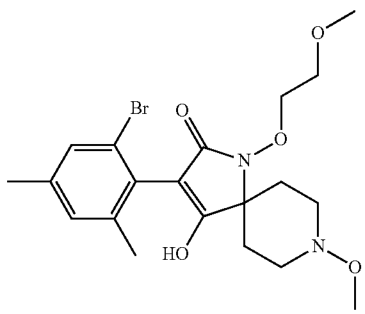 | 148-153° C. | LC/MS: 455/457 (M + H)⁺<br>$R_t$ = 1.60 min |
| P2ii.58 | 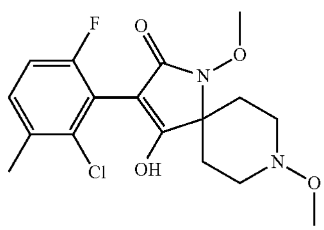 [SMILES: CON1CCC2(CC1)C(O)=C(c1c(F)ccc(C)c1Cl)C(=O)N2OC] | 83-86° C. | LC/MS: 371/373 (M + H)⁺<br>$R_t$ = 1.52 min |
| P2ii.59 | 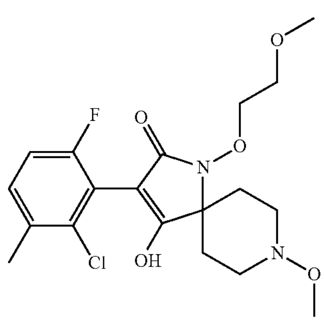 [SMILES: COCCON1C(=O)C(c2c(F)ccc(C)c2Cl)=C(O)C12CCN(OC)CC2] | 55-57° C. | LC/MS: 415/417 (M + H)⁺<br>$R_t$ = 1.53 min |
| P2ii.60 | 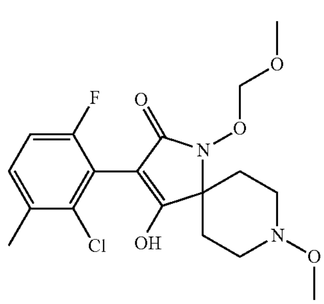 [SMILES: COCON1C(=O)C(c2c(F)ccc(C)c2Cl)=C(O)C12CCN(OC)CC2] | 155-158° C. | LC/MS: 401/403 (M + H)⁺<br>$R_t$ = 1.51 min |

TABLE P2ii-continued

Physical data of compounds of formula II

| Compound No. | Structures | Melting Point | MS/NMR |
|---|---|---|---|
| P2ii.61 | 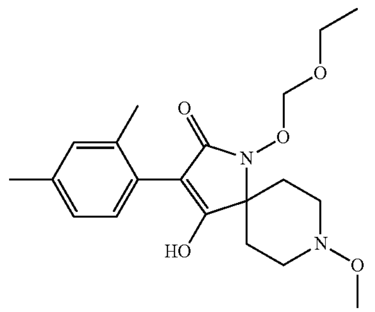 [SMILES: CCOCON1C(=O)C(c2ccc(C)cc2C)=C(O)C12CCN(OC)CC2] | powder | LC/MS: 377 (M + H)$^+$<br>R$_t$ = 1.66 min |
| P2ii.62 | 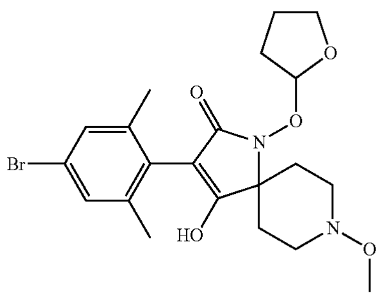 | 91-92° C. | LC/MS: 467/469 (M + H)$^+$<br>R$_t$ = 1.71 min |
| P2ii.63 | 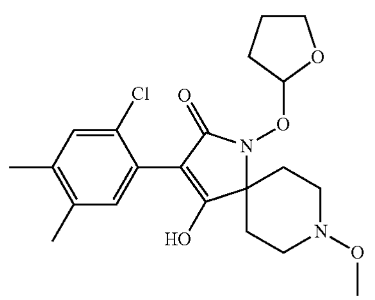 | 84-85° C. | LC/MS: 423/425 (M + H)$^+$<br>R$_t$ = 1.71 min |
| P2ii.64 | 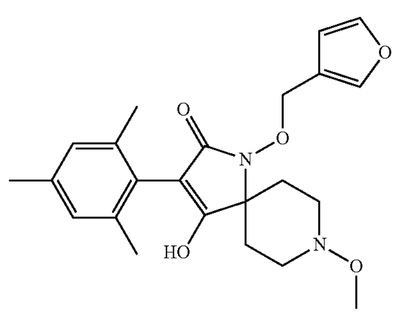 [SMILES: CON1CCC2(CC1)C(O)=C(c1c(C)cc(C)cc1C)C(=O)N2OCc1ccoc1] | 154-157° C. | LC/MS: 413 (M + H)$^+$<br>R$_t$ = 1.77 min |
| P2ii.65 | 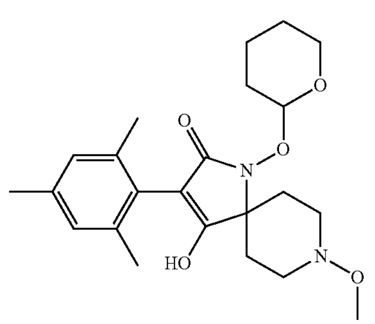 | 103-106° C. | LC/MS: 417 (M + H)$^+$<br>R$_t$ = 1.77 min |

TABLE P2ii-continued

Physical data of compounds of formula II

| Compound No. | Structures | Melting Point | MS/NMR |
|---|---|---|---|
| P2ii.66 | 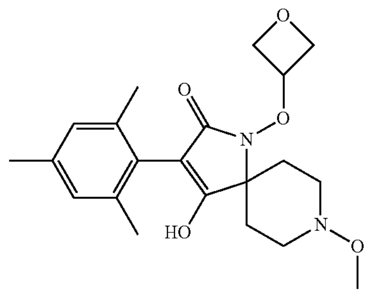 | 88-91° C. | LC/MS: 389 (M + H)+<br>$R_t$ = 1.54 min |
| P2ii.67 | 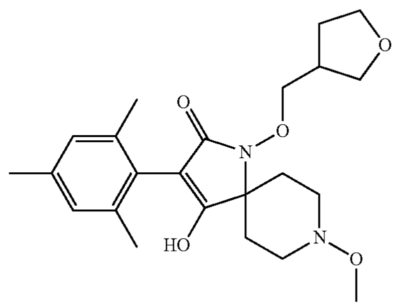 [SMILES: CON1CCC2(CC1)C(O)=C(c1c(C)cc(C)cc1C)C(=O)N2OCC1CCOC1] | 69-72° C. | LC/MS: 417 (M + H)+<br>$R_t$ = 1.64 min |
| P2ii.68 | 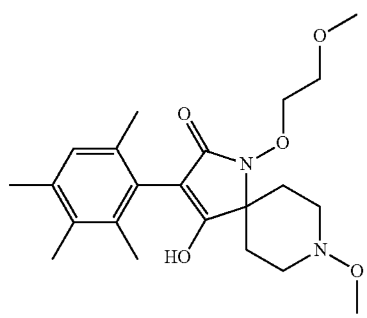 | gum | LC/MS: 405 (M + H)+<br>$R_t$ = 1.65 min |
| P2ii.69 | 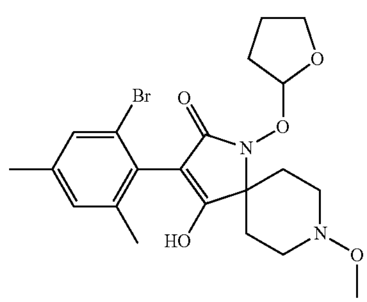 | gum | LC/MS: 467/469 (M + H)+<br>$R_t$ = 1.66 min |
| P2ii.70 | 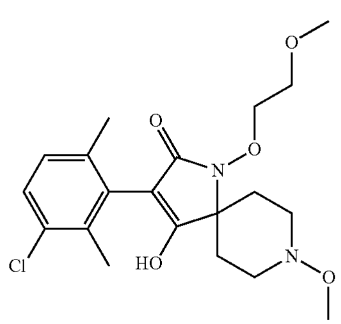 [SMILES: COCCON1C(=O)C(c2c(C)ccc(Cl)c2C)=C(O)C12CCN(OC)CC2] | gum | LC/MS: 411/413 (M + H)+<br>$R_t$ = 1.61 min |

TABLE P2ii-continued

Physical data of compounds of formula II

| Compound No. | Structures | Melting Point | MS/NMR |
|---|---|---|---|
| P2ii.71 | 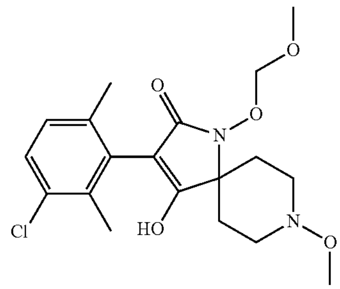 [SMILES: COCON1C(=O)C(c2c(C)ccc(Cl)c2C)=C(O)C12CCN(OC)CC2] | gum | LC/MS: 397/399 (M + H)+<br>R$_t$ = 1.60 min |
| P2ii.72 | 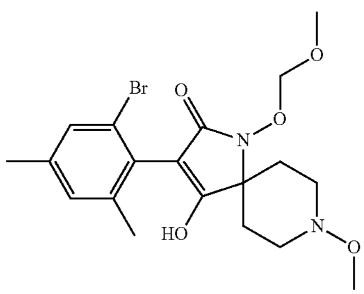 | 167-171° C. | LC/MS: 441/443 (M + H)+<br>R$_t$ = 1.58 min |
| P2ii.73 | 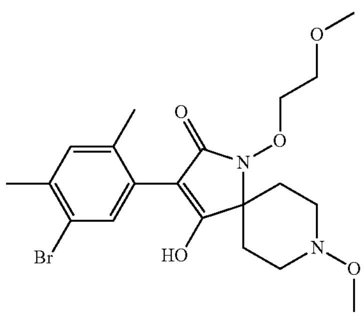 | 63-64° C. | LC/MS: 455/457 (M + H)+<br>R$_t$ = 1.72 min |
| P2ii.74 | 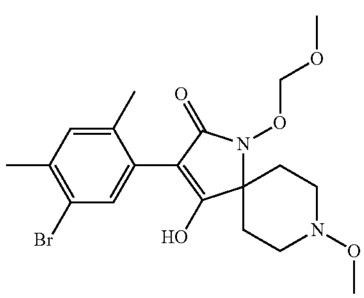 | 79-80° C. | LC/MS: 441/443 (M + H)+<br>R$_t$ = 1.70 min |
| P2ii.75 | 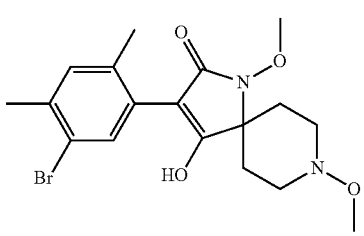 | 86-87° C. | LC/MS: 411/413 (M + H)+<br>R$_t$ = 1.69 min |

TABLE P2ii-continued

Physical data of compounds of formula II

| Compound No. | Structures | Melting Point | MS/NMR |
|---|---|---|---|
| P2ii.76 | 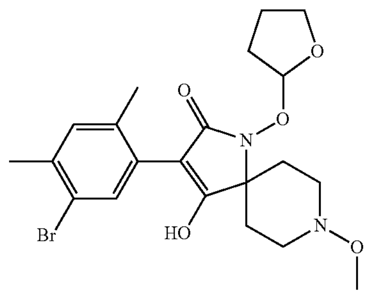 | 96-97° C. | LC/MS: 467/469 (M + H)$^+$<br>R$_t$ = 1.78 min |
| P2ii.77 | 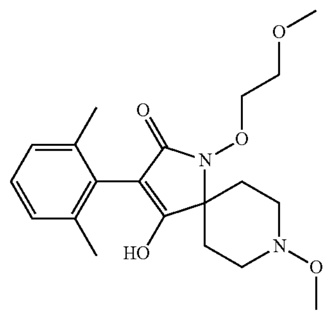 [SMILES: COCCON1C(=O)C(c2c(C)cccc2C)=C(O)C12CCN(OC)CC2] | 141-144° C. | LC/MS: 377 (M + H)$^+$<br>R$_t$ = 1.49 min |
| P2ii.78 | 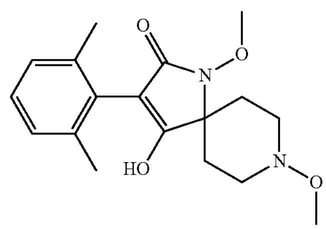 [SMILES: CON1CCC2(CC1)C(O)=C(c1c(C)cccc1C)C(=O)N2OC] | 153-155° C. | LC/MS: 333 (M + H)$^+$<br>R$_t$ = 1.44 min |
| P2ii.79 | 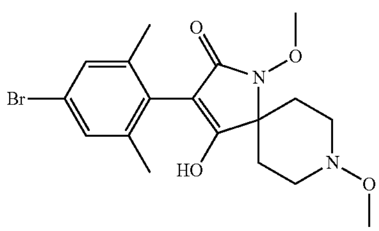 | 188-191° C. | LC/MS: 411/413 (M + H)$^+$<br>R$_t$ = 1.63 min |
| P2ii.80 | 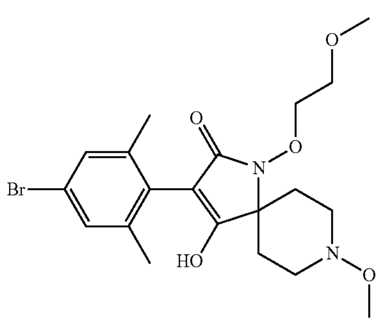 | 163-167° C. | LC/MS: 455/457 (M + H)$^+$<br>R$_t$ = 1.67 min |

TABLE P2ii-continued

Physical data of compounds of formula II

| Compound No. | Structures | Melting Point | MS/NMR |
|---|---|---|---|
| P2ii.81 | 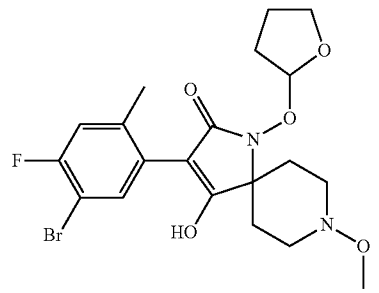 [SMILES: CON1CCC2(CC1)C(O)=C(c1cc(Br)c(F)cc1C)C(=O)N2OC1CCCO1] | gum | LC/MS: 471/473 (M + H)+<br>$R_t$ = 1.70 min |
| P2ii.82 | 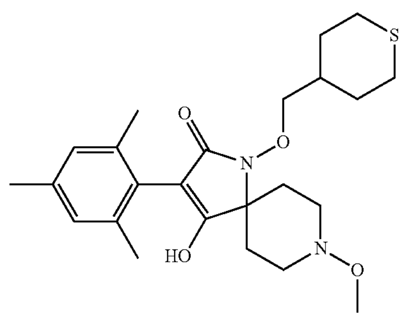 [SMILES: CON1CCC2(CC1)C(O)=C(c1c(C)cc(C)cc1C)C(=O)N2OCC1CCSCC1] | 95-98° C. | LC/MS: 447 (M + H)+<br>$R_t$ = 1.89 min |
| P2ii.83 | 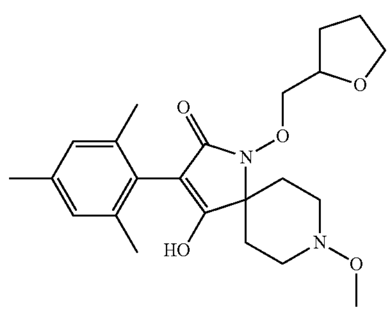 | 155-157° C. | LC/MS: 413 (M + H)+<br>$R_t$ = 1.75 min |
| P2ii.84 | 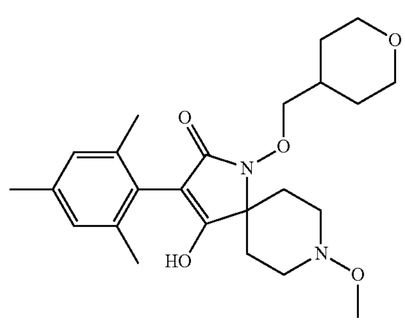 [SMILES: CON1CCC2(CC1)C(O)=C(c1c(C)cc(C)cc1C)C(=O)N2OCC1CCOCC1] | 100-103° C. | LC/MS: 431 (M + H)+<br>$R_t$ = 1.70 min |
| P2ii.85 | 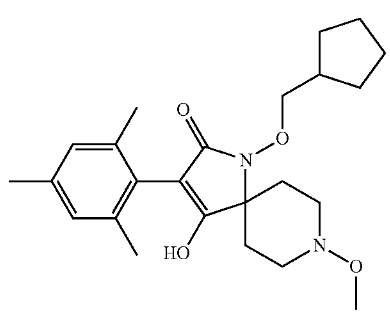 [SMILES: CON1CCC2(CC1)C(O)=C(c1c(C)cc(C)cc1C)C(=O)N2OCC1CCCC1] | 74-77° C. | LC/MS: 415 (M + H)+<br>$R_t$ = 1.98 min |

TABLE P2ii-continued

Physical data of compounds of formula II

| Compound No. | Structures | Melting Point | MS/NMR |
|---|---|---|---|
| P2ii.86 | 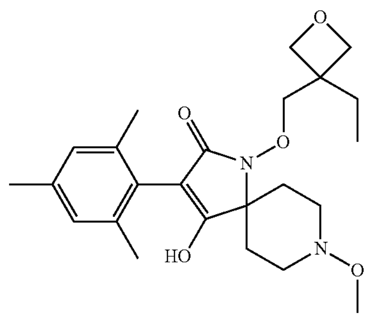 [SMILES: CCC1(CON2C(=O)C(c3c(C)cc(C)cc3C)=C(O)C23CCN(OC)CC3)COC1] | 88-91° C. | LC/MS: 431 (M + H)⁺<br>$R_t$ = 1.62 min |
| P2ii.87 | 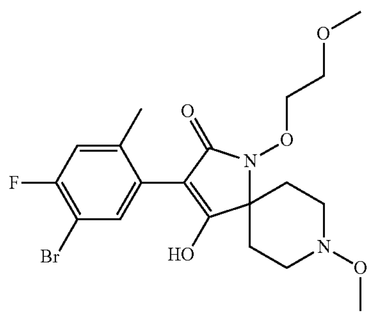 [SMILES: COCCON1C(=O)C(c2cc(Br)c(F)cc2C)=C(O)C12CCN(OC)CC2] | 71-74° C. | LC/MS: 459/461 (M + H)⁺<br>$R_t$ = 1.66 min |
| P2ii.88 | 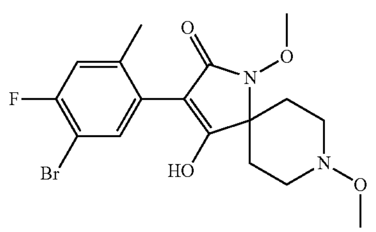 [SMILES: CON1CCC2(CC1)C(O)=C(c1cc(Br)c(F)cc1C)C(=O)N2OC] | solid | LC/MS: 415/417 (M + H)⁺<br>$R_t$ = 1.63 min |
| P2ii.89 | 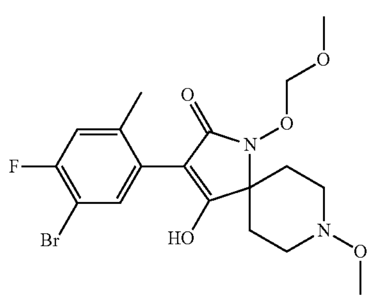 [SMILES: COCON1C(=O)C(c2cc(Br)c(F)cc2C)=C(O)C12CCN(OC)CC2] | 64-67° C. | LC/MS: 445/447 (M + H)⁺<br>$R_t$ = 1.65 min |
| P2ii.90 | 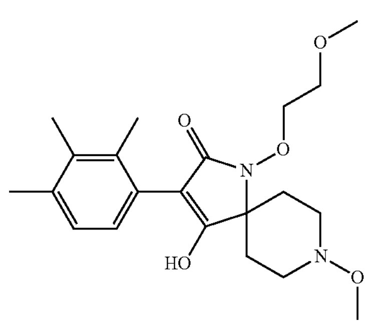 | solid | LC/MS: 391 (M + H)⁺<br>$R_t$ = 1.62 min |

TABLE P2ii-continued
Physical data of compounds of formula II
| Compound No. | Structures | Melting Point | MS/NMR |
|---|---|---|---|
| P2ii.91 | 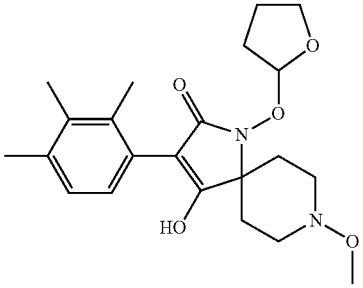 | foam | LC/MS: 403 (M + H)+<br>R$_t$ = 1.68 min |
| P2ii.92 | 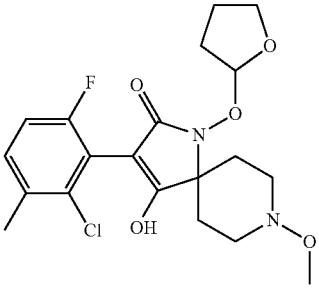 | 86-89° C. | LC/MS: 427/429 (M + H)+<br>R$_t$ = 1.61 min |
| P2ii.93 | 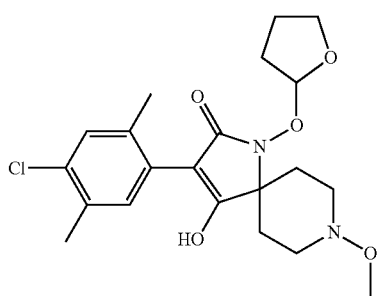 [SMILES: CON1CCC2(CC1)C(O)=C(c1cc(C)c(Cl)cc1C)C(=O)N2OC1CCCO1] | 88-91° C. | LC/MS: 423/425 (M + H)+<br>R$_t$ = 1.74 min |
| P2ii.94 | 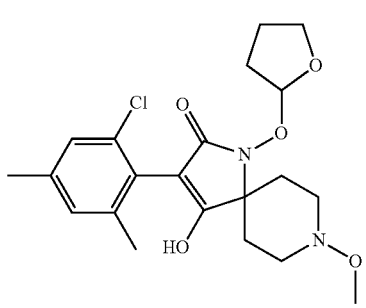 | 84-88° C. | LC/MS: 423/425 (M + H)+<br>R$_t$ = 1.63 min |

TABLE P2ii-continued
Physical data of compounds of formula II
| Compound No. | Structures | Melting Point | MS/NMR |
|---|---|---|---|
| P2ii.95 | 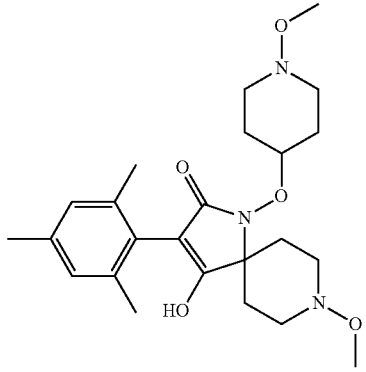 | solid | LC/MS: 446 (M + H)+<br>R_t = 1.62 min |
| P2ii.96 | 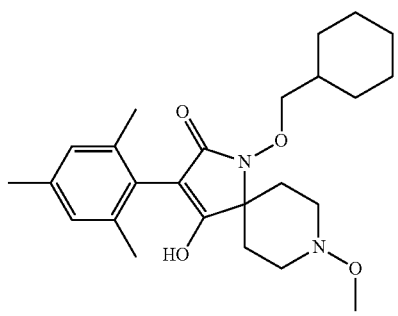 | 169-172° C. | LC/MS: 429 (M + H)+<br>R_t = 2.05 min |
| P2ii.97 | 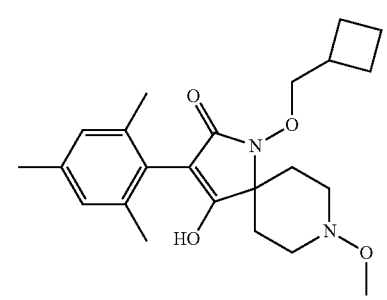 [SMILES: CON1CCC2(CC1)C(O)=C(c1c(C)cc(C)cc1C)C(=O)N2OCC1CCC1] | 113-115° C. | LC/MS: 401 (M + H)+<br>R_t = 1.89 min |
| P2ii.98 | 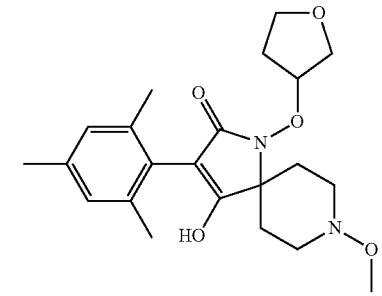 | 135-138° C. | LC/MS: 403 (M + H)+<br>R_t = 1.57 min |

TABLE P2ii-continued

Physical data of compounds of formula II

| Compound No. | Structures | Melting Point | MS/NMR |
|---|---|---|---|
| P2ii.99 | 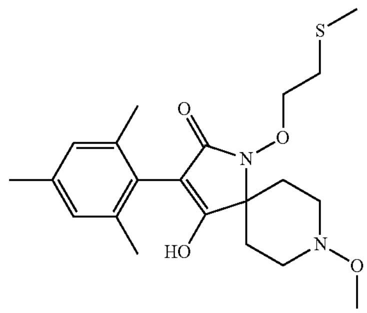 | 113-115° C. | LC/MS: 407 (M + H)$^+$<br>$R_t$ = 1.72 min |
| P2ii.100 | 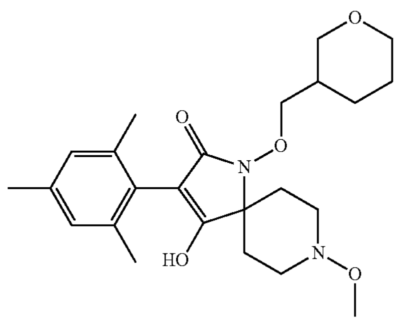 [SMILES: CON1CCC2(CC1)C(O)=C(c1c(C)cc(C)cc1C)C(=O)N2OCC1CCCOC1] | 98-101° C. | LC/MS: 431 (M + H)$^+$<br>$R_t$ = 1.72 min |
| P2ii.101 | 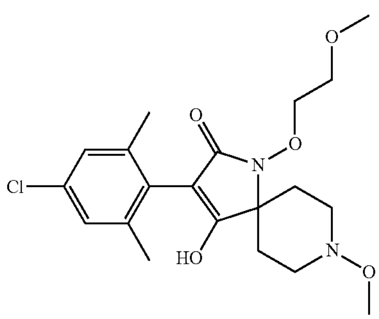 [SMILES: COCCON1C(=O)C(c2c(C)cc(Cl)cc2C)=C(O)C12CCN(OC)CC2] | 161-164° C. | LC/MS: 411/413 (M + H)$^+$<br>$R_t$ = 1.63 min |
| P2ii.102 | 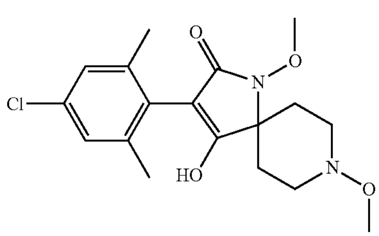 [SMILES: CON1CCC2(CC1)C(O)=C(c1c(C)cc(Cl)cc1C)C(=O)N2OC] | 88-92° C. | LC/MS: 367/369 (M + H)$^+$<br>$R_t$ = 1.58 min |
| P2ii.103 | 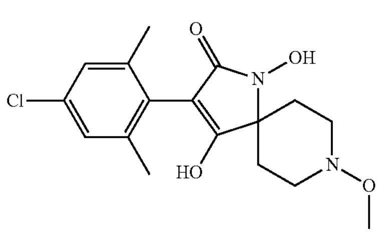 [SMILES: CON1CCC2(CC1)C(O)=C(c1c(C)cc(Cl)cc1C)C(=O)N2O] | solid | LC/MS: 353/355 (M + H)$^+$<br>$R_t$ = 1.37 min |

EXAMPLE 20, step 2

TABLE P2ii-continued

Physical data of compounds of formula II

| Compound No. | Structures | Melting Point | MS/NMR |
|---|---|---|---|
| P2ii.104 | 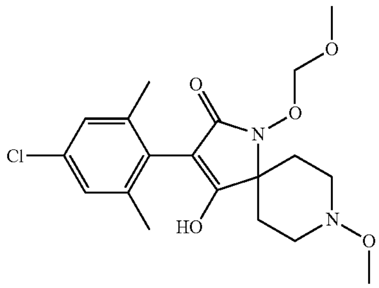 [SMILES: COCON1C(=O)C(c2c(C)cc(Cl)cc2C)=C(O)C12CCN(OC)CC2] | 176-178° C. | LC/MS: 397/399 (M + H)+<br>$R_t$ = 1.64 min |
| P2ii.105 | 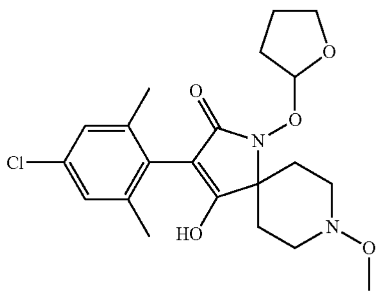 [SMILES: CON1CCC2(CC1)C(O)=C(c1c(C)cc(Cl)cc1C)C(=O)N2OC1CCCO1] | 137-139° C. | LC/MS: 421/423 (M − H)−<br>$R_t$ = 1.69 min |

Intermediates from Table P3ii can be prepared by analogous procedures.

TABLE P3ii

Physical data of intermediates

| Compound No. | Structures | Melting Point | MS/NMR |
|---|---|---|---|
| P3ii.1 | EXAMPLE 11, step 4<br>EXAMPLE 16, step 2 | 140-142° C. | LC/MS: 351 (M + H)+<br>$R_t$ = 1.59 min |
| P3ii.2 | EXAMPLE 16, step 1 | 153-156° C. | LC/MS: 318 (M + H)+<br>$R_t$ = 1.66 min |
| P3ii.3 | 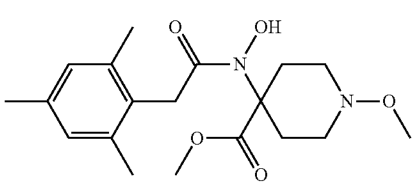 | 199-200° C. | LC/MS: 365 (M + H)+<br>$R_t$ = 1.68 min |

TABLE P3ii-continued

Physical data of intermediates

| Compound No. | Structures | Melting Point | MS/NMR |
|---|---|---|---|
| P3ii.4 | EXAMPLE 12, step 1 | 108-110° C. | LC/MS: 403 (M + H)+<br>$R_t$ = 1.98 min |
| P3ii.5 | 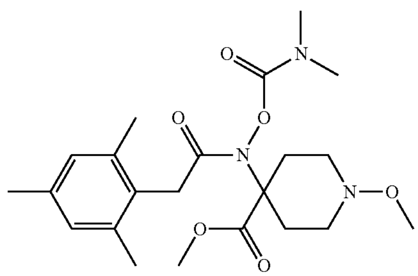 | gum | LC/MS: 436 (M + H)+<br>$R_t$ = 1.91 min |
| P3ii.6 | EXAMPLE 17, step 1 | 107-109° C. | LC/MS: 435 (M + H)+<br>$R_t$ = 2.03 min |
| P3ii.7 | 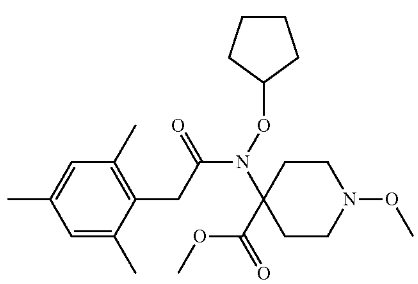 | gum | LC/MS: 433 (M + H)+<br>$R_t$ = 2.19 min |
| P3ii.8 | EXAMPLE 18, step 1 | gum | LC/MS: 447 (M + H)+<br>$R_t$ = 2.23 min |

TABLE P3ii-continued

Physical data of intermediates

| Compound No. | Structures | Melting Point | MS/NMR |
|---|---|---|---|
| P3ii.9 | 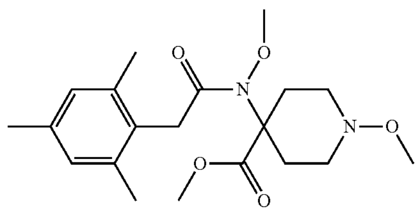 | gum | LC/MS: 379 (M + H)$^+$<br>$R_t$ = 1.89 min |
| P3ii.10 | 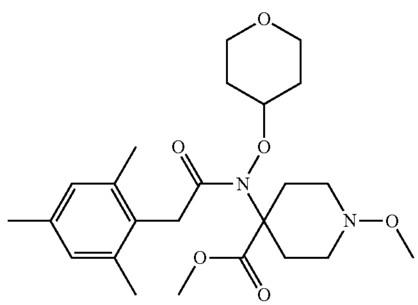 | gum | LC/MS: 449 (M + H)$^+$<br>$R_t$ = 1.89 min |
| P3ii.11 | 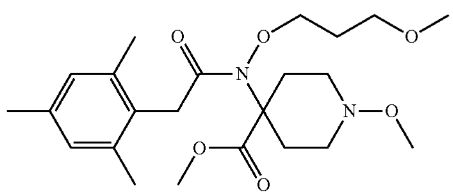 | 55-57° C. | LC/MS: 437 (M + H)$^+$<br>$R_t$ = 1.95 min |
| P3ii.12 | 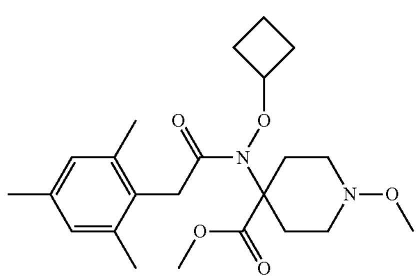 | gum | LC/MS: 419 (M + H)$^+$<br>$R_t$ = 2.09 min |
| P3ii.13 | 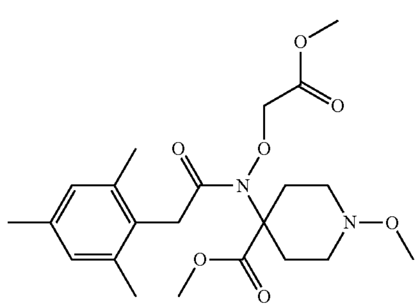 | gum | LC/MS: 437 (M + H)$^+$<br>$R_t$ = 1.86 min |
| P3ii.14 | 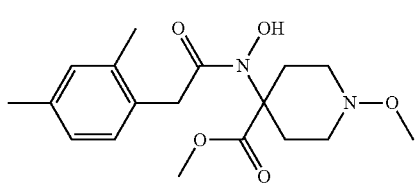 | solid | LC/MS: 351 (M + H)$^+$<br>$R_t$ = 1.59 min |

TABLE P3ii-continued

Physical data of intermediates

| Compound No. | Structures | Melting Point | MS/NMR |
|---|---|---|---|
| P3ii.15 | 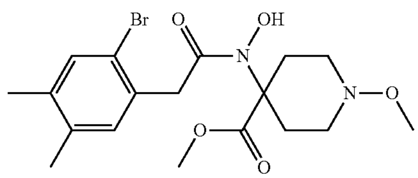 | 166-167° C. | LC/MS: 429/431 (M + H)$^+$<br>$R_t$ = 1.71 min |
| P3ii.16 | 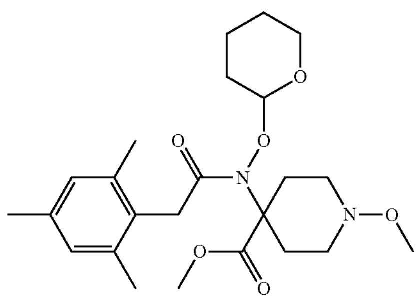 | gum | LC/MS: 449 (M + H)$^+$<br>$R_t$ = 2.08 min |
| P3ii.17 | 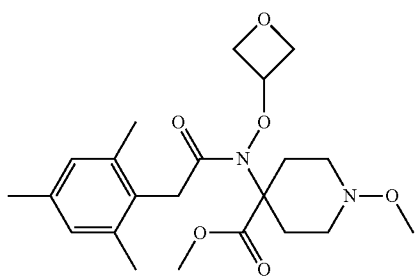 | gum | LC/MS: 421 (M + H)$^+$<br>$R_t$ = 1.80 min |
| P3ii.18 | 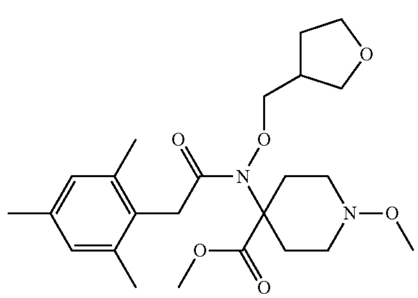 | gum | LC/MS: 449 (M + H)$^+$<br>$R_t$ = 1.88 min |
| P3ii.19 | 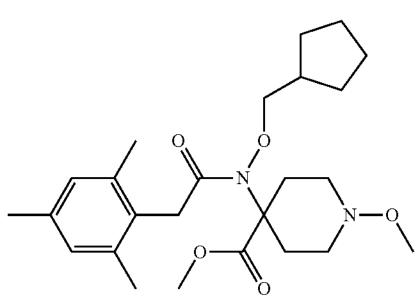 | gum | LC/MS: 447 (M + H)$^+$<br>$R_t$ = 2.25 min |

TABLE P3ii-continued
Physical data of intermediates
| Compound No. | Structures | Melting Point | MS/NMR |
|---|---|---|---|
| P3ii.20 | 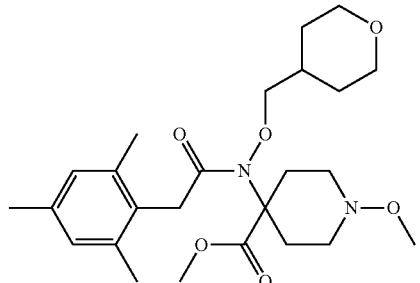 | gum | LC/MS: 463 (M + H)+<br>R$_t$ = 1.93 min |
| P3ii.21 | 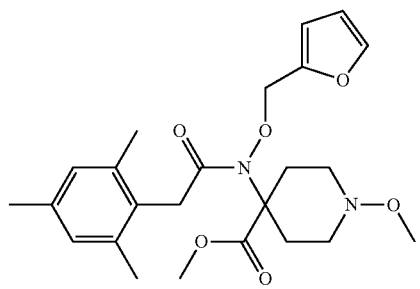 | gum | LC/MS: 445 (M + H)+<br>R$_t$ = 2.05 min |
| P3ii.22 | 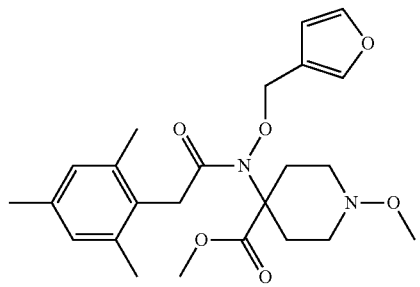 | gum | LC/MS: 445 (M + H)+<br>R$_t$ = 1.98 min |
| P3ii.23 | 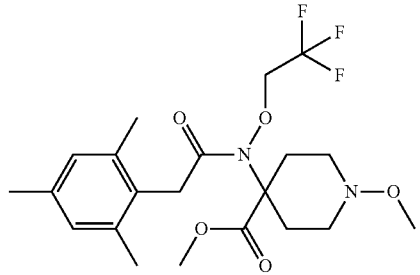 | gum | LC/MS: 447 (M + H)+<br>R$_t$ = 2.03 min |
| P3ii.24 | 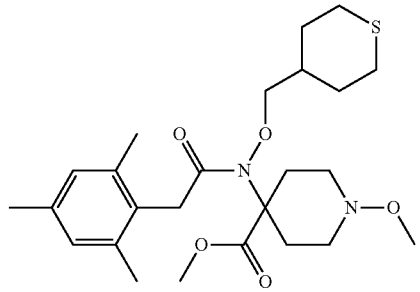 | gum | LC/MS: 479 (M + H)+<br>R$_t$ = 2.10 min |

TABLE P3ii-continued
Physical data of intermediates
| Compound No. | Structures | Melting Point | MS/NMR |
|---|---|---|---|
| P3ii.25 | 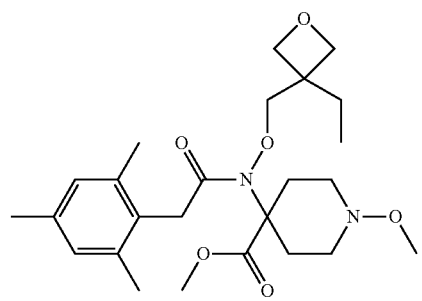 | gum | LC/MS: 463 (M + H)+<br>R$_t$ = 1.94 min |
| P3ii.26 | 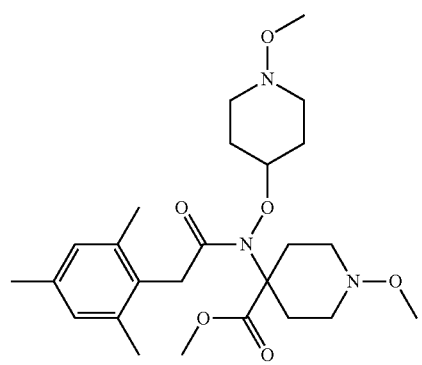<br>EXAMPLE 19, step 2 | gum | LC/MS: 478 (M + H)+<br>R$_t$ = 1.97 min |
| P3ii.27 | 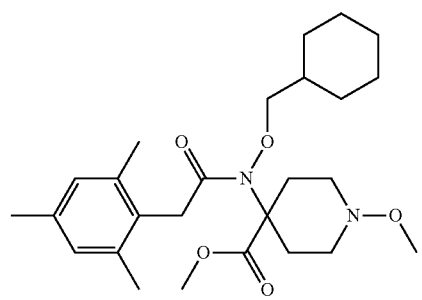 | gum | LC/MS: 461 (M + H)+<br>R$_t$ = 2.31 min |
| P3ii.28 | 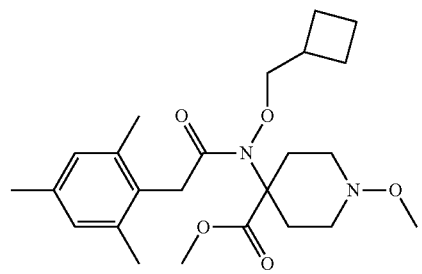 | gum | LC/MS: 433 (M + H)+<br>R$_t$ = 2.17 min |

TABLE P3ii-continued

Physical data of intermediates

| Compound No. | Structures | Melting Point | MS/NMR |
|---|---|---|---|
| P3ii.29 | 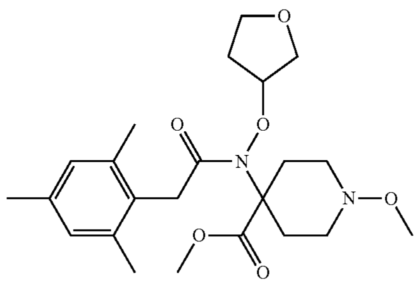 | 115-117° C. | LC/MS: 435 (M + H)+<br>$R_t$ = 1.85 min |
| P3ii.30 | 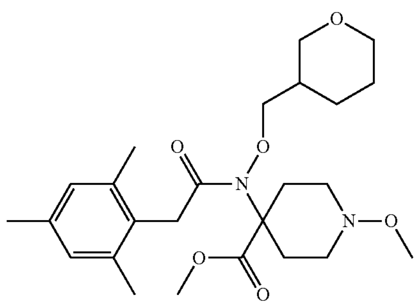 | gum | LC/MS: 463 (M + H)+<br>$R_t$ = 2.01 min |
| P3ii.31 | 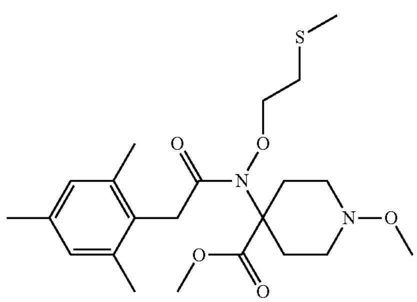 | gum | LC/MS: 439 (M + H)+<br>$R_t$ = 2.03 min |
| P3ii.32 | 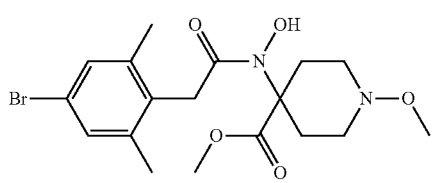 [SMILES: COC(=O)C1(N(O)C(=O)Cc2c(C)cc(Br)cc2C)CCN(OC)CC1] | solid | LC/MS: 429/431 (M + H)+<br>$R_t$ = 1.73 min |
| P3ii.33 | 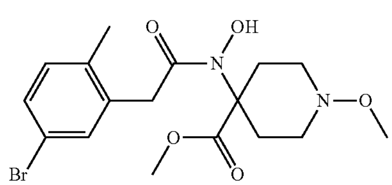 | solid | LC/MS: 415/417 (M + H)+<br>$R_t$ = 1.67 min |
| P3ii.34 | 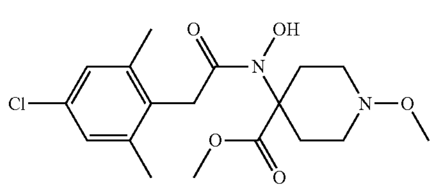 | 228-231° C. | LC/MS: 385/387 (M + H)+<br>$R_t$ = 1.71 min |

EXAMPLE 20, step 1

TABLE P3ii-continued

Physical data of intermediates

| Compound No. | Structures | Melting Point | MS/NMR |
|---|---|---|---|
| P3ii.35 | 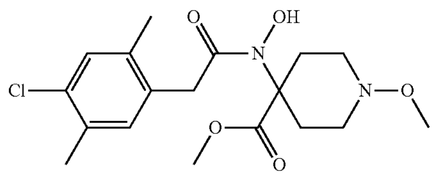 [SMILES: COC(=O)C1(N(O)C(=O)Cc2cc(C)c(Cl)cc2C)CCN(OC)CC1] | | LC/MS: 385/387 (M + H)$^+$ <br> R$_t$ = 1.86 min |
| P3ii.36 | 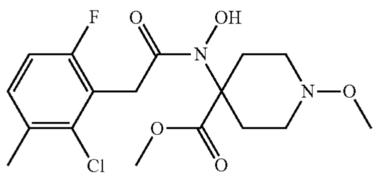 | | LC/MS: 389/391 (M + H)$^+$ <br> R$_t$ = 1.59 min |
| P3ii.37 | 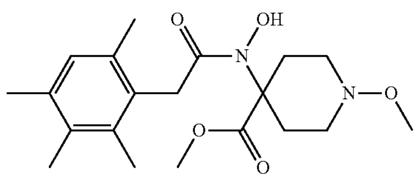 | | LC/MS: 379 (M + H)$^+$ <br> R$_t$ = 1.91 min |
| P3ii.38 | 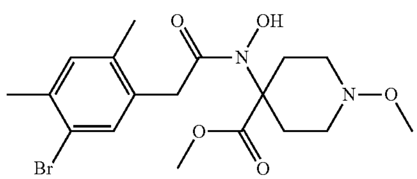 | 162-163° C. | LC/MS: 429/431 (M + H)$^+$ <br> R$_t$ = 1.76 min |
| P3ii.39 | 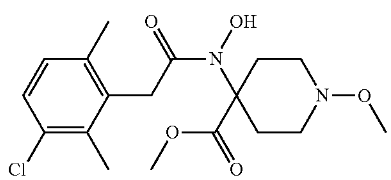 [SMILES: COC(=O)C1(N(O)C(=O)Cc2c(C)ccc(Cl)c2C)CCN(OC)CC1] | | LC/MS: 385/387 (M + H)$^+$ <br> R$_t$ = 1.67 min |
| P3ii.40 | 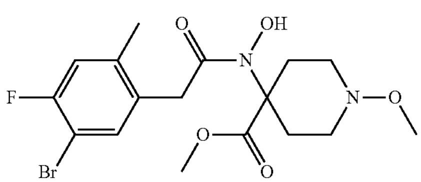 [SMILES: COC(=O)C1(N(O)C(=O)Cc2cc(Br)c(F)cc2C)CCN(OC)CC1] | | LC/MS: 433/435 (M + H)$^+$ <br> R$_t$ = 1.69 min |
| P3ii.41 | 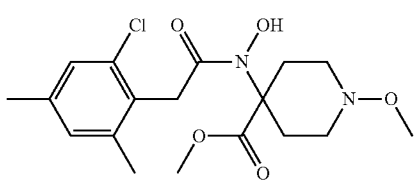 | | LC/MS: 385/387 (M + H)$^+$ <br> R$_t$ = 1.69 min |
| P3ii.42 | 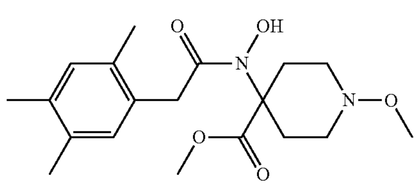 | | LC/MS: 365 (M + H)$^+$ <br> R$_t$ = 1.67 min |

TABLE P3ii-continued

Physical data of intermediates

| Compound No. | Structures | Melting Point | MS/NMR |
|---|---|---|---|
| P3ii.43 | 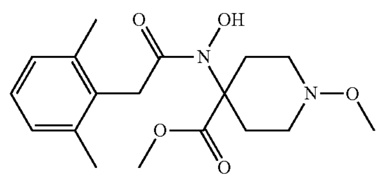 [SMILES: COC(=O)C1(N(O)C(=O)Cc2c(C)cccc2C)CCN(OC)CC1] | | LC/MS: 351 (M + H)+<br>$R_t$ = 1.55 min |
| P3ii.44 | 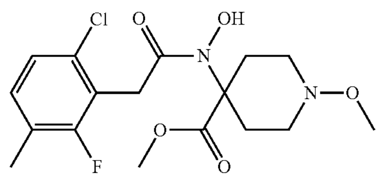 | | LC/MS: 389/391 (M + H)+<br>$R_t$ = 1.62 min |
| P3ii.45 | 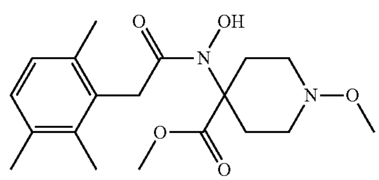 | | LC/MS: 365 (M + H)+<br>$R_t$ = 1.66 min |
| P3ii.46 | 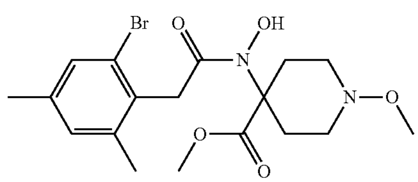 | | LC/MS: 429/431 (M + H)+<br>$R_t$ = 1.67 min |
| P3ii.47 | 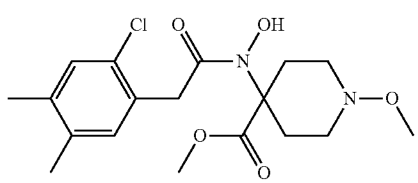 | | LC/MS: 385/387 (M + H)+<br>$R_t$ = 1.71 min |
| P3ii.48 | 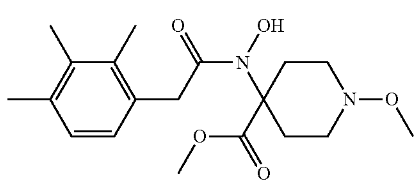 | | LC/MS: 365 (M + H)+<br>$R_t$ = 1.65 min |
| P3ii.49 | EXAMPLE 23, step 3 | 100-103° C. | LC/MS: 380/382 (M + H)+<br>$R_t$ = 1.99 min |

Intermediates from Table P4ii can be prepared by analogous procedures.

TABLE P4ii

Physical data of intermediates

| Compound No. | Structures | Melting Point | MS/NMR |
|---|---|---|---|
| P4ii.1 | EXAMPLE 11, step 2 | 130-131° C. | $^1$H-NMR (CDCl$_3$): 1.55-2.35 (br signals, total 4H), 2.60-3.45 (br signals, total 4H), 3.52 (s, 3H), 5.19 (br s, 1H), 5.42 (br s, 1H). IR (CN): ν 2227.8 cm$^{-1}$. LC/MS (ES+): 172 (M + H)$^+$; R$_t$ = 0.31 min. |
| P4ii.2 | EXAMPLE 11, step 3 | Oil | $^1$H-NMR (CDCl$_3$): 1.50-2.40 (br signals, total 4H), 2.76 (br m, 2H), 3.01-3.32 (br m, 2H), 3.52 (s, 3H), 3.76 (s, 3H), 5.58 (br s, 2H). IR (COOMe): ν 1731.3 cm$^{-1}$. LC/MS (ES+): 205 (M + H)$^+$; R$_t$ = 0.31 min. |
| P4ii.3 | EXAMPLE 23, step 2 | Oil | $^1$H-NMR (CDCl$_3$): 1.19 (t, 3H), 1.59-2.29 (br signals, total 4H), 2.64-3.43 (br signals, total 4H), 3.52 (s, 3H), 3.80 (q, 2H), 5.37 (br s, 1H). IR (CN): ν 2235.3 cm$^{-1}$. LC/MS (ES+): 200 (M + H)$^+$; R$_t$ = 1.21 min. |
| P4ii.4 | example 25, step 1 | 180° C. | $^1$H-NMR (CD$_3$OD): 1.54-2.29 (br signals, total 4H), 2.82 (br m, 2H), 3.07-3.26 (br signals, total 2H), 3.49 (s, 3H). LC/MS (ES+): 191 (M + H)$^+$; R$_t$ = 0.22 min. |

Examples of compounds of formula I where Q is iii are disclosed in WO2009/049851.

BIOLOGICAL EXAMPLES

Example B1

*Myzus Persicae* (Green Peach Aphid): Mixed Population, Feeding/Residual Contact Activity, Preventive Sunflower leaf discs are placed on agar in a 24-well microtiter plate and sprayed with test solutions. After drying, the leaf discs are infested with an aphid population of mixed ages. After an incubation period of 6 DAT, samples are checked for mortality. The results are summarized in the following Table.

TABLE B1

| | Concentration | A Mortality | B |
|---|---|---|---|
| Cpd. T1iii.067 of Table T1iii, wherein G is CO$_2$C$_2$H$_5$ | 200 ppm | 50% | 80% |

TABLE B1-continued

| | Concentration | A Mortality | B |
|---|---|---|---|
| Cpd. P1.2 of Table P1 | 200 ppm | 95% | 90% |

A: neonicotinoid insecticides susceptible *Myzus persicae* (mixed age population)
B: neonicotinoid insecticides resistant *Myzus persicae* (mixed age population)

Example B2

Determination of the Cross-Resistance Status of Compounds of Formula I when Applied Against Agronomically Important Pest Species Resistant to One or More Commercially Available Class of Insecticide Resistance may be defined as 'a heritable change in the sensitivity of a pest population that is reflected in the repeated failure of a product to achieve the expected level of control when used according to the label recommendation for that pest species'. (IRAC) Cross-resistance occurs when resistance to one insecticide confers resistance to another insecticide via the same biochemical mechanism. This can happen within insecticide chemical groups or between insecticide chemical groups. Cross-resistance may occur even if the resistant insect has never been exposed to one of the chemical classes of insecticide.

The level of resistance and therefore the impact on the performance of the insecticide can be measured by the use of a 'Resistance Factor'. The resistance factor can be calculated by dividing the concentration of an insecticide that provides a set level of mortality (i.e. 80%) for the 'resistant' strain with the concentration of the same insecticide that provides the same level of mortality for the 'susceptible' insect of the same species and life-stage. Although there are no set rules, a low value (1-10) indicates no cross-resistance and only natural levels of variation and a high value (50+) provides strong evidence of cross-resistance.

a) Neonicotinoid and Pyrethroid Resistant Strain of the Green Peach Aphid (*Myzus persicae*)

*Myzus persicae* strains utilised:

Standard screening strain of *Myzus persicae* (Neonicotinoid susceptible)

FRC-P strain of *Myzus persicae* (Neonicotinoid resistant)

Bioassay Method:

*Myzus persicae*: mixed population, contact activity, curative on pea seedlings

Pea seedlings, infested with an aphid population of mixed ages, are treated with the test solutions in a spray chamber. 6 days after treatment, samples are checked for mortality.

TABLE B2a

| Compound of formula I | Resistance Factor (RF$_{80}$)* |
|---|---|
| 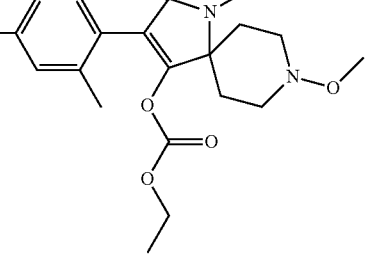 | 1 |
| | <1 |
| | <1 |
| | 4 |
| | 4 |
| | 4 |
| | 1 |
| Thiamethoxam (Neonicotinoid) | >250 |

*Resistance factor (RF$_{80}$) = Lowest concentration tested that provides greater than 80% mortality of resistant aphids/Lowest concentration tested that provides greater than 80% mortality of susceptible aphids.

There is no evidence of cross-resistance between the tested compounds of formula I and the neonicotinoid in this population of neonicotinoid resistant *Myzus persicae*. This is demonstrated by the high RF observed for thiamethoxam and low resistance factors for the compounds of formula I. This indicates that the expected level of control provided by the tested compounds of formula I is unlikely to be greatly different when applied against neonicotinoid resistant and susceptible *Myzus persicae*.

Although not presented, the FRC strain is also known to be pyrethroid resistant and therefore the data suggests that there is also no cross-resistance with this insecticide chemistry in this strain.

b) Neonicotinoid Resistant Strain of the Brown Planthopper (*Nilaparvata lugens*)

*Nilaparvata lugens* strains utilised:

Standard screening strain of *Nilaparvata lugens* (Neonicotinoid susceptible)

IND3 strain of *Nilaparvata lugens* (Neonicotinoid resistant)

Bioassay Method:

*Nilaparvata lugens*: larvicide, feeding/contact activity, preventive

Rice seedlings are treated with the diluted test solutions in a turn table spray chamber. After drying, they are infested with 20 $N_3$ nymphs. 6 and 12 days after the treatment samples are checked for mortality, growth regulation, and effects on the $F_1$ generation.

TABLE B2b

| Compound of formula I | Resistance Factor $(RF_{80})$* |
|---|---|
| 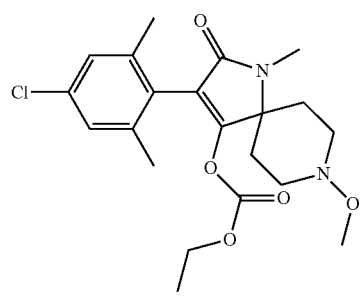 [SMILES: CCOC(=O)OC1=C(c2c(C)cc(Cl)cc2C)C(=O)N(C)C12CCN(OC)CC2] | 4 |
| 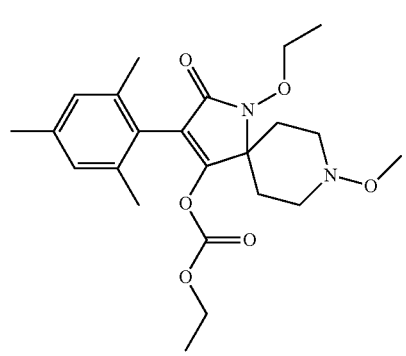 | <1 |
| 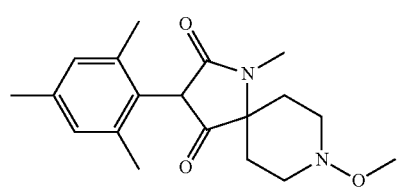 | 1 |

TABLE B2b-continued

| Compound of formula I | Resistance Factor $(RF_{80})$* |
|---|---|
| 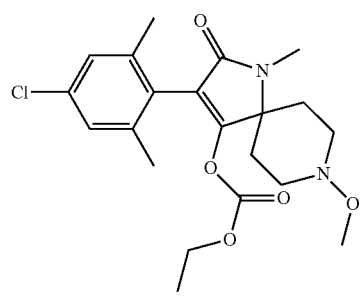 [SMILES: CCOC(=O)OC1=C(c2c(C)cc(Cl)cc2C)C(=O)N(C)C12CCN(OC)CC2] | 1 |
| Thiamethoxam (Neonicotinoid) | >64 |

*Resistance factor $(RF_{80})$ = Lowest concentration tested that provides greater than 80% mortality of resistant hoppers/Lowest concentration tested that provides greater than 80% mortality of susceptible hoppers.

There is no evidence of cross-resistance between the tested compounds of formula I and the neonicotinoid in this population of neonicotinoid resistant *Nilaparvata lugens*. This is demonstrated by the high RF observed for thiamethoxam and low resistance factors for the tested compounds of formula I. This indicates that the expected level of control provided by the STAR compounds is unlikely to be greatly different when applied against neonicotinoid resistant and susceptible *Nilaparvata lugens*.

c) Neonicotinoid and Pyrethroid Resistant Strain of the Tobacco Whitefly (*Bemisia tabaci*)

*Bemisia tabaci* strains utilised:

Standard screening strain of *Bemisia tabaci* (Neonicotinoid susceptible)

ALM07 strain of *Nilaparvata lugens* (Neonicotinoid and pyrethroid resistant) and originally provided by Rothamsted Research, UK. (>250 RF in residual mortality bioassay of adult whitefly with thiamethoxam).

Bioassay Method:

*Bemisia tabaci*: residual activity, preventive egg lay

Cotton seedlings, with all but a single leaf removed are treated with the diluted test solutions in a turn table spray chamber. 24 hours after drying, they are infested with 20 adult whitefly. 3 days after exposure, the total number of adult whitefly and the total number of whitefly eggs laid on the leaf are counted. Percentage control of egg lay is calculated and corrected for control mortality.

TABLE B2c

| Compound of formula I | Resistance Factor (RF$_{50}$)* |
|---|---|
| 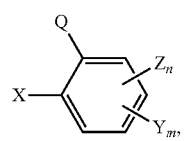 | 4 |

*Resistance factor (RF$_{50}$) = Concentration tested that provides 50% control of resistant whitefly egg lay/concentration that provides 50% control of susceptible whitefly egg lay.

There is no evidence of cross-resistance between the tested compound and neonicotinoid in this population of neonicotinoid resistant Bemisia tabaci. This is demonstrated by the low resistance factor for the tested compound of formula I in the egg lay bioassay, compared to high RF observed for thiamethoxam in adult mortality bioassays. A direct comparison of cross-resistance is not possible for these compounds as they act on different life stages.

The invention claimed is:

1. A method of controlling insects from the order hemiptera in plants, which insects are resistant to a neonicotinoid insecticide, which method comprises applying to said neonicotinoid resistant insects a compound of formula I

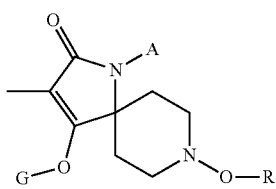

in which Q is
i i

X, Y and Z independently of each other are $C_{1-4}$alkyl, $C_{3-6}$cycloalkyl, $C_{1-4}$haloalkyl, $C_{1-4}$alkoxy, halogen, phenyl or phenyl substituted by $C_{1-4}$alkyl, $C_{1-4}$haloalkyl, halogen or cyano;

m and n, independently of each other, are 0, 1, 2 or 3 and m+n is 0, 1, 2 or 3;

G is hydrogen, a metal, an ammonium, a sulfonium or a latentiating group;

R is hydrogen, $C_{1-6}$alkyl, $C_{1-6}$haloalkyl, $C_{1-6}$cyanoalkyl, benzyl, $C_{1-4}$alkoxy($C_{1-4}$)alkyl, $C_{1-4}$alkoxy($C_{1-4}$)alkoxy($C_{1-4}$)alkyl or a group selected from G;

A is $C_{1-6}$alkyl;

or an agrochemically acceptable salt or an N-oxide thereof.

2. A method according to claim 1 of controlling insects from the Aphididae family, which insects are resistant to a neonicotinoid insecticide, which method comprises applying to said neonicotinoid resistant insects a compound of formula I.

3. A method of protecting a crop of useful plants susceptible to and/or under attack by insects from the order hemiptera, which insects are resistant to a neonicotinoid insecticide, which method comprises applying to said crop, treating a plant propagation material of said crop with, and/or applying to said neonicotinoid resistant insects, a compound of formula I according to claim 1.

4. A method of controlling resistance to one or more neonicotinoid insecticides in insects from the order hemiptera, which comprises alternately applying a compound of formula I according to claim 1 and a neonicotinoid insecticide to said insects or to a crop of useful plants susceptible to and/or under attack from said insects.

5. The method according to claim 1, wherein said insects is one or more of as an example Acyrthosiphum pisum, Aphis citricola, Aphis craccivora, Aphis fabae, Aphis frangulae, Aphis glycines, Aphis gossypii, Aphis nasturtii, Aphis pomi, Aphis spiraecola, Aulacorthum solani, Brachycaudus helichrysi, Brevicoryne brassicae, Diuraphis noxia, Dysaphis devecta, Dysaphis plantaginea, Eriosoma lanigerum, Hyalopterus pruni, Lipaphis erysimi, Macrosiphum avenae, Macrosiphum euphorbiae, Macrosiphum rosae, Myzus cerasi F., Myzus nicotianae, Myzus persicae, Nasonovia ribisnigri, Pemphigus bursarius, Phorodon humuli, Rhopalosiphum insertum Wa, Rhopalosiphum maidis Fitch, Rhopalosiphum padi L., Schizaphis graminum Rond., Sitobion avenae, Toxoptera aurantii, Toxoptera citricola, Phylloxera vitifoliae, Bemisia tabaci, Myzus persicae, Nilaparvata lugens, Aphis gossypii, Trialeurodes vaporariorum, Bactericera cockerelli.

6. The method according to claim 5, wherein said insects are one or more of as an example Bemisia tabaci, Myzus persicae, Nilaparvata lugens, Aphis gossypii, Trialeurodes vaporariorum, Bactericera cockerelli.

7. The method according to claim 3, wherein said crop of useful plants is chosen from cereals; beet; fruit; leguminous crops; cucurbits; fibre plants; vegetables; tobacco, nuts, coffee, eggplants, sugarcane, tea, pepper, grapevines, hops, the plantain family, latex plants, lawn, turf, fodder grass, and ornamentals.

8. The method according to claim 1, wherein compound of formula (I) is in a composition, said composition additionally comprising an agriculturally acceptable diluent or carrier.

9. A method of controlling plant viruses spread by insects from the order hemiptera, the method comprising applying a compound of formula I according to claim 1 to neonicotinoid resistant insects of the order hemiptera, which insects carry said plant viruses.

10. A method of controlling a plant virus in a crop of useful plants susceptible to or under attack by neonicotinoid resistant insects of the order hemiptera, which insects carry said plant virus, the method comprises applying to said crop, treating a plant propagation material of said crop with, or applying to said insects, a compound of formula I according to claim 1.

11. The method according to claim 9, wherein said virus is one or more of Sobemovirus, Caulimovirus (Caulimoviridae), Closterovirus (Closteroviridae), Sequivirus (Sequiviridae), Enamovirus (Luteoviridae), Luteovirus (Luteoviridae), Polerovirus (Luteoviridae), Umbravirus, Nanovirus (Nanoviridae), Cytorhabdovirus (Rhabdoviridae), Nucleorhabdovirus (Rhabdoviridae).

12. The method according to claim 9, wherein said insect is one or more of as an example Acyrthosiphum pisum, Aphis citricola, Aphis craccivora, Aphis fabae, Aphis frangulae, Aphis glycines, Aphis gossypii, Aphis nasturtii, Aphis pomi, Aphis spiraecola, Aulacorthum solani, Brachycaudus helichrysi, Brevicoryne brassicae, Diuraphis noxia, Dysaphis devecta, Dysaphis plantaginea, Eriosoma lanigerum, Hyalopterus pruni, Lipaphis erysimi, Macrosiphum avenae, Macrosiphum euphorbiae, Macrosiphum rosae, Myzus cerasi F., Myzus nicotianae, Myzus persicae, Nasonovia ribisnigri, Pemphigus bursarius, Phorodon humuli, Rhopalosiphum insertum Wa, Rhopalosiphum maidis Fitch, Rhopalosiphum padi L., Schizaphis graminum Rond., Sitobion avenae, Toxoptera aurantii, Toxoptera citricola,Phylloxera vitifoliae, Bemisia tabaci, Myzus persicae, Nilaparvata lugens, Aphis gossypii, Trialeurodes vaporariorum, Bactericera cockerelli.

13. A method according to claim 3 wherein the method comprises applying to the propagation material of said crop a neonicotinoid insecticide followed by the foliar application of a compound of the formula (I) beginning with the 3-to 5leaf crop stage.

14. The method of claim 1, wherein A is methyl.

* * * * *